(12) United States Patent
Banerjee et al.

(10) Patent No.: US 12,378,257 B2
(45) Date of Patent: Aug. 5, 2025

(54) METABOLICALLY STABLE PYRIMIDINYL DIHYDROQUINOXALINONES AS TUBULIN POLYMERIZATION INHIBITORS

(71) Applicant: UNIVERSITY OF TENNESSEE RESEARCH FOUNDATION, Memphis, TN (US)

(72) Inventors: Souvik Banerjee, Fort Smith, AR (US); Wei Li, Germantown, TN (US); Duane D. Miller, Collierville, TN (US); Zhongzhi Wu, Collierville, TN (US); Satyanarayana Pochampally, Memphis, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 17/725,465

(22) Filed: Apr. 20, 2022

(65) Prior Publication Data

US 2023/0286995 A1    Sep. 14, 2023

Related U.S. Application Data

(60) Provisional application No. 63/317,931, filed on Mar. 8, 2022, provisional application No. 63/177,183, filed on Apr. 20, 2021.

(51) Int. Cl.
| | | |
|---|---|---|
| *C07D 491/048* | (2006.01) |
| *A61P 35/00* | (2006.01) |
| *C07D 401/14* | (2006.01) |
| *C07D 403/04* | (2006.01) |
| *C07D 403/14* | (2006.01) |
| *C07D 413/14* | (2006.01) |
| *C07D 471/04* | (2006.01) |
| *C07D 498/04* | (2006.01) |

(52) U.S. Cl.
CPC ......... *C07D 491/048* (2013.01); *A61P 35/00* (2018.01); *C07D 401/14* (2013.01); *C07D 403/04* (2013.01); *C07D 403/14* (2013.01); *C07D 413/14* (2013.01); *C07D 471/04* (2013.01); *C07D 498/04* (2013.01)

(58) Field of Classification Search
CPC C07D 491/048; C07D 401/14; C07D 403/04; C07D 403/14; C07D 413/14; C07D 471/04; C07D 498/04; A61P 35/00
USPC .................................... 514/255.05
See application file for complete search history.

(56) References Cited

U.S. PATENT DOCUMENTS

| | | | |
|---|---|---|---|
| 9,751,884 B2 * | 9/2017 | Xie .......................... A61P 35/02 |
| 2014/0315886 A1 * | 10/2014 | Suzuki ................ C07D 417/14 |
| | | | 514/266.21 |
| 2015/0141407 A1 | 5/2015 | Xie et al. |
| 2016/0009663 A1 | 1/2016 | Qian et al. |
| 2020/0190066 A1 | 6/2020 | Luo et al. |

OTHER PUBLICATIONS

Banerjee et al J. Med. Chem, 2021, 64(17), 13072-13095 (Year: 2021).*
Jiang et al ACS Med Chem Lett, 2020, 11, 83-89 (Year: 2020).*
International Search Report dated Aug. 30, 2022 in respect of PCT Application No. PCT/US2022/025637.

* cited by examiner

*Primary Examiner* — Yevgeny Valenrod
(74) *Attorney, Agent, or Firm* — James Parrett, Esq.

(57) ABSTRACT

The invention encompasses novel dihydroquinoxalinone compounds with significantly improved water solubility and reduced toxicity to achieve higher therapeutic indexes and the treatment of cancer, virus infections, and inflammation using the same.

3 Claims, 54 Drawing Sheets

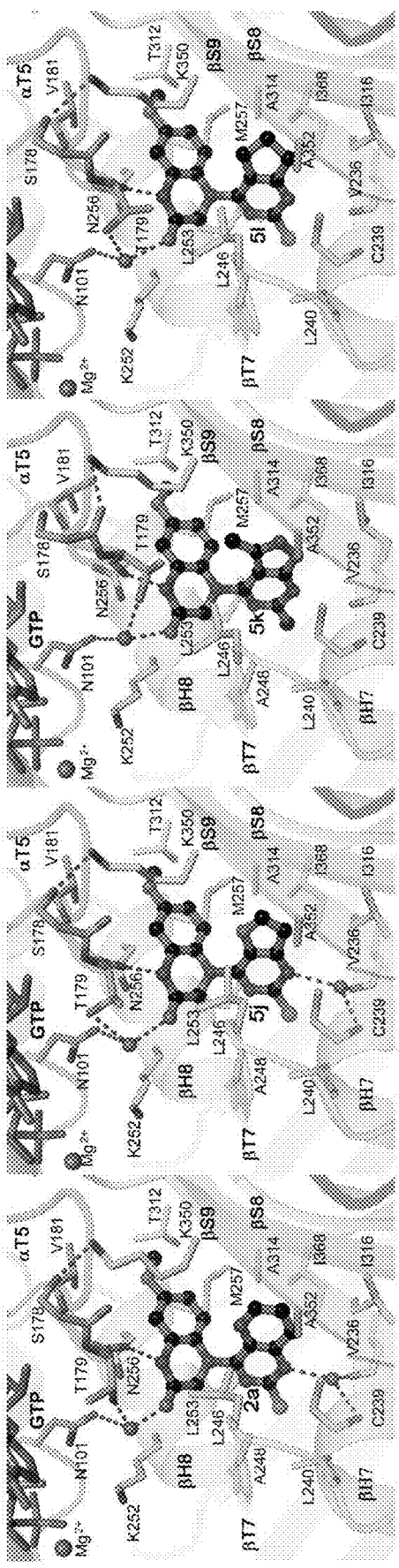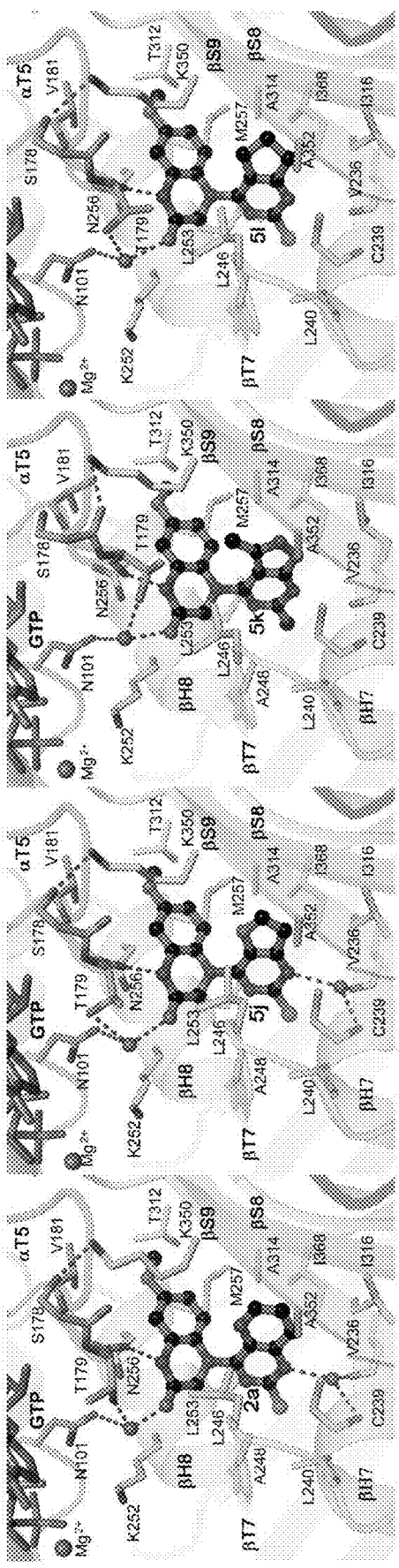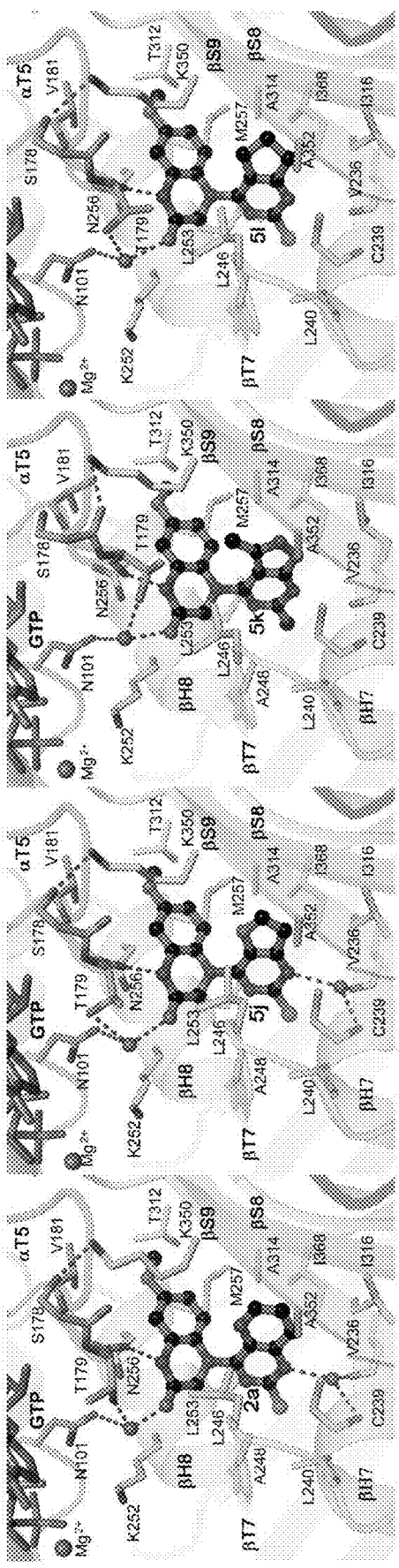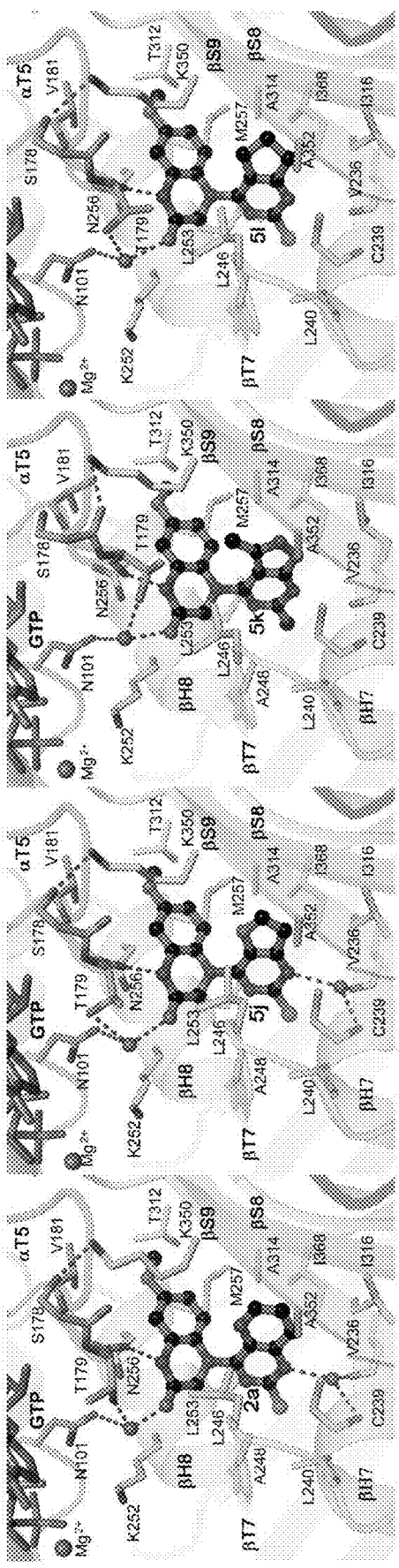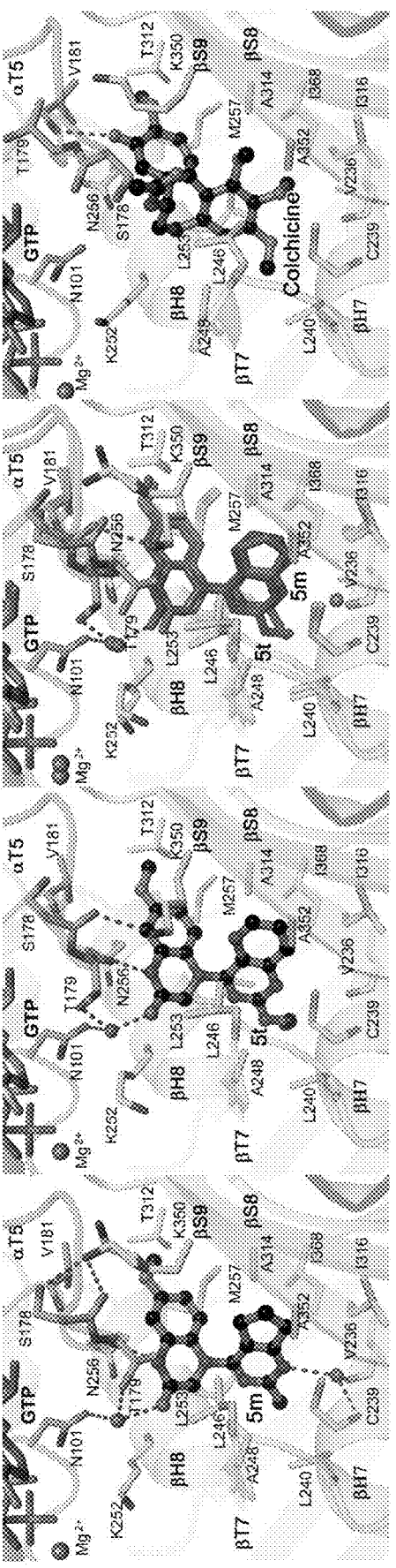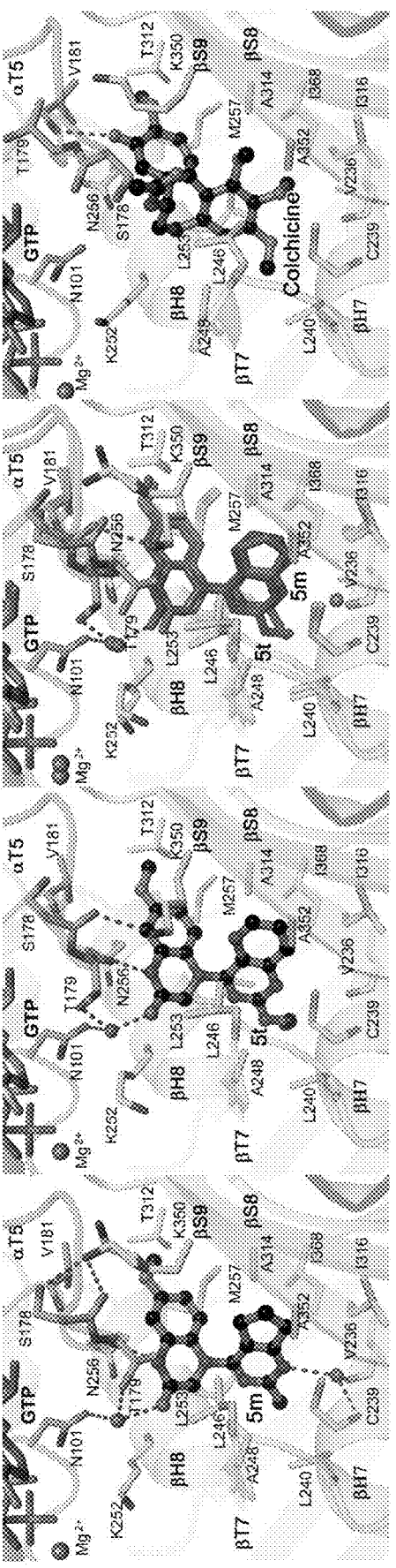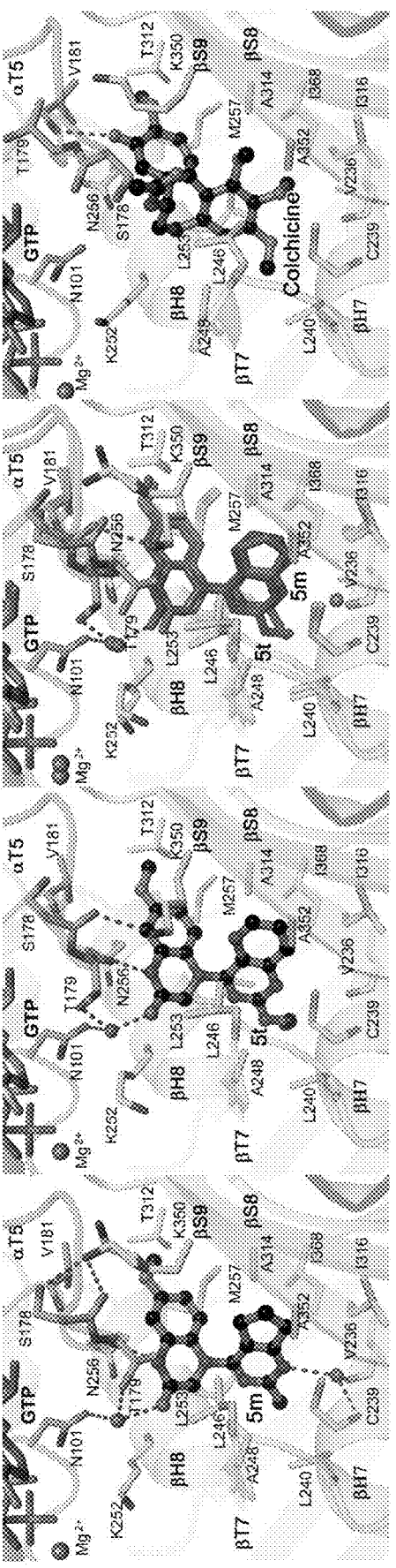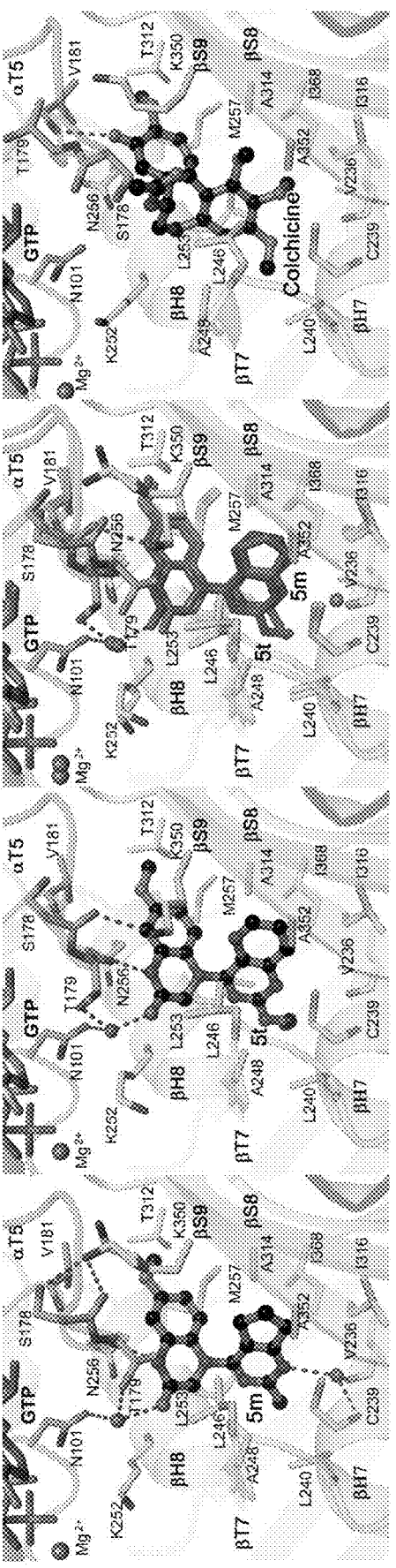
FIGURE 6A FIGURE 6B FIGURE 6C FIGURE 6D
FIGURE 6E FIGURE 6F FIGURE 6G FIGURE 6H

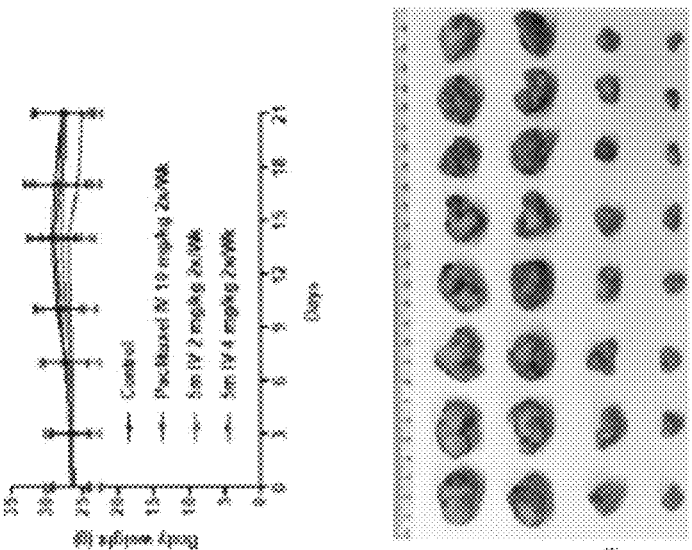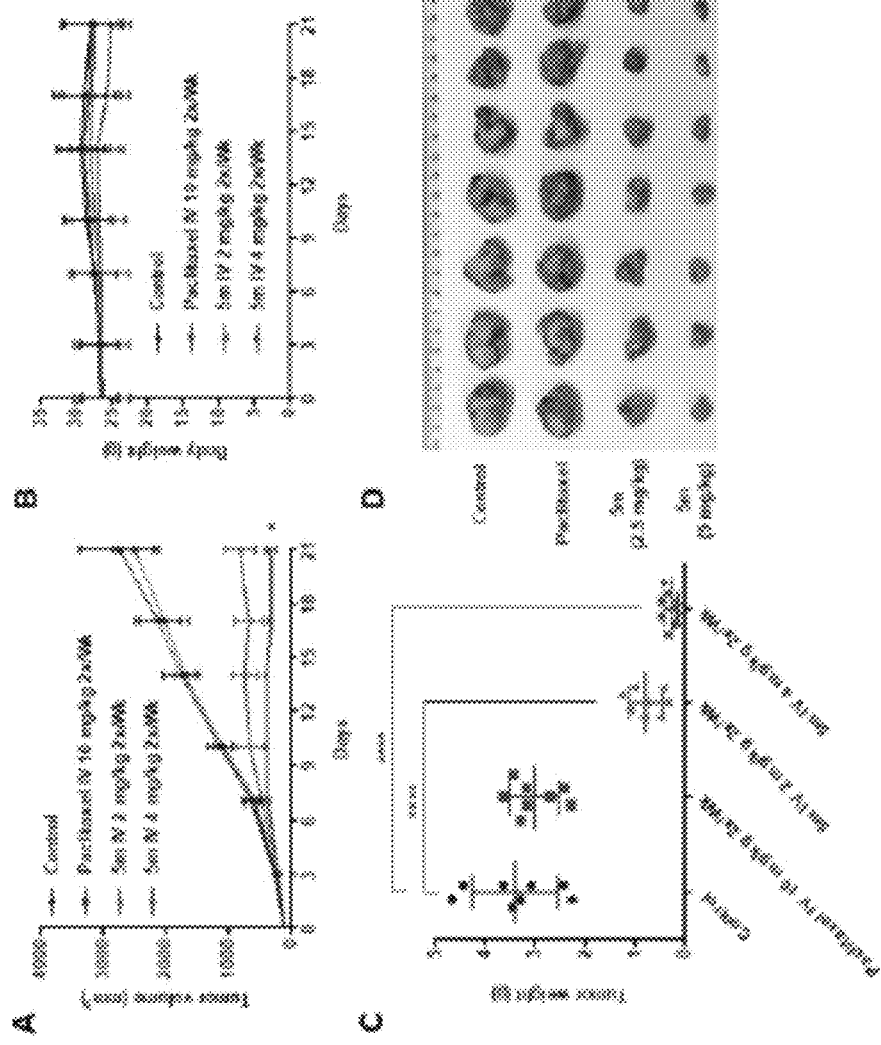
FIGURE 10A
FIGURE 10B
FIGURE 10C
FIGURE 10D

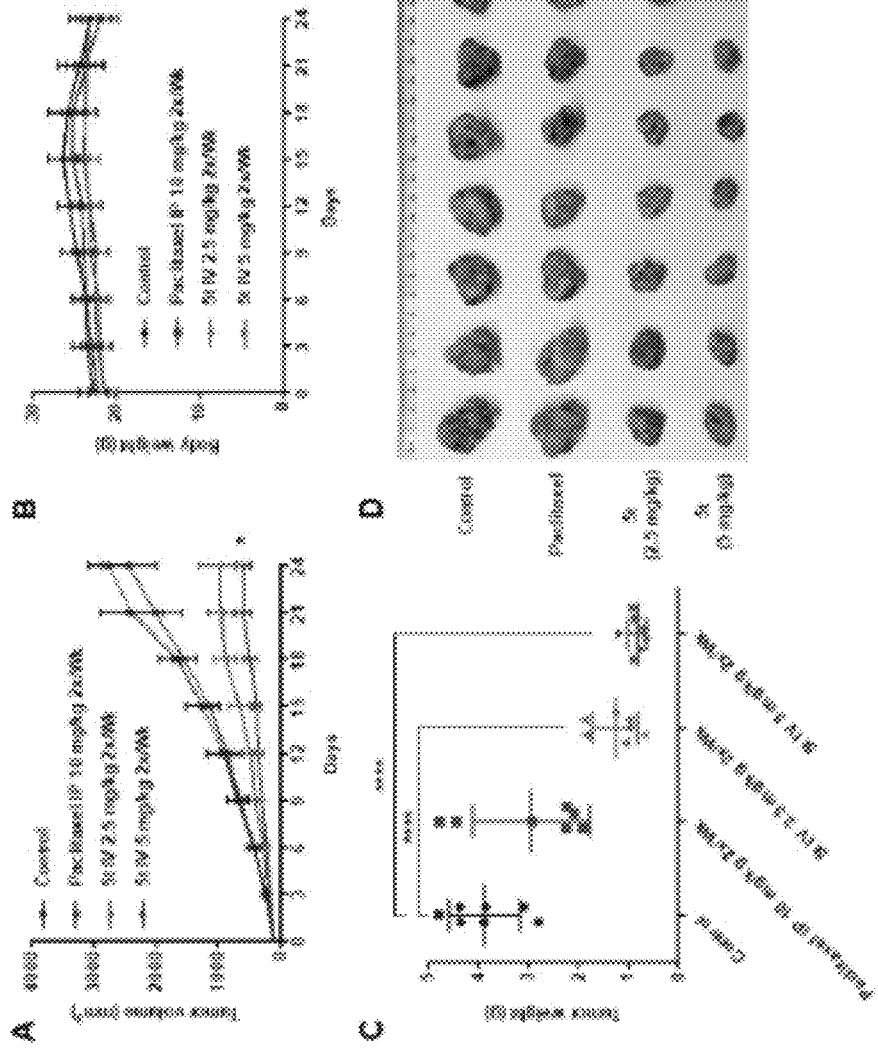
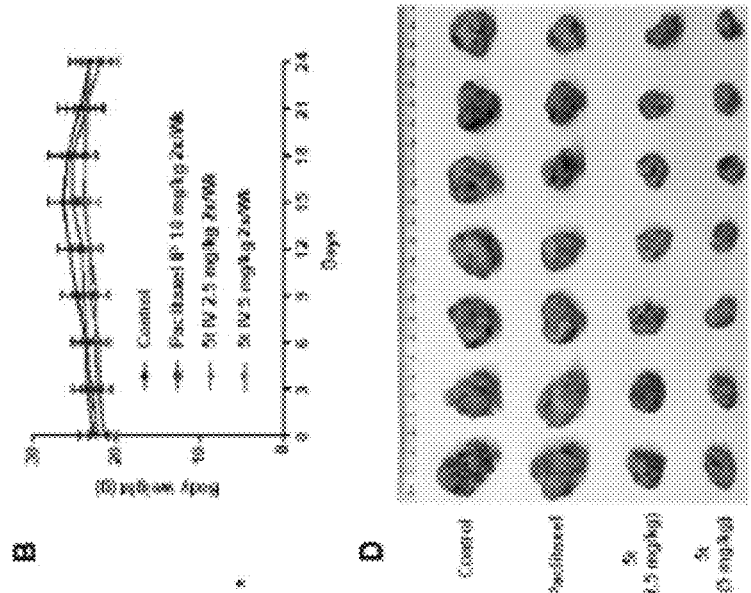
FIGURE 11A FIGURE 11B FIGURE 11C FIGURE 11D

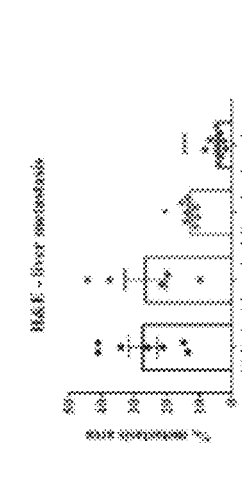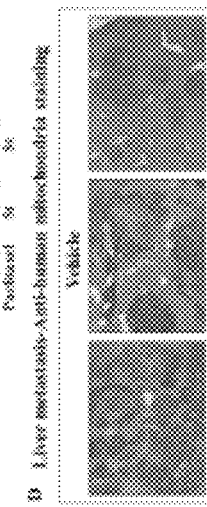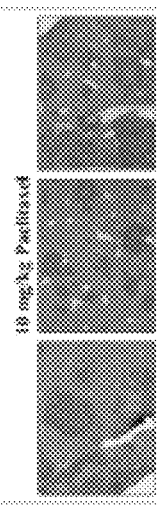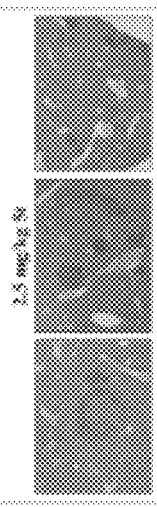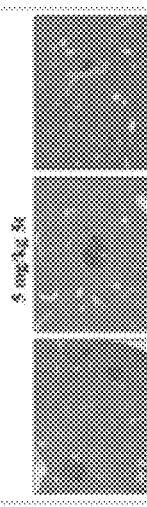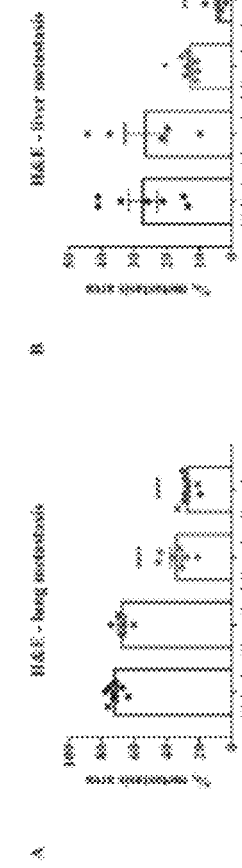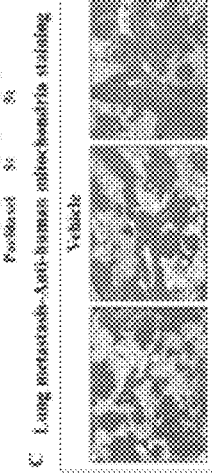
FIGURE 14A  FIGURE 14B
FIGURE 14C  FIGURE 14D

*a* Reagents and conditions: (i) *t*-BuOK/*t*-BuOH; (ii) POCl₃, 90 °C; (iii) IPA/HCl, rt, 5 - 6 h; (iv) Zn/AcOH, CH₂Cl₂; (v) Chloroacetyl chloride/K₂CO₃, acetone, 0 °C; (vi) NaH, THF, 0 °C to rt; (vii) Oxone, methanol/water, rt.

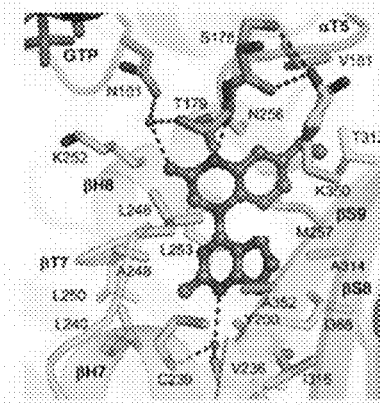 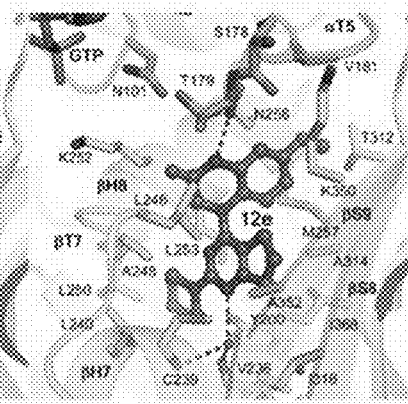 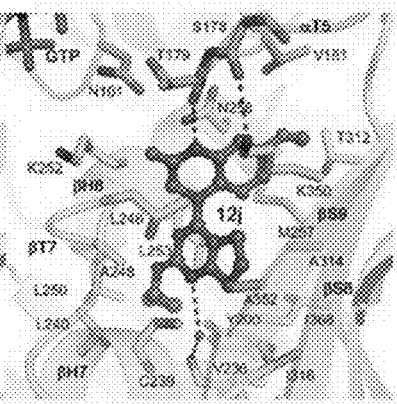
FIG. 26A  FIG. 26B  FIG. 26C
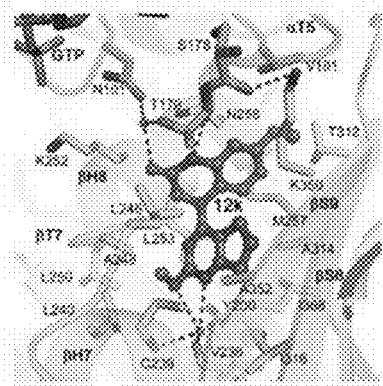
FIG. 26D
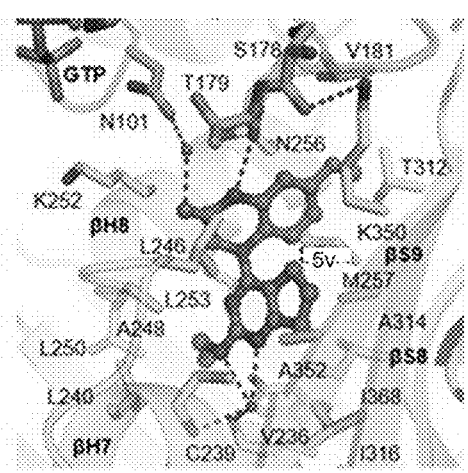
FIG. 26E FIGURE 29A
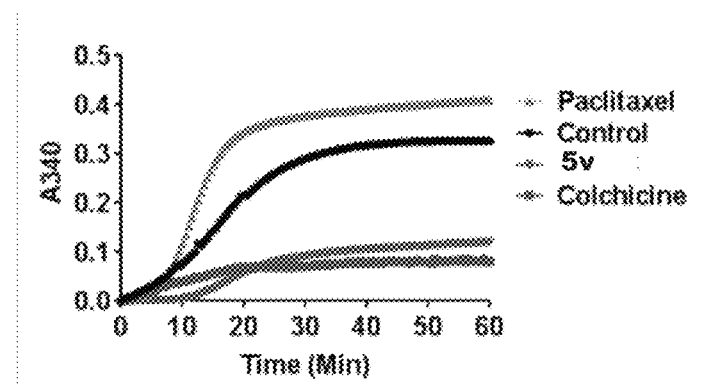
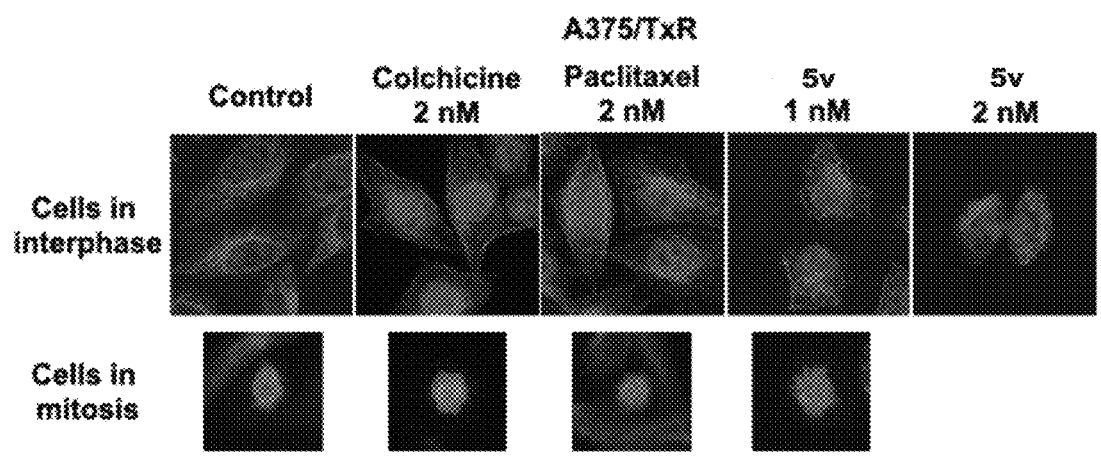
FIGURE 29B

FIGURE 34A
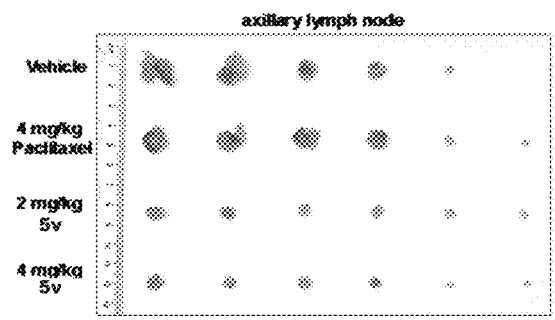
axillary lymph node
FIGURE 34B
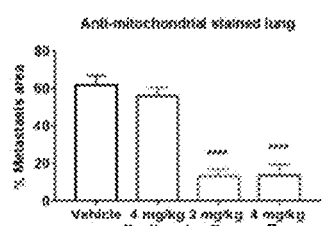
Anti-mitochondrial stained lung
FIGURE 34C
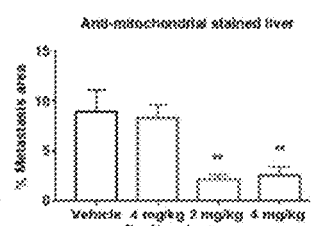
Anti-mitochondrial stained liver
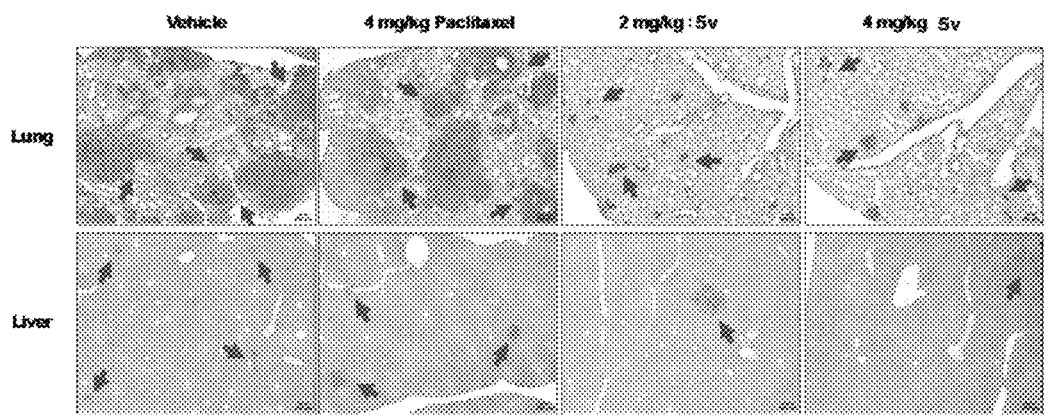
FIGURE 34D

Colony formation

Western blot

Scheme for 5v

*Reagents and conditions: (i) NaHCO₃, H₂O, rt; (ii) POCl₃, 100 °C; (iii) IPA/HCl, 50 °C; (iv) Zn/AcOH, CH₂Cl₂; (v) Chloroacetyl chloride/K₂CO₃, acetone, 0 °C; (vi) NaH, THF, 0 °C to rt; (vii) Oxone, methanol/water, rt; (viii) EtNH₂/Dioxane, 100 °C.

METABOLICALLY STABLE PYRIMIDINYL DIHYDROQUINOXALINONES AS TUBULIN POLYMERIZATION INHIBITORS

CROSS REFERENCE TO RELATED APPLICATIONS

This application claims the benefit of priority of U.S. Provisional Application No. 63/177,183, filed on Apr. 20, 2021, and 63/317,931, filed on Mar. 8, 2022, hereby incorporated by reference.

GOVERNMENT INTEREST STATEMENT

This invention was made with government support under Grant Numbers R01CA148706, 1S100D010678-01, RR-026377-01, and 1S100D016226, awarded by the National Institutes of Health. The government has certain rights in the invention.

BACKGROUND OF THE INVENTION

Dynamic microtubules (MTs) are crucial elements of cellular cytoskeleton and known to have important contributions in cell proliferation, migration and mitosis. Assembly as well as disassembly of MTs depend on the polymerization and depolymerization of tubulin. Thus, disruption of MT dynamics has been a well-established strategy in anticancer therapy, given MTs are deeply involved in mitosis.

Three of the major classes of tubulin inhibitors that have been extensively used for clinical intervention of cancer are taxanes, vinca alkaloids, and epothilones. However, development of multidrug resistance (MDR), peripheral neuropathy as well as narrow therapeutic index often restrict the efficacies of these drugs in the clinic. Colchicine binds at the interface of the αβ-tubulin dimer. Colchicine and other small molecules that bind to the colchicine site have been observed to inhibit the ability of tubulin dimers to polymerize and form functional microtubules. Thus, colchicine binding site inhibitors (CBSIs) have demonstrated substantial cytotoxicity in a number of studies. Although colchicine itself is prone to efflux transporters as well as β3-tubulin (Class III β-tubulin) mediated MDR, small molecule CBSIs are significantly less vulnerable to these MDR mechanisms responsible for limited clinical efficacy of current FDA approved tubulin inhibitors. However, clinical applications of small molecule CBSIs have been constrained by the substantial undesired toxicities against normal cells, low solubility as well as low oral bioavailability.

In recent years, there has been extensive research on a new class of small molecule CBSIs, particularly vascular disrupting agents (VDAs), that target the colchicine binding site. VDAs have profound advantages over angiogenesis inhibitors (AIs) by disrupting established blood vessel networks in the tumor and, thereby, introducing extensive necrosis as well as apoptosis via vascular collapse. It is noteworthy to mention that VDAs are known to predominantly block the blood flow in solid tumors, leaving the blood vessels in normal tissues intact. Currently, a significant number of VDA agents targeting the colchicine site are in advanced clinical trials for the treatment of diverse cancer types.

For instance, a phosphate analogue of combretastatin A-4 (CA-4P) is in phase III trials targeting anaplastic thyroid cancer, and in phase II trials from the treatment of non-small-cell lung cancer (NSCLC). Verubulin (MPC-6827), Azixa, was introduced a few years ago as a highly potent tubulin polymerization inhibitor with strong ability to initiate vascular disruption by rapid collapse of tumor blood flow and inhibition of tumor growth. Verubulin has exhibited low nanomolar efficacy against diverse cancers, including melanoma, brain, prostate, and breast cancers. Verubulin was advanced to Phase I and Phase II clinical trials, however, and was subsequently withdrawn from the clinical trials for potential cardiovascular toxicities.

These successes have resulted in intensive research in VDAs leading to a number of recent reports on small molecule VDA drug-like candidates with significantly high antiproliferative activities. Most of the recent colchicine binding VDAs have drawn considerable attention for their dual mechanism of action as antimitotic as well as vascular disrupting agents resulting in high expectations for success in cancer chemotherapy.

SUMMARY OF THE INVENTION

An embodiment of the invention encompasses compounds having a structure of Formula I:

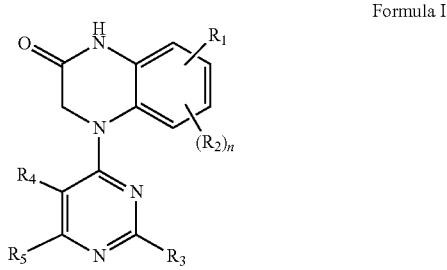

Formula I wherein $R_1$ is a halide, $C_1$-$C_4$ alkyl, $C_1$-$C_4$ alkoxy, $C_1$-$C_4$ haloalkyl, $C_1$-$C_4$ haloalkoxy, Ph, O($C_5$-$C_{10}$ aryl), OPh, ($C_1$-$C_3$ alkyl)phenyl, —O($C_1$-$C_3$ alkyl)phenyl, —$NH_2$, —NH ($C_1$-$C_4$ alkyl), —N($C_1$-$C_4$ alkyl)$_2$, hydroxyl, cyano, or $C_2$-$C_5$ ether;

$R_2$ is at least one of hydrogen, halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, hydroxyl, cyano, or $C_2$-$C_5$ ether;

$R_3$ is hydrogen, halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, —NH($C_1$-$C_4$ heteroalkyl), —NHPh, —NH($C_3$-$C_{10}$ aryl), —NH($C_3$-$C_{10}$ heteroaryl), —NH($C_3$-$C_{10}$ cycloalkyl), —NH($C_3$-$C_{10}$ heterocyclyl), hydroxyl, cyano, NCS, $C_3$-$C_6$ heterocyclyl, or $C_2$-$C_5$ ether, wherein the heterocyclyl has at least one of O, N, or S, or wherein the heterocyclyl may optionally be substituted, wherein the substitutions of the heterocyclyl include halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, hydroxyl, cyano, or $C_2$-$C_5$ ether;

$R_4$ and $R_5$ are at least one of halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, hydroxyl, cyano, $C_2$-$C_5$ ether, or wherein when taken together $R_4$ and $R_5$ form a 5 or 6-membered cycloalkyl ring, or a 5 or 6-membered heterocycle ring having at least one N, O, or S atom, wherein the cycloalkyl or heterocycle ring may optionally have at least one unsaturation, wherein the cycloalkyl or heterocycle ring may optionally be substituted, wherein the substitutions of the cycloalkyl or heterocycle ring include halide, $C_1$-$C_4$ alkyl, $C_1$-$C_4$ alkoxy, $C_1$-$C_4$ haloalkyl, —$NH_2$, —$NH(C_1$-$C_4$ alkyl), —$N(C_1$-$C_4$ alkyl)$_2$, hydroxyl, cyano, or $C_2$-$C_5$ ether;

provided that if $R_4$ and $R_5$ taken together form a phenyl ring, then said phenyl ring is substituted, or if $R_4$ and $R_5$ taken together form a pyridine ring, then $R_3$ is not chlorine; and n is 1 to 3;

or a stereoisomer, pharmaceutically acceptable salt, hydrate, N-oxide, or combinations thereof.

Another embodiment of the invention encompasses compounds having a structure of Formula IA:

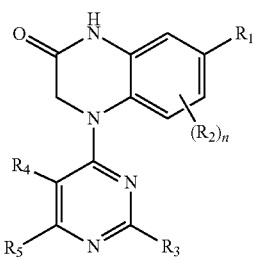

Formula IA wherein $R_1$ is a halide, $C_1$-$C_4$ alkyl, $C_1$-$C_4$ alkoxy, $C_1$-$C_4$ haloalkyl, $C_1$-$C_4$ haloalkoxy, Ph, O($C_5$-$C_{10}$ aryl), OPh, ($C_1$-$C_3$ alkyl)phenyl, —O($C_1$-$C_3$ alkyl)phenyl, —$NH_2$, —NH($C_1$-$C_4$ alkyl), —N($C_1$-$C_4$ alkyl)$_2$, hydroxyl, cyano, or $C_2$-$C_5$ ether;

$R_2$ is at least one of hydrogen, halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, hydroxyl, cyano, or $C_2$-$C_5$ ether;

$R_3$ is hydrogen, halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, —NH($C_1$-$C_4$ heteroalkyl), —NHPh, —NH($C_3$-$C_{10}$ aryl), —NH($C_3$-$C_{10}$ heteroaryl), —NH($C_3$-$C_{10}$ cycloalkyl), —NH($C_3$-$C_{10}$ heterocyclyl), hydroxyl, cyano, NCS, $C_3$-$C_6$ heterocyclyl, or $C_2$-$C_5$ ether, wherein the heterocyclyl has at least one of O, N, or S, and wherein the heterocyclyl may optionally be substituted, wherein the substitutions of the heterocyclyl include halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, hydroxyl, cyano, or $C_2$-$C_5$ ether;

$R_4$ and $R_5$ are taken together to form a 5 or 6-membered cycloalkyl ring, or a 5 or 6-membered heterocycle ring having at least one N, O, or S atom, wherein the cycloalkyl or heterocycle ring may optionally have at least one unsaturation, wherein the cycloalkyl or heterocycle ring may optionally be substituted, wherein the substitutions of the cycloalkyl or heterocycle ring include halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, hydroxyl, cyano, or $C_2$-$C_5$ ether;

provided that if $R_4$ and $R_5$ taken together form a phenyl ring, then said phenyl ring is substituted, or if $R_4$ and $R_5$ taken together form a pyridine ring, then $R_3$ is not chlorine; and n is 1 to 3;

or a stereoisomer, pharmaceutically acceptable salt, hydrate, N-oxide, or combinations thereof.

Yet another embodiment of the invention encompasses compounds having a structure of Formula II:

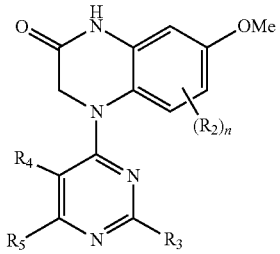

Formula II wherein $R_2$ is at least one of hydrogen, halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, hydroxyl, cyano, or $C_2$-$C_5$ ether;

$R_3$ is hydrogen, halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, —NH($C_1$-$C_4$ heteroalkyl), —NHPh, —NH($C_3$-$C_{10}$ aryl), —NH($C_3$-$C_{10}$ heteroaryl), —NH($C_3$-$C_{10}$ cycloalkyl), —NH($C_3$-$C_{10}$ heterocyclyl), hydroxyl, cyano, NCS, $C_3$-$C_6$ heterocyclyl, or $C_2$-$C_5$ ether, wherein the heterocyclyl has at least one of O, N, or S, and wherein the heterocyclyl may optionally be substituted, wherein the substitutions of the heterocyclyl include halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, hydroxyl, cyano, or $C_2$-$C_5$ ether;

$R_4$ and $R_5$ are at least one of halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, hydroxyl, cyano, $C_2$-$C_5$ ether, or wherein when taken together $R_4$ and $R_5$ form a 5 or 6-membered cycloalkyl ring, or a 5 or 6-membered heterocycle ring having at least one N, O, or S atom, wherein the cycloalkyl or heterocycle ring may optionally have at least one unsaturation, wherein the cycloalkyl or heterocycle ring may optionally be substituted, wherein the substitutions of the cycloalkyl or heterocycle ring include halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, hydroxyl, cyano, or $C_2$-$C_5$ ether;

provided that if $R_4$ and $R_5$ taken together form a phenyl ring, then said phenyl ring is substituted, or if $R_4$ and $R_5$ taken together form a pyridine ring, then $R_3$ is not chlorine; and n is 1 to 3;

or a stereoisomer, pharmaceutically acceptable salt, hydrate, N-oxide, or combinations thereof.

In another embodiment, the invention encompasses pharmaceutical compositions comprising a compound of formula II and a pharmaceutically acceptable excipient.

An embodiment of the invention encompasses a compound of formula I represented by any one of the following compounds 5j-5r, 5t-5v or 12a-12m and 12o-12q:

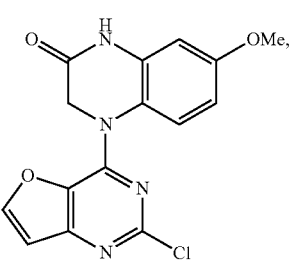

5j

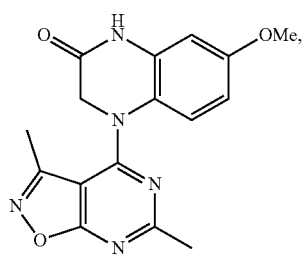
5k
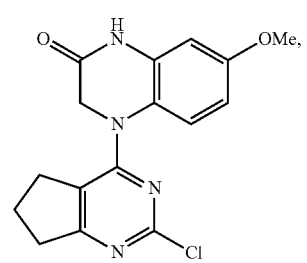
5l
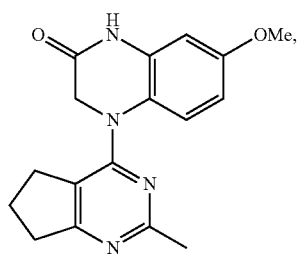
5m
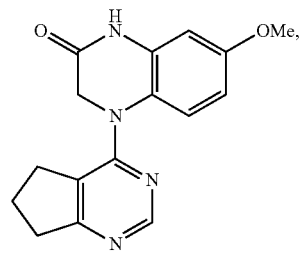
5n
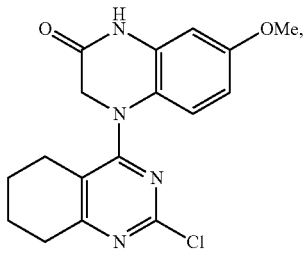
5o
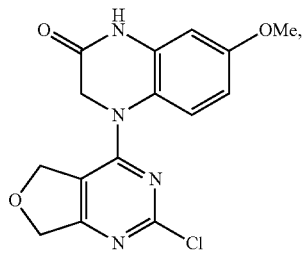
5p
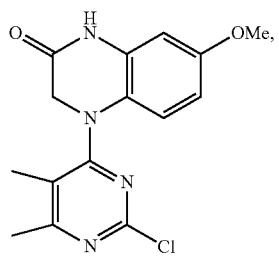
5q
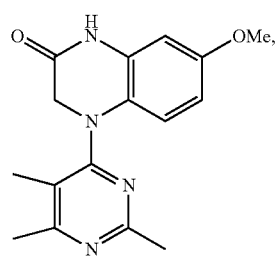
5r
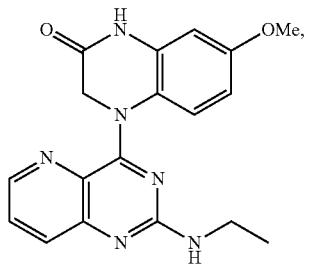
5t
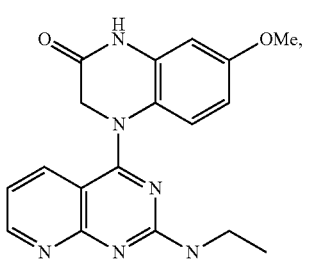
5u
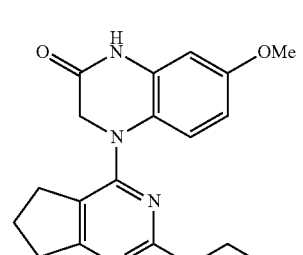
5v
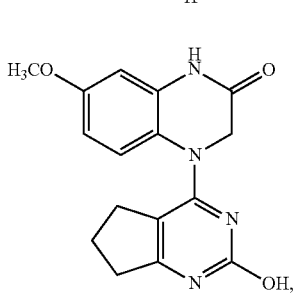
12a

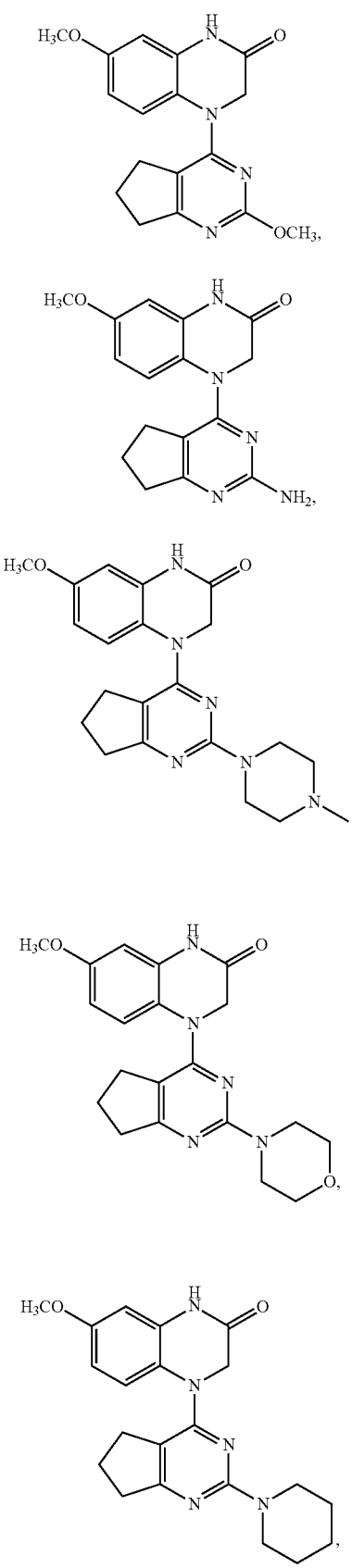

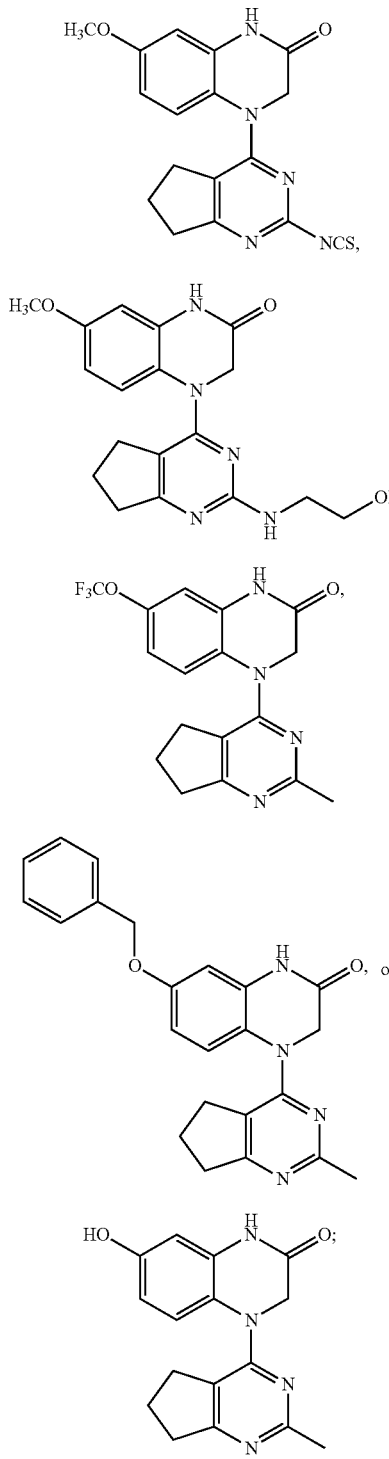

or a stereoisomer, pharmaceutically acceptable salt, hydrate, N-oxide, or combinations thereof.

In another embodiment, the invention encompasses pharmaceutical compositions comprising a compound of any one of formulas 5j-5r, 5t-5v or 12a-12m and 12o-12q and a pharmaceutically acceptable excipient.

An embodiment of the invention encompasses the compound represented by 5s:

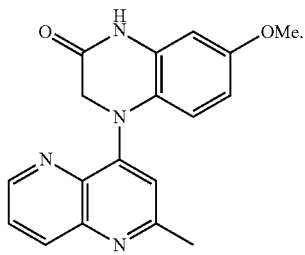

Another embodiment of the invention encompasses methods of treating cancer in a subject in need thereof by administering a therapeutically effective amount of a compound of structure of Formula I to the subject, wherein the structure of Formula I is

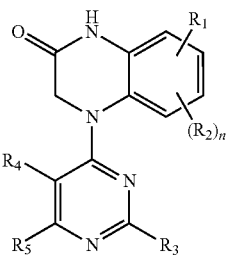

Formula I wherein
$R_1$ is a halide, $C_1$-$C_4$ alkyl, $C_1$-$C_4$ alkoxy, $C_1$-$C_4$ haloalkyl, $C_1$-$C_4$ haloalkoxy, Ph, O($C_5$-$C_{10}$ aryl), OPh, ($C_1$-$C_3$ alkyl)phenyl, —O($C_1$-$C_3$ alkyl)phenyl, —$NH_2$, —NH($C_1$-$C_4$ alkyl), —N($C_1$-$C_4$ alkyl)$_2$, hydroxyl, cyano, or $C_2$-$C_5$ ether;

$R_2$ is at least one of hydrogen, halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, hydroxyl, cyano, or $C_2$-$C_5$ ether;

$R_3$ is hydrogen, halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, —NH($C_1$-$C_4$ heteroalkyl), —NHPh, —NH($C_3$-$C_{10}$ aryl), —NH($C_3$-$C_{10}$ heteroaryl), —NH($C_3$-$C_{10}$ cycloalkyl), —NH($C_3$-$C_{10}$ heterocyclyl), hydroxyl, cyano, NCS, $C_3$-$C_6$ heterocyclyl, or $C_2$-$C_5$ ether, wherein the heterocyclyl has at least one of O, N, or S, and wherein the heterocyclyl may optionally be substituted, wherein the substitutions of the heterocyclyl include halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, hydroxyl, cyano, or $C_2$-$C_5$ ether;

$R_4$ and $R_5$ are at least one of halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, hydroxyl, cyano, $C_2$-$C_5$ ether, or wherein when taken together $R_4$ and $R_5$ form a 5 or 6-membered cycloalkyl ring, or a 5 or 6-membered heterocycle ring having at least one N, O, or S atom, wherein the cycloalkyl or heterocycle ring may optionally have at least one unsaturation, wherein the cycloalkyl or heterocycle ring may optionally be substituted, wherein said substitutions of the cycloalkyl or heterocycle ring include halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, hydroxyl, cyano, or $C_2$-$C_5$ ether;

provided that if $R_4$ and $R_5$ taken together form a phenyl ring, then said phenyl ring is substituted, or if $R_4$ and $R_5$ taken together form a pyridine ring, then $R_3$ is not chlorine; and n is 1 to 3;

or a stereoisomer, pharmaceutically acceptable salt, hydrate, N-oxide, or combinations thereof. Yet in another embodiment of the method, the cancer is at least one of drug resistant tumors; metastatic cancer; or drug resistant cancer. In one embodiment of the method, the cancer is at least one of prostate cancer, breast cancer, ovarian cancer, melanoma, lung cancer, colon cancer, leukemia, lymphoma, head and neck, pancreatic, esophageal, renal cancer or CNS cancer.

Another embodiment of the invention encompasses methods of treating cancer in a subject in need thereof by administering a therapeutically effective amount of a compound of structure of Formula I to the subject, wherein the structure of Formula IA is

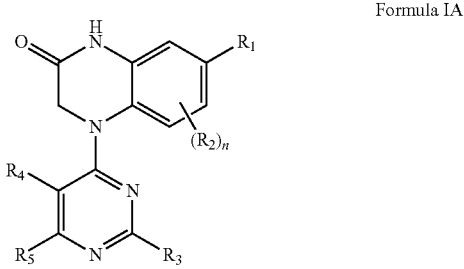

Formula IA wherein $R_1$ is a halide, $C_1$-$C_4$ alkyl, $C_1$-$C_4$ alkoxy, $C_1$-$C_4$ haloalkyl, $C_1$-$C_4$ haloalkoxy, Ph, O($C_5$-$C_{10}$ aryl), OPh, ($C_1$-$C_3$ alkyl)phenyl, —O($C_1$-$C_3$ alkyl)phenyl, —NH$_2$, —NH($C_1$-$C_4$ alkyl), —N($C_1$-$C_4$ alkyl)$_2$, hydroxyl, cyano, or $C_2$-$C_5$ ether;

$R_2$ is at least one of hydrogen, halide, $C_1$-$C_4$ alkyl, $C_1$-$C_4$ alkoxy, $C_1$-$C_4$ haloalkyl, —NH$_2$, —NH($C_1$-$C_4$ alkyl), —N($C_1$-$C_4$ alkyl)$_2$, hydroxyl, cyano, or $C_2$-$C_5$ ether;

$R_3$ is hydrogen, halide, $C_1$-$C_4$ alkyl, $C_1$-$C_4$ alkoxy, $C_1$-$C_4$ haloalkyl, —NH$_2$, —NH($C_1$-$C_4$ alkyl), —N($C_1$-$C_4$ alkyl)$_2$, —NH($C_1$-$C_4$ heteroalkyl), —NHPh, —NH($C_3$-$C_{10}$ aryl), —NH($C_3$-$C_{10}$ heteroaryl), —NH($C_3$-$C_{10}$ cycloalkyl), —NH($C_3$-$C_{10}$ heterocyclyl), hydroxyl, cyano, NCS, $C_3$-$C_6$ heterocyclyl, or $C_2$-$C_5$ ether, wherein the heterocyclyl has at least one of O, N, or S, and wherein the heterocyclyl may optionally be substituted, wherein the substitutions of the heterocyclyl include halide, $C_1$-$C_4$ alkyl, $C_1$-$C_4$ alkoxy, $C_1$-$C_4$ haloalkyl, —NH$_2$, —NH($C_1$-$C_4$ alkyl), —N($C_1$-$C_4$ alkyl)$_2$, hydroxyl, cyano, or $C_2$-$C_5$ ether;

$R_4$ and $R_5$ are taken together to form a 5 or 6-membered cycloalkyl ring, or a 5 or 6-membered heterocycle ring having at least one N, O, or S atom, wherein the cycloalkyl or heterocycle ring may optionally have at least one unsaturation, wherein the cycloalkyl or heterocycle ring may optionally be substituted, wherein the substitutions of the cycloalkyl or heterocycle ring include halide, $C_1$-$C_4$ alkyl, $C_1$-$C_4$ alkoxy, $C_1$-$C_4$ haloalkyl, —NH$_2$, —NH($C_1$-$C_4$ alkyl), —N($C_1$-$C_4$ alkyl)$_2$, hydroxyl, cyano, or $C_2$-$C_5$ ether;

provided that if $R_4$ and $R_5$ taken together form a phenyl ring, then said phenyl ring is substituted, or if $R_4$ and $R_5$ taken together form a pyridine ring, then $R_3$ is not chlorine; and n is 1 to 3;

or a stereoisomer, pharmaceutically acceptable salt, hydrate, N-oxide, or combinations thereof. In yet another embodiment of the method, the cancer is at least one of drug resistant tumors; metastatic cancer; or drug resistant cancer. In one embodiment of the method, the cancer is at least one of prostate cancer, breast cancer, ovarian cancer, melanoma, lung cancer, colon cancer, leukemia, lymphoma, head and neck, pancreatic, esophageal, renal cancer or CNS cancer.

An embodiment of the invention encompasses methods of treating cancer in a subject in need thereof by administering a therapeutically effective amount of a compound of structure of Formula II to the subject, wherein the structure of Formula II is

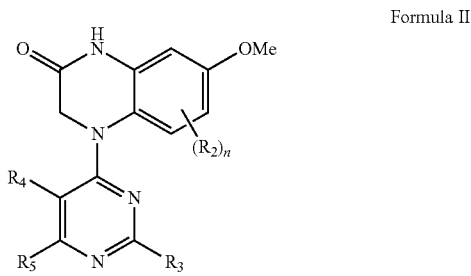

Formula II wherein $R_2$ is at least one of hydrogen, halide, $C_1$-$C_4$ alkyl, $C_1$-$C_4$ alkoxy, $C_1$-$C_4$ haloalkyl, —NH$_2$, —NH($C_1$-$C_4$ alkyl), —N($C_1$-$C_4$ alkyl)$_2$, hydroxyl, cyano, or $C_2$-$C_5$ ether;

$R_3$ is hydrogen, halide, $C_1$-$C_4$ alkyl, $C_1$-$C_4$ alkoxy, $C_1$-$C_4$ haloalkyl, —NH$_2$, —NH($C_1$-$C_4$ alkyl), —N($C_1$-$C_4$ alkyl)$_2$, —NH($C_1$-$C_4$ heteroalkyl), —NHPh, —NH($C_3$-$C_{10}$ aryl), —NH($C_3$-$C_{10}$ heteroaryl), —NH($C_3$-$C_{10}$ cycloalkyl), —NH($C_3$-$C_{10}$ heterocyclyl), hydroxyl, cyano, NCS, $C_3$-$C_6$ heterocyclyl, or $C_2$-$C_5$ ether, wherein the heterocyclyl has at least one of O, N, or S, and wherein the heterocyclyl may optionally be substituted, wherein the substitutions of the heterocyclyl include halide, $C_1$-$C_4$ alkyl, $C_1$-$C_4$ alkoxy, $C_1$-$C_4$ haloalkyl, —NH$_2$, —NH($C_1$-$C_4$ alkyl), —N($C_1$-$C_4$ alkyl)$_2$, hydroxyl, cyano, or $C_2$-$C_5$ ether;

$R_4$ and $R_5$ are at least one of halide, $C_1$-$C_4$ alkyl, $C_1$-$C_4$ alkoxy, $C_1$-$C_4$ haloalkyl, —NH$_2$, —NH($C_1$-$C_4$ alkyl), —N($C_1$-$C_4$ alkyl)$_2$, hydroxyl, cyano, $C_2$-$C_5$ ether, or wherein when taken together $R_4$ and $R_5$ form a 5 or 6-membered cycloalkyl ring, or a 5 or 6-membered heterocycle ring having at least one N, O, or S atom, wherein the cycloalkyl or heterocycle ring may optionally have at least one unsaturation, wherein the cycloalkyl or heterocycle ring may optionally be substituted, wherein the substitutions of the cycloalkyl or heterocycle ring include halide, $C_1$-$C_4$ alkyl, $C_1$-$C_4$ alkoxy, $C_1$-$C_4$ haloalkyl, —NH$_2$, —NH($C_1$-$C_4$ alkyl), —N($C_1$-$C_4$ alkyl)$_2$, hydroxyl, cyano, or $C_2$-$C_5$ ether;

provided that if $R_4$ and $R_5$ taken together form a phenyl ring, then said phenyl ring is substituted, or if $R_4$ and $R_5$ taken together form a pyridine ring, then $R_3$ is not chlorine; and n is 1 to 3;

or a stereoisomer, pharmaceutically acceptable salt, hydrate, N-oxide, or combinations thereof. In another embodiment, the invention encompasses pharmaceutical compositions comprising a compound of formula II and a pharmaceutically acceptable excipient. In one embodiment of the method, the cancer is at least one of drug resistant tumors; metastatic cancer; or drug resistant cancer. In yet another embodiment of the method, cancer is at least one of prostate cancer, breast cancer, ovarian cancer, melanoma, lung cancer, colon cancer, leukemia, lymphoma, head and neck, pancreatic, esophageal, renal cancer or CNS cancer.

An embodiment of the invention encompasses methods of treating cancer in a subject in need thereof by administering a therapeutically effective amount of a compound of formula I represented by any one of the following compounds 5j-5r, 5t-5v or 12a-12m and 12o-12q:

5j
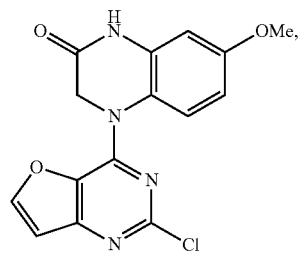

5k
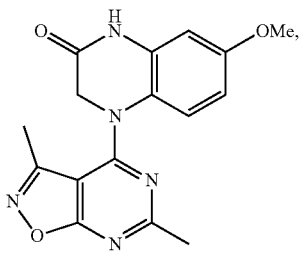

5l
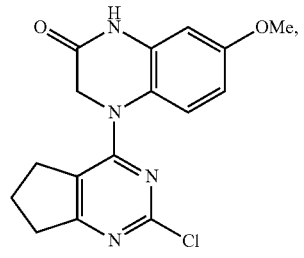

5m
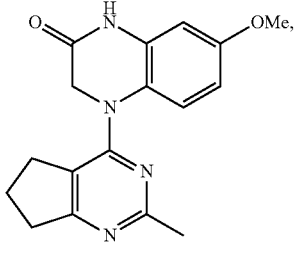

5n
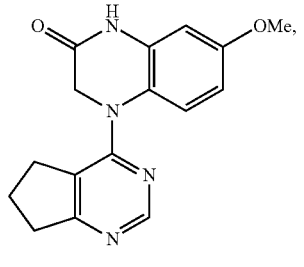

5o
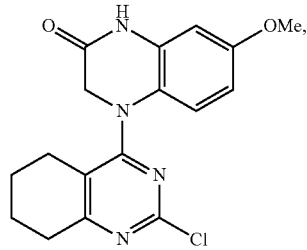

5p
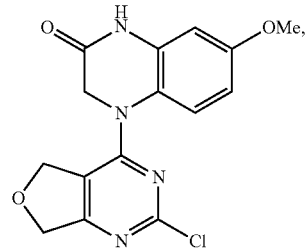

5q
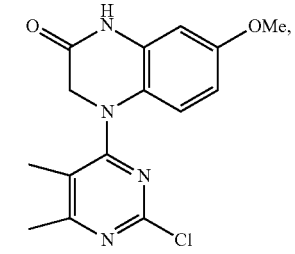

5r
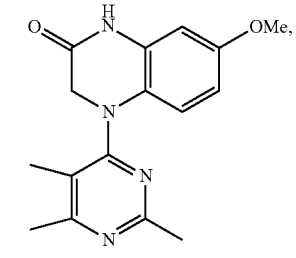

5t
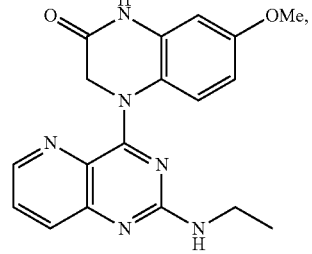

5u
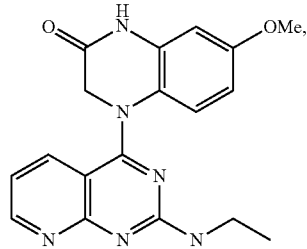

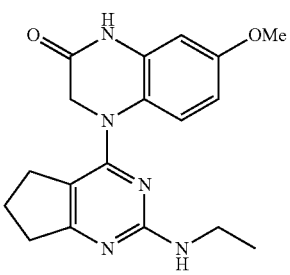
5v
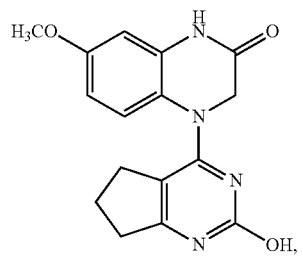
12a
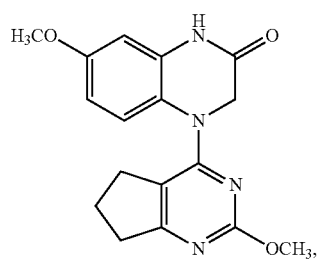
12b
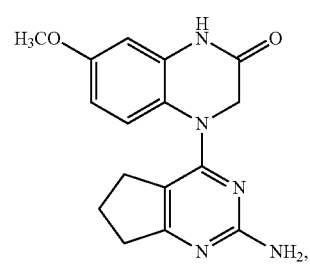
12c
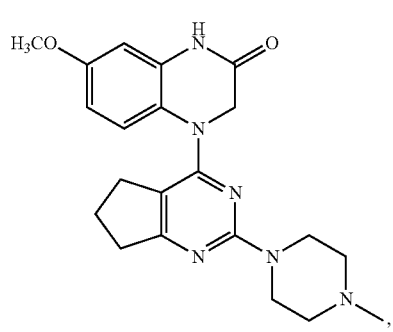
12d
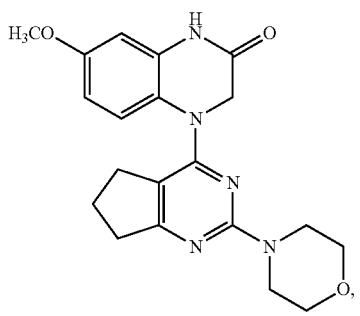
12e
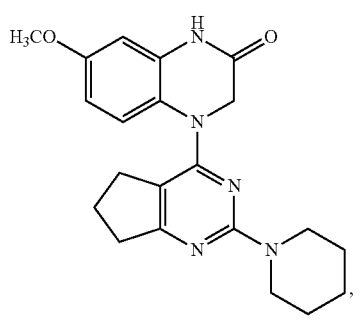
12f
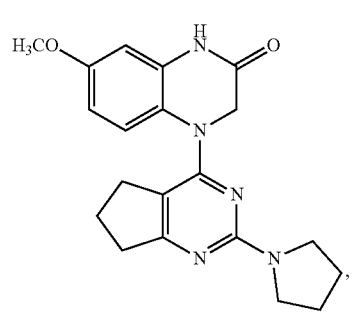
12g
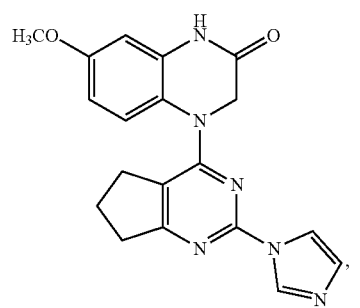
12h or a stereoisomer, pharmaceutically acceptable salt, hydrate, N-oxide, or combinations thereof.

In another embodiment, the invention encompasses pharmaceutical compositions for treating cancer comprising a compound of any one of formulas 5j-5r, 5t-5v or 12a-12m and 12o-12q or its stereoisomer, pharmaceutically acceptable salt, hydrate, N-oxide, or combinations thereof, and a pharmaceutically acceptable excipient.

An embodiment of this invention encompasses treating cancer with the compound represented by 5s:

In one embodiment of method, the cancer is at least one of drug resistant tumors; metastatic cancer; or drug resistant cancer. In yet another embodiment of the method, the cancer is at least one of prostate cancer, breast cancer, ovarian cancer, melanoma, lung cancer, colon cancer, leukemia, lymphoma, head and neck, pancreatic, esophageal, renal cancer or CNS cancer.

An embodiment of the invention encompasses methods of treating cancer in a subject in need thereof by administering a therapeutically effective amount of compound 5s:

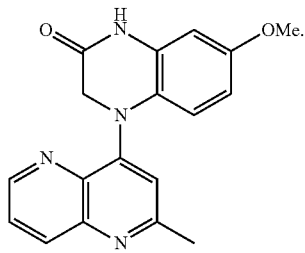
5s

In one embodiment of method, the cancer is at least one of drug resistant tumors; metastatic cancer; or drug resistant cancer. In yet another embodiment of the method, the cancer is at least one of prostate cancer, breast cancer, ovarian cancer, melanoma, lung cancer, colon cancer, leukemia, lymphoma, head and neck, pancreatic, esophageal, renal cancer or CNS cancer.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 5A illustrates the tubulin polymerization assay of 5m (10 µM) and 5t (10 µM) using tubulin protein from bovine brain origin. An identical concentration of colchicine and paclitaxel were used, colchicine was used as a positive control and paclitaxel was used as the negative control. FIG. 5B illustrates a comparison between the morphology and α-tubulin distribution of A375/TxR melanoma cells in interphase (top) and mitosis (bottom) after treatment with 2 nM of colchicine, paclitaxel, 5m and 5t in vitro.

FIGS. 6A-6H illustrate the X-ray co-crystal structures of tubulin-RB3-SLD-TTL proteins in complex with 2a, 5j, 5k, 5l, 5m, 5t and colchicine. FIG. 6A illustrates the complex with 2a at a 2.6 Å resolution. FIG. 6B illustrates the complex with 5j at a 2.9 Å resolution.

FIG. 6C illustrates the complex with 5k at 2.8 Å resolution. FIG. 6D illustrates the complex with 5l at 2.9 Å resolution. FIG. 6E illustrates the complex with 5m at 2.7 Å resolution. FIG. 6F illustrates the complex with 5t at 2.9 Å resolution. FIG. 6G illustrates an overlap of the complexes with 5m and 5t FIG. 6H illustrates the complex with colchicine bound tubulin complex (PDB 5XIW). The tubulin α-monomer is shown in cyan, and the β-monomer is shown in gold for FIGS. 6A-6H.

FIG. 7A illustrates representative colony formation images of A375/TxR cells after the treatment of 5m with various concentrations for a week. FIG. 7B illustrates representative colony formation images of A375/TxR cells after the treatment of 5t with various concentrations for a week. Colony formation rate is expressed as % of colony area density±SEM. *p=0.0004, **p<0.0001.

FIG. 8A illustrates representative images of wound healing as captured by IncuCyte after 12 h or 24 h treatment with 5m and blue lines demonstrates the wound edges of cell monolayer. FIG. 8B illustrates representative images of wound healing as captured by IncuCyte after 12 h or 24 h treatment with 5t and blue lines demonstrates the wound edges of cell monolayer. Wound closure is shown as the percent of relative wound density at each time point.

FIG. 9A illustrates cell cycle analysis of compounds 5m and 5t against A375/TxR cells. A375/TxR cells were incubated with 1 nM, 2 nM and 5 nM of 5m or 5t for 24 h without serum starvation. Cells were harvested, stained with propidium iodide (PI) and then analyzed by flow cytometry. Quantification of cell cycle distribution was analyzed by GraphPad based on two independent experiments in triplicate. FIG. 9B illustrates the induction of cell apoptosis by compounds 5m and 5t A375/TxR cells were treated with 5m or 5t for 24 h with the concentration range shown in panel A. Cells were collected and stained with FITC-labelled Annexin V and PI and analyzed by flow cytometry. The histograms on the right represent the percentage of the sum of the early and late apoptotic cells of two independent experiments in triplicate. *p=0.0001, **p<0.0001 vs. control.

FIGS. 10A-10D illustrate the dihydroquinoxalinone pyrimidine analogue 5m inhibition of the tumor growth in A375/TxR xenograft study. In this study, 10 mg/kg paclitaxel treatment was included as the reference control. 5m was intravenously (IV) administered with two different doses (2 and 4 mg/kg) for every 2 times per week. Similarly, paclitaxel was administered at a dose of 10 mg/kg (IV) with the same frequency as 5m. FIG. 10A illustrates the tumor growth of the inoculated tumor and FIG. 10B illustrates the mice body weight as measured during the therapy. FIG. 10C illustrates the final weight of the tumors that were excised after 21 days of treatment. FIG. 10D illustrates an image with all tumors as captured. The significant differences between groups were determined by one-way ANOVA followed by Dunnett's multiple comparison test. (*p<0.05, ****p<0.0001 vs. control). Data=mean±SD.

FIGS. 11A-D illustrate that dihydroquinoxalinone pyrimidine analogue t inhibited the tumor growth of A375/TxR xenografts in NSG mice. The mice were treated with intravenous injections with 2.5 mg/kg or 5 mg/kg 5t twice per week. Paclitaxel-treated group (10 mg/kg) was used as positive control. FIG. 11A illustrates the tumor growth curve of inoculated A375/TxR xenografts. FIG. 11B graphically illustrates the changes of mice body weight. FIG. 11C graphically illustrates the final tumor weight at the study endpoint. FIG. 11D illustrates the representative tumor images in this study. Data are presented as the mean±SD. *p<0.05, ****p<0.0001 vs. control, as analyzed by one-way ANOVA followed by Dunnett's multiple comparison test.

FIG. 13A illustrates the number of lung metastases that were counted in all the mice by averaging the percentage of metastatic area of 3 to 4 representative H&E images of each mouse (**p<0.0001 vs. control). FIG. 13B illustrates the number of liver metastases that were counted in all the mice by averaging the percentage of metastatic area of 3 to 4 representative H&E images of each mouse (**p<0.0001 vs. control). FIG. 13C illustrates the anti-human mitochondria immunohistochemistry (IHC) staining of lung tissues that confirmed the presence of melanoma metastases in vehicle or paclitaxel-treated mice and the metastases were reduced with 5m treatment. FIG. 13D illustrates the anti-human mitochondria IHC staining of liver tissues that confirmed the presence of melanoma metastases in vehicle or paclitaxel-treated mice and the metastases were reduced with 5m treatment. The images were acquired by Keyence BZ-X700 microscope and brown staining indicates the metastases.

FIGS. 14A-D illustrate the in vivo efficacy of 5t in lung or liver spontaneous metastasis. FIG. 14A illustrates a scatter plot of mean±SEM that shows the quantification of metastases present in the lung through counting the average of the percentage of metastatic area in 3 to 4 representative H&E images of each mouse (*p=0.016, ****p<0.0001 vs. control). FIG. 14B illustrates a scatter plot of mean±SEM that shows the quantification of metastases present in the liver through counting the average of the percentage of metastatic area in 3 to 4 representative H&E images of each mouse (*p=0.016, ****p<0.0001 vs. control). FIG. 14C illustrates the IHC staining for anti-human specific mitochondria to detect metastases in lung sections. FIG. 14D illustrates the IHC staining for anti-human specific mitochondria to detect metastases in liver sections. The images were acquired by Keyence BZ-X700 microscope and brown staining indicates the metastases.

FIG. 15A illustrates representative H&E stained images of lungs in mice treated with vehicle, 10 mg/kg paclitaxel, 2 mg/kg 5m and 4 mg/kg 5m for 21 days. FIG. 15B illustrates representative H&E-stained images of livers harvested in the same treatment groups as in FIG. 15A, where in both figures, examples of metastases are indicated by yellow arrows.

FIG. 17A illustrates representative H&E-stained images of lungs in mice treated with vehicle, 10 mg/kg paclitaxel, 2.5 mg/kg 5t and 5 mg/kg 5t for 24 days. FIG. 17B illustrates representative H&E-stained images of livers in the same treatment groups as in FIG. 17A.

FIG. 18 illustrates representative images of whole lungs and livers treated with vehicle, 10 mg/kg paclitaxel, 2.5 mg/kg 5t and 5 mg/kg 5t for 24 days after staining with anti-human mitochondria antibody, wherein the brown staining decreased in compound 5t-treated lungs or livers as compared to the vehicle or paclitaxel group.

FIG. 19A illustrates tumor growth inhibition of A375/TxR xenografts in NSG mice by treatment with vehicle, 10 mg/kg paclitaxel IV, or 2 mg/kg or 4 mg/kg 5m IV. FIG. 19B illustrates tumor growth inhibition of DU-145/VxR xenografts in NSG mice by treatment with vehicle (control), 20 mg/kg Compound 17ya PO, or 1 mg/kg 5m IV. FIG. 19C illustrates tumor growth inhibition of MDA-MB-231/VxR xenografts in NSG mice by treatment with vehicle, 10 mg/kg paclitaxel IP, 20 mg/kg Compound 17ya PO, or 2 mg/kg 5m IV. FIG. 19D illustrates tumor growth inhibition of 22RV1 xenografts in NSG mice by treatment with vehicle (control) or 1 mg/kg 5m IV. FIG. 19E illustrates tumor growth inhibition as shown by the images of the A2780/TxR ovarian cancer xenografts grown in left ovaries (right ovary was left unchanged as a control, as shown in the figure) in mice by treatment with vehicle (control), 5 mg/kg paclitaxel IV, 1 mg/kg 5m IV, or 20 mg/kg Compound 17ya PO. FIG. 19F illustrates tumor weights of these A2780/TxR ovarian cancer xenografts shown in FIG. 19E. Data presented in FIGS. 19B, 19C, 19E and 19F demonstrate that 5m possessed activity that was unexpectedly superior compared to 17ya. Data were expressed as the mean±SEM and analyzed two-way ANOVA followed by Dunnett's multiple comparison test using GraphPad Prism 9 software (San Diego, CA). Statistical significance is presented as *p<0.05, p<0.01, * p<0.001, and ****p<0.0001.

FIG. 21A illustrates the effect of 5m and PTX compared to vehicle treated control (control) on growth of PDAC cells in a clonogenic assay. Colony formation in Mia PaCa-2 and PANC-1 cell lines treated with 5m or paclitaxel (PTX), both compounds at 1 nM, 2.5 nM, and 5 nM were compared in the representative colony formation images shown. Bar graphs demonstrate that for Mia PaCa-2, colony formation was completely inhibited by 5m at the lowest dose (1 nM), whereas for PTX complete inhibition was only seen at 5 nM. Whereas for PANC-1 cells, the potency of inhibition of colony formation was comparable for 5m and PTX with only the 5 nM doses demonstrating nearly complete inhibition of colony formation.

**p<0.0001. FIG. 21B illustrates representative images of wound healing as captured by IncuCyte. Cells were live monitored with IncuCyte and pictures obtained every 2 h. Compared with the control (vehicle), wound closure is shown as the wound width in microns (μm) at each time point, as summarized in the bar graph. 5m (2 nM) and PTX (4 nM) both inhibited cell migration over 48 hours in Mia PaCa-2 cell cultures compared to control. As the bar graph demonstrated, 5m (2 nM) more effectively inhibited wound healing as compared to PTX (4 nM) at each time point. * p<0.001, and ****p<0.0001.

FIG. 22A illustrates the ability of compound 5m to dose dependently increase proportion of cells in G2/M phase in PANC-1 and Mia PaCa-2 cell lines, suggesting mitotic arrest in PDAC cell lines. FIG. 22B illustrates that compound 5m and PTX induced apoptosis in Mia PaCa-2 cells as measured by increased cleaved PARP to PARP ratio. Induction of apoptosis by 5m was dose-dependent and more potent as compared to PTX in the Mia PaCa-2 cell line. For example, this ratio was comparable for 10 nM of 5m as compared to 20 nM of PTX.

FIG. 23A illustrates the effect of compound 5m (2 mg/kg) as compared to control (vehicle) on tumor volume as measured over 42 days. As can be seen, 5m (2 mg/kg) significantly reduced tumor growth vs. control. FIG. 23B illustrates the effect of compound 5m as compared to control on body weight over 42 days. The body weight is represented as weight change %. As can be seen, limited global toxicity was observed with 5m as body weight trended toward slightly reduced compared to control. FIG. 23C graphically illustrates the effect of compound 5m (2 mg/kg) as compared to control on ex vivo tumor volume as measured over 42 days. FIG. 23D graphically illustrates the effect of compound 5m (2 mg/kg) as compared to control on ex vivo tumor weight over 42 days. FIG. 23E illustrates a comparison of the excised tumor sizes after treatment with compound 5m as compared to control. As seen in FIG. 23, tumor volumes and tumor weights were significantly reduced by the treatment of 5m (2 mg/kg) over control for 42 days, which can also be appreciated in the pictures of the excised tumors. Data are presented as means±standard errors of the means (SEM). Significant differences related to control groups are presented by P values<0.05 (* p<0.05,  p<0.01, * p<0.001, **** p<0.001), as measured by two tailed, unpaired Welch's t test or two-way ANOVA followed by Šidák's or Dunnett's multiple comparison. $IC_{50}$ were calculated by nonlinear regression. All data were analyzed using GraphPad Prism 9.

FIG. 24A illustrates the effect of compound 5m as compared to control on tumor volume. 5m dose-dependently inhibited xenograft tumor growth compared to control. FIG. 24B illustrates the effect of compound 5m as compared to control on body weight (weight change %). After 49 days of treatment with 5m at two doses, there was no differences seen in body weight for the treated animals compared with control, indicating that 5m lacks significant global toxicity. FIG. 24C graphically illustrates the effect of compound 5m as compared to control on ex vivo tumor volume ($mm^3$). FIG. 24D graphically illustrates the effect of compound 5m as compared to control on ex vivo tumor weight (g). Consistent with the results for tumor volume, 5m dose-dependently inhibited xenograft tumor growth compared to control as measured by ex vivo tumor volume and ex vivo tumor weight. FIG. 24E photographically illustrates a comparison of the excised tumor sizes after treatment with compound 5m as compared to control. Tumor volume was calculated by the equation: volume ($mm^3$)=0.5×(length× $width^2$). All animals were euthanized at the end of the study. Tumors were excised, recorded with ex vivo weight and size and imaged. Data are presented as means±standard errors of the means (SEM). Significant differences related to control groups are presented by P values<0.05 (* p<0.05,  p<0.01, * p<0.001, **** p<0.001), as measured two tailed, unpaired Welch's t test, or one-way ANOVA followed by Dunnett's multiple comparison, or two-way ANOVA followed by Šidák's or Dunnett's multiple comparison. $IC_{50}$ were calculated by nonlinear regression. All data were analyzed using GraphPad Prism 9 (GraphPad Software Inc.).

FIGS. 26A-E illustrates the crystal structures of tubulin-RB3_SLD (sT2R) complexes with compounds 5m (unlabeled), 12e, 12j, 12k, and 5v. FIG. 26A illustrates the original complex with compound 5m (unlabeled) at a 2.7 Å resolution (PDB ID: PDB 6X1F). FIG. 26B illustrates the crystal structure with compound 12e at a 2.27 Å resolution. FIG. 26C illustrates the crystal structure with compound 12j at a 2.70 Å resolution. FIG. 26D illustrates the crystal structure with compound 12k at a 2.10 Å resolution. FIG. 26E illustrates the crystal structure with compound 5v at a 2.40 Å resolution. The tubulin α-monomer and β-monomer are shown in cyan and gold, respectively.

FIG. 28A graphically illustrates the tumor growth curve over time comparing treatment with a control (vehicle), 10 mg/kg (1×/week) paclitaxel, and compound 2.5 mg/kg (2×/week) 12k. Statistical significance was determined using two-way ANOVA followed by multiple comparisons test. FIG. 28B graphically illustrates the percentage of body weight (% Body Weight) change during treatment days comparing treatment with a control, paclitaxel, and compound 12k. FIG. 28C graphically illustrates the ex vivo tumor volume comparing treatment with a control, paclitaxel, and compound 12k. FIG. 28D graphically illustrates the ex vivo tumor weight after treatment with a control, paclitaxel, and compound 12k. FIG. 28E illustrates pictures of isolated tumors in 35 mm petri dishes after treatment with a control, paclitaxel, and compound 12k. Data are presented as the mean+/−SEM. Significant differences between groups were determined by one-way ANOVA, followed by Dunnett's multiple comparison test (p<0.005, *p<0.0005, ****p<0.0001).

FIGS. 29A-B illustrates that 5v induced tubulin depolymerization and disrupts the microtubule network. FIG. 29A graphically illustrates tubulin depolymerization was induced by 5v at 10 µM in the tubulin mixture containing porcine brain tubulin (3 mg/mL) and GTP (1 mM) at 37° C. 10 µM of colchicine and paclitaxel were used as positive and negative controls. FIG. 29B illustrates representative immunofluorescence images of A375/TxR cells in the interphase or mitotic phase treated with colchicine (2 nM), paclitaxel (2 nM), or 5v (1 nM or 2 nM) for 24 h. Tubulin (red) was stained with α-tubulin antibody. The nucleus (blue) was stained with DAPI.

FIG. 30A illustrates that five Taxol-sensitive cancer cell lines (A375, M14, MDA-MB-231, PC3, and DU145) were treated with colchicine, paclitaxel (Taxol), Azixa, and 5v ranging from 0.1 nM to 3 µM for 72 h. Cell viability is expressed relative to DMSO control. FIG. 30B illustrates the anti-proliferative activity of 5v against five Taxol-resistant cancer cell lines (A375/TxR, M14/LCC6MDR1, MDA-MB-231/TxR, PC3/TxR, and DU145/TxR). FIG. 30C illustrates representative colony images of A375/TxR cells treated with 5v (0.5 nM, 1 nM, and 2 nM) for 7 days and the quantification of colony formation density of treatment group as of control group. Data are presented as the grand mean±SEM, ****  $P<0.0001$.

FIG. 31A illustrates the migration ability of A375/TxR cells upon treatment with 5v (0.5 nM, 1 nM, 2 nM, or 5 nM) was investigated by scratch wound assay. Representative wound pictures were acquired after 5v exposure at 0 h, 24 h, and 48 h by IncuCyte. Percentage wound closure relative to cells at 0 h±SEM of each group was calculated by IncuCyte Scratch Wound Module at each of the time points. FIG. 31B illustrates the measurement of apoptotic A375/TxR cells treated with 5v (1 nM, 2 nM, or 5 nM) by Annexin V/PI staining. Bar graphs represent the % of apoptotic cells±SEM for each group. FIG. 31C illustrates cell cycle distribution of A375/TxR cells with the same treatment in B. The percentage of cells in the G1, S, or G2/M phase of each treatment group was plotted. , $P<0.01$; *, $P<0.001$; ****, $P<0.0001$.

FIG. 31A illustrates tumor volume±SD of A375/TxR melanoma xenografts. Mice were dosed with the vehicle, 4 mg/kg paclitaxel, 2 mg/kg 5v, or 4 mg/kg 5v two times a week intravenously. FIG. 31B illustrates mouse body weight change±SD of tumor-bearing mice. FIG. 31C illustrates a representative image of resected tumors in vehicle group and treatment groups. FIG. 31A illustrates the final tumor wet weight±SD for each group. Statistical significance was evaluated by Dunnett's multiple comparison test, *, $P<0.001$; **, $P<0.0001$ versus vehicle.

FIG. 33A illustrates representative images of tumor sections stained with H&E, Ki67, CD31, and cleaved caspase-3. Keyence microscope magnification, 20×. Scale bar, 50 µm. Yellow arrows in H&E stained tumor sections indicate necrotic tumor cells. FIG. 33B illustrates the quantification of the mean Ki67, CD31, and cleaved caspase-3 expression±SD in tumor sections relative to the vehicle control group. Statistical significance was evaluated by Dunnett's multiple comparison test, *, $P<0.05$; *, $P<0.001$; **, $P<0.0001$ verse vehicle.

FIGS. 34A-D illustrates that 5v suppressed the spontaneous metastasis of A375/TxR subcutaneous tumors. FIG. 34A illustrates a representative image of axillary lymph node collected from each group in A375/TxR xenograft model. FIG. 34B illustrates anti-human mitochondrial IHC staining was used to detect metastases in lung sections of each group of mice. FIG. 34C graphically illustrates anti-human mitochondrial IHC staining was used to detect metases in liver sections of each group of mice. The bar graph represents the area of metastases present in the lung (FIG. 34B) and liver (FIG. 34C) in each group. FIG. 34D are representative images of anti-human mitochondria stained lung (top) or liver (bottom) metastases in each group. Both lung and liver metastases are indicated with red arrows. Keyence microscope magnification, 20×. Scale bar: 200 µm. , $P<0.01$; **, $P<0.0001$ versus vehicle.

FIG. 36A graphically illustrates the body weight of mice when 5 mg/kg 5v was administered into 3 NSG mice by intraperitoneal (IP) injection with dose frequency as 5 times a week. FIG. 36B graphically illustrates the body weight of mice when 10 mg/kg 5v was administered into 3 NSG mice by intraperitoneal (IP) injection with dose frequency as 5 times a week. FIG. 36C graphically illustrates the body weight of mice when 5 mg/kg 5v was administered into 4 NSG mice by intravenous (IV) injection with dose frequency as 2 times a week. FIG. 36D graphically illustrates the body weight of mice when 10 mg/kg 5v was administered into 4 NSG mice by intravenous (IV) injection with dose frequency as 2 times a week.

FIG. 39A illustrates the IC$_{50}$ values expressed in nM for compounds 5m, 12k, and 5v HC in two different cell lines of head and neck cancer, A-253 and Detroit 562. FIG. 39B is a graph of the cell viability (%) vs. concentration (nM) for A-253 cell line. FIG. 39C is a graph of the cell viability (%) vs. concentration (nM) for Detroit-562 cell line. IC$_{50}$ values were calculated as described elsewhere herein. Similarly, cytotoxicity experiments were performed as described elsewhere herein.

FIG. 40A illustrates the graph of Confluence % vs Time Elapsed (hrs.) for 12k in the A-253 cell line. FIG. 40B illustrates the graph of Confluence % vs Time Elapsed (hrs.) for 12k in the Detroit 562 cell line. FIG. 40C illustrates the graph of Confluence % vs Time Elapsed (hrs.) for compound 17ya in the A-253 cell line. FIG. 40D illustrates the graph of Confluence % vs Time Elapsed (hrs.) for compound 17ya in the A-253 cell line. Compound 12k or 17ya were added in increasing concentrations into wells seeded with indicated number of cell lines for the indicated cell lines, and monitored for % confluence over a period of 62 h. Both compounds demonstrated a dose-responsive decrease in cell proliferation in both A-253 and Detroit 562 cells, however, 12k was more potent in both cell lines.

FIG. 41A illustrates the effect of compound 12k on colony formation in the A-253 cell line. FIG. 41B illustrates the effect of compound 12k on colony formation in the Detroit 562 cell line. Colony formation experiments were performed as described elsewhere herein.

FIG. 42A illustrates that compound 12k induces apoptosis in the A-253 cell line. FIG. 42B illustrates that compound 12k induces apoptosis in the Detroit 562 cell line.

FIG. 46A illustrates the effect of compound 5m on 231-BrM2 cells (200,000) were injected intracardiac (IC) into 8-9 week old NSG females and drug therapy started 2 days after IC injection; animals were dosed twice per week via IV route. All mice were euthanized on Day 24 of treatment and brain signal shown at endpoint after bio-imaging ex vivo. Representative images of the whole brain from vehicle (top) and 5m treated (bottom) mice are shown in FIG. 46A. FIG. 46B illustrates that in an independent experiment to measure overall survival (OS), 231-BrM2 cells (100,000) were IC injected into 8-9-week old NSG females and therapy begun 24 h later. Animals were dosed twice per week via IV route. Mice were bio-imaged once per week and animals removed from the study once moribund by local IACUC criteria. Total photon flux data of live mice (head only) are shown up to Day 28. Note that 2 of 6 vehicle mice were moribund/censored post-imaging on Day 24, resulting in the decreased mean flux on Day 28. The y-axes are plotted on log 10 scale. The survival data is shown in FIG. 51 below.

FIG. 49A illustrates the vehicle treated mouse. FIG. 49B illustrates the mouse treated with compound 5m. Using identical capture times (1 minute), the reduction in photon flux in the ex vivo brains can be further appreciated; the observed photon flux in the 5m treated ex vivo brain (see far right image; $1.51 \times 10^7$ p/s) is reduced compared to the vehicle treated brain (panel second from left; $6.01 \times 10^7$ p/s). Animals were imaged using a Perkin Elmer XMRS instrument.

FIG. 50A illustrates the effect on bone ex-vivo. FIG. 50B illustrates the effect on lungs ex-vivo. FIG. 50A illustrates the effect on spleen ex-vivo.

FIG. 54A illustrates the graphical representation of the effect of compound 5m and vehicle. FIG. 54B illustrates the ex vivo imaging for the vehicle treated mouse and the mouse treated with compound 5m. A single representative mouse from each cohort was tracked over time (using identical bio-imaging capture times). Again, by day 14, the difference in total photon flux between vehicle-treated compared to 5m treated mouse started to diverge, again indicating that 5m delayed metastatic progression, with a 6.7 fold increased metastasis on day 28, despite each mouse showing similar starting values for BrnMets photon flux (7.5×10$^5$ vs. 6.3× 10$^5$). Further, the representative vehicle treated mouse died on day 28 whereas the 5m treated mouse lived until day 35. Animals were imaged using a Perkin Elmer XMRS instrument.

Figure 1:
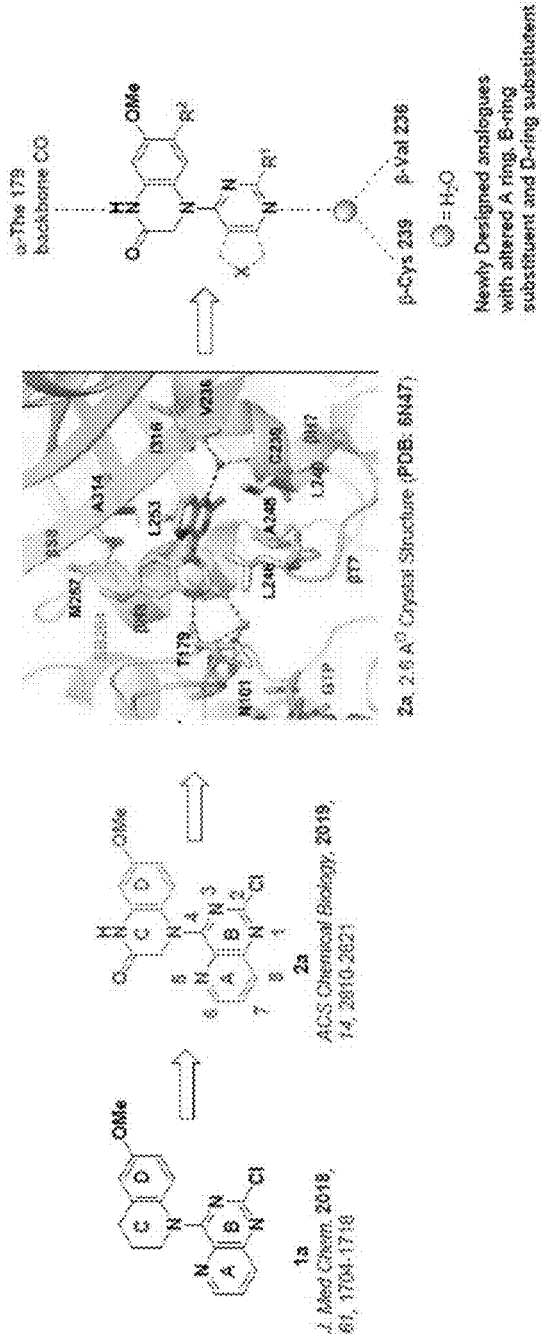
FIG. 1 illustrates heterocyclic-pyridopyrimidine 1a and dihydroquinoxalinone 2a and the x-ray crystal structure of 2a illustrating binding with the colchicine site in tubulin.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

Heterocyclic-pyridopyrimidine 1a (see FIG. 1) and hydroquinoxalinone 2a (see FIG. 1), were found to be potent tubulin polymerization inhibitors with significant vascular disrupting capabilities. The X-ray co-crystal structures demonstrated that 1a and 2a bind to the colchicine site in tubulin (FIG. 1). Crystal structures unveil that the pyrimidine portion of these molecules form water mediated hydrogen bonds with the β-C239 and β-V236, making these analogues one of the most potent inhibitors of tubulin polymerization. Additionally, in compound 2a and its derivatives, the dihydroquinoxalinone moiety forms a hydrogen bond with the α-T179. Thus, Compound 2a, is a strong inhibitor of microtubule polymerization and has improved metabolic stability against human ($t_{1/2}$=5.5 hrs), mouse ($t_{1/2}$=1 hr), and rat ($t_{1/2}$=5.07 hrs) liver microsomes. Compound 2a was found to have single digit nanomolar potency against diverse melanoma, prostate, lung and breast cancer cell lines. However, compound 2a has poor water solubility making it very difficult to work in either intraperitoneal or intravenous in vivo experiments. Also, Compound 2a in a maximum tolerated dose (MTD) study showed toxicity above 1 mg/kg dose leading to loss of body weight and death of mice, a highly undesirable property.

Figure 2:
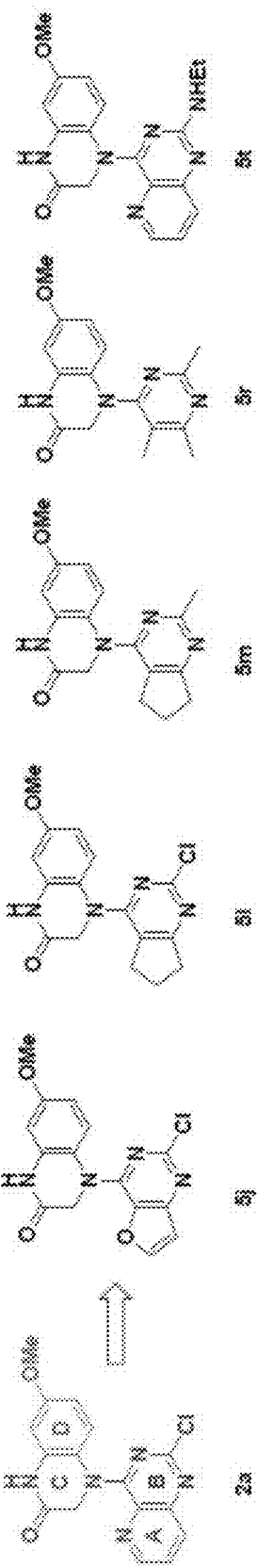
FIG. 2 illustrates examples of the compounds of the invention, e.g., 5j, 5l, 5m, 5r, and 5t.

To address the shortcomings, the invention encompasses novel dihydroquinoxalinone compounds with significantly improved water solubility and reduced toxicity to achieve higher therapeutic indexes. The invention encompasses a novel class of pyrimidine analogues with different A rings (see FIG. 1). The compounds of the invention include A rings such as a) fused heterocyclic-pyrimidines; b) fused saturated-cycloalkane-pyrimidines; or c) ring-open substituted pyridine-pyrimidine analogues with dihydroquinoxalinone head groups, among others, as shown in FIG. 2. Not to be limited by theory, however, the invention is based upon the belief that switching from the fused pyridopyrimidine tail group to other fused-heterocyclic-pyrimidines as well as fused-saturated-hydrocarbon-pyrimidine tail groups would provide two advantages: a) improved water solubility; and b) reduced toxicity while retaining key hydrogen bonding interactions, one with T-5 loop of α-tubulin monomer and the other with H-7 helix of the β-monomer mediated by water. By incorporating these different structures within the molecule, the invention sought to overcome the shortcomings of solubility and toxicity found in other compounds.

Not to be limited by theory, it is believed that the embodiment encompassing fused hydrocarbon ring in the tail group should make the compounds more capable of forming hydrophobic interactions with the predominately hydrophobic pocket in β-tubulin, thus causing stronger tubulin binding and improved anticancer efficacy.

The invention encompasses compounds having a structure of Formula I:

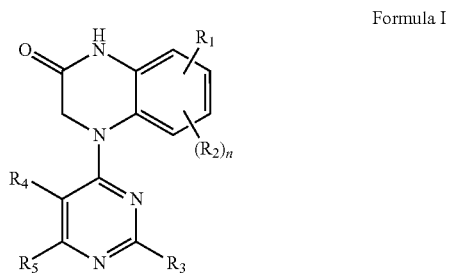

Formula I wherein $R_1$ is a halide, $C_1$-$C_4$ alkyl, $C_1$-$C_4$ alkoxy, $C_1$-$C_4$ haloalkyl, $C_1$-$C_4$ haloalkoxy, Ph, O($C_5$-$C_{10}$ aryl), OPh, ($C_1$-$C_3$ alkyl)phenyl, —O($C_1$-$C_3$ alkyl)phenyl, —NH$_2$, —NH ($C_1$-$C_4$ alkyl), —N($C_1$-$C_4$ alkyl)$_2$, hydroxyl, cyano, or $C_2$-$C_5$ ether;

$R_2$ is at least one of hydrogen, halide, $C_1$-$C_4$ alkyl, $C_1$-$C_4$ alkoxy, $C_1$-$C_4$ haloalkyl, —NH$_2$, —NH($C_1$-$C_4$ alkyl), —N($C_1$-$C_4$ alkyl)$_2$, hydroxyl, cyano, or $C_2$-$C_5$ ether;

$R_3$ is hydrogen, halide, $C_1$-$C_4$ alkyl, $C_1$-$C_4$ alkoxy, $C_1$-$C_4$ haloalkyl, —NH$_2$, —NH($C_1$-$C_4$ alkyl), —N($C_1$-$C_4$ alkyl)$_2$, —NH($C_1$-$C_4$ heteroalkyl), —NHPh, —NH($C_3$-$C_{10}$ aryl), —NH($C_3$-$C_{10}$ heteroaryl), —NH($C_3$-$C_{10}$ cycloalkyl), —NH($C_3$-$C_{10}$ heterocyclyl), hydroxyl, cyano, NCS, $C_3$-$C_6$ heterocyclyl, or $C_2$-$C_5$ ether, wherein the heterocyclyl has at least one of O, N, or S, and wherein the heterocyclyl may optionally be substituted, wherein the substitutions of the heterocyclyl include halide, $C_1$-$C_4$ alkyl, $C_1$-$C_4$ alkoxy, $C_1$-$C_4$ haloalkyl, —NH$_2$, —NH($C_1$-$C_4$ alkyl), —N($C_1$-$C_4$ alkyl)$_2$, hydroxyl, cyano, or $C_2$-$C_5$ ether; and $R_4$ and $R_5$ are at least one of halide, $C_1$-$C_4$ alkyl, $C_1$-$C_4$ alkoxy, $C_1$-$C_4$ haloalkyl, —NH$_2$, —NH($C_1$-$C_4$ alkyl), —N($C_1$-$C_4$ alkyl)$_2$, hydroxyl, cyano, $C_2$-$C_5$ ether, or wherein when taken together $R_4$ and $R_5$ form a 5 or 6-membered cycloalkyl ring, or a 5 or 6-membered heterocycle ring having at least one N, O, or S atom, wherein the cycloalkyl or heterocycle ring may optionally have at least one unsaturation, wherein the cycloalkyl or heterocycle ring may optionally be substituted, wherein the substitutions of the cycloalkyl or heterocycle ring include halide, $C_1$-$C_4$ alkyl, $C_1$-$C_4$ alkoxy, $C_1$-$C_4$ haloalkyl, —NH$_2$, —NH($C_1$-$C_4$ alkyl), —N($C_1$-$C_4$ alkyl)$_2$, hydroxyl, cyano, or $C_2$-$C_5$ ether;

provided that if $R_4$ and $R_5$ taken together form a phenyl ring, then said phenyl ring is substituted, or if $R_4$ and $R_5$ taken together form a pyridine ring, then $R_3$ is not chlorine;

n is 1-3;

or a stereoisomer, pharmaceutically acceptable salt, hydrate, N-oxide, or combinations thereof.

The invention encompasses compounds having a structure of formula IA:

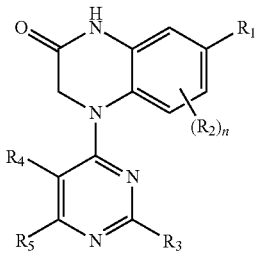

Formula IA wherein $R_1$ is a halide, $C_1$-$C_4$ alkyl, $C_1$-$C_4$ alkoxy, $C_1$-$C_4$ haloalkyl, $C_1$-$C_4$ haloalkoxy, Ph, O($C_5$-$C_{10}$ aryl), OPh, ($C_1$-$C_3$ alkyl)phenyl, —O($C_1$-$C_3$ alkyl)phenyl, —$NH_2$, —NH($C_1$-$C_4$ alkyl), —N($C_1$-$C_4$ alkyl)$_2$, hydroxyl, cyano, or $C_2$-$C_5$ ether;

$R_2$ is at least one of hydrogen, halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, hydroxyl, cyano, or $C_2$-$C_5$ ether;

$R_3$ is hydrogen, halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, —NH($C_1$-$C_4$ heteroalkyl), —NHPh, —NH($C_3$-$C_{10}$ aryl), —NH($C_3$-$C_{10}$ heteroaryl), —NH($C_3$-$C_{10}$ cycloalkyl), —NH($C_3$-$C_{10}$ heterocyclyl), hydroxyl, cyano, NCS, $C_3$-$C_6$ heterocyclyl, or $C_2$-$C_5$ ether, wherein the heterocyclyl has at least one of O, N, or S, and wherein the heterocyclyl may optionally be substituted, wherein the substitutions of the heterocyclyl include halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, hydroxyl, cyano, or $C_2$-$C_5$ ether; and $R_4$ and $R_5$ are taken together to form a 5 or 6-membered cycloalkyl ring, or a 5 or 6-membered heterocycle ring having at least one N, O, or S atom, wherein the cycloalkyl or heterocycle ring may optionally have at least one unsaturation, wherein the cycloalkyl or heterocycle ring may optionally be substituted, wherein the substitutions of the cycloalkyl or heterocycle ring include halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, hydroxyl, cyano, or $C_2$-$C_5$ ether;

provided that if $R_4$ and $R_5$ taken together form a phenyl ring, then said phenyl ring is substituted, or if $R_4$ and $R_5$ taken together form a pyridine ring, then $R_3$ is not chlorine;

n is 1-3;

or a stereoisomer, pharmaceutically acceptable salt, hydrate, N-oxide, or combinations thereof.

The invention encompasses compounds having a structure of Formula II:

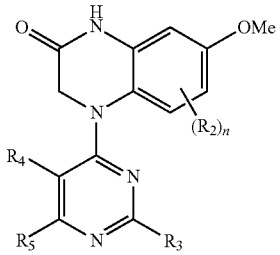

Formula II wherein $R_2$ is at least one of hydrogen, halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, hydroxyl, cyano, or $C_2$-$C_5$ ether;

$R_3$ is hydrogen, halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, —NH($C_1$-$C_4$ heteroalkyl), —NHPh, —NH($C_3$-$C_{10}$ aryl), —NH($C_3$-$C_{10}$ heteroaryl), —NH($C_3$-$C_{10}$ cycloalkyl), —NH($C_3$-$C_{10}$ heterocyclyl), hydroxyl, cyano, NCS, $C_3$-$C_6$ heterocyclyl, or $C_2$-$C_5$ ether, wherein the heterocyclyl has at least one of O, N, or S, and wherein the heterocyclyl may optionally be substituted, wherein the substitutions of the heterocyclyl include halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, hydroxyl, cyano, or $C_2$-$C_5$ ether; and $R_4$ and $R_5$ are at least one of halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, hydroxyl, cyano, $C_2$-$C_5$ ether, or wherein when taken together $R_4$ and $R_5$ form a 5 or 6-membered cycloalkyl ring, or a 5 or 6-membered heterocycle ring having at least one N, O, or S atom, wherein the cycloalkyl or heterocycle ring may optionally have at least one unsaturation, wherein the cycloalkyl or heterocycle ring may optionally be substituted, wherein the substitutions of the cycloalkyl or heterocycle ring include halide, $C_1$-$C_4$ alkyl, $C_1$-$C_4$ alkoxy, $C_1$-$C_4$ haloalkyl, —$NH_2$, —NH($C_1$-$C_4$ alkyl), —N($C_1$-$C_4$ alkyl)$_2$, hydroxyl, cyano, or $C_2$-$C_5$ ether;

provided that if $R_4$ and $R_5$ taken together form a phenyl ring, then said phenyl ring is substituted, or if $R_4$ and $R_5$ taken together form a pyridine ring, then $R_3$ is not chlorine;

n is 1-3;

or a stereoisomer, pharmaceutically acceptable salt, hydrate, N-oxide, or combinations thereof. In another embodiment, the invention encompasses pharmaceutical compositions comprising a compound of formula II and a pharmaceutically acceptable excipient.

The invention encompasses compounds having a structure of Formula IIA:

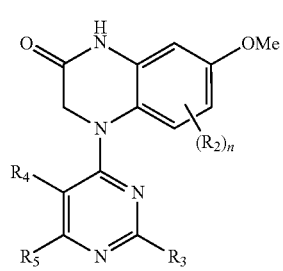

Formula IIA wherein
- $R_2$ is at least one of hydrogen, halide, $C_1$-$C_4$ alkyl, $C_1$-$C_4$ alkoxy, $C_1$-$C_4$ haloalkyl, —$NH_2$, —$NH(C_1$-$C_4$ alkyl), —$N(C_1$-$C_4$ alkyl)$_2$, hydroxyl, cyano, or $C_2$-$C_5$ ether;
- $R_3$ is hydrogen, halide, $C_1$-$C_4$ alkyl, $C_1$-$C_4$ alkoxy, $C_1$-$C_4$ haloalkyl, —$NH_2$, —$NH(C_1$-$C_4$ alkyl), —$N(C_1$-$C_4$ alkyl)$_2$, —$NH(C_1$-$C_4$ heteroalkyl), —NHPh, —$NH(C_3$-$C_{10}$ aryl), —$NH(C_3$-$C_{10}$ heteroaryl), —$NH(C_3$-$C_{10}$ cycloalkyl), —$NH(C_3$-$C_{10}$ heterocyclyl), hydroxyl, cyano, NCS, $C_3$-$C_6$ heterocyclyl, or $C_2$-$C_5$ ether, wherein the heterocyclyl has at least one of O, N, or S, and wherein the heterocyclyl may optionally be substituted, wherein the substitutions of the heterocyclyl include halide, $C_1$-$C_4$ alkyl, $C_1$-$C_4$ alkoxy, $C_1$-$C_4$ haloalkyl, —$NH_2$, —$NH(C_1$-$C_4$ alkyl), —$N(C_1$-$C_4$ alkyl)$_2$, hydroxyl, cyano, or $C_2$-$C_5$ ether; and
- $R_4$ and $R_5$ are taken together to form a 5 or 6-membered cycloalkyl ring, or a 5 or 6-membered heterocycle ring having at least one N, O, or S atom, wherein the cycloalkyl or heterocycle ring may optionally have at least one unsaturation, wherein the cycloalkyl or heterocycle ring may optionally be substituted, wherein the substitutions of the cycloalkyl or heterocycle ring include halide, $C_1$-$C_4$ alkyl, $C_1$-$C_4$ alkoxy, $C_1$-$C_4$ haloalkyl, —$NH_2$, —$NH(C_1$-$C_4$ alkyl), —$N(C_1$-$C_4$ alkyl)$_2$, hydroxyl, cyano, or $C_2$-$C_5$ ether;
- provided that if $R_4$ and $R_5$ taken together form a phenyl ring, then said phenyl ring is substituted, or if $R_4$ and $R_5$ taken together form a pyridine ring, then $R_3$ is not chlorine;
- n is 1-3;
- or a stereoisomer, pharmaceutically acceptable salt, hydrate, N-oxide, or combinations thereof.

In another embodiment, the invention encompasses pharmaceutical compositions comprising a compound of formula II and a pharmaceutically acceptable excipient.

An embodiment of the invention encompasses a compound of formula I, IA, II, or IIA represented by any one of the following compounds 5j-5r, 5t-5v or 12a-12m and 12o-12q:

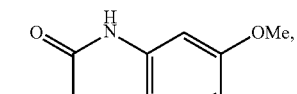

5j

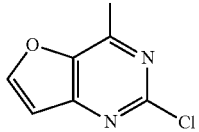

5k

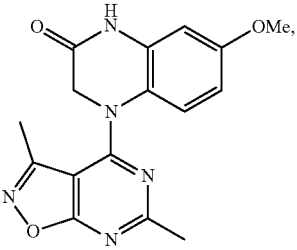

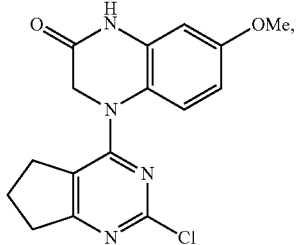

5l

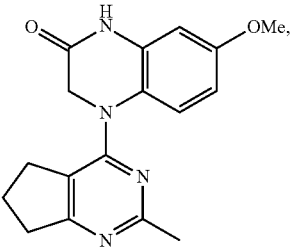

5m

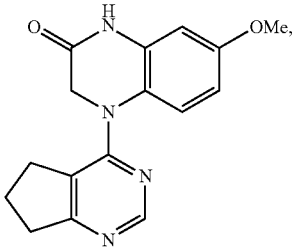

5n

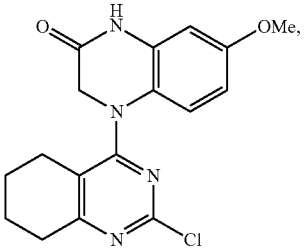

5o

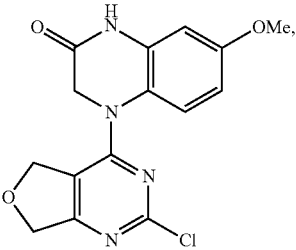

5p

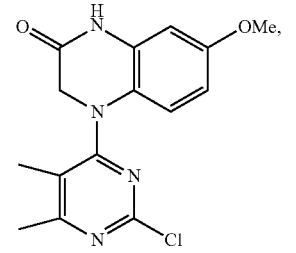

5q

5r 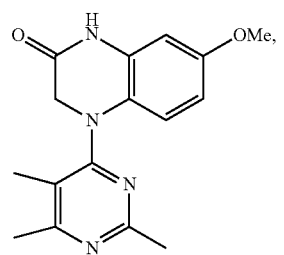
5t 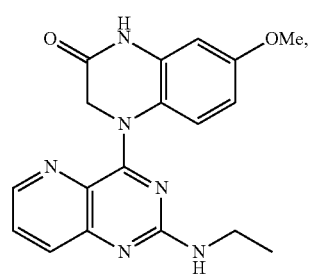
5u 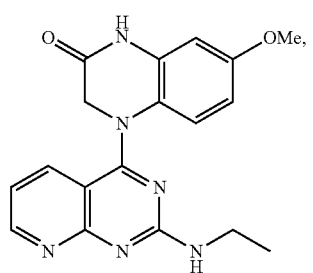
5v 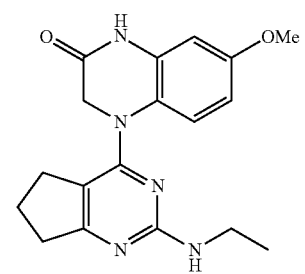
12a 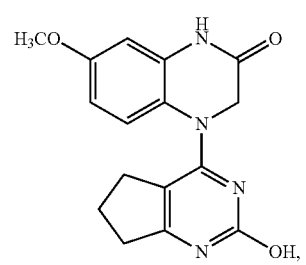
12b 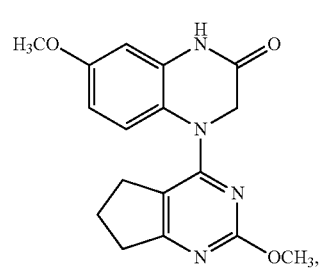
12c 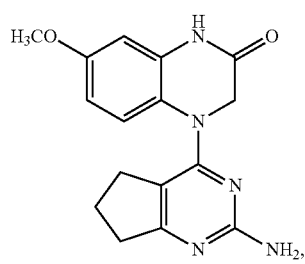
12d 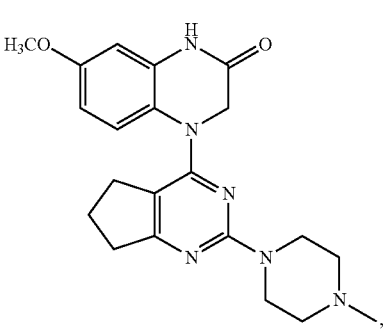
12e 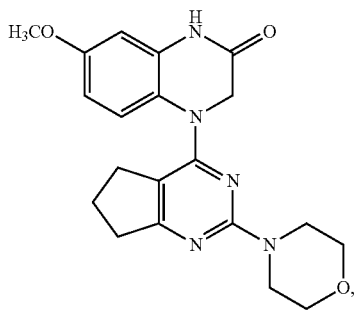
12f 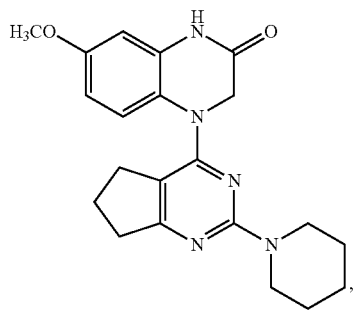
12g 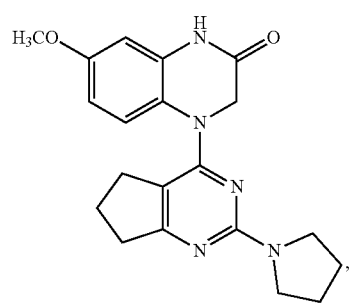

12h 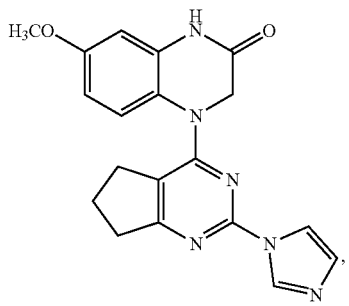

12i 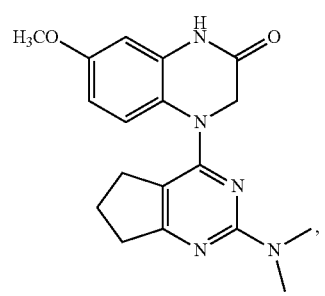

12j 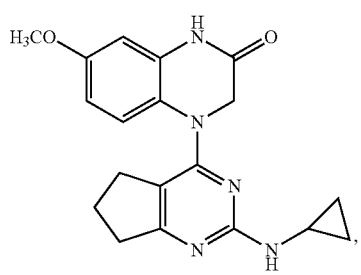

12k 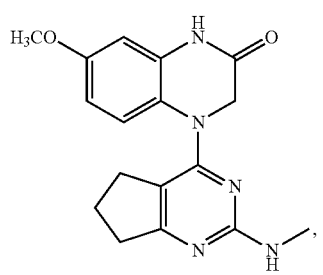

12l 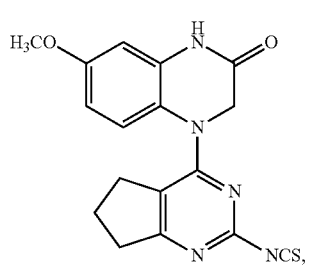

12m 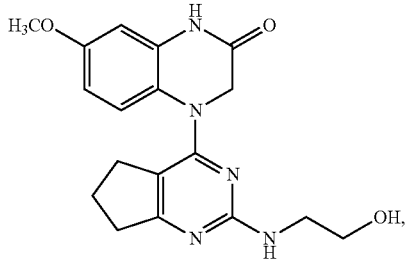

12o 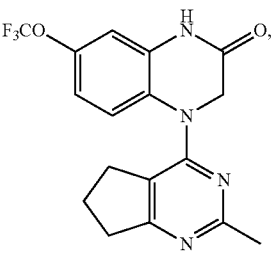

12p 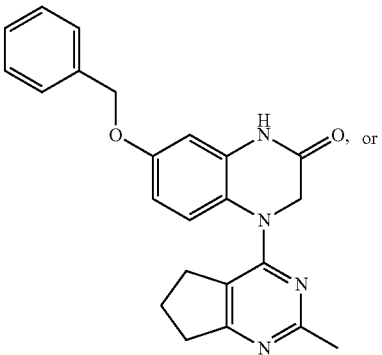

12q 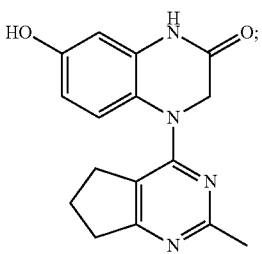

or a stereoisomer, pharmaceutically acceptable salt, hydrate, N-oxide, or combinations thereof.

In another embodiment, the invention encompasses pharmaceutical compositions comprising a compound of any one of formulas 5j-5r, 5t-5v or 12a-12m and 12o-12q and a pharmaceutically acceptable excipient.

An embodiment of the invention encompasses the compound represented by 5s:

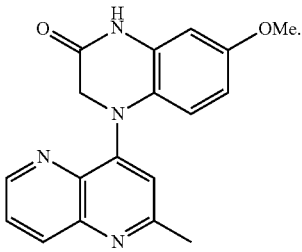

5s

The invention encompasses compounds having a structure of Formula III:

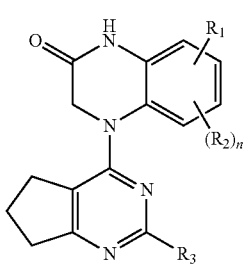

Formula III wherein
- R$_1$ is a halide, C$_1$-C$_4$ alkyl, C$_1$-C$_4$ alkoxy, C$_1$-C$_4$ haloalkyl, C$_1$-C$_4$ haloalkoxy, Ph, O(C$_5$-C$_{10}$ aryl), OPh, (C$_1$-C$_3$ alkyl)phenyl, —O(C$_1$-C$_3$ alkyl)phenyl, —NH$_2$, —NH(C$_1$-C$_4$ alkyl), —N(C$_1$-C$_4$ alkyl)$_2$, hydroxyl, cyano, or C$_2$-C$_5$ ether;
- R$_2$ is at least one of hydrogen, halide, C$_1$-C$_4$ alkyl, C$_1$-C$_4$ alkoxy, C$_1$-C$_4$ haloalkyl, —NH$_2$, —NH(C$_1$-C$_4$ alkyl), —N(C$_1$-C$_4$ alkyl)$_2$, hydroxyl, cyano, or C$_2$-C$_5$ ether;
- R$_3$ is hydrogen, halide, C$_1$-C$_4$ alkyl, C$_1$-C$_4$ alkoxy, C$_1$-C$_4$ haloalkyl, —NH$_2$, —NH(C$_1$-C$_4$ alkyl), —N(C$_1$-C$_4$ alkyl)$_2$, —NH(C$_1$-C$_4$ heteroalkyl), —NHPh, —NH(C$_3$-C$_{10}$ aryl), —NH(C$_3$-C$_{10}$ heteroaryl), —NH(C$_3$-C$_{10}$ cycloalkyl), —NH(C$_3$-C$_{10}$ heterocyclyl), hydroxyl, cyano, NCS, C$_3$-C$_6$ heterocyclyl, or C$_2$-C$_5$ ether, wherein the heterocyclyl has at least one of O, N, or S, and wherein the heterocyclyl may optionally be substituted, wherein the substitutions of the heterocyclyl include halide, C$_1$-C$_4$ alkyl, C$_1$-C$_4$ alkoxy, C$_1$-C$_4$ haloalkyl, —NH$_2$, —NH(C$_1$-C$_4$ alkyl), —N(C$_1$-C$_4$ alkyl)$_2$, hydroxyl, cyano, or C$_2$-C$_5$ ether; and
- n is 1-3;

or a stereoisomer, pharmaceutically acceptable salt, hydrate, N-oxide, or combinations thereof.

The invention encompasses compounds having a structure of formula IIIA:

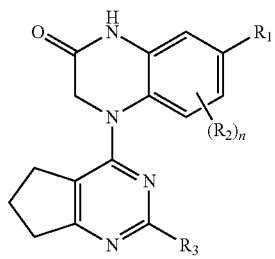

Formula IIIA wherein
- R$_1$ is a halide, C$_1$-C$_4$ alkyl, C$_1$-C$_4$ alkoxy, C$_1$-C$_4$ haloalkyl, C$_1$-C$_4$ haloalkoxy, Ph, O(C$_5$-C$_{10}$ aryl), OPh, (C$_1$-C$_3$ alkyl)phenyl, —O(C$_1$-C$_3$ alkyl)phenyl, —NH$_2$, —NH(C$_1$-C$_4$ alkyl), —N(C$_1$-C$_4$ alkyl)$_2$, hydroxyl, cyano, or C$_2$-C$_5$ ether;
- R$_2$ is at least one of hydrogen, halide, C$_1$-C$_4$ alkyl, C$_1$-C$_4$ alkoxy, C$_1$-C$_4$ haloalkyl, —NH$_2$, —NH(C$_1$-C$_4$ alkyl), —N(C$_1$-C$_4$ alkyl)$_2$, hydroxyl, cyano, or C$_2$-C$_5$ ether;
- R$_3$ is hydrogen, halide, C$_1$-C$_4$ alkyl, C$_1$-C$_4$ alkoxy, C$_1$-C$_4$ haloalkyl, —NH$_2$, —NH(C$_1$-C$_4$ alkyl), —N(C$_1$-C$_4$ alkyl)$_2$, —NH(C$_1$-C$_4$ heteroalkyl), —NHPh, —NH(C$_3$-C$_{10}$ aryl), —NH(C$_3$-C$_{10}$ heteroaryl), —NH(C$_3$-C$_{10}$ cycloalkyl), —NH(C$_3$-C$_{10}$ heterocyclyl), hydroxyl, cyano, NCS, C$_3$-C$_6$ heterocyclyl, or C$_2$-C$_5$ ether, wherein the heterocyclyl has at least one of O, N, or S, and wherein the heterocyclyl may optionally be substituted, wherein the substitutions of the heterocyclyl include halide, C$_1$-C$_4$ alkyl, C$_1$-C$_4$ alkoxy, C$_1$-C$_4$ haloalkyl, —NH$_2$, —NH(C$_1$-C$_4$ alkyl), —N(C$_1$-C$_4$ alkyl)$_2$, hydroxyl, cyano, or C$_2$-C$_5$ ether; and
- n is 1-3;

or a stereoisomer, pharmaceutically acceptable salt, hydrate, N-oxide, or combinations thereof.

The invention encompasses compounds having a structure of formula IIIB:

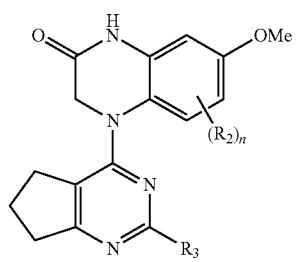

Formula IIIB wherein
- R$_2$ is at least one of hydrogen, halide, C$_1$-C$_4$ alkyl, C$_1$-C$_4$ alkoxy, C$_1$-C$_4$ haloalkyl, —NH$_2$, —NH(C$_1$-C$_4$ alkyl), —N(C$_1$-C$_4$ alkyl)$_2$, hydroxyl, cyano, or C$_2$-C$_5$ ether;
- R$_3$ is hydrogen, halide, C$_1$-C$_4$ alkyl, C$_1$-C$_4$ alkoxy, C$_1$-C$_4$ haloalkyl, —NH$_2$, —NH(C$_1$-C$_4$ alkyl), —N(C$_1$-C$_4$ alkyl)$_2$, —NH(C$_1$-C$_4$ heteroalkyl), —NHPh, —NH(C$_3$-C$_{10}$ aryl), —NH(C$_3$-C$_{10}$ heteroaryl), —NH(C$_3$-C$_{10}$ cycloalkyl), —NH(C$_3$-C$_{10}$ heterocyclyl), hydroxyl, cyano, NCS, C$_3$-C$_6$ heterocyclyl, or C$_2$-C$_5$ ether, wherein the heterocyclyl has at least one of O, N, or S, and wherein the heterocyclyl may optionally be substituted, wherein the substitutions of the heterocyclyl include halide, C$_1$-C$_4$ alkyl, C$_1$-C$_4$ alkoxy, C$_1$-C$_4$ haloalkyl, —NH$_2$, —NH(C$_1$-C$_4$ alkyl), —N(C$_1$-C$_4$ alkyl)$_2$, hydroxyl, cyano, or C$_2$-C$_5$ ether; and
- n is 1-3;

or a stereoisomer, pharmaceutically acceptable salt, hydrate, N-oxide, or combinations thereof.

An embodiment of the invention encompasses a compound of formula III represented by any one of the following compounds 5l-5n, 5v, 12a-12m and 12o-12q:

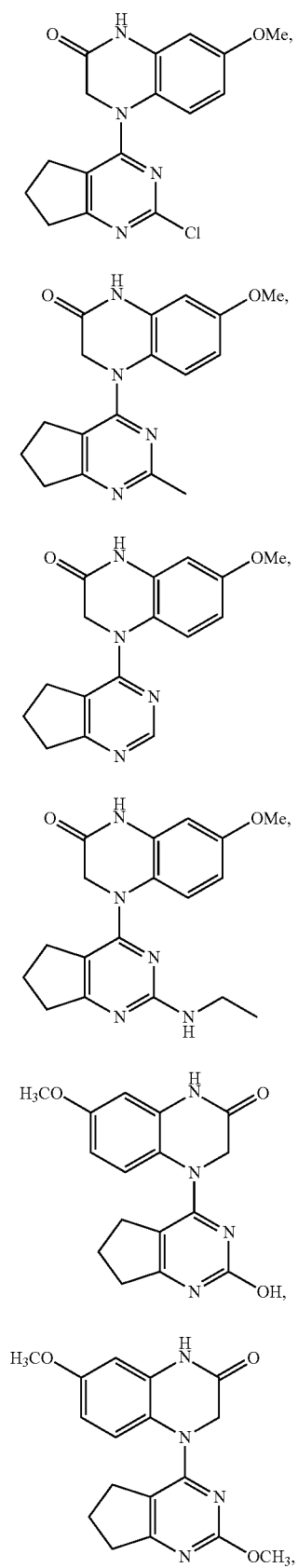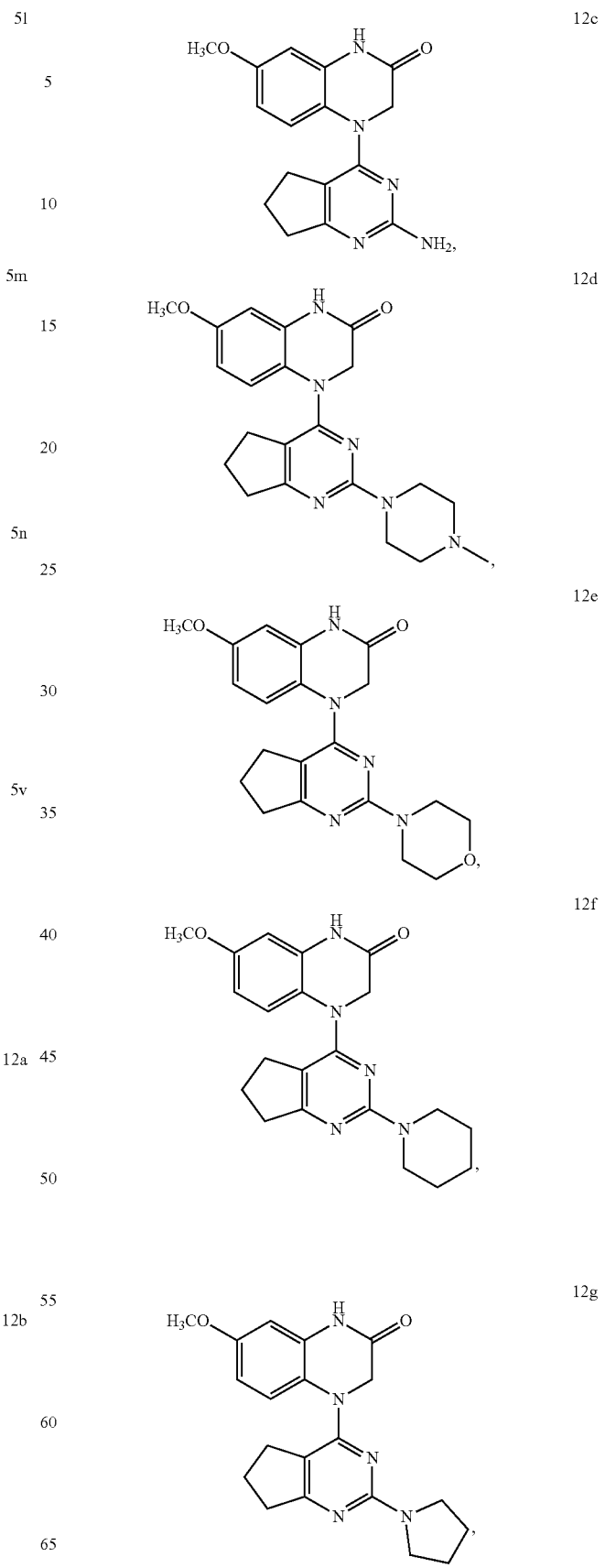

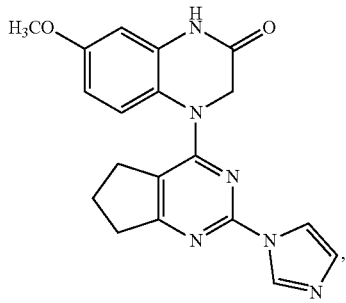

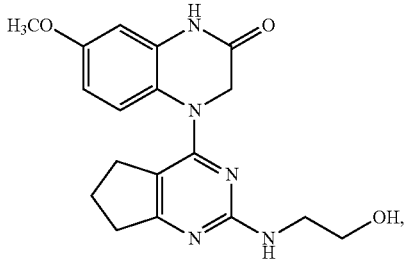

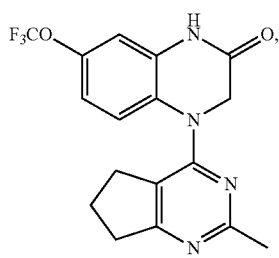

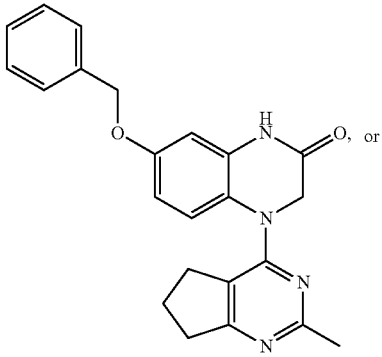

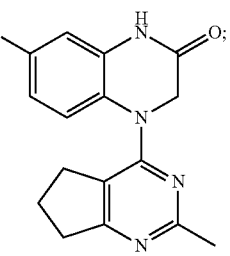

or a stereoisomer, pharmaceutically acceptable salt, hydrate, N-oxide, or combinations thereof.

In another embodiment, the invention encompasses pharmaceutical compositions comprising a compound of Formula III represented by any one of 5l-5n, 5v, 12a-12m and 12o-12q and a pharmaceutically acceptable excipient.

An embodiment of the invention encompasses the compound represented by 5s:

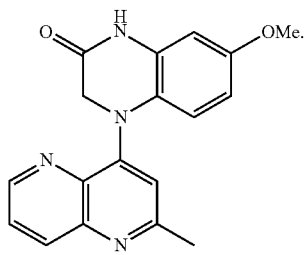

The invention includes "pharmaceutically acceptable salts" of the compounds of the invention, as described above, which may be produced by reaction of a compound of this invention with an acid or base. Certain compounds, particularly those possessing acid or basic groups, can also be in the form of a salt, preferably a pharmaceutically acceptable salt. As used herein, the term "pharmaceutically acceptable salt" refers to those salts that retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. Other salts are known to those of skill in the art and can readily be adapted for use in accordance with the present invention.

Suitable pharmaceutically acceptable salts of amines of compounds used in the method of the invention may be prepared from an inorganic acid or from an organic acid. In one embodiment, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isothionates, nitrates, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

Examples of organic salts of amines include, but are not limited to, aliphatic, cycloaliphatic, aromatic, araliphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates gluconates, glutamates, glycolates, glucorate, glucoheptanoates, glycerophosphates, gluceptates, glycollylarsanilates, glutarates, glutamate, heptanoates, hexanoates, hydroxymaleates, hydroxycarboxlic acids, hexylresorcinates, hydroxybenzoates, hydroxynaphthoates, hydrofluorates, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, naphthalenesulfonates, 2-naphthalenesulfonates, nicotinates, nitrates, napsylates, N-methylglucamines, oxalates, octanoates, oleates, pamoates, phenylacetates, picrates, phenylbenzoates, pivalates, propionates, phthalates, phenylacetate, pectinates, phenylpropionates, palmitates, pantothenates, polygalacturates, pyruvates, quinates, salicylates, succinates, stearates, sulfanilate, subacetates, tartrates, theophyllineacetates, p-toluenesulfonates (tosylates), trifluoroacetates, terephthalates, tannates, teoclates, trihaloacetates, triethiodide, tricarboxylates, undecanoates and valerates.

Examples of inorganic salts of carboxylic acids or hydroxyls may be selected from ammonium, alkali metals to include lithium, sodium, potassium, cesium; alkaline earth metals to include calcium, magnesium, aluminum; zinc, barium, cholines, quaternary ammoniums.

Examples of organic salts of carboxylic acids or hydroxyl may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolies, piperazines, procain, tris(hydroxymethyl)methylamines, triethylamines, triethanolamines, trimethylamines, tromethamines and ureas.

Typical salts include, but are not limited to, hydrofluoric, hydrochloric, hydrobromic, hydroiodic, boric, nitric, perchloric, phosphoric, sulfuric, acetate, citrate, maleate, malate, or mesylate. Preferred salts include hydrofluoric, hydrochloric, hydrobromic, hydroiodic, acetate, citrate, maleate, or mesylate. More preferred salts include hydrochloric, acetate, or maleate.

The salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of an existing salt for another ion or suitable ion-exchange resin.

Pharmaceutical Composition

The invention also encompasses pharmaceutical compositions including a pharmaceutically acceptable carrier and at least one of the compounds described above. Typically, the pharmaceutical composition may include at least one compound described above or its pharmaceutically acceptable salt, and at least one pharmaceutically acceptable excipient. The term "pharmaceutically acceptable excipient" refers to any suitable adjuvants, carriers, excipients, flavorant, or stabilizers, and can be used in pharmaceutical formulations either in solid or liquid form. Such forms include, but are not limited to, tablets, capsules, powders, solutions, suspensions, or emulsions.

Upon improvement of a subject's condition, a maintenance dose of a compound, composition or formulation may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

The solid unit dosage forms can be of the conventional type. The solid form can be a capsule and the like, such as an ordinary gelatin type containing the compounds and a carrier. Carriers include, but are not limited to, lubricants and inert fillers such as, lactose, sucrose, or cornstarch. The formulations may be tabulated with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, the formulation may include excipients and used in the form of tablets, capsules, elixirs, suspensions, syrups, and the like. Such compositions and preparations should contain at least 0.1% of active compound. The percentage of the compound in these compositions can, of course, be varied and can conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 0.1 mg and 80 mg of active compound, or alternatively about 1 mg and 800 mg, or alternatively about 2 mg to 108 mg.

The formulations may be orally administered with an inert diluent, or with an assimilable edible carrier, or they can be enclosed in hard or soft shell capsules, or they can be compressed into tablets, or they can be incorporated directly with the food of the diet. Formulations may be an oral formulation, intraperitoneal, intravenous, among others.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds or pharmaceutical compositions used in the method of the present invention may also be administered in injectable dosages by solution or suspension of these materials in a physiologically acceptable diluent with a pharmaceutical adjuvant, carrier or excipient. Such adjuvants, carriers and/or excipients include, but are not limited to, sterile liquids, such as water and oils, with or without the addition of a surfactant and other pharmaceutically and physiologically acceptable components. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

The formulation may also be administered parenterally. Solutions or suspensions of these formulations can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

When administering the formulations in the methods of the invention, the formulations may be administered systemically, or sequentially. Administration can be accomplished in any manner effective for delivering the compounds or the pharmaceutical compositions to the desired site. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

The invention encompasses methods of treating cancer by providing at least one compound of the invention or as least one composition to a subject in need thereof in a therapeutically effective amount sufficient to treat the cancer in the subject. Drug resistance is the major cause of cancer chemotherapy failure. Therefore, the invention may also encompasses treating a subject that has been previously treated with hormone, chemotherapy, radiotherapy, or biological therapy; comprising administering to the subject at least one compound of the invention to a subject in need thereof.

The invention also encompasses methods of treating as least one of drug resistant tumors; metastatic cancer; or drug resistant cancer. The invention also encompasses methods of treating at least one of prostate cancer, breast cancer, ovarian cancer, skin cancer (e.g., melanoma), lung cancer, colon cancer, leukemia, lymphoma, head and neck, pancreatic, esophageal, renal cancer or CNS cancer (e.g., glioma, glioblastoma).

The invention also encompasses treating cancer using the drugs of the invention, wherein the cancer is adrenocortical carcinoma, anal cancer, bladder cancer, brain tumor, brain stem tumor, breast cancer, glioma, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, central nervous system (CNS) cancer, endometrial cancer, esophageal cancer, extrahepatic bile duct cancer, Ewing's family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic leukemia, oral cavity cancer, liver cancer, lung cancer, non-small cell lung cancer, small cell, lymphoma, AIDS-related lymphoma, central nervous system (primary), lymphoma, cutaneous T-cell lymphoma, Hodgkin's disease, non-Hodgkin's disease, malignant mesothelioma, melanoma, Merkel cell carcinoma, metastatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian cancer, ovarian epithelial cancer, ovarian germ cell tumor, ovarian low malignant potential tumor, pancreatic cancer, exocrine pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cancer, renal cell cancer, salivary gland cancer, Sezary syndrome, skin cancer, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, Wilms' tumor, or any combination thereof. In another embodiment the subject has been previously treated with hormone, chemotherapy, radiotherapy or biological therapy. Preferably, the cancer is melanoma, breast cancer, ovarian cancer, prostate cancer, or pancreatic cancer.

Despite the significant advancements in breast cancer therapy, effective treatment of metastatic breast cancer (MBC) remains challenging. Major metastasis sites in MBC overall include the bone (41%), lung (22%), liver (8%) and brain (7%). While exact distribution in these major metastasis sites depends on MBC subtypes, the most frequent site is to the bone, and the most difficult site to treat is the brain. Patients with bone-destroying lesions (osteolytic) are particularly susceptible to fractures and chronic pain.

In a preferred embodiment, the invention encompasses methods of treating cancers with the compounds of Formula III (including Formula IIIA and Formula IIIB) wherein the cancers include melanoma, breast cancer, pancreatic cancer, prostate cancer, metastatic bone cancer, or metastatic brain cancer. In another preferred embodiment, the invention encompasses methods of treating breast cancer with the compounds of Formula III (including Formula IIIA and Formula IIIB) wherein the breast cancer includes at least one of advanced breast cancer; metastatic breast cancer; AR-positive breast cancer; ER-positive breast cancer; AR-positive breast cancer with or without expression of ER, PR and/or HER2; triple-positive breast cancer (ER, PR and HER2-positive), AR-positive breast cancer with or without expression of ER; ER-positive breast cancer with or without expression of AR; AR-positive and ER-positive breast cancer; refractory breast cancer; AR-positive refractory breast cancer; ER-positive refractory breast cancer; AR-positive metastatic breast cancer; ER-positive metastatic breast cancer.

In another preferred embodiment, the invention encompasses methods of treating triple negative breast cancer with the compounds of Formula III (including Formula IIIA and Formula IIIB).

As used herein, the term "metastatic cancer" refers to a cancer that spreads (metastasized) from its original site to another area of the body. Virtually all cancers have the potential to spread. Whether metastases develop depends on the complex interaction of many tumor cell factors, including the type of cancer, the degree of maturity (differentiation) of the tumor cells, the location and how long the cancer has been present, as well as other incompletely understood factors. Metastases spread in three ways—by local extension from the tumor to the surrounding tissues, through the bloodstream to distant sites or through the lymphatic system to neighboring or distant lymph nodes. Each kind of cancer may have a typical route of spread. The tumor is called by the primary site (for example, breast cancer that has spread to the brain is called metastatic breast cancer to the brain). In one embodiment of the invention, a compound of the invention is useful in treating metastatic breast cancer to the bone. In one embodiment of the invention, a compound of the invention is useful in preventing the development of metastatic breast cancer to the bone in a patient suffering from breast cancer. In another embodiment of the invention, a compound of the invention is useful in treating metastatic breast cancer to the brain. In one embodiment of the invention, a compound of the invention is useful in preventing the development of metastatic breast cancer to the brain in a patient suffering from breast cancer.

As used herein, the term "drug-resistant cancer" refers to cancer cells that acquire resistance to hormone or chemotherapy. Cancer cells can acquire resistance to hormone or chemotherapy by a range of mechanisms, including the mutation or overexpression of the drug target, inactivation of the drug, or elimination of the drug from the cell. Tumors that recur after an initial response to hormone or chemotherapy may be resistant to multiple drugs (they are multidrug resistant). In the conventional view of drug resistance, one or several cells in the tumor population acquire genetic changes that confer drug resistance. Accordingly, the reasons for drug resistance, inter alia, are: a) some of the cells that are not killed by the hormone or chemotherapy mutate (change) and become resistant to the drug. Once they multiply, there may be more resistant cells than cells that are sensitive to the chemotherapy; b) gene amplification in which a cancer cell may produce hundreds of copies of a particular gene. This gene triggers an overproduction of protein that renders the anticancer drug ineffective; c) cancer cells may pump the drug out of the cell as fast as it is going in using a molecule called P-glycoprotein; d) cancer cells may stop taking in the drugs because the protein that transports the drug across the cell wall stops working; e) the cancer cells may learn how to repair the DNA breaks caused by some anti-cancer drugs; f) cancer cells may develop a mechanism that inactivates the drug. One major contributor to multidrug resistance is overexpression of P-glycoprotein (P-gp). This protein is a clinically important transporter protein belonging to the ATP-binding cassette family of cell membrane transporters. It can pump substrates including anticancer drugs out of tumor cells through an ATP-dependent mechanism. Thus, the resistance to anticancer agents used in chemotherapy is the main cause of treatment failure in malignant disorders, provoking tumors to become resistant. Drug resistance is the major cause of cancer hormone or chemotherapy failure.

The invention also encompasses methods of treating viral infections by administering compounds of the invention, wherein the viral infection is caused by a Flaviviridae, or Herpesviridae (PMID: 31861082) virus. An embodiment of the invention encompasses methods of treating a viral infection by administering compounds of the invention, wherein the infection is caused by SARS-CoV, MERS-CoV, COVID-19 or SARS-CoV-2. Another embodiment of the invention encompasses methods of treating a viral infection wherein the infection is caused by COVID-19. Another embodiment of the invention encompasses methods of treating herpesvirus viral infections or latent infections wherein the viral infection is caused by HSV, VZV, CMV, EBV, or PRV. Another embodiment of the invention encompasses methods of treating viral infections in which the infection is caused by flaviviruses. Another embodiment of the invention encompasses methods wherein the flavivirus infection is caused by Dengue, West Nile, Hepatitis C, or Zika. Another embodiment of the invention encompasses methods of treating viral infections wherein the viral infection is caused by an influenza virus. In another embodiment, the influenza virus is influenza A. In another embodiment, the influenza virus is influenza B. In another embodiment, the influenza virus is influenza D. In another embodiment, the influenza virus is influenza C.

An embodiment of the invention encompasses methods of treating viral infections by administering compounds of the invention in which the infection is caused by a coronavirus. Another embodiment of the invention encompasses, methods of treating a viral infection by administering compounds of the invention wherein the viral infection is caused by SARS-CoV, MERS-CoV, or SARS-CoV-2. A preferred embodiment of the invention encompasses methods of treating a subject with SARS-CoV-2 infection by administering compounds of the invention. A further embodiment of the invention encompasses methods of treating a subject with SARS-CoV-2 infection at high risk for acute respiratory distress syndrome (ARDS) or severe acute respiratory syndrome (SARS). Another embodiment of the invention encompasses methods wherein treating a subject with SARS-CoV-2 infection reduces mortality. Another embodiment of the invention encompasses methods wherein treating a subject with SARS-CoV-2 infection at high risk for acute respiratory distress syndrome (ARDS) or severe acute respiratory syndrome (SARS) reduces mortality. Another embodiment of the invention encompasses methods wherein treating a subject with SARS-CoV-2 infection reduces morbidity. Another embodiment of the invention encompasses methods wherein treating a subject with SARS-CoV-2 infection at high risk for acute respiratory distress syndrome (ARDS) or severe acute respiratory syndrome (SARS) reduces morbidity. Another embodiment of the invention encompasses methods wherein treating a subject with SARS-CoV-2 infection reduces respiratory failure, days in ICU, days on mechanical ventilator, or improves WHO Ordinal Scale for Clinical Improvements. Another embodiment of the invention encompasses methods wherein treating a subject with SARS-CoV-2 infection at high risk for acute respiratory distress syndrome (ARDS) or severe acute respiratory syndrome (SARS) reduces respiratory failure, days in ICU, days on mechanical ventilator, or improves WHO Ordinal Scale for Clinical Improvements. Another embodiment of the invention encompasses methods wherein treating a subject with SARS-CoV-2 infection reduces mortality or respiratory failure in subjects >60 years of age. Another embodiment of the invention encompasses methods wherein treating a subject with SARS-CoV-2 infection at high risk for acute respiratory distress syndrome (ARDS) or severe acute respiratory syndrome (SARS) reduces mortality or respiratory failure in subjects >60 years of age. Another embodiment of the invention encompasses methods wherein treating a subject with SARS-CoV-2 infection reduces mortality or respiratory failure when dosed in combination with remdesivir and/or dexamethasone and/or molnupiravir and/or sotrovimab and/or bebtelovimab and/or tocilizumab and/or baricitinib and/or convalescent plasma and/or bamlanivimab/etesevimab and/or casirivimab/imdevimab and/or ensovibep and/or nirmatrelvir/ritonavir. Another embodiment of the invention encompasses methods wherein treating a subject with SARS-CoV-2 infection at high risk for acute respiratory distress syndrome (ARDS) or severe acute respiratory syndrome (SARS) reduces mortality or respiratory failure when dosed in combination with remdesivir and/or dexamethasone and/or molnupiravir and/or sotrovimab and/or bebtelovimab and/or tocilizumab and/or baricitinib and/or convalescent plasma and/or bamlanivimab/etesevimab and/or casirivimab/imdevimab and/or ensovibep and/or nirmatrelvir/ritonavir. As used herein, the reduction in mortality, morbidity, or respiratory failure, days in ICU, days on mechanical ventilator, and the like means the reduction is in comparison to a subject (or subject population) treated with placebo. Likewise, any improvement, such as in WHO Ordinal Scale for Clinical Improvements, means an improvement in comparison to a subject (or subject population) treated with placebo.

Yet another embodiment of the invention encompasses methods of treating a virus infection by administering compounds of the invention further comprise at least one additional therapy. An embodiment of the method of treating a virus infection further comprises a second antiviral therapy such as a neuraminidase inhibitor, remdesivir, hydroxychloroquine, azithromycin, or hemagglutinin inhibitor. An embodiment of the method of treating a virus further comprises medications that modulate the immune system or host cell factors such as dexamethasone or another corticosteroid, an IL-6 inhibitor such as tocilizumab, interferons, an IL-1 inhibitor, or a kinase inhibitor such as baricitinib. Yet another embodiment of the invention, the methods further comprise an antibody therapy such as high titer COVID-19 convalescent plasma, IVIG, a monoclonal antibody therapy such as casirivimab plus imdevimab, bamlanivimab, or bamlanivimab plus etesevimab. An embodiment of the method further comprises an additional therapy such as a remdesivir and/or dexamethasone or other corticosteroids. An embodiment of the method further comprises an additional therapy such as tocilizumab. An embodiment of the method further comprises an additional therapy such as baricitinib. An embodiment of the method further comprises an additional therapy such as high titer COVID-19 convalescent plasma. An embodiment of the method further comprises an additional therapy such as IVIG. An embodiment of the method further comprises an additional therapy such as casirivimab plus imdevimab. An embodiment of the method further comprises an additional therapy such as bamlanivimab. An embodiment of the method further comprises an additional therapy such as bamlanivimab plus etesevimab. Yet another embodiment of the methods includes a second antiviral therapy that is at least one of favipiravir, lopinavir, ritonavir, remdesivir, janus kinase inhibitors, hydroxychloroquine, azithromycin, amantadine, rimantadine, ribavirin, idoxuridine, trifluridine, vidarabine, acyclovir, ganciclovir, foscarnet, zidovudine, didanosine, peramivir, zalcitabine, stavudine, famciclovir, oseltamivir, zanamivir, or valaciclovir. Yet another embodiment of the methods includes a second therapy that is at least one of vitamins C or D, zinc, famotidine, ivermectin, or angiotensin converting enzyme inhibitor (ACEI) or angiotensin receptor binding (ARB) agent.

An embodiment of the invention encompasses methods of treating a virus infection by administering compounds of the invention, wherein the compound of the invention is administered in an amount of about 0.1 mg to about 100 mg. Another embodiment of the invention of treating virus infections by administering compounds of the invention encompasses methods wherein the compound of the invention is administered in an amount of about 1 to about 90 mg. Another embodiment of the invention of treating virus infections by administering compounds of the invention encompasses methods wherein the compound of the invention is administered in an amount of about 3 to about 30 mg.

Another embodiment of the invention of encompasses methods wherein the compound of the invention is administered in an amount of about 9 mg to about 18 mg. Another embodiment of the invention encompasses methods wherein the compound of the invention is administered in an amount of about 4 mg to about 45 mg. In yet another embodiment of the method encompasses at least one pharmaceutically acceptable excipient.

The methods of treating viral infections by administering compounds of the invention may be administered in conjunction with other antiviral therapies to treat the infection or disease associated with the viral infection, e.g., combination therapy. Suitable antiviral agents contemplated for use in combination with the methods of the invention may include nucleoside and nucleotide reverse transcriptase inhibitors (NRTIs), non-nucleoside reverse transcriptase inhibitors (NNRTIs), protease inhibitors and other antiviral drugs. Examples of suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emtricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4(1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfinavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

Other antiviral agents include, but are not limited to, neuraminidase inhibitors, hemagglutinin inhibitor, hydroxychloroquine, azithromycin, or medications that modulate the immune system or host cell factors such dexamethasone. Examples include, but are not limited to, favipiravir, lopinavir, ritonavir, remdesivir, janus kinase inhibitors, hydroxychloroquine, azithromycin, amantadine, rimantadine, ribavirin, idoxuridine, trifluridine, vidarabine, acyclovir, ganciclovir, foscarnet, zidovudine, didanosine, peramivir, zalcitabine, stavudine, famciclovir, oseltamivir, zanamivir, and valaciclovir. An embodiment of the method further comprises an additional therapy such as a remdesivir and/or dexamethasone. An embodiment of the method further comprises an additional therapy such as casirivimab plus indevimab. An embodiment of the method further comprises an additional therapy such as bamlanivimab.

The methods of treating viral infections may further comprise other therapies. For example, the methods may include a second antiviral therapy such as a neuraminidase inhibitor, remdesivir, hydroxychloroquine, azithromycin, or hemagglutinin inhibitor. Other therapies included in the methods are medications that modulate the immune system or host cell factors such as dexamethasone; corticosteroids; an IL-6 inhibitor such as tocilizumab; interferons; an IL-1 inhibitor; or a kinase inhibitor such as baricitinib. The methods may further comprise an antibody therapy such as high titer COVID-19 convalescent plasma, IVIG, a monoclonal antibody therapy such as casirivimab plus imdevimab, bamlanivimab, or bamlanivimab plus etesevimab. The methods may further comprise tocilizumab or baricitinib. The methods may further comprise an additional therapy such as high titer COVID-19 convalescent plasma; IVIG; casirivimab plus imdevimab; bamlanivimab; or bamlanivimab plus etesevimab. The methods may include a second antiviral therapy that is at least one of favipiravir, lopinavir, ritonavir, remdesivir, janus kinase inhibitors, hydroxychloroquine, azithromycin, amantadine, rimantadine, ribavirin, idoxuridine, trifluridine, vidarabine, acyclovir, ganciclovir, foscarnet, zidovudine, didanosine, peramivir, zalcitabine, stavudine, famciclovir, oseltamivir, zanamivir, or valaciclovir. The methods may include a second therapy that is at least one of vitamins C or D, zinc, famotidine, ivermectin, or angiotensin converting enzyme inhibitor (ACEI) or angiotensin receptor binding (ARB) agent.

The invention is also directed to methods of treating inflammation with the compounds and formulations described above. The compounds and formulations thereof have utility in treating inflammation by disrupting tubulin polymerization. The formulations may optionally comprise additional active ingredients, whose activity is useful for treating diseases associated with inflammation, treat adverse effect associated with the compounds or dosages of a particular formulation, and/or delay or extend the release of the ingredients.

Yet another embodiment of the invention encompasses methods of treating harmful inflammation by administering a compound of the invention wherein the inflammation results from viral infection caused by SARS-CoV, MERS-CoV, COVID-19 or SARS-CoV-2 viruses.

An embodiment of the invention encompasses methods of treating inflammation wherein the compound of the invention is administered in an amount of about 0.1 mg to about 100 mg. Another embodiment of the invention encompasses methods of treating inflammation wherein the compound of the invention is administered in an amount of about 1 to about 90 mg. Another embodiment of the invention of treating inflammation by administering compounds of the invention encompasses methods wherein the compound of the invention is administered in an amount of about 3 to about 30 mg. Another embodiment of the invention encompasses methods of treating inflammation wherein the compound of the invention is administered in an amount of about 9 mg to about 18 mg. Another embodiment of the invention encompasses methods of treating inflammation wherein the compound of the invention is administered in an amount of about 4 mg to about 45 mg. In yet another embodiment of the methods of treating inflammation encompass at least one pharmaceutically acceptable excipient.

Methods of the invention may be used to treat inflammation caused by the following diseases including, but not limited to, chronic inflammatory diseases and autoimmune diseases. Examples include virally induced inflammation, arthritis, gout, acute respiratory distress syndrome (ARDS), systemic acute respiratory syndrome (SARS), allergies, Alzheimer's disease, asthma, autoimmune diseases, cardiovascular disease, cancer, chronic obstructive pulmonary disease, coeliac disease, Crohn's disease, diabetes type I, diabetes type II, endometriosis, fatty liver disease, glomerulonephritis, hepatitis, inflammatory bowel disease, multiple sclerosis, muscular dystrophies such as Duchenne muscular dystrophy, obesity, Parkinson's disease, periodontitis, psoriasis, rheumatoid arthritis, sinusitis, tuberculosis, ulcerative colitis. a) prevention, treatment, or reversal of arthritis; b) prevention, treatment, or reversal of an arthritic condition such as Behcet's disease (autoimmune vasculitis), bursitis, calcium pyrophosphate dihydrate crystal (CPPD), deposition disease (or pseudogout), carpal tunnel syndrome, connective tissue disorders, Crohn's diseases, Ehlers-Danlos syndrome (EDS), fibromyalgia, gout, infectious arthritis, inflammatory bowel disease (IBD), juvenile arthritis, systemic lupus erythematosus (SLE), Lyme's disease, Marfan syndrome, myositis, osteoarthritis, polyarteritis nodosa, polymyalgia rheumatica, psoriasis, psoriatic arthritis, Raynaud's phenomenon, reflex sympathetic dystrophy syndrome, Reiter's syndrome, rheumatoid arthritis, scleroderma, Sjogrens' syndrome, tendonitis or ulcerative colitis; c) preventing, treatment, or reversing an autoimmune disease.

Methods of the invention may be used to treat inflammation caused by viruses including those of the superfamilies of Coronaviridae, and possibly Flaviviridae and Herpesviridae. Also, the methods of the invention may be used to treat inflammation caused by viruses including, but not limited to, RSV, KSHV, CMV, DENV, CHIKV, TBEV, VSV, ZIKV, HCV, SARS, MERS-CoV, and COVID-19. Preferably, the methods of the invention treat inflammation caused by SARS-CoV, MERS-CoV, or COVID-19. The methods of the invention may also be used to treat inflammation caused by herpes viruses such as herpes simplex virus (HSV-1, HSV-2), varicella zoster virus (VZV), cytomegalovirus (CMV), or Epstein-Barr virus (EBV).

The methods of the invention may be used to treat inflammation caused by SARS-CoV, MERS-CoV, or SARS-CoV-2, and in particular SARS-CoV-2 infection. The methods of the invention may be used to treat subjects with SARS-CoV-2 infection at high risk for acute respiratory distress syndrome (ARDS) or severe acute respiratory syndrome (SARS). The subject may have a SARS-CoV-2 infection that reduces mortality. Another embodiment of the invention encompasses methods wherein treating a subject with SARS-CoV-2 infection at high risk for acute respiratory distress syndrome (ARDS) or severe acute respiratory syndrome (SARS) reduces mortality. Another embodiment of the invention encompasses methods wherein treating a subject with SARS-CoV-2 infection reduces morbidity. Another embodiment of the invention encompasses methods wherein treating a subject with SARS-CoV-2 infection at high risk for acute respiratory distress syndrome (ARDS) or severe acute respiratory syndrome (SARS) reduces morbidity. Another embodiment of the invention encompasses methods wherein treating a subject with SARS-CoV-2 infection reduces respiratory failure, days in ICU, days on mechanical ventilator, or improves WHO Ordinal Scale for Clinical Improvements. Another embodiment of the invention encompasses methods wherein treating a subject with SARS-CoV-2 infection at high risk for acute respiratory distress syndrome (ARDS) or severe acute respiratory syndrome (SARS) reduces respiratory failure, days in ICU, days on mechanical ventilator, or improves WHO Ordinal Scale for Clinical Improvements. Another embodiment of the invention encompasses methods wherein treating a subject with SARS-CoV-2 infection reduces mortality or respiratory failure in subjects >60 years of age. Another embodiment of the invention encompasses methods wherein treating a subject with SARS-CoV-2 infection at high risk for acute respiratory distress syndrome (ARDS) or severe acute respiratory syndrome (SARS) reduces mortality or respiratory failure in subjects >60 years of age. Another embodiment of the invention encompasses methods wherein treating a subject with SARS-CoV-2 infection reduces mortality or respiratory failure when dosed in combination with remdesivir and/or dexamethasone. Another embodiment of the invention encompasses methods wherein treating a subject with SARS-CoV-2 infection at high risk for acute respiratory distress syndrome (ARDS) or severe acute respiratory syndrome (SARS) reduces mortality or respiratory failure when dosed in combination with remdesivir and/or dexamethasone.

Biological Activity

Fourteen compounds were synthesized and tested for in vitro anticancer potency against a panel of melanoma and breast cancer cell lines. The results are illustrated in Table 1, below.

TABLE 1

Cytotoxic effects of dihydroquinoxalinone-pyrimidine analogues against various human melanoma and breast cancer cell lines.

| | | $IC_{50}$ (nM) | | | | | | |
| --- | --- | --- | --- | --- | --- | --- | --- | --- |
| | | Melanoma | | | Breast | | | |
| SL | Compound ID | A375 | M14 | RPMI-7951 | MDA-MB-231 | MDA-MB-453 | MDA-MB-468 | logP |
| 9  | 5i | >1000 | >1000 | >1000 | >1000 | 692.6 ± 101.9 | 940.3 ± 299.5 | 2.23 |
| 10 | 5j | 11.9 ± 3.2 | 5.6 ± 1.2 | 14.8 ± 3.7 | 5.4 ± 0.6 | 1.4 ± 0.3 | 6.4 ± 1.3 | 1.6 |
| 11 | 5k | 14.3 ± 4.1 | 6.7 ± 2.2 | 7.0 ± 2.3 | 9.3 ± 1.6 | 4.6 ± 1.1 | 7.5 ± 1.6 | 2.46 |
| 12 | 5l | 5.5 ± 0.7 | 5.9 ± 1.5 | 6.8 ± 2.5 | 25.7 ± 6.2 | 3.7 ± 1.2 | 5.6 ± 2.2 | 2.74 |
| 13 | 5m | 1.4 ± 0.2 | 1.4 ± 0.4 | 1.5 ± 0.4 | 4.0 ± 0.8 | 0.5 ± 0.1 | 1.8 ± 0.4 | 2.96 |
| 14 | 5n | 13.4 ± 1.9 | 19.1 ± 5.3 | 14.0 ± 3.9 | 54.0 ± 9.9 | 7.3 ± 1.5 | 15.6 ± 3.8 | 2.05 |
| 15 | 5o | >1000 | >1000 | >1000 | >1000 | 256.2 ± 59.5 | >1000 | 3.16 |
| 16 | 5p | 31.8 ± 4.4 | 23.3 ± 3.0 | 27.2 ± 3.9 | 36.8 ± 4.5 | 19.3 ± 3.5 | 22.8 ± 4.6 | 1.47 |
| 17 | 5q | >1000 | >1000 | >1000 | >1000 | >1000 | >1000 | 2.76 |
| 18 | 5r | 9.0 ± 1.0 | 9.8 ± 1.7 | 8.9 ± 1.5 | 18.0 ± 2.7 | 4.3 ± 0.9 | 5.2 ± 2.2 | 2.97 |
| 19 | 5s | 15.0 ± 2.1 | 18.3 ± 2.9 | 14.4 ± 2.4 | 23.9 ± 4.1 | 12.9 ± 2.3 | 18.5 ± 4.1 | 1.96 |
| 20 | 5t | 1.1 ± 0.2 | 1.0 ± 0.1 | 0.8 ± 0.1 | 1.2 ± 0.2 | 1.0 ± 0.2 | 4.3 ± 0.7 | 1.72 |
| 21 | 5u | 5.8 ± 1.0 | 5.4 ± 0.7 | 4.8 ± 0.8 | 6.7 ± 1.2 | 4.5 ± 0.9 | 10.5 ± 1.6 | 2.51 |
| 22 | 5v | 0.7 ± 0.1 | 0.6 ± 0.1 | 0.5 ± 0.1 | 0.7 ± 0.1 | 0.43 ± 0.10 | 0.8 ± 0.1 | 2.39 |

Ten newly designed dihydroquinoxalinone analogues were highly potent, particularly 5l, 5m, 5r, 5t 5u, and 5v demonstrated promising cytotoxic activities against all tested cell lines with $IC_{50}$ values ranging from 0.4-26 nM.

Figure 3:
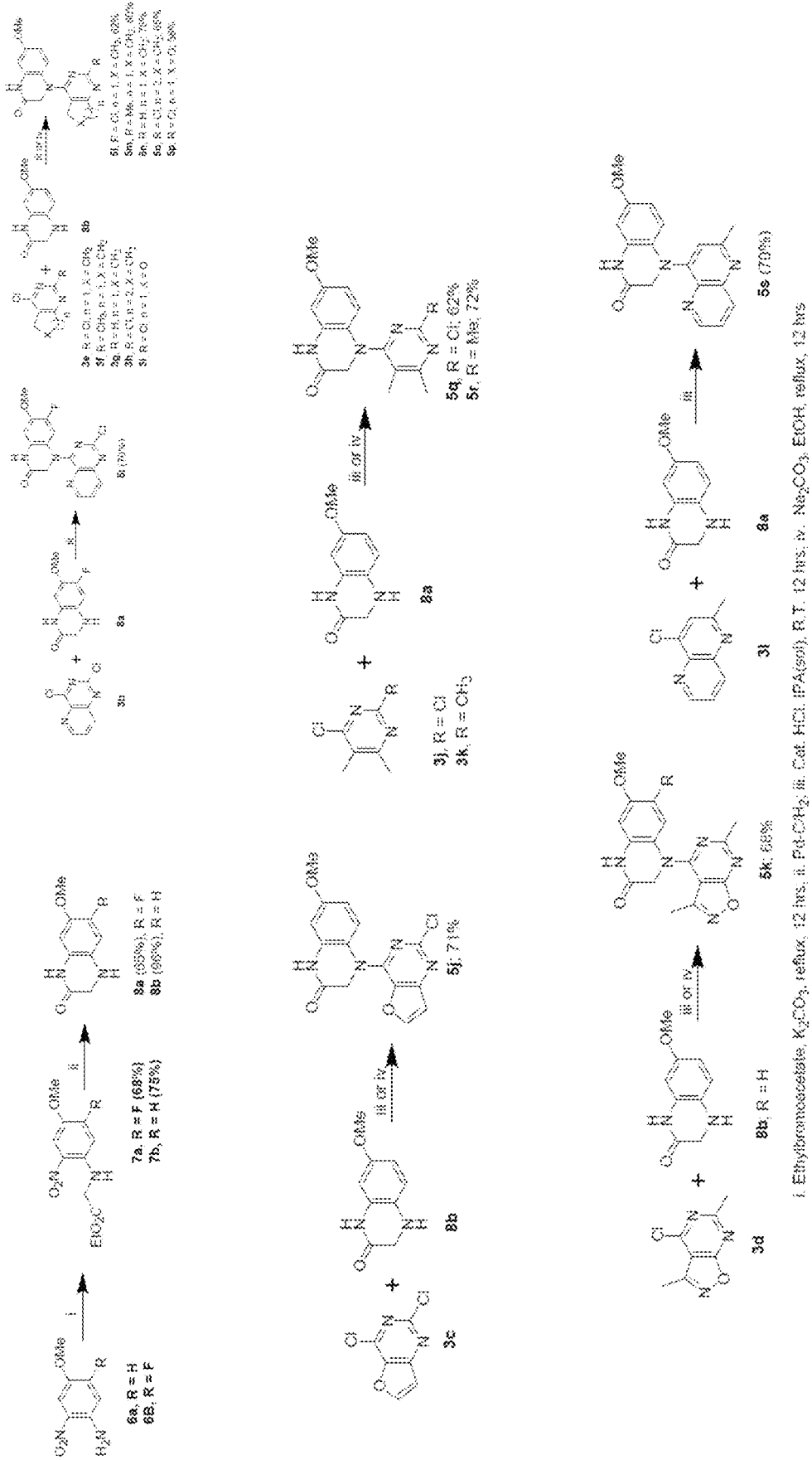
FIG. 3 illustrates the synthesis of modified A- and B-ring dihydroquinoxalinone analogues.

Compound 5p was moderately active as well with an $IC_{50}$ value in the range of 19-37 nanomolar. Two compounds were prepared having A ring opened pyrimidine analogues, 5q and 5r, as shown in FIG. 3. Compound 5r was found to be very potent with $IC_{50}$ values ranging from 4 nanomolar to 18 nanomolar (see Table 1). Compound 5q with chloro-substituted B-ring was found to be inactive. Thus, the A ring is flexible and can be modified to attain improved potency as well as water solubility. Pyridopyrimidine analogue 5s was prepared as the nitrogen atom at the 1-position of 1a and 2a was involved in water mediated hydrogen bonding with the β-C239 and β-V236 of tubulin. Compound 5s had diminished potency compared to the pyrimidine counterpart 2a with $IC_{50}$ values ranging from 13 to 24 nM. Further, the chlorine atom attached to the B-ring was located in a pocket between β-H7 and β-T7 loop. The pocket is hydrophobic in nature and has more free space that allowed for further synthetic modification. Thus, three ethylamine substituted B-ring analogues were synthesized, 5t 5u, and 5v. See FIG. 4. The ethylamine moiety is able to form hydrogen bonding with the β-H7 and β-T7 backbone and improve water solubility of the analogues for better efficacy in vivo. Compound 5v exhibited the highest potency with pM range $IC_{50}$ values from 0.4 to 0.8 nM.

Since a major clinical limitation for existing tubulin inhibitors such as taxanes is their high susceptibility to efflux pumps, compounds 5m, 5t and 5v were evaluated in additional cancer cell lines (A375/TxR, M14/LCC6MDR1, MB-231/TxR, and A549/TxR) that are highly resistant to taxanes (Table 2). Paclitaxel, colchicine, verubulin, and Compound 17ya [(2-(1H-indolyl-3-yl)-1H-imidazol-4-yl) (3,4,5-trimethxoylphenyl)] have been used as the controls for the side-by-side comparison. Unlike paclitaxel which significantly lost potency in these cell lines, 5m, 5t 5v, and verubulin retained their potency (Table 2). Compounds 5m, 5t and 5v exhibited one of the most potent cytotoxic activity against melanoma and breast cancers (Table 1). The $IC_{50}$ values of the compounds 5m, 5t and 5v ranged from 0.3 to 5 nanomolar against taxane-resistant melanoma, breast, and lung cancer cells (Table 2). It is apparent from Table 2 that the compound 5v is as potent as verubulin against taxane resistant cell lines, and conceivable that 5m and 5t are almost equipotent. Compounds 5m, 5t and 5v were unlike Compound 17ya in that they retained low nM (1.2 to 2.9 nM) activity in the Compound 17ya resistant triple negative breast cancer cells (MDA-MD-231/VxR; grown in the presence of 100 nM Compound 17ya) which is comparable to their activity in the MDA-MB-231 parental line (1.0 to 2.2 nM). In contrast, Compound 17ya activity revealed at least a 100-fold resistance (903.4 nM vs 6.1 nM).

TABLE 2

Cytotoxic effects of 5m, 5t, 5v against resistant melanoma, breast and lung cancer cell lines

| Cancer Type | Cell Lines | $IC_{50}$ ± SEM (nM) | | | | | | |
|---|---|---|---|---|---|---|---|---|
| | | 5m | 5t | 5v | Paclitaxel | Colchicine | Verubulin | Compound 17ya |
| Melanoma | A375 | 1.1 ± 0.1 | 1.5 ± 0.3 | 0.4 ± 0.04 | 0.6 ± 0.1 | 10.6 ± 1.4 | 0.7 ± 0.1 | ND |
| | A375/TxR | 1.1 ± 0.2 | 1.3 ± 0.2 | 0.3 ± 0.03 | 103.8 ± 13.2 | 23.6 ± 3.2 | 0.7 ± 0.1 | ND |
| | M14 | 1.3 ± 0.2 | 1.4 ± 0.3 | 0.3 ± 0.04 | 0.6 ± 0.1 | 8.1 ± 1.0 | 1.0 ± 0.1 | ND |
| | M14/LCC6MDR1 | 1.4 ± 0.3 | 1.4 ± 0.2 | 0.3 ± 0.03 | 306.2 ± 40.3 | >1000 | 1.2 ± 0.2 | ND |
| Breast | MDA-MB-231 | 1.7 ± 0.4 | 2.2 ± 0.7 | 1.0 ± 0.2 | 2.3 ± 0.4 | 18.9 ± 3.2 | 1.9 ± 0.4 | 6.1 ± 1.1 |
| | MDA-MB-231/TxR | 1.5 ± 0.3 | 1.1 ± 0.2 | 0.6 ± 0.1 | >50 | 15.8 ± 2.3 | 1.4 ± 0.3 | 5.6 ± 0.9 |
| | MDA-MB-231/VxR | 2.3 ± 0.4 | 2.9 ± 0.4 | 1.2 ± 0.3 | 3.4 ± 0.5 | 24.0 ± 4.4 | 2.0 ± 0.4 | 903.4 |
| Lung | A549 | 4.5 ± 0.8 | 4.4 ± 0.6 | ND | 9.8 ± 2.1 | 77.6 ± 2.1 | ND | ND |
| | A549/TxR | 2.8 ± 1.1 | 5.4 ± 1.7 | ND | >1000 | 202.9 ± 1.7 | ND | ND |
| Prostate | DU-145 | ND | ND | 1.8 ± 0.3 | ND | ND | ND | ND |
| | DU-145/TxR | ND | ND | 1.9 ± 0.3 | ND | ND | ND | ND |
| | DU-145/VxR | 3.7 ± 0.6 | 1.8 ± 0.4 | 1.0 ± 0.1 | ND | ND | ND | 127.9 ± 14.5 |

A major obstacle in drug discovery is the inadequate in vivo stability of compounds which leads to rapid loss of pharmacological activity and adverse effects due to the formation of potentially toxic metabolites. Therefore, the half-life and clearance of compound 5m in human and mouse liver microsomes was measured. Table 3 summarizes the data.

TABLE 3

In vitro metabolic stability of compound 5m in human and mouse liver microsomes. Verapamil was used in this study as an assay control and the data was presented as mean (% CV).

| Compounds | Metabolic stability in human | | Metabolic stability in rat | | Metabolic stability in mouse | |
|---|---|---|---|---|---|---|
| | $t_{1/2}$ (min) | $Cl_{int}$ (mL/min/kg) | $t_{1/2}$ (min) | $Cl_{int}$ (mL/min/kg) | $t_{1/2}$ (min) | $Cl_{int}$ (mL/min/kg) |
| 5m | 53.6 (7.9) | 13.0 (8.0) | 7.97 (0.7) | 86.9 (0.7) | 14.4 (2.9) | 48.0 (2.9) |
| Verapamil | 7.94 (1.2) | 87.3 (1.2) | 4.47 (3.7) | 155.0 (3.7) | 3.92 (3.3) | 177.0 (3.3) |

The results indicated that compound 5m had acceptable microsomal stability that was substantially higher in humans compared to rodents.

An in vivo pharmacokinetic study of compound 5m in rats after intravenous and oral administration demonstrated a low cumulative urinary excretion in unchanged form that indicated a high degree of metabolic conversion. The in vivo terminal half-life was 14.7 h long, likely due to the large volume distribution. The systemic exposure quantified as area under concentration-time curve was on a per mg dose basis nearly twice as high as what has been observed for verubulin in mice [data not shown]. Oral bioavailability of 5m was 3.2%. Table 4 summarizes the data.

TABLE 4

Pharmacokinetic parameters of compound 5m after intravenous and oral administration to male Sprague-Dawley rats.
Data is presented as mean (% CV).

| Route (dose) | Intravenous (2 mg/kg) | Oral (5 mg/kg) |
| --- | --- | --- |
| $C_{max}$ (ng/ml) | 806 (17.8) | 34.7 (105) |
| $t_{max}$ (min) | 5.00 (0) | 22.5 (38.5) |
| $AUC_{0-inf}$ (min · µg/mL) | 58.0 (25.9) | 4.62 (96.7) |
| Volume of distribution (L/kg) | 23.7 (26.4) | — |
| Clearance (mL/min/kg) | 36.9 (34.1) | — |
| $t_{1/2}$ (h) | 14.7 (30.2) | — |
| Bioavailability (%) | — | 3.2 |
| Cumulative urinary excretion (%) | 0.00134 (46.3) | — |

Evaluation of Anti-Tumor Activity of Compound 5m in Pancreatic Cancer

Pancreatic ductal adenocarcinoma (PDAC) is a lethal malignancy with high mortality. Compound 5m is one of many dihydroquinoxalinones reported herein that function as tubulin inhibitors that targets the colchicine binding site, supporting their use in PDAC and various other cancer types. The in vitro effects of Compound 5m on the PDAC cell lines in comparison with one of the first-line treatment options, paclitaxel, were surprising. This supported in vivo testing of Compound 5m was effective in luciferase labeled Mia PaCa-2 cell line, Mia PaCa-2-luc, for live monitoring of tumor progression and evaluating anti-tumor effect in subcutaneous mouse models. 5m demonstrated significant tumor growth inhibition with limited global toxicity in Mia PaCa-2-luc xenografts (FIG. 23). Similarly, PANC-1-luc xenografts treated with 5m also demonstrated potent and dose-dependent anticancer activity for Compound 5m in PDAC. The results of Example 7 showed that Compound 5m effectively inhibited cell proliferation, colony formation, and cell migration dose-dependently at low nanomolar concentrations. Immunoblotting also confirmed that Compound 5m induced cell apoptosis in a dose-dependent manner. Cell cycle arrest assay confirmed that Compound 5m arrested cells in the G2/M phase. In vivo studies indicated that Compound 5m significantly inhibited tumor growth in of PDAC tumors significantly in subcutaneous xenograft models with little to no low toxicity effect. The preclinical data demonstrated that Compound 5m inhibited proliferation, cell migration, and induced apoptosis in PDAC cells, indicating a chemotherapy agent in treating PDAC.

Inhibition of Tubulin Polymerization.

To determine that the compounds exhibited potent antiproliferative activities due to their binding to microtubules, cell-free tubulin polymerization assay with two compounds, 5m and 5t as well as the reference compounds, colchicine and paclitaxel was performed. As shown in FIG. 5, compounds 5m and 5t significantly inhibited microtubule polymerization, similar to colchicine serving as a positive control. The negative control paclitaxel showed the expected accelerated microtubule nucleation and growth, thus, causing polymerization enhancement. In agreement with the tubulin polymerization assay, compounds 5m and 5t demonstrated the soluble cytoplasmic tubulin that associated with microtubule fragmentations, resulting in heavy disruption in microtubule dynamics in interphasic A375/TxR cells (FIG. 5B). While cells in the vehicle control group, during interphase, were observed with regular microtubule network that wrapped towards the nucleus with uncondensed chromosomes. Colchicine or paclitaxel treated cells also showed the intact tubulin network with normal filamentous arrangement at the concentration of 2 nM. Compared with the mitotic cells which had normal functioning mitotic spindles in control, colchicine or paclitaxel group, 2 nM of 5m-treated cells appeared defective in the assembly of the mitotic spindle with the formation of multipolar spindles and misaligned chromosomes. Similar results were observed in mitotic cells with 2 nM of 5t treatment.

X-Ray Crystallographic Analyses of Compounds 5j, 5k, 5l, 5m, and 5t in Complex with Tubulin.

The molecular interactions of the compounds with the colchicine binding site were studied by the tubulin crystal structures in complex with 5j (PDB: 6X1C, 2.9 Å resolution), 5k (PDB: 6X1E, 2.9 Å resolution), 5l (PDB: 6X1E, 2.9 Å resolution), 5m (PDB: 6X1F, 2.7 Å resolution), and 5t (PDB: 7LZ8, 2.9 Å resolution) (FIGS. 6B-6G). These crystal structures demonstrated that the designed analogues bound to the colchicine binding site as expected.

All five designed analogues possessed binding orientations with A and B rings deep into the β-tubulin pocket and the C and D rings in the interface with α-tubulin (FIGS. 6B-6G). Most of the molecular interactions of the co-crystallized ligands with the tubulin are hydrophobic in nature, including β-A352 from the sheet S9, β-A314 and β-I316 from the sheet S8, β-I368 from the sheet S10, β-L253 and β-M257 from the helix H8, β-L246 and β-A248 from the loop T7, β-L240, β-C239 and β-V236 from the helix H7, as observed for the compounds 1a and 2a. The NH group, from the amide moiety of C-ring, acts as a hydrogen bond donor to the backbone carbonyl group α-T179 from the loop T5. The carbonyl group of amide moiety in C-ring forms an additional water mediated hydrogen bonding with the α-T179 and α-N101 as observed in 2a. Two of the compounds, 5j and 5m, also retained a water mediated H-bonding between the N-atom in B-ring as well as β-C239 and β-V236 from the helix H7. Like compounds 1a and 2a, all the co-crystallized structures present a new H-bonding between α-S178 from loop T5 and β-K350 from the sheet S9. Hence, these findings suggest that the new analogues with hydrophobic A-ring as well as amide C-ring have stronger interactions with both α- and β-tubulin monomers and, thus, bring them closer together to a tighter conformation leading to a possibility of H-bonding between residues from α- and β-monomers. The co-crystal structure of 5m binds to the colchicine binding site better than other compounds. The strongest binding of 5m to the tubulin stands by the experimental findings of low single digit nano molar $IC_{50}$ values (1-5 nM) against different regular and paclitaxel-resistant melanoma, breast as well as lung cancer cell lines. The dihydroquinoxalinone analogues with saturated hydrophobic A-rings (5l, 5m) have stronger binding than the previously published 1a as well as 2a resulting in potentially improved antitumor efficacy.

Inhibition of colony formation and migration of taxol-resistant melanoma cells. Based on the results of cytotoxic effects of dihydroquinoxalinone analogues against diverse taxol-sensitive (parental) as well as taxol-resistant cancer cell lines (Tables 1 and 2), two analogues, 5m and 5t were selected to perform the further in vitro and in vivo experiments to investigate the anticancer mechanisms against A375/TxR cells. Since cancer cells proliferate through forming colonies, repressing colony formation was regarded as a key attribute of good anticancer drugs. A clonogenic assay was carried out to investigate the potency of 5m and 5t to inhibit colony formation.

Figure 7A:
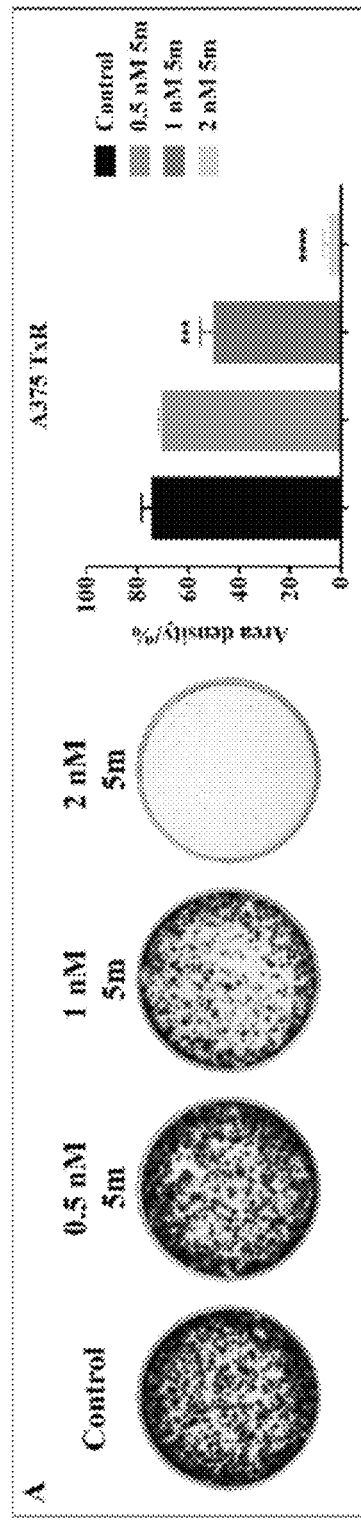
FIGS. 7A and 7B illustrate the effects of compounds 5m and 5t on clonogenic assay.
Figure 7B:
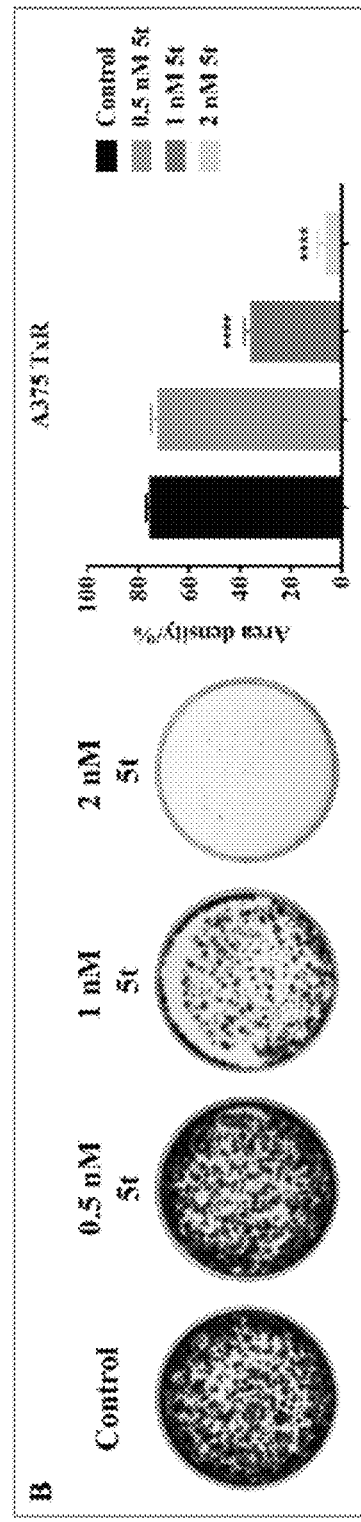

FIGS. 7A and 7B illustrate the newly synthesized compounds suppressed the colony formation of A375/TxR cells in a concentration-dependent manner. Compared with the control group, compounds 5m and 5t demonstrated the reduction of the number and size of colonies and suppressed the cell growth for a long exposure time (7 days) even at a very low concentration (1 nM). Compounds 5m and 5t completely inhibited the colony formation at high dose, i.e., 2 nM (FIG. 7A).

Figures 8A, 8B:
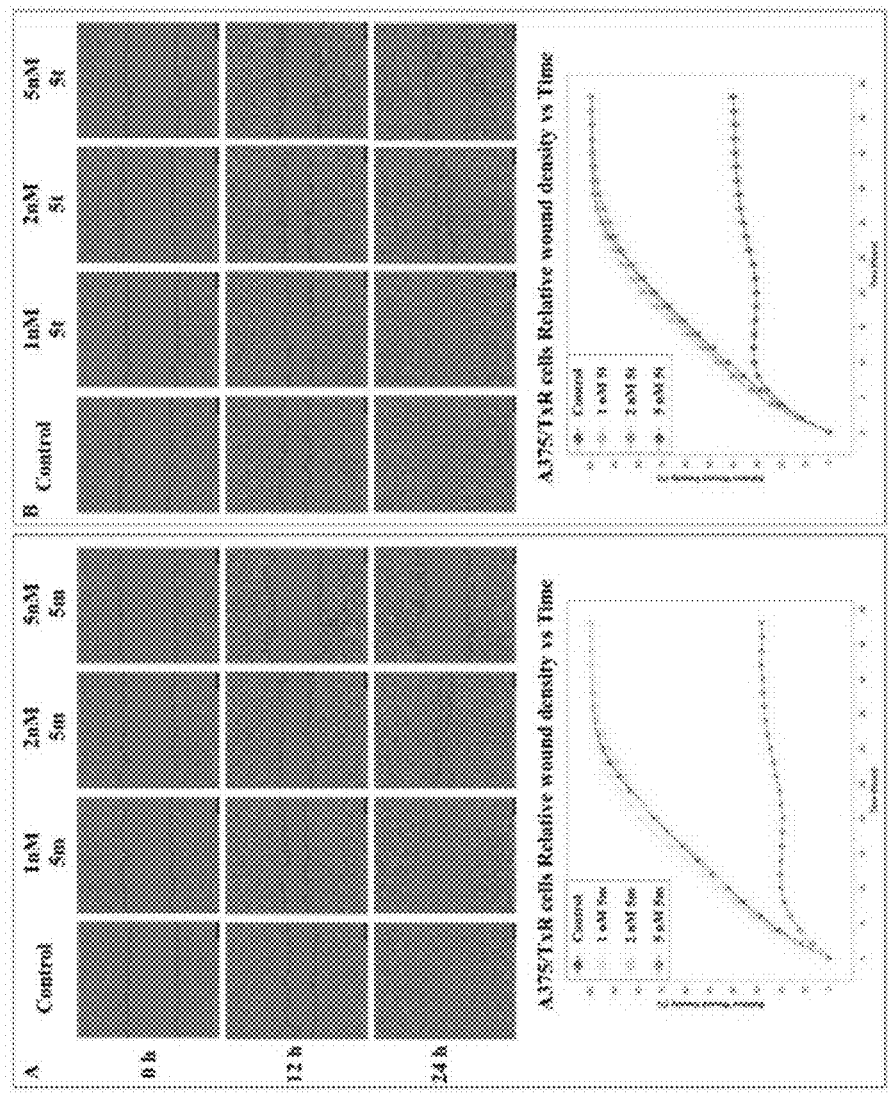
FIGS. 8A and 8B illustrate the effects of compounds 5m and 5t on A375/TxR cell migration. Scratches were created by the wound maker.

As cancer cell migration is very essential in the tumor progression and metastasis, and metastasis is the most common contributing factor leading to the high mortality rates in cancer patients, compounds 5m and 5t were tested to inhibit the migration of A375/TxR cells by using wound healing assay. FIG. 8A illustrates that after 24 h of wounding the cell monolayer DMSO-treated control cells filled the wounded area, while the wound in the 2 nM or 5 nM 5m treated cells healed slowed than that in the control group. The 5 nM of 5m markedly inhibited the migration of A375/TxR cells even after incubation for 12 h. FIG. 8B illustrates that 5t treatment had strong capacity to suppress the A375/TxR cell migration, and its potency was equivalent to 5m. Collectively, the results indicated that 5m and 5t were potent to inhibit the colony formation and migration of cancer cells.

Figure 9A:
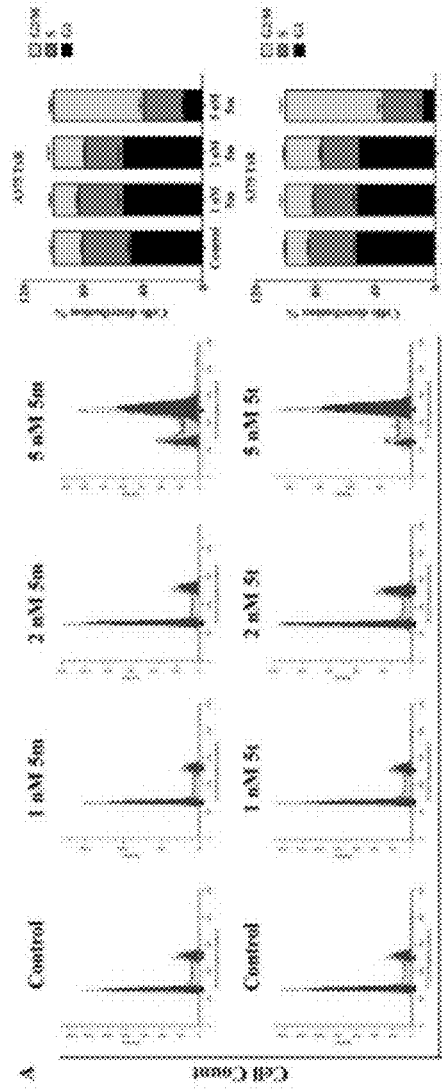
FIGS. 9A and 9B illustrate compounds 5m and 5t induced G2/M phase cell cycle arrest and cell apoptosis in A375/TxR cells.

Compounds 5m and 5t treatment caused G2/M cell cycle arrest and cell apoptosis of A375/TxR cells. Considering the pivotal role of the inhibition of microtubule polymerization in disrupting cell cycle progression and the mitotic spindle defects observed in 5m and 5t-treated A375/TxR cells as illustrated in FIG. 5B, a flow cytometry-based cell cycle analysis was performed to evaluate the effects of 5m and 5t on cell mitosis. A375/TxR cells were treated with compound 5m or 5t at different concentrations (1 nM, 2 nM and 5 nM) for 24 h without serum starvation. FIG. 9A illustrates in comparison with a normal cell cycle distribution (G1: 48%; S: 33%; G2/M: 19%) in the control cells, 5m or 5t treatment induced the significant cell cycle arrest at the phase of G2/M concentration-dependently. At the concentration of 2 nM, 5m and 5t arrested the A375/TxR cells in G2/M phase with the percentage of 60% and 64%, respectively. The results demonstrated that 5m and 5t could potently induce cell cycle arrest at G2/M phase against A375/TxR cells and affect the cell mitosis even without serum starvation.

Figure 9B:
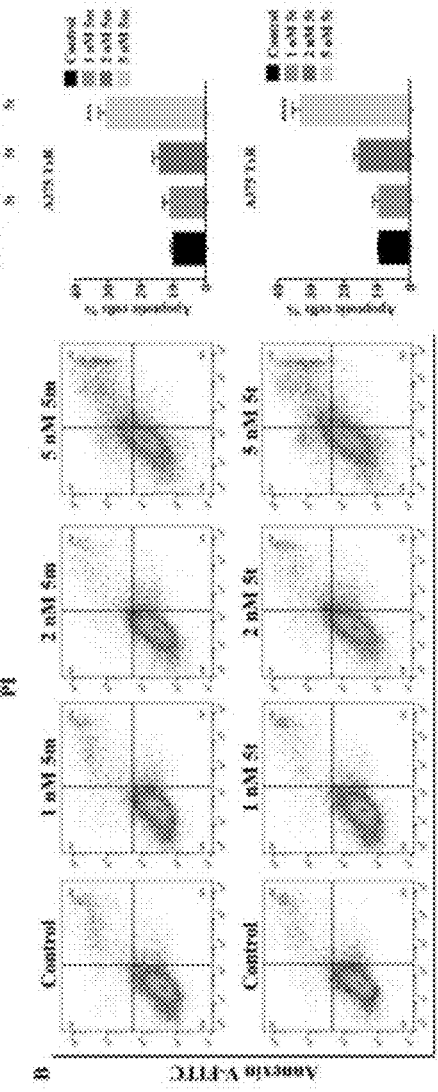

The cell cycle distribution was analyzed using ModFit LT™ software, and a significant apoptosis peak in subG1 region (we gated this cell population out to quantify the percentage of cells in G2/M phase correctively in FIG. 9A) after 24 h of treatment with 5m or 5t was observed. The Annexin V-FITC/PI staining assay verified the effects of 5m and 5t on cell apoptosis induction in A375/TxR cells using the same treatment as in cell cycle analysis. The total percentage of apoptotic cells was namely the sum of the early and late apoptotic cells versus the total number of cells. From FIG. 9B it can be observed that the percentage of apoptotic cells after 24 h treatment was only 9% in the control group, while the apoptotic cells increased to 30% and 33%, individually, after the treatment with 2 nM of 5m and 5t Additionally, compounds 5m and 5t induced the cell apoptosis of A375/TxR in a concentration-dependent manner. Taken together, compounds 5m and 5t significantly caused the apoptosis of tumor cells, which were consistent with their activities in antiproliferation and cell cycle arrest.

In Vivo Experiments with Compounds 5m and 5t against A375/TxR Xenograft Models. Compounds 5m and 5t were tested for treating tumor in A375/TxR xenograft models to determine the potential of the dihydroquinoxalinone pyrimidine analogues for treating cancer treatment in vivo. A375/TxR melanoma cells were developed to become resistance against paclitaxel therapy. This tumor model is useful to study the therapeutic benefits of newer agents over the existing therapy where acquired drug resistance is a major problem. Treatment with compound 5m inhibited the A375/TxR melanoma tumor growth in a dose-dependent manner (FIG. 10A). At a dose of 4 mg/kg, 5m significantly suppressed the tumor growth throughout the study period (p=0.0452). Treatment with 2 mg/kg 5m also resulted in the tumor reduction of 70.45% compared with the control compared with that of 4 mg/kg (88.18% vs. control). Paclitaxel therapy was ineffective and showed the similar tumor growth trend with vehicle-treated group, suggesting the drug resistance. Individual mouse body weight was monitored during the study. The results showed consistent body weight gain without any obvious adverse reactions caused by the test compound (FIG. 10B). At the study endpoint, the tumors were collected and weighed. The tumor weight in mice treated with 2 mg/kg and 4 mg/kg 5m were decreased 76.7% and 91.8%, respectively, in comparison with that in vehicle group (FIGS. 10C and 10D). Comparatively higher dose of paclitaxel (10 mg/kg) showed no benefits in tumor weight reduction. The in vivo antitumor efficacy of compound 5t was assessed in the same A375/TxR melanoma model, where paclitaxel treatment was used as positive control. Since the $IC_{50}$ of 5t (1.3 nM) is slightly higher than 5m (1.1 nM) in A375/TxR cells, the dose of 5t was increased during treatment in mice-bearing A375/TxR tumors to 2.5 mg/kg and 5 mg/kg. Both 2.5 mg/kg and 5 mg/kg 5t treatments demonstrated superior antitumor efficacies in contrast to the control and paclitaxel treatment groups (FIG. 11A). Compared to the vehicle-treated group, treatment with 2.5 mg/kg and 5 mg/kg 5t decreased the final A375/TxR tumor volume in mice as a ratio of 64.63% and 78.38% (p=0.0374), respectively. There was no marked difference in body weight between different treatment groups compared to control (FIG. 11B). Furthermore, compound 5t was dose-dependently reduced the tumor weight of mice (67.38% of decrease in 2.5 mg/kg and 78.65% decrease in 5 mg/kg treatment group versus vehicle group), and the results were significant (p<0.0001) (FIG. 11C). The picture of all tumors in this study further confirmed the potency of t in vivo (FIG. 11D). Taken together, compound 5t demonstrated enhanced antitumor efficacy against paclitaxel-resistant melanoma model without clear side effects.

Figure 12:
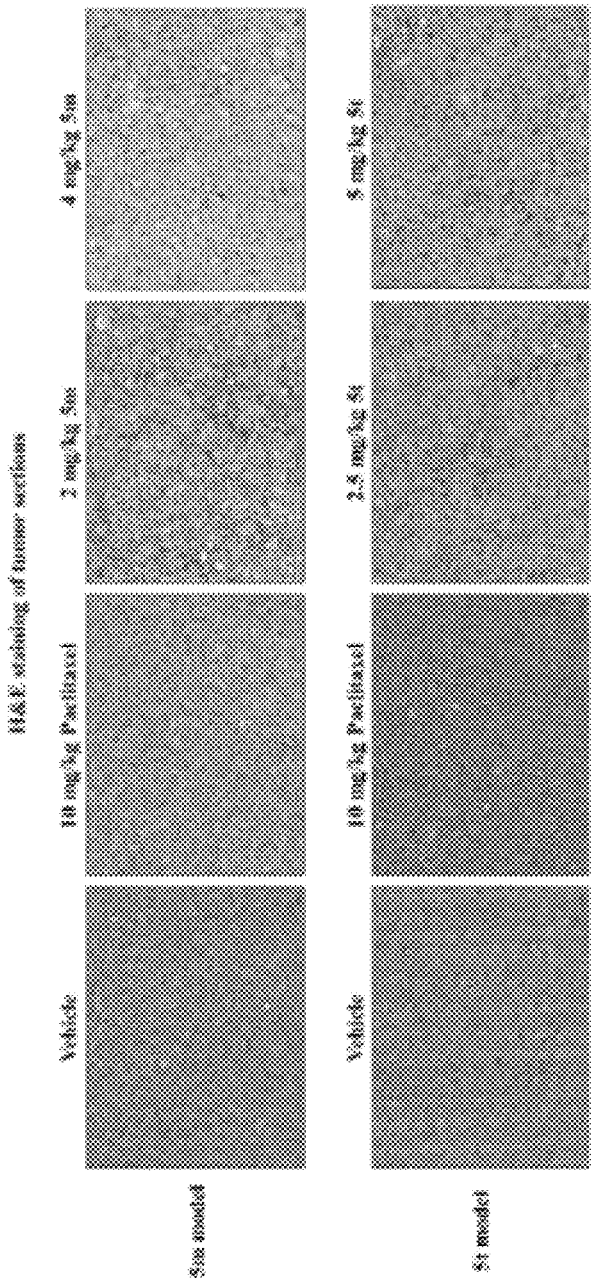
FIG. 12 illustrates the necrosis in A375/TxR tumors caused by 5m or 5t treatment. The tumors were harvested, fixed, embedded, sectioned and stained with hematoxylin and eosinophillin (H&E), slides from 5m xenograft model (5m model, top panel) and 5t xenograft model (bottom panel) were scanned by a Panoramic FLASH III system and representative images were captured using CaseViewer.

Compounds 5m and 5t treatment induced tumor necrosis in vivo. Due to the strong effects of compounds 5m and 5t in cell apoptosis induction observed in vitro, the disruptive effects of 5m and 5t in vivo using tumors in A375/TxR xenograft models was studied as exhibited in FIGS. 10 and 11. After measurement and imaging, tumors were fixed in 10% buffered formalin, embedded in paraffin and sectioned for H&E staining. As displayed in FIG. 12, in the vehicle-treated group the tumor cells exhibited a normal shape with a round and intact nucleus, and the tumor cells arranged tightly and constantly. Paclitaxel-treated tumor cells showed similar cell morphology and distribution. In contrast, after 5m or 5t treatment, tumor cells arranged loosely and unevenly, and extensive necrotic area with several necrotic cells could be observed clearly in tumors, and the tumor necrosis area increased in a dose-dependent manner. These results confirmed the potent antitumor ability of 5m and 5t.

Compounds 5m and 5t treatments inhibited spontaneous lung and liver metastasis. Malignant melanoma is a dangerous disease with aggressive potential for metastasis, a process that tumor cells spread from a primary site to visceral organs. One major step of metastasis is the developments of tumor microenvironments in visceral organs that are suitable for the survival and growth of tumor cells. Many studies reported that a spontaneous metastasis xenograft model was widely used to study this critical step of metastasis, such as the occurrence of pulmonary or brain metastasis caused by melanoma. Compounds 5m and 5t were studied for inhibiting spontaneous melanoma metastasis in vivo, using the lung and liver tissues of A375/TxR subcutaneous xenograft models (see above) in which spontaneous lung metastases would occur. First, H&E staining of lung tissues of 5m xenograft model was performed.

Figures 13A, 13B, 13C, 13D:
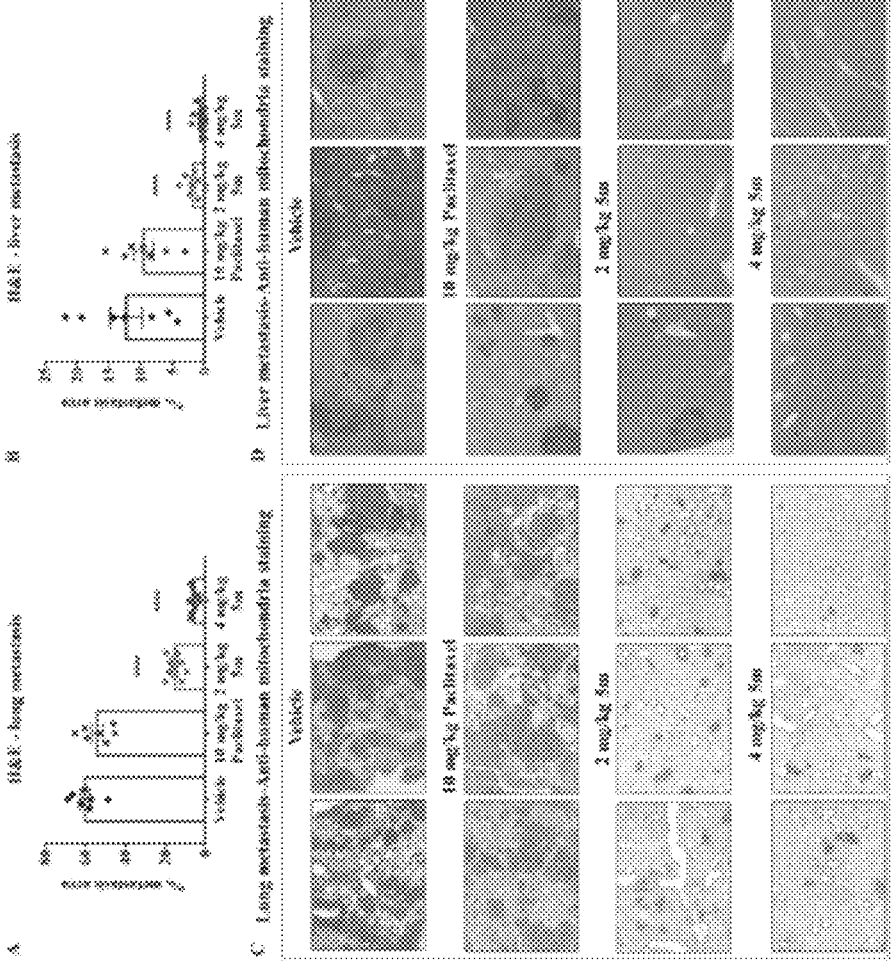
FIGS. 13A-D illustrate the anti-lung and liver spontaneous metastases effect by compound 5m in a A375/TxR subcutaneous xenograft model. After 21 days of treatment, the mice bearing A375/TxR tumors described in FIGS. 10A-D were sacrificed, and the lung and liver tissues were harvested, fixed and stained with H&E or anti-human mitochondria antibody.
Figure 15A:
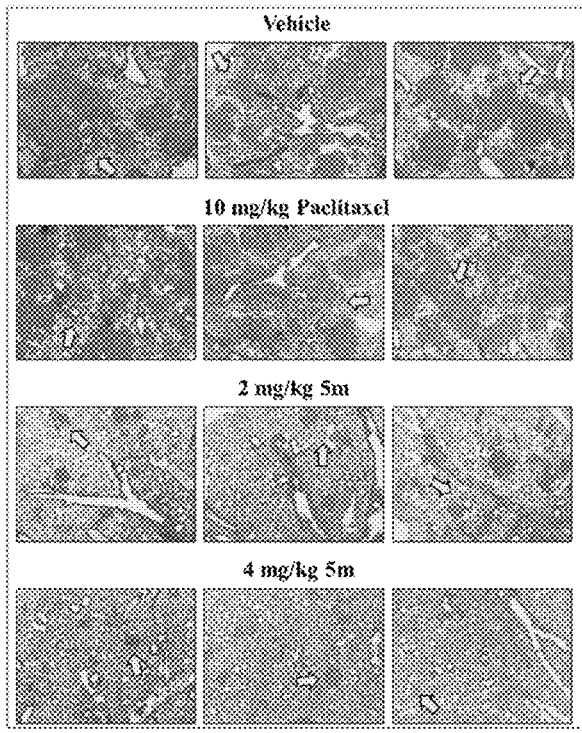
FIGS. 15A and 15B illustrate the histopathological evaluation of tumor nodules in lung and liver tissues of 5m subcutaneous xenograft model.
Figure 15B:
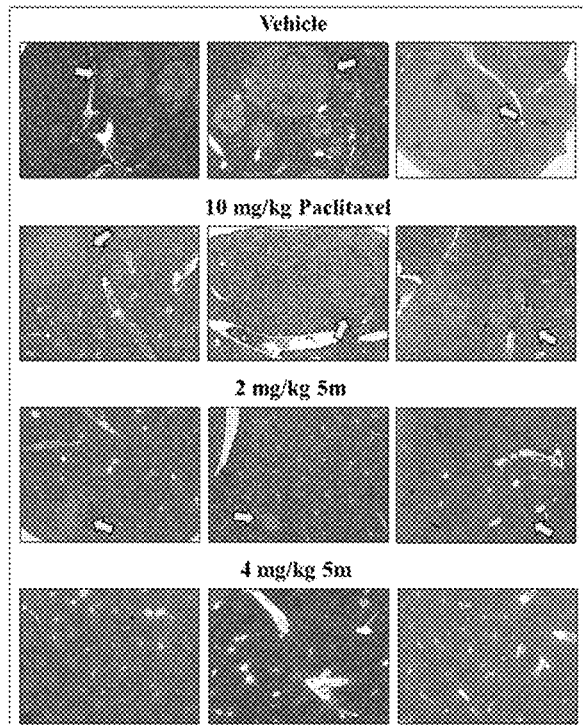
Figure 16:
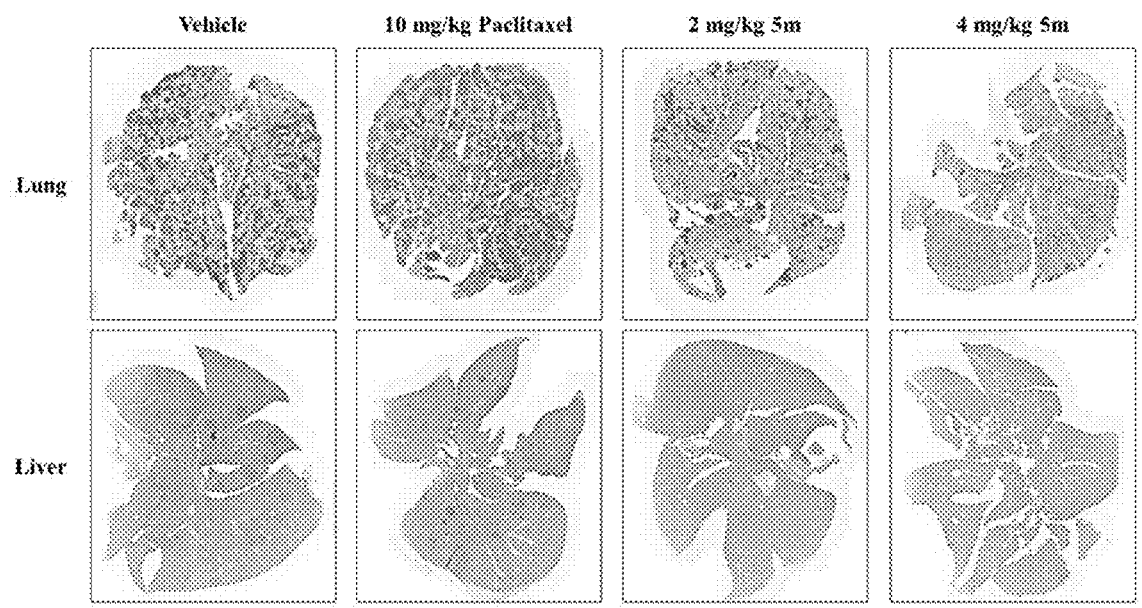
FIG. 16 illustrates that compound 5m exhibited potent anti-metastasis effects in anti-human mitochondria IHC staining with representative images of whole lungs and livers treated with vehicle, 10 mg/kg paclitaxel, 2 mg/kg 5m and 4 mg/kg 5m for 21 days after staining with anti-human mitochondria antibody. The brown staining decreased in 5m-treated lungs as compared to that in vehicle or paclitaxel group and the livers in 5m-treated groups were clearer than that in vehicle or paclitaxel groups.
Figure 17A:
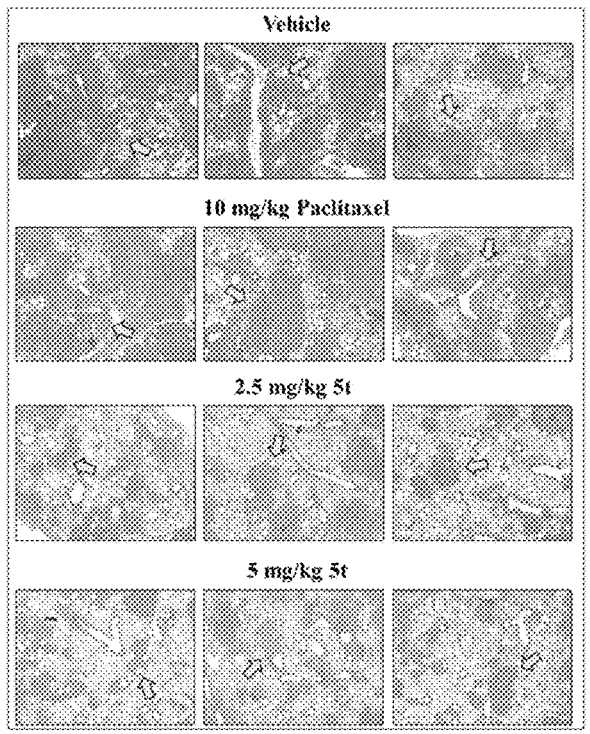
FIG. 17A and FIG. 17B illustrate the histopathological evaluation of melanoma metastasis of tissues in 5t subcutaneous xenograft model.
Figure 17B:
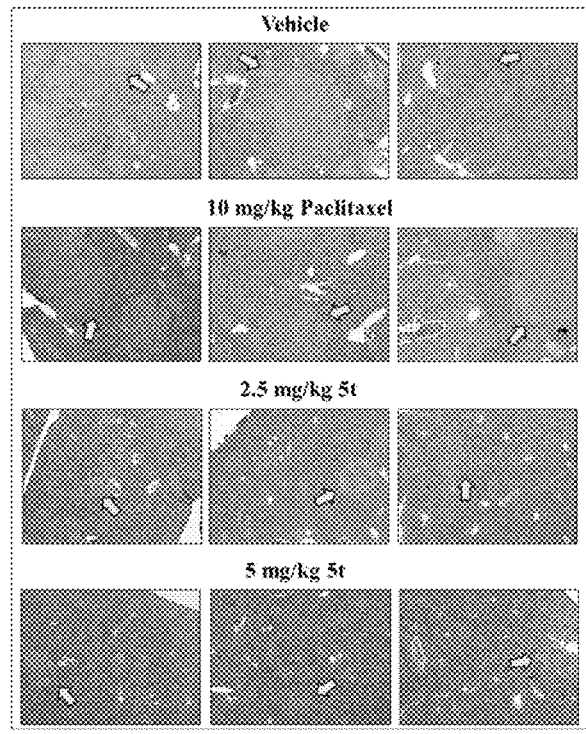
Figure 18:
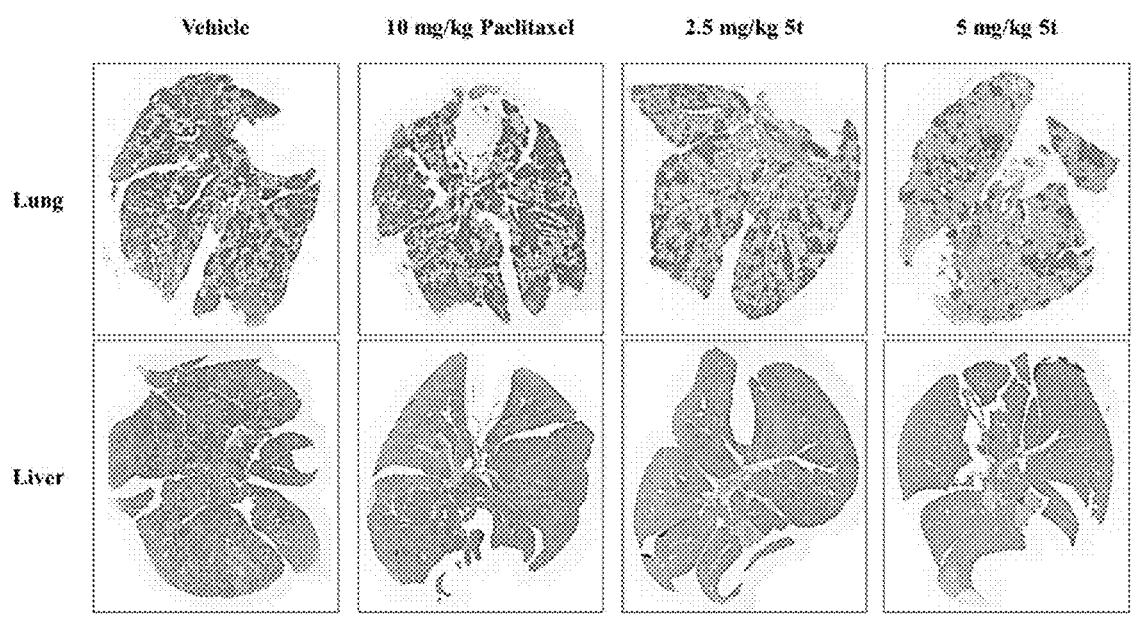
FIG. 18 illustrates that compound 5t treatment reduced melanoma metastasis in anti-human mitochondria IHC staining.

FIG. 15A illustrates multiple macrometastases (yellow arrows) as observed in the control group, indicating severe melanoma lung metastasis. While 5m-treated group displayed limited number of metastases with smaller size, and 5m treatment suppressed the lung metastasis dose-dependently. Paclitaxel treatment group was used as the positive control, it had no effect on the lung spontaneous metastasis compared to the vehicle treatment. FIG. 13A graphically illustrates the quantitative analysis of tumor burden in the lungs further confirmed the inhibiting effect of 5m on the migration of metastatic tumor cells. Since the liver is another major organ for tumor cells to seed on and grow, the H&E staining of liver tissues was performed. The reduction of metastases on the hepatic surface in the 5m treatment group confirmed the efficacy of 5m in repressing the spontaneous migration of melanoma as illustrated in FIG. 15B and FIG. 13B. The livers of 4 mg/kg 5m-treated mice were all clean, demonstrating the strong inhibiting effect of 5m on liver metastasis. Significant inhibition of tumor migration by 5m treatment was further confirmed by the reduced density (brown-stained tissues) of anti-human mitochondria immunostains in lung or liver sections, which were consistent with the results obtained through H&E staining (FIGS. 13C, 13D, and FIG. 16). Given the promising data acquired from 5m xenograft model, the H&E staining for the lung and liver tissues in 5t xenograft model were performed. In accordance with the final tumor weight, relative to the control or paclitaxel group from 5m xenograft model, the number of lung and liver metastases increased in the control or paclitaxel group from 5t xenograft model, validating the tumor progression difference between two xenograft models as illustrated in FIG. 17 and FIGS. 14A-B. H&E staining results exhibited the strong effect of 5t treatment on suppression of lung and liver metastasis following a dose-dependent manner. Moreover, the anti-human mitochondria IHC staining also showed the metastases in 5t-treated mice were sparse and smaller, and when the dose of 5t increased, the number and size of metastases decreased as shown in FIGS. 14C and 14D and FIG. 18. These data support the roles of 5m and 5t as potent tubulin-destabilizing agents in the inhibition of melanoma spontaneous metastases into the lungs and livers of mice.

Compound 5m Overcame Resistance to Taxane and/or Compound 17Ya or Castration in In Vivo Xenograft Models of Melanoma (A375/TxR), Prostate Cancer (DU-145/VxR and 22RV1), Breast Cancer (MDA-MD-231/Vx), and Ovarian Cancer (A2780/TxR).

Figure 19A:
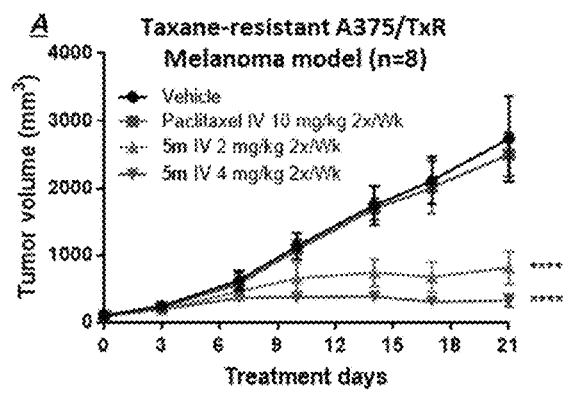
FIG. 19A-19F illustrate that compound 5m treatment is able to potently overcome taxane resistance and/or Compound 17ya resistance or castration resistance in xenografts derived from a variety of cancers including taxane resistant melanoma (A375/TxR), Compound 17ya resistant prostate cancer (DU-145/VxR), taxane- and Compound 17ya resistant breast cancer (MDA-MB-231/VxR), castration resistant prostate cancer (22RV1), and taxane resistant ovarian cancer (A2780/TxR).

To determine whether the dihydroquinoxalinone pyrimidine analogues had the potential for the cancer treatment in vivo, compound 5m was selected as a representative compound for treating tumor in A375/TxR xenograft models. A375/TxR melanoma cells were developed to become resistance against paclitaxel therapy. Thus, this tumor model might be very useful to study the therapeutic benefits of newer agents over the existing therapy where acquired drug resistance is a major problem. We found that 5m treatment strongly inhibited the A375/TxR melanoma tumor growth in a dose-dependent manner (FIG. 19A). At a dose of 4 mg/kg, 5m significantly suppressed the tumor growth throughout the study period (p=0.0452). Treatment with 2 mg/kg of 5m also resulted in the tumor reduction of 70.5% compared with the control, which was slightly lower than that of 4 mg/kg (88.2% vs. control). As expected, 10 mg/kg paclitaxel therapy was ineffective and showed the similar tumor growth trend with vehicle-treated group, suggesting the taxane drug resistance.

Figure 19B:
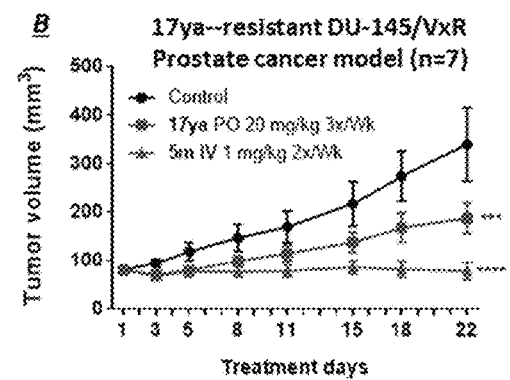

To evaluate the effect of 5m over Compound 17ya resistance (VxR) [Compound 17ya is (2-(1H-indolyl-3-yl)-1H-imidazol-4-yl)(3,4,5-trimethxoylphenyl)], Compound 17ya-resistant DU-145/VxR cells and MDA-MB-231/VxR cells were generated by incubating cells with Compound 17ya continually. When the cells were resistant to 100 nM of Compound 17ya, both cell lines were confirmed resistant to Compound 17ya and expanded for the in vivo studies. Interestingly, both DU-145/VxR cells and MDA-MB-231/VxR cells grow slow in mice bearing the tumors. We waited for 16 days until the average tumor volume reached ~80 mm$^3$ and started the treatments. During the therapy period, we saw a significant tumor inhibition effect of 5m over DU-145/VxR xenografts (FIG. 19B). The endpoint average tumor volume of 1 mg/kg IV 5m (2×/wk) group was almost the same as the starting point, which was 80 mm$^3$, while the endpoint average tumor volume of control group was around 340 mm$^3$. Surprisingly, a high dose of 20 mg/kg PO Compound 17ya (3×/wk) was still effective in this Compound 17ya resistant prostate cancer model. [Unlike 5m, compound 17ya possesses high oral bioavailability.] Its endpoint average tumor volume was between the control and 5m groups, which was about 190 mm$^3$. Nonetheless, the >20-fold higher dose of Compound 17ya had inferior efficacy to 5m.

Figure 19C:
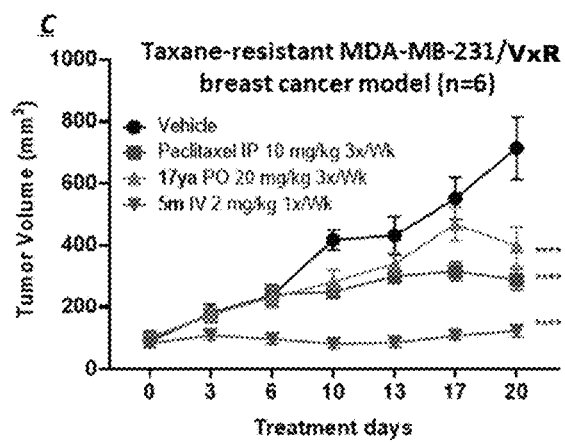

We also used an orthotopic MDA-MB-231/VxR xenograft model to determine the effect of 5m on triple negative breast cancer (TNBC) that was resistant to compound 17ya. This time, we included both 10 mg/kg paclitaxel and 20 mg/kg Compound 17ya as controls. To relieve the discomfort of mice with IV injections, we increased dose of 5m to 2 mg/kg and reduced the dose frequency from 2 times a week to 1 time a week. Similar to the DU-145/VxR xenograft model, 20 mg/kg Compound 17ya (3×/wk) was effective in suppressing the growth of MDA-MB-231/VxR xenografts, although its antitumor efficacy was weaker than either paclitaxel (10 mg/kg IV 3×/wk) or 5m (1 mg/kg IV 1×/wk) treatment, suggesting that Compound 17ya may still have antitumor activity even when Compound 17ya resistance developed (FIG. 19C). The tumor growth inhibition of 5m treatment group was still evident, as reflected by the flat tumor growth curve shown in FIG. 19C. And its antitumor effect was greater than paclitaxel or Compound 17ya even at a very low dose and with less dose frequency. Compound 17ya and 5m both work through the colchicine binding site of tubulin, and so it is unexpected that 5m would be able to overcome resistance to Compound 17ya, even at much lower doses than Compound 17ya. Further, it is expected that other compounds of this invention which possess a distinct structure and consequently distinct binding mode compared to 17ya will also be able to overcome 17ya resistant tumors.

Figure 19D:
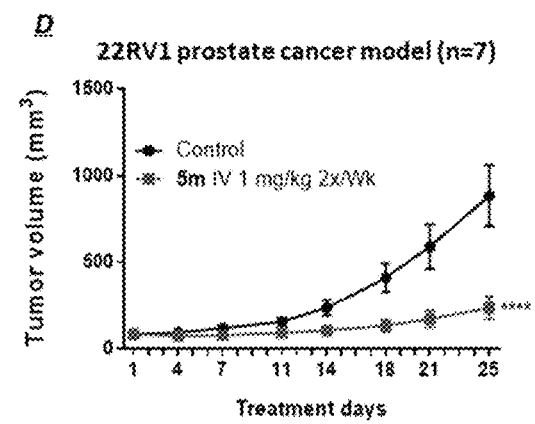

An additional animal study was carried out to determine the effect of 5m on castration-resistant prostate cancer using 22RV1 cells. We separated the mice into untreated control group and 1 mg/kg 5m treatment group based on tumor volume and mouse body weight. This is our first time to evaluate the efficacy of 5m to overcome the castration resistance of 22RV1 prostate cancer xenograft model, so we kept the original dose and dose frequency of 5m (1 mg/kg, IV, 2 times/week) once the mice were ready for the treatments. As shown in FIG. 19D, 1 mg/kg 5m was remarkable in inhibiting the growth of 22RV1 xenografts (p<0.0001), demonstrating the strong antitumor capacity of 5m on castration resistant prostate cancer models.

Figure 19E:
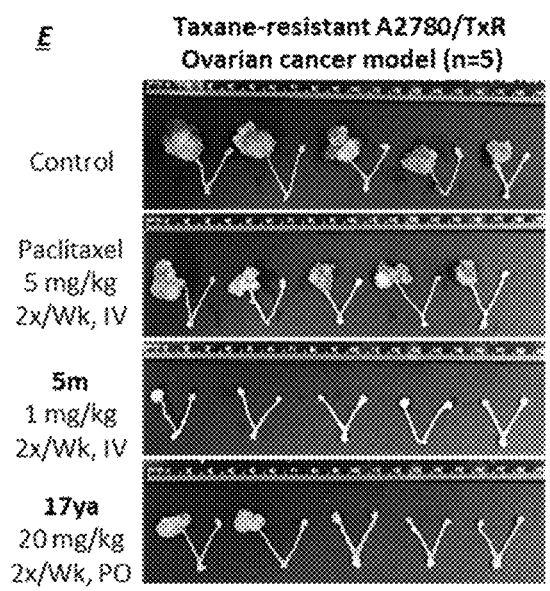
Figure 19F:
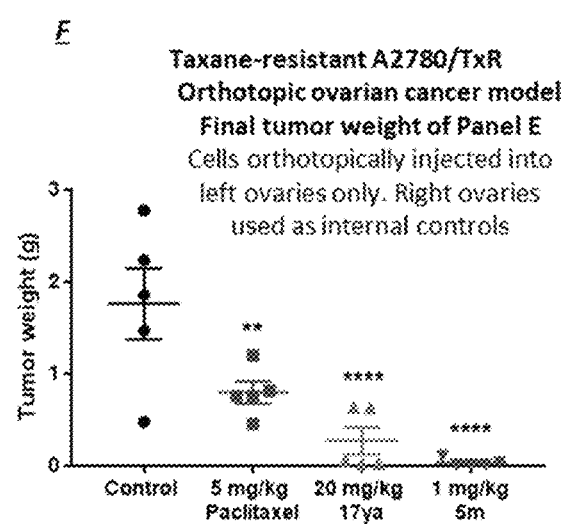

Moreover, apart from melanoma, prostate and breast cancer models, we also tested the effect of 5m on an aggressive orthotopic ovarian cancer model. And we chose paclitaxel-resistant A2780/TxR cells for this study. Similar to other models, we treated the mice for 3 weeks and harvested all the tumors at the study endpoint. As displayed in FIG. 19E, we confirmed that paclitaxel had limited effect on this aggressive A2780/TxR model even with the dose of 5 mg/kg by IV injection. While at the dose of 1 mg/kg 5m was able to suppress the tumor growth significantly with only 1 of 5 mice having visible tumor. And in 20 mg/kg Compound 17ya, there were 2 mice having visible tumors and the tumor size was bigger than that in 5m treatment group. Furthermore, the tumor weight of each group confirmed the strong antitumor efficacy of 5m on A2780/TxR ovary cancer model, and its potency was greater than paclitaxel and Compound 17ya (FIG. 19F). While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

Analogs of compounds 10 and 12a-12q were tested for their cytotoxicity activity against a panel of cancer cell lines such as melanoma (A375, M14), breast (MDA-MB-231, MDA-MB-453), pancreatic (Mia PaCa-2, PANC-1), and prostate (PC3, PC3/TxR) cancers. Half-maximal inhibitory concentration values ($IC_{50}$) for cell growth inhibition are summarized in Example 9. This study revealed that the size of the heteroatom has significant impact on the cytotoxic potency with decreasing size of the heteroatom tending to increase the potency. For example, the thioether 10 ($IC_{50}$ 3.4±0.5 nM, A375 cell lines), ether 12b ($IC_{50}$≈3.2±0.5 nM), and secondary amine 12k ($IC_{50}$ 1.2±0.2 nM) were relatively small and possessed single digit nM potencies. However, substitution of cyclic derivatives such as N-methyl piperazine 12d ($IC_{50}$≈542.8±111.0 nM), morpholine 12e ($IC_{50}$≈13.6±2.0 nM), piperidine 12f ($IC_{50}$≈436.1±76.2 nM), and pyrrolidine 12g ($IC_{50}$≈82.1±12.9 nM) have turned out to be relatively low in potency except the morpholine derivative which showed moderate to high potency. An aromatic heterocycle, i.e., imidazole 12h ($IC_{50}$≈5.7±0.9 nM) showed good potency. The tertiary amine 12i ($IC_{50}$≈22.6±4.5 nM) derivative showed moderate potency. Results obtained with compound 12k paved the way to study the pharmacological potency of secondary amines such as N-ethyl 5v ($IC_{50}$≈1.6±0.3 nM) and N-cyclopropyl 12j ($IC_{50}$≈1.4±0.3 nM) which were high potency. Of the molecules investigated, 12k was the best among the three secondary amines. Adding on an extra hydrogen bonding donor such as a —OH group in the ethanolamine moiety of 12m ($IC_{50}$≈8.6±0.2 nM) decreased potency slightly when compared with 5v (the ethylamine version) and the isothiocyanate derivative 12l ($IC_{50}$≈3.3±0.5 nM) has also shown very good potency. The unprotected phenolic OH at C2 position on the pyrimidine (2-Py) ring 12a ($IC_{50}$≈646.5±124.2 nM) drastically reduced potency as do other electron withdrawing groups, such as sulfone derivative 11 ($IC_{50}$≈84.9±17 nM). On the other hand, a free amine 12c at the same position resulted in improved potency ($IC_{50}$≈2.01±0.4 nM). Compounds 12o-12p (i.e., $OCF_3$, OBn and OH) as replacements of the OMe group were not well tolerated, leading to a decrease in potency. A general trend with the aryl substituent was that 4-OMe compounds had the highest affinity, those with 4-$OCF_3$ (12o, $IC_{50}$≈43.1±6.9), OH (12q, $IC_{50}$≈19.0±2.9) were intermediate in potency, and compounds with OBn (12p) substitution was least in potency.

EXAMPLES

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

Chemistry: General Methods. All nonaqueous reactions were performed in oven-dried glassware under an inert atmosphere of dry nitrogen. All the reagents and solvents were purchased from Aldrich (St. Louis, MO), Alfa-Aesar (Ward Hill, MA), Combi-Blocks (San Diego, CA), Ark Pharm (Libertyville, IL) and used without further purification. Analytical thin-layer chromatography was performed on silica gel GHLF 10 cm×20 cm Analtech TLC Uniplates (Analtech, Newark, DE) and were visualized by fluorescence quenching under UV light. Biotage SP1 flash chromatography purification system (Charlotte, NC) (Biotage SNAP cartridge, silica, 50 g and 100 g) was used to purify the compounds. $^1$H NMR and $^{13}$C NMR spectra were recorded on a Varian Inova-500 spectrometer (500 MHz) (Agilent Technologies, Santa Clara, CA) or a Bruker Ascend 400 (400 MHz) (Billerica, MA) spectrometer. Chemical shifts are reported in ppm on the δ scale and referenced to the appropriate solvent residual peaks ($CDCl_3$, 7.26 ppm for $^1$H and 77.23 ppm for $^{13}$C; DMSO-$d_6$, 2.50 ppm for $^1$H and 39.51 ppm for $^{13}$C). Mass spectra were collected on a Bruker ESQUIRE electrospray/ion trap instrument in the positive and negative modes. High resolution mass spectrometer (HRMS) data were acquired on a Waters Xevo G2-S qTOF (Milford, MA) system equipped with an Acquity I class UPLC system. Porcine brain tubulin (catalog no. T-238P) was purchased from Cytoskeleton, Inc. The purity of all tested compounds was determined to be ≥95% by $^1$H NMR and HPLC. The HPLC method used to determine purity is as follows: Compound purity was analyzed using an Agilent 1100 HPLC system (Santa Clara, CA) with a Zorbax SB-C18 column, particle size 3.5 μm, 4.6 mm×150 mm, from Agilent. Mobile phases consist of water with 0.1% formic acid (A) and acetonitrile with 0.1% formic acid (B). A flow rate of 1 mL/min was used. The gradient elution started at 50% B. It reached 100% B from 0 to 9 min, was maintained at this from 9 to 12 min, and was then decreased to 50% B from 12 to 15 min and stopped. Compound purity was monitored with a DAD detector set at 254 nm.

Example 1: Synthesis of ethyl 2-((5-fluoro-4-methoxy-2-nitrophenyl)amino) acetate (7a) or ethyl 2-((4-methoxy-2-nitrophenyl)amino) acetate (7b) (FIG. 3)

Synthesis of ethyl 2-((5-fluoro-4-methoxy-2-nitrophenyl) amino) acetate (7a) or ethyl 2-((4-methoxy-2-nitrophenyl) amino) acetate (7b). An amount of 25 g commercially available 5-fluoro-4-methoxy-2-nitroaniline (148.7 mmol), compound 6a, or 25 g of 4-methoxy-2-nitroaniline, compound 6b, was taken in a 1000 mL three necked flask. A volume of 100 mL ethyl bromoacetate (901.8 mmol) was poured into the flask slowly under argon atmosphere. An amount of 102.7 g $K_2CO_3$ (743.5 mmol) was added to the solution. The mixture was heated to reflux over 12 h. The mixture was cooled to room temperature and diluted with EtOAc (250 mL). The organic layer was extracted with water, dried over $MgSO_4$ and evaporated to dryness giving the crude. The crude was then purified through column chromatography in 20% $Et_2O$/hexanes yielding compound 7a or 7b as red colored solid powder (20 gm, 53-55%). $^1H$ NMR (7a) ($CDCl_3$, 400 MHz) δ 8.31 (bs, 1H), 7.87 (d, 1H, J=7.19 Hz), 6.45 (d, 1H, J=7.12 Hz), 4.30 (q, 2H, J=7.28 Hz), 4.10 (m, 2H), 3.82 (s, 3H), 1.33 (t, 3H, J=7.19 Hz). $^1$HNMR (7b) ($CDCl_3$, 400 MHz) δ 8.30 (bs, 1H), 7.68 (m, 1H), 7.18 (m, 1H), 6.69 (d, 1H, J=8.27 Hz), 4.30 (q, 2H, J=7.28 Hz), 4.10 (s, 2H), 3.82 (s, 3H), 1.33 (t, 3H, J=7.19 Hz).

Example 2: Synthesis of 6-fluoro-7-methoxy-3,4-dihydroquinoxalin-2(1H)-one (8a) or 7-methoxy-3,4-dihydroquinoxalin-2(1H)-one (8b)

Synthesis of 6-fluoro-7-methoxy-3,4-dihydroquinoxalin-2(1H)-one (8a) or 7-methoxy-3,4-dihydroquinoxalin-2(1H)-one (8b): An amount of 19 g of compound 7a (69.7 mmol) or 7b (74.7 mmol) was dissolved in 150 mL of 3% $CH_2Cl_2$ in MeOH. An amount of 2 gm 10% Pd—C was added to the solution carefully. The reaction was then continued under $H_2$ atmosphere for 5 h, upon which point the reaction was concluded to be completed as per TLC. The reaction was filtered through Celite® bed and the filtrate was evaporated to dryness giving the pure compound 8a (8.88 gm, 45.3 mmol, 65%) or 8b (12.47 gm, 71.7 mmol, 96%) as light brown solid. $^1H$ NMR (8a) (DMSO-$d_6$, 400 MHz) δ 10.16 (bs, 1H), 6.60 (m, 2H), 5.8 (s, 1H), 3.63 (m, 5H). $^1H$ NMR (8b) (DMSO-$d_6$, 400 MHz) δ 10.16 (bs, 1H), 6.60 (d, 1H, J=8.0 Hz), 6.38 (m, 2H), 3.63 (s, 6H). Compound 8a and 8b were then taken for the final coupling step without further purification.

Example 3: General procedure for the preparation of dihydroquinaxolinone-pyrimidine/pyridine analogues (5i-5s) (FIG. 3)

Compounds 5i-5s were prepared by following procedure A or procedure B.

Procedure A. A solution of commercially available 2,4-dichloro pyrimidine/pyridine analogue, 3b-3l, (1 eq) was taken in 10 mL dry isopropanol followed by addition of solid head group 8a or 8b (1 eq). Catalytic amount of concentrated HCl (3-4 drops) was added to the solution and the solution was stirred under argon atmosphere for 12 h. Reaction was diluted with water and extracted with methylene chloride (3×30 mL). The organic layer was neutralized with saturated sodium bicarbonate solution and was then dried over $MgSO_4$. The organic layer was concentrated, and the resulting crude material was then purified using silica column (20%-30% EtOAc in $CH_2Cl_2$) to yield pure product as solid.

Procedure B. Commercially available pyrimidine/pyridine analogues, 3b-3l, (1 eq) was taken in 10 mL dry ethanol followed by addition of solid head group 8a or 8b (1 eq). Sodium carbonate (2 eq) was added to the solution and the solution was brought to reflux under argon atmosphere for 12 h. Reaction was diluted with water, extracted with methylene chloride (3×30 mL), and then dried over $MgSO_4$. The organic layer was concentrated, and the resulting crude was then purified using silica column (20%-30% EtOAc in $CH_2Cl_2$) to yield pure product as solid.

Synthesis of 4-(2-chloropyrido[3,2-d]pyrimidin-4-yl)-6-fluoro-7-methoxy-3,4-dihydroquinoxalin-2(1H)-one (5i) (FIG. 3): Compound 5i was prepared following procedure A of the general procedure for the preparation of 5i-5s. An amount of 200 mg of 3b (1 mmol) was added in a solution of 216 mg of compound 8a (1.1 mmol) in 20 mL of anhydrous isopropanol in followed by addition of catalytic amount of HCl (3-4 drops). Crude was then purified through flash silica (30% EtOAc/$CH_2Cl_2$) yielding the pure product as light yellow solid (252 mg, 0.7 mmol, 70%). $^1H$ NMR (400 MHz, DMSO-$d_6$) δ 10.72 (s, 1H), 8.81 (d, J=3.2 Hz, 1H), 8.21 (d, J=8.3 Hz, 1H), 7.90 (dd, J=8.6, 4.2 Hz, 1H), 7.34 (d, J=12.6 Hz, 1H), 6.77 (d, J=8.3 Hz, 1H), 5.03 (s, 2H), 3.85 (s, 3H). $^{13}C$ NMR (101 MHz, DMSO) δ 167.13, 160.52, 155.64, 149.36, 149.02, 145.80, 145.68, 145.30, 135.77, 132.86, 129.42, 128.59, 120.97, 112.44, 112.21, 56.52, 51.84. HRMS [$C_{16}H_{12}ClFN_5O_2^+$] calcd 360.0664, found 360.0650. HPLC purity 96.20% ($t_R$=2.60 min).

Synthesis of 4-(2-chlorofuro[3,2-d]pyrimidin-4-yl)-7-methoxy-3,4-dihydroquinoxalin-2(1H)-one (5j) (FIG. 3): Compound 5j was prepared following procedure A of the general procedure for the preparation of 5i-5s. An amount of 188 mg of 3c (1 mmol) was added in a solution of 196 mg of compound 8b (1.1 mmol) in 20 mL of anhydrous isopropanol in followed by addition of catalytic amount of HCl (3-4 drops). Crude was then purified through flash silica (30% EtOAc/$CH_2Cl_2$) yielding the pure product as light yellow solid (235 mg, 0.71 mmol, 71%). $^1H$ NMR (400 MHz, DMSO-$d_6$) δ 10.75 (s, 1H), 8.30 (d, J=2.0 Hz, 1H), 7.34 (d, J=8.8 Hz, 1H), 7.06 (d, J=2.0 Hz, 1H), 6.72-6.49 (m, 2H), 4.67 (s, 2H), 3.77 (s, 3H). $^{13}C$ NMR (101 MHz, DMSO) δ 167.28, 157.98, 155.11, 153.16, 152.50, 146.50, 133.85, 133.26, 124.46, 119.66, 107.81, 107.52, 101.89, 55.84, 31.17. HRMS [$C_{15}H_{12}ClN_4O_3^+$] calcd 331.0598, found 331.0584. HPLC purity 96.27% ($t_R$=2.53 min).

Synthesis of 4-(3,6-dimethylisoxazolo[5,4-d]pyrimidin-4-yl)-7-methoxy-3,4-dihydroquinoxalin-2(1H)-one (5k) ((FIG. 3; R is H): Compound 5k was prepared following procedure B of the general procedure for the preparation of 5i-5s. An amount of 184 mg of 3d (1 mmol) was added in a solution of 196 mg of compound 8b (1.1 mmol) in 20 mL of anhydrous EtOH followed by addition of $K_2CO_3$ (276 mg, 2 mmol). Crude purified through flash silica (30% EtOAc/$CH_2Cl_2$) yielding the pure product as white solid (221 mg, 0.68 mmol, 68%). $^1H$ NMR (400 MHz, DMSO-$d_6$) δ 10.79 (s, 1H), 7.21 (d, J=8.8 Hz, 1H), 6.80-6.44 (m, 2H), 4.51 (s, 2H), 3.75 (s, 3H), 2.60 (s, 3H), 1.65 (s, 3H). $^{13}C$ NMR (101 MHz, DMSO) δ 177.03, 168.19, 167.80, 157.86, 156.97, 154.52, 133.63, 122.77, 121.17, 108.55, 102.80, 97.97, 55.91, 50.35, 26.16, 12.69. HRMS [$C_{16}H_{16}N_5O_3^+$] calcd 326.1253, found 326.1294. HPLC purity 99.6% ($t_R$=2.37 min).

Synthesis of 4-(2-chloro-6,7-dihydro-5H-cyclopenta[d]pyrimidin-4-yl)-7-methoxy-3,4-dihydroquinoxalin-2(1H)-one (5l): Compound 5l was prepared following procedure A of the general procedure for the preparation of 5i-5s. An amount of 188 mg of 3e (1 mmol) was added in a solution of 196 mg of compound 8b (1.1 mmol) in 20 mL of anhydrous isopropanol followed by addition of catalytic amount of HCl (3-4 drops). Crude was then purified through flash silica (30% EtOAc/CH$_2$Cl$_2$) yielding the pure product as white solid (205 mg, 0.62 mmol, 62%). $^1$H NMR (400 MHz, DMSO-d$_6$) δ 10.72 (s, 1H), 6.93 (d, J=8.5 Hz, 1H), 6.60 (d, J=9.5 Hz, 2H), 4.44 (s, 2H), 3.74 (s, 3H), 2.78 (t, J=7.6 Hz, 2H), 2.18 (t, J=7.1 Hz, 2H), 1.97-1.73 (m, 2H). $^{13}$C NMR (101 MHz, DMSO) 177.90, 167.34, 157.61, 157.28, 156.94, 132.64, 122.80, 119.87, 118.46, 106.80, 101.63, 55.32, 49.25, 33.33, 30.32, 21.98. HRMS [$C_{16}H_{16}ClN_4O_2^+$] calcd 331.0962, found 331.0974. HPLC purity 99.4% ($t_R$=2.59 min).

Synthesis of 7-methoxy-4-(2-methyl-6,7-dihydro-5H-cyclopenta[d]pyrimidin-4-yl)-3,4-dihydroquinoxalin-2(1H)-one (5m): Compound 5m was prepared following procedure A of the general procedure for the preparation of 5i-5s. An amount of 220 mg of 3f (1.3 mmol) was added in a solution of 256 mg of compound 8b (1.4 mmol) in 20 mL of anhydrous isopropanol followed by addition of catalytic amount of HCl (3-4 drops). Crude was then purified through flash silica (30% EtOAc/CH$_2$Cl$_2$) yielding the pure product as reddish solid (323 mg, 1.04 mmol, 80%). $^1$H NMR (400 MHz, DMSO-d$_6$) δ 10.66 (s, 1H), 6.79 (d, J=9.2 Hz, 1H), 6.58 (s, 2H), 4.43 (s, 2H), 3.73 (s, 3H), 2.74 (t, J=7.3 Hz, 2H), 2.47 (s, 3H), 2.17 (t, J=6.8 Hz, 2H), 1.92-1.74 (m, 2H). $^{13}$C NMR (101 MHz, DMSO) δ 175.16, 167.81, 165.09, 156.33, 156.22, 132.23, 121.84, 121.07, 116.34, 106.79, 101.64, 55.27, 49.09, 33.51, 30.42, 25.30, 21.88. HRMS [$C_{17}H_{19}N_4O_2^+$] calcd 311.1508, found 331.1525. HPLC purity 99.9% ($t_R$=1.94 min).

Synthesis of 4-(6,7-dihydro-5H-cyclopenta[d]pyrimidin-4-yl)-7-methoxy-3,4-dihydroquinoxalin-2(1H)-one (5n): Compound 5n was prepared following procedure A of the general procedure for the preparation of 5i-5s. An amount of 200 mg of 3g (1.3 mmol) was added in a solution of 249 mg of compound 8b (1.4 mmol) in 20 mL of anhydrous isopropanol followed by addition of catalytic amount of HCl (3-4 drops). Crude was then purified through flash silica (30% EtOAc/CH$_2$Cl$_2$) yielding the pure product as off white solid (300 mg, 1.01 mmol, 78%). $^1$H NMR (400 MHz, DMSO-d$_6$) δ 10.68 (s, 1H), 8.59 (s, 1H), 6.95-6.71 (m, 1H), 6.66-6.35 (m, 2H), 4.44 (s, 2H), 3.74 (s, 3H), 2.80 (t, J=7.6 Hz, 2H), 2.24 (t, J=7.2 Hz, 2H), 1.94-1.69 (m, 2H). $^{13}$C NMR (101 MHz, DMSO) δ 174.69, 167.69, 156.48, 156.37, 156.35, 132.31, 121.88, 120.91, 119.69, 106.78, 101.67, 55.28, 49.21, 33.59, 30.73, 21.80. HRMS [$C_{16}H_{17}N_4O_2^+$] calcd 297.1352, found 297.1346. HPLC purity 97.9% ($t_R$=1.66 min).

Synthesis of 4-(2-chloro-5,6,7,8-tetrahydroquinazolin-4-yl)-7-methoxy-3,4-dihydroquinoxalin-2(1H)-one (5o): Compound 5o was prepared following procedure A of the general procedure for the preparation of 5i-5s. An amount of 203 mg of 3h (1 mmol) was added in a solution of 196 mg of compound 8b (1.1 mmol) in 20 mL of anhydrous isopropanol followed by addition of catalytic amount of HCl (3-4 drops). Crude was then purified through flash silica (30% EtOAc/CH$_2$Cl$_2$) yielding the pure product as white solid (224 mg, 0.65 mmol, 65%). $^1$H NMR (400 MHz, DMSO-d$_6$) δ 10.59 (s, 1H), 7.60 (d, J=9.0 Hz, 1H), 6.88-6.20 (m, 2H), 4.57 (s, 2H), 3.75 (s, 3H), 2.83 (s, 1H), 2.68 (d, J=3.7 Hz, 2H), 2.57 (s, 1H), 1.79 (dd, J=10.1, 6.9 Hz, 4H). $^{13}$C NMR (101 MHz, DMSO) δ 169.38, 167.81, 160.56, 157.03, 132.55, 125.40, 120.96, 119.07, 107.75, 101.84, 55.52, 47.76, 32.70, 24.98, 22.27, 21.92. HRMS [$C_{17}H_{18}ClN_4O_2^+$] calcd 345.1118, found 345.1133. HPLC purity 95.40% ($t_R$=3.33 min).

Synthesis of 4-(2-chloro-5,7-dihydrofuro[3,4-d]pyrimidin-4-yl)-7-methoxy-3,4-dihydroquinoxalin-2(1H)-one (5p): Compound 5p was prepared following procedure B of the general procedure for the preparation of 5i-5s. An amount of 200 mg of 3i (1.04 mmol) was added in a solution of 205 mg of compound 8b (1.15 mmol) in 20 mL of anhydrous EtOH followed by addition of Na$_2$CO$_3$ (244 mg, 2.3 mmol). Crude was then purified through flash silica (25% EtOAc/CH$_2$Cl$_2$) yielding the pure product as off white solid (201 mg, 0.6 mmol, 58%). $^1$H NMR (400 MHz, DMSO-d$_6$) δ 10.75 (s, 1H), 7.14 (d, J=8.7 Hz, 1H), 6.65 (d, J=8.7 Hz, 1H), 6.59 (s, 1H), 4.79 (s, 2H), 4.53 (s, 2H), 4.34 (s, 2H), 3.76 (s, 3H). $^{13}$C NMR (101 MHz, DMSO) δ 207.03, 173.02, 167.65, 158.36, 156.93, 134.16, 123.91, 119.19, 113.73, 107.30, 102.22, 71.68, 55.88, 49.23, 31.17. HRMS [$C_{15}H_{14}ClN_4O_3^+$] calcd 333.0754, found 333.0754. HPLC purity 99.08% ($t_R$=2.37 min).

Synthesis of 4-(2-chloro-5,6-dimethylpyrimidin-4-yl)-7-methoxy-3,4-dihydroquinoxalin-2(1H)-one (5q): Compound 5q was prepared following procedure A of the general procedure for the preparation of 5i-5s. An amount of 200 mg of 3j (1.1 mmol) was added in a solution of 221 mg of compound 8b (1.2 mmol) in 20 mL of anhydrous isopropanol followed by addition of catalytic amount of conc. HCl (3-4 drops). Crude was then purified through flash silica (30% EtOAc/CH$_2$Cl$_2$) yielding the pure product as white solid (217 mg, 0.68 mmol, 62%). $^1$H NMR (400 MHz, DMSO-d$_6$) δ 10.60 (s, 1H), 7.60 (d, J=9.0 Hz, 1H), 6.63 (d, J=8.9 Hz, 1H), 6.55 (d, J=2.4 Hz, 1H), 4.56 (s, 2H), 3.73 (s, 3H), 2.38 (s, 3H), 2.17 (s, 3H). $^{13}$C NMR (101 MHz, DMSO) δ 169.08, 167.82, 159.95, 156.95, 156.85, 132.78, 125.55, 120.85, 117.97, 107.78, 101.79, 55.75, 47.77, 23.55, 14.30. HRMS [$C_{15}H_{16}ClN_4O_2^+$] calcd 319.0962, found 319.0962. HPLC purity 95.9% ($t_R$=3.00 min).

Synthesis of 7-methoxy-4-(2,5,6-trimethylpyrimidin-4-yl)-3,4-dihydroquinoxalin-2(1H)-one (5r): Compound 5r was prepared following procedure B of the general procedure for the preparation of 5i-5s. An amount of 200 mg of 3k (1.3 mmol) was added in a solution of 250 mg of compound 8b (1.4 mmol) in 20 mL of anhydrous EtOH followed by addition of Na$_2$CO$_3$. Crude was then purified through flash silica (30% EtOAc/CH$_2$Cl$_2$) yielding the pure product as white solid (280 mg, 0.94 mmol, 72%). $^1$H NMR (400 MHz, DMSO-d$_6$) δ 10.65 (s, 1H), 6.89-6.22 (m, 3H), 4.18 (s, 2H), 3.70 (s, 3H), 2.36 (s, 3H), 1.72 (s, 3H). $^{13}$C NMR (101 MHz, DMSO) δ 167.72, 166.24, 163.53, 158.90, 155.04, 130.42, 123.65, 117.65, 115.26, 107.04, 102.07, 55.20, 50.79, 25.16, 22.08, 14.15. HRMS [$C_{16}H_{19}N_4O_2^+$] calcd 299.1508, found 299.1517. HPLC purity 99.6% ($t_R$=1.74 min).

Synthesis of 7-methoxy-4-(2-methyl-1,5-naphthyridin-4-yl)-3,4-dihydroquinoxalin-2(1H)-one (5s) (FIG. 3): Compound 5s was prepared following procedure A of the general procedure for the preparation of 5i-5s. An amount of 200 mg of 3l (1.1 mmol) was added in a solution of 219 mg of compound 8b (1.2 mmol) in 20 mL of anhydrous isopropanol followed by addition of catalytic amount of conc. HCl (3-4 drops). Crude was then purified through flash silica (30% EtOAc/CH$_2$Cl$_2$) yielding the pure product as yellowish red solid (247 mg, 0.77 mmol, 70%). $^1$H NMR (400 MHz, DMSO-$d_6$) δ 10.65 (s, 1H), 8.75 (dd, J=4.0, 1.6 Hz, 1H), 8.24 (dd, J=8.5, 1.6 Hz, 1H), 7.69 (dd, J=8.5, 4.1 Hz, 1H), 7.01 (s, 1H), 6.71 (d, J=8.8 Hz, 1H), 6.61 (s, 1H), 6.48 (dd, J=8.8, 2.8 Hz, 1H), 4.61 (s, 2H), 3.72 (s, 3H), 2.52 (s, 3H). $^{13}$C NMR (101 MHz, DMSO) δ 167.60, 160.28, 156.33, 150.47, 147.88, 144.75, 137.20, 137.12, 132.49, 125.12, 125.06, 122.13, 114.51, 108.55, 102.37, 55.73, 54.10, 25.36. HRMS [$C_{18}H_{17}N_4O_2^+$] calcd 321.1352, found 321.1353. HPLC purity 98.6% ($t_R$=1.70 min).

Figure 4:
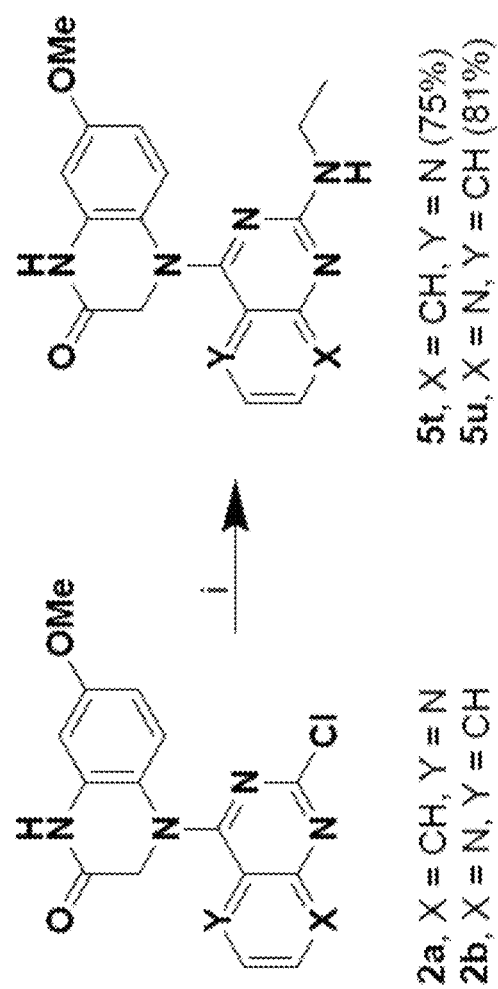
FIG. 4 illustrates the synthesis of ethylamine substituted B-ring dihydroquinoxalinone analogues 5t-5u.

Example 4: Procedure for the Preparation of 5t-5v (FIG. 4)

Compound 2a or 2b (1 eq) were dissolved in 3 ml of isopropanol in a microwave tube, to which ethyl amine (5 eq) was added. The reaction was carried out for 30 minutes under microwave condition (150 watt) at 80° C. Reaction mixture was brought to pH 7 using 10% HCl. The precipitates were filtered and dried under air to give pure product as solid. The crude was then purified using flash chromatography using 50%-60% EtOAc/$CH_2Cl_2$ to yield pure product as brownish yellow solid.

Synthesis of 4-(2-(ethylamino)pyrido[3,2-d]pyrimidin-4-yl)-7-methoxy-3,4-dihydroquinoxalin-2(1H)-one (5t): Compound 5t was prepared following the general procedure for the preparation of 5t-5u starting with 345 mg of 2a (1 mmol) and 331 mL of ethylamine (5 mmol). Crude was purified through flash silica (55% EtOAc/$CH_2Cl_2$) yielding the pure product as brownish yellow solid (263 mg, 0.75 mmol, 75%). $^1$H NMR (400 MHz, CDCl$_3$) δ 8.83 (s, 1H), 8.36 (dd, J=4.1, 1.6 Hz, 1H), 7.81 (d, J=8.3 Hz, 1H), 7.46 (dd, J=8.6, 4.1 Hz, 1H), 6.96 (d, J=8.9 Hz, 1H), 6.49 (dd, J=8.9, 2.7 Hz, 1H), 6.39 (d, J=2.7 Hz, 1H), 4.97 (s, 2H), 3.76 (s, 3H), 3.57-3.36 (m, 2H), 1.24 (t, J=7.2 Hz, 3H). $^{13}$C NMR (101 MHz, CDCl$_3$) δ 168.51, 159.98, 158.60, 157.03, 150.17, 143.07, 133.60, 130.84, 127.60, 124.24, 123.32, 108.48, 101.64, 55.58, 51.63, 36.45, 15.08. HRMS [$C_{18}H_{19}N_6O_2^+$] calcd 351.1569, found 351.1568. HPLC purity 96.74% ($t_R$=2.41 min).

Synthesis of 4-(2-(ethylamino)pyrido[2,3-d]pyrimidin-4-yl)-7-methoxy-3,4-dihydroquinoxalin-2(1H)-one (5u): Compound 5u was prepared following the general procedure for the preparation of 5t-5u starting with 345 mg of 2b (1 mmol) and 331 mL of ethylamine (5 mmol). Crude was purified through flash silica (55% EtOAc/$CH_2Cl_2$) yielding the pure product as yellowish solid (284 mg, 0.81 mmol, 81%). $^1$H NMR (400 MHz, DMSO-$d_6$) δ 10.79 (s, 1H), 8.65 (s, 1H), 7.66-7.25 (m, 2H), 6.88 (s, 1H), 6.78-6.53 (m, 2H), 6.43 (d, J=8.9 Hz, 1H), 4.38 (s, 2H), 3.72 (s, 3H), 3.40 (dt, J=13.7, 7.0 Hz, 2H), 1.18 (t, J=7.1 Hz, 3H). $^{13}$C NMR (101 MHz, DMSO) δ 168.18, 162.41, 161.01, 156.76, 156.00, 135.04, 132.00, 124.10, 121.23, 116.33, 108.09, 102.57, 55.75, 51.32, 35.88, 15.05, 0.56. HRMS [$C_{18}H_{19}N_6O_2^+$] calcd 351.1569, found 351.1572. HPLC purity 95.01% ($t_R$=2.41 min).

Synthesis of 4-(2-(ethylamino)-6,7-dihydro-5H-cyclopenta[d]pyrimidin-4-yl)-7-methoxy-3,4-dihydroquinoxalin-2(1H)-one (5v). Compound 5v was prepared following the general procedure for the preparation of 5t starting with 345 mg of 5l (1 mmol) and 331 mL of ethylamine (5 mmol). Crude was purified through flash silica (55% EtOAc/$CH_2Cl_2$) yielding the pure product as yellowish solid (284 mg, 0.81 mmol, 81%). $^1$H NMR (400 MHz, DMSO-$d_6$) δ 10.60 (s, 1H), 6.77 (d, J=8.4 Hz, 1H), 6.71 (t, J=4.9 Hz, 1H), 6.57 (d, J=9.6 Hz, 2H), 4.35 (s, 1H), 3.72 (s, 3H), 3.72 (s, 2H), 3.31-3.20 (m, 2H), 2.59 (t, J=7.4 Hz, 2H), 2.12-2.00 (m, 2H), 1.83-1.68 (m, 2H), 1.11 (t, J=7.0 Hz, 2H). HRMS [$C_{18}H_{22}N_5O_2$]+, exact mass 340.1773, obtained 340.1768.

Example 5: Biology

Cell Culture and Reagents. Human melanoma cell lines A375, RPMI-7951, human breast cancer cell lines MDA-MB-231, MDA-MB-453, MDA-MB-468 and human lung cancer cell line A549 were purchased from American Type Culture Collection (ATCC, Manassas, VA). M14 and M14 multidrug-resistant daughter line M14/LCC6MDR1 were gifts from Dr. Robert Clarke from Georgetown University. Melanoma cells and breast cancer cells were cultured in Dulbecco's modified Eagle's medium (DMEM) (Corning, Manassas, VA) supplemented with 10% fetal bovine serum (FBS, Atlanta Biologicals, Lawrenceville, GA) and 1% antibiotic/antimycotic solution (Sigma-Aldrich, St. Louis, MO). A549 cells were cultured with RPMI 1640 medium (Gibco, Carlsbad, CA) supplemented with 10% fetal bovine serum and 1% antibiotic/antimycotic mixture. Paclitaxel-resistant A375/TxR, MDA-MB-231/TxR and A549/TxR cells were developed by the sequential treatment with paclitaxel and maintained in medium with 100 nM paclitaxel at 37° C. in a humidified atmosphere with 5% $CO_2$. Taxanes were removed from the media a week before the actual experiment. Compound 17ya resistant MDA-MB-231/VxR cell line was developed by the sequential treatment with Compound 17ya and maintained in medium with 100 nM Compound 17ya in a cell culture incubator. Compound 17ya was removed from the culture media two weeks before the actual experiment. For biological studies, dihydroquinoxalinone pyrimidine analogues were prepared in DMSO (ATCC) at a stock concentration of 20 mM and stored in −20° C. in refrigerator. Prior to experiments, stocks were diluted with the proper culture medium.

Cytotoxicity Assay (e.g., Tables 1 and 2).

Depending on their growth rate, cancer cells were seeded at a concentration of 3,500-5,000 cells per well in 96-well plate. On next day, the culture medium was replaced with the fresh medium containing the test compounds at concentrations ranging from 0.1 nM to 3 μM in four replicates. After 72 h of incubation, MTS reagent (Promega, Madison, WI) was added to the each well in dark and incubated at 37° C. for 1-2 h depending on the cell type. Absorbance was recorded at 490 nm using a microplate reader (BioTek Instruments Inc., Winooski, VT). $IC_{50}$ values were calculated by GraphPad Prism software (San Diego, CA).

Microsomal Stability Assay (Table 3).

Liver microsomal incubations (1 mg microsomal protein/mL) with human (Corning Life Sciences, Oneonta, NY), rat, and mouse microsomes (Sekisui XenoTech, Kansas City, KS) were assessed for compound 5m or other compounds of the invention and verapamil (1 μg/mL), in the presence of NADPH (Acros Organics, Fair Lawn, NJ) (1 mM). At predefined times (0, 5, 10, 30, 45, and 60 min), aliquots (50 μL) were removed and the reaction was quenched by addition of 200 μL ice-cold methanol containing internal standard. Samples were briefly vortexed and centrifuged at 3,200×g for 5 min at 4° C. Supernatants were collected and analyzed by LC-MS/MS. In vitro half-life and intrinsic clearance were assessed per standard procedures. See Obach, R. S., "Cytochrome P450-catalyzed metabolism of ezlopitant alkene (CJ-12,458), a pharmacologically active metabolite of ezlopitant: enzyme kinetics and mechanism of an alkene hydration reaction," *Drug. Metab. Dispos.*, 2001, 29(7), 1057-67.

In Vivo Pharmacokinetics in Rats (Table 4).

All animal studies were performed in adherence to the NIH Principles of Laboratory Animal Care and were only initiated after prior approval by the Institutional Animal Care and Use Committee of the University of Tennessee health Science Center. Catheterized male and female Sprague-Dawley rats (225-250 g; Harlan Bioscience, Indianapolis, IN) were kept at a 12 h light/card cycle with access to food and water ad libitum. Groups of 4 rats (2 male and 2 female) received either a single intravenous (IV) dose of 2 mg/kg of compound 5m by injection via a femoral vein catheter, or a single oral dose of 5 mg/kg of compound 5m by oral gavage. The compound was formulated in PEG300 (40%) and water (60%). After drug administration, blood samples (200 µL) were collected via a jugular vein catheter at up to 10 predefined time points over 24 h. Plasma was immediately separated by centrifugation (6,000×g for 10 min at 4° C.) and stored at −70° C. until analysis. For urinary excretion, urine was cumulatively collected after intravenous administration, the volume recorded, and a specimen stored at −70° C. until analysis.

Quantification of Compound Concentrations

For quantification of compound 5m concentrations in plasma and urine samples were processed by protein precipitation with 4 volumes of methanol and analyzed by LC-MS/MS. Chromatographic separations were carried out on a Phenomenex C18, 2.6 µm, 100×4.6 mm column (Phenomenex, Torrance CA) using a Nexera XR liquid chromatograph (Shimadzu Corp., Columbia, MD). The mobile phase consisted of a) 95% water and 5% acetonitrile with 2 mM ammonium formate and 0.1% formic acid, and b) 95% acetonitrile and 5% water with 2 mM ammonium formate and 0.1% formic acid. Compound 5m and internal standard [(2-(1H-indolyl-3-yl)-1H-imidazol-4-yl)(3,4,5-trimethxoylphenyl)] methanone were eluted in a gradient at 0.5 m/min. The eluate was led directly into an API 4500 triple quadruple mass spectrometer (Applied Biosystem, Foster City, CA) equipped with a turbospray ion source, operated in the positive ion mode at a source temperature of 500° C. with a capillary voltage of 4500 kV. Nitrogen was used as the source gas, curtain gas, and collision gas. The characteristic mass transfers monitored were m/x 311.1/296.0 for compound 5m and m/z 378.4/210.1 for the internal standard. Concentrations were calculated by weighted least-square regression ($1/x^2$) using calibration standards of 5m ranging from 2.93-3000 ng/mL and quality controls at the concentration of 20, 200, and 2000 ng/mL. The obtained plasma concentration-time profiles were analyzed by standard noncompartmental pharmacokinetic analysis using the software package WinNonlin 8.0 (Cetera, Princeton, NJ).

Figure 5A:
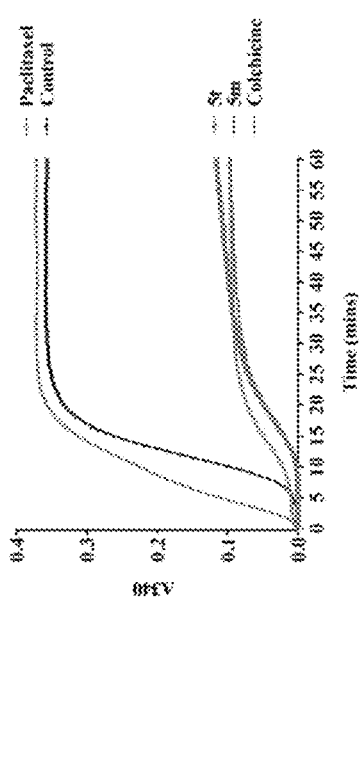
FIGS. 5A and 5B illustrate the binding patterns of compounds 5m and 5t with tubulin and their localization within the cell.
Figure 5B:
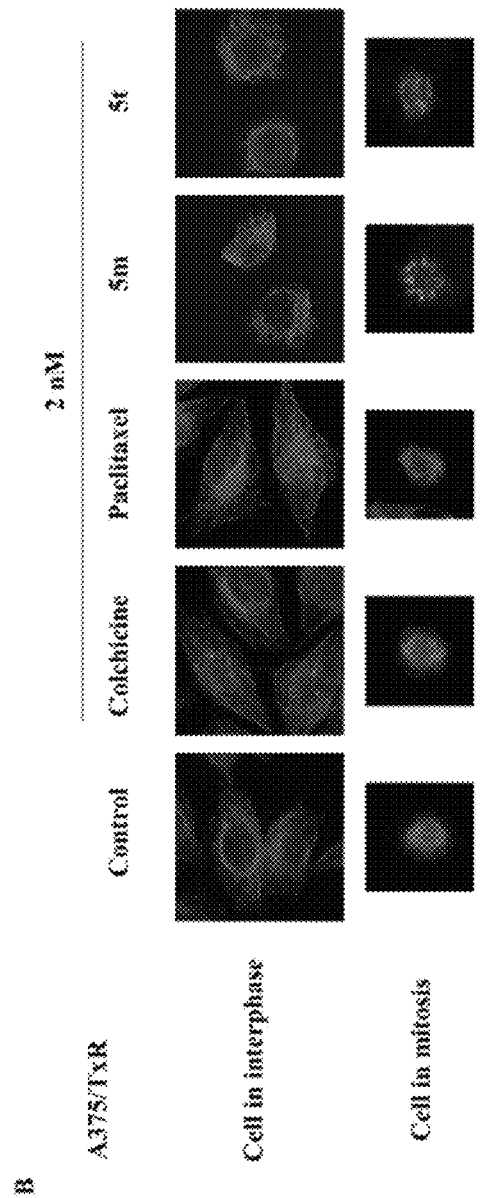

Tubulin Polymerization Assay (FIG. 5A).

Tubulin polymerization reaction was initiated by adding 100 µL of tubulin protein from bovine brain origin (3 mg/ml, Cytoskeleton, Denver, CO) into 10 µM of test compounds in general tubulin buffer (80 mM PIPES, 2.0 mM $MgCl_2$, 0.5 mM EGTA, and 1 mM GTP) according to the manufacturer protocol. The reaction kinetics were recorded in every thirty seconds for 1 h at 37° C. and a microplate reader equipped with absorbance settings at 340 nm wavelength was used for this purpose. The experiment was performed in duplicates.

Clonogenic Assay (FIG. 7).

In case of clonogenic assay, A375/TxR cells were seeded in 6-well plates at very low concentration (1000 cells/well). When each single cell had split into 4 cells in each well, cells were treated with 5m or 5t at different concentrations (0.5 nM, 1 nM and 2 nM) or media only and incubated for 7 days. Medium was replaced with fresh drug once during the treatment. Cells were then fixed with cold methanol and stained with 0.5% crystal violet. Colony area density was quantified using the Keyence Hybrid Cell Count module.

Wound Healing Assay (FIG. 8).

The scratch assay was performed with 5m or 5t treatment (1 nM, 2 nM and 5 nM) using IncuCyte S3 live cell imager. Briefly, A375/TxR cells (50000 cells/well) were seeded in 96-well ImageLock plates (Essen BioScience) and allowed to attach overnight. Then a WoundMaker™ (Essen BioScience) was used to create uniform scratches in all wells and cell debris was washed away with grow medium for three times. Growth medium or medium containing 5m or 5t was added to each well and the plates were monitored by IncuCyte every two hours for up to 2 days. The representative images and the relative wound density calculation were processed using the IncuCyte™ Scratch Wound Software Module.

Cell Cycle and Cell Apoptosis Analysis (FIG. 9).

A375/TxR cells were seeded into the 10-mm dishes ($2 \times 10^6$/well) and treated with 5m or 5t at concentrations of 1 nM, 2 nM and 5 nM for 24 h. Cells were trypsinized, washed and fixed in ice-cold 70% ethanol overnight. Next, the cells were incubated with 100 µg/ml RNase A for 1 h followed by the staining of propidium iodide. After 5 min of incubation, the samples were analyzed by Bio-Rad ZE5 instrument in the University of Tennessee Health Science Center (UTHSC) Flow Cytometry and Cell Sorting core. Data was processed by ModFit LT™ software (Verity Software House, Topsham, ME). For cell apoptosis analysis, after the same treatments as in cell cycle analysis, $10^5$ cells were collected, washed, resuspended in Annexin-V-FITC binding buffer (eBioscience, Grand Island, NY) and stained with Annexin-V-FITC (eBioscience) and propidium iodide based on the kit instructions. Then the samples were incubated for 10 mins in dark and analyzed using Bio-Rad ZE5.

Immunofluorescence Staining (FIG. 5B).

A375/TxR cells (100000 cells) were seeded into six-well plates with glass coverslips in each well and incubated for overnight. 2 nM of colchicine, paclitaxel, 5m or 5t were added into the cells and treated for 24 h. Immunofluorescence staining was performed by incubating α-tubulin antibody (Thermo Scientific, Rockford, IL) for overnight at 4° C. and subsequently Alexa Fluor 647 conjugated goat anti-mouse IgG (Molecular Probes, Eugene, OR) as secondary antibody at room temperature for 1 h. The coverslips were washed three times with PBS and mounted in a glass slide with DAPI containing Prolong Diamond Antifade mounting medium (Invitrogen, Eugene, OR). The photographs were acquired and processed with a Keyence BZ-X700 microscope (Itasca, IL).

In Vivo A375/TxR Melanoma Xenograft Model (FIGS. 10 and 11).

All animal experiments were performed according to the guidelines from the National Institute of Health (NIH) and the Institutional Animal Care and Use Committee (IACUC) at the University of Tennessee Health Science Center (UTHSC, Memphis, TN). Equivalent numbers of male and female pathogen-free Nod-Skid-Gamma (NSG) mice (n=8 mice per group) at age 6-8 weeks of age were maintained under controlled environmental conditions with 12:12 hours light-dark cycle in the animal facility. A375/TxR melanoma cells were suspended in FBS and phenol red-free medium and diluted with Matrigel solution prior to the inoculation. A total of $2 \times 10^6$ A375/TxR cells in 100 µL solution were inoculated in the right flank of each mouse using an insulin syringe. Mice were anesthetized with 2-4% isoflurane inhalation before tumor cell inoculation. The tumor growth was carefully monitored, and the tumor volume was calculated as a×b$^{2×0.5}$ using a caliper, where a and b represented the larger and smaller diameter, respectively. Vehicle or drug treatment was initiated when the tumor reached to around 100 mm$^3$. Paclitaxel was dissolved in ethanol and diluted in a 1:1:18 ratio of ethanol:Cremophor EL:PBS solution. 5m was formulated in PEG300 solution and further diluted with isotonic saline (ratio 1:4). Both paclitaxel (10 mg/kg) and 5m (2 mg/kg and 4 mg/kg) were administered into mice intravenously (IV) via a tail vein injection every two times per week (2×/Wk) in a total 3-week time period. In another separate study, the A375/TxR tumor xenograft model was also established in the NSG mice (50% male and 50% female) by following the above-mentioned protocol (n=7-8 mice per group). Compound 5t was dissolved in PEG300 solution using a water-bath sonication and further diluted with sterile saline (PEG300:saline=3:7 ratio). The tumor-bearing mice (average 90-100 mm$^3$ tumor volume) were treated with two different dosages of compound 5t by intravenous injection in a total 7 doses within 24 days. At the end of the study, mice were euthanized by an overdose with isoflurane and the tumor samples were obtained from the mice to analyze tumor size and also various histological factors.

Histological and Anti-Mitochondria IHC Staining (FIGS. 12-18).

Fixed lung, liver and tumor tissues were paraffin-embedded and cut into 4 μm-thick sections. Histological processing of specimens was carried out by dewaxing, staining with hematoxylin and eosin (H&E), rehydrating and sealing to attach to glass slides. Anti-mitochondria IHC staining to visualize metastasis was performed according to previously published protocols. See, Deng et al., "An orally Available Tubulin Inhibitor, Compound 17ya, Suppresses Triple-Negative Breast Cancer Tumor Growth and Metastasis and Bypasses Taxane Resistance," *Mol. Cancer Ther.*, 2020, 19(2), 16146-16154. Briefly, lung and liver slides were stained with anti-human mitochondria antibody (AbCAM, Cambridge, MA, Cat #ab92824) with 1:1000 dilution overnight after blocking with 10% of horse serum. The following day, the slides were incubated with secondary anti-mouse antibody, visualized with DAB agent (Sigma-Aldrich, Cat #D5637), counterstained in Gill's hematoxylin and mounted with Permount™ mounting media. Representative tissue images were captured by Keyence BZ-X700 microscope. Representative whole lung or liver images were digitally scanned by a Panoramic FLASH III system (3D Histech). Lung or liver metastatic burden of each mouse was quantified by measuring the percentage of metastasis area in 3-4 representative fields per H&E staining tissue with Keyence Hybrid Cell Count module.

In Vivo Xenograft Models of Taxane-Resistance and/or Compound 17Ya Resistance (FIGS. 19A-19C, 19E and 19F)

FIG. 19A (A375/TxR): All animal experiments were performed according to the guidelines from the National Institute of Health (NIH) and the Institutional Animal Care and Use Committee at UTHSC (Memphis, TN). Equivalent numbers of male and female pathogen-free NSG mice (n=8 mice per group) at age 6-8 weeks of age were maintained under controlled environmental conditions with 12:12 hours light-dark cycle in the animal facility. A375/TxR melanoma cells were suspended in FBS and phenol red-free medium and diluted with Matrigel solution prior to the inoculation. A total of 2×10$^6$ A375/TxR cells in 100 μL of solution were inoculated in the right flank of each mouse using an insulin syringe. Mice were anesthetized with 2-4% isoflurane inhalation before tumor cell inoculation. The tumor growth was carefully monitored, and the tumor volume was calculated as a×b$^2$×0.5 using a caliper, where a and b represent the larger and smaller diameter, respectively. Vehicle or drug treatment was initiated when the tumor reached to around 100 mm$^3$. Paclitaxel was dissolved in ethanol and diluted in a 1:1:18 ratio of ethanol:Cremophor EL:PBS solution. 5m was formulated in PEG300 solution and further diluted with isotonic saline (1:4 ratio). Both paclitaxel (10 mg/kg) and 5m (2 mg/kg and 4 mg/kg) were administered into mice intravenously via a tail vein injection two times per week (2×/Wk) in a total 3-week time period, and the tumor volume of each mouse was measured during the therapy until reaching the study endpoint.

FIG. 19B: For DU-145/VxR (Compound 17ya resistant; Compound 17ya is (2-(1H-indol-3-yl)imidazol-4-yl)(3,4,5-trimethoxyphenyl)methanone) xenograft model, 21 male aged of 5 to 6 weeks old NSG mice were used. Then 2.5×10$^6$ DU-145/VxR cells suspended in 100 μL of solution consisting of 50% of FBS and phenol red-free medium and 50% Matrigel were inoculated in the right flank of each NSG mouse. After around 16 days, mice were randomized into 3 groups [untreated control; 20 mg/kg Compound 17ya (PO, 3 times/week); 1 mg/kg 5m (IV, 2 times/week)] and treatments initiated. During the treatments, we monitored the tumor growth by measuring the tumor volume three times per week. And after 22 days of drug treatment, we terminated the study.

FIG. 19C: For MDA-MB-231/VxR (Compound 17ya resistant) xenograft model, we injected 2.5×10$^5$ MDA-MB-231/VxR cells suspended in 10 μL of HBSS solution orthotopically into the left and right site of mammary fat pad. Tumor growth was monitored externally using a caliper. When the average tumor volume of each mouse reached 100 mm$^3$, mice were randomized into 4 groups, including vehicle (ethanol:Cremophor EL:PBS solution=1:1:18, IP, 3 times/week), 10 mg/kg paclitaxel (ethanol:Cremophor EL:PBS solution=1:1:18, IP, 3 times/week), 20 mg/kg Compound 17ya (PEG300:water=3:7, PO, 3 times/week) and 2 mg/kg 5m (PEG300:saline=1:4, IV, 1 time/week). Mice were dosed for 20 days before the study ended. FIG. 19E and FIG. 19F: The ovarian cancer xenograft model was built by intraperitoneally injecting 5×10$^5$ A2780/TxR cells into the bursa of the left ovary with the right unchanged ovary as a control. Anesthesia and analgesics were used to minimize the suffering of the animals. After a week, all 20 female mice were randomized into 4 groups based on the body weight. The 4 groups include untreated control, 5 mg/kg paclitaxel (IV, 2 times/week), 20 mg/kg Compound 17ya (PO, 2 times/week) and 1 mg/kg 5m (IV, 2 times/week). The tumor progression was monitored using bioluminescence imaging via intraperitoneally injecting D-luciferin into mice. After dosing mice for 3 weeks, all the mice were euthanized and ovaries were collected, weighed and imaged.

In Vivo Xenograft Models of Castration Resistance (22RV)

FIG. 19D: Similarly, for 22RV1 prostate cancer xenograft model, we inoculated 2.5×10$^6$ 22RV1 cells subcutaneously into the right flank of each mouse. The cells were prepared in the mixture of FBS and phenol red-free DMEM medium and Matrigel (1:1 ratio). When the average tumor volume reached around 100 mm$^3$, which used 11 days, all 14 male mice were randomly divided into 2 groups, namely untreated control group and 1 mg/kg 5m group. 1 mg/kg 5m was administrated with IV injection with dose frequency of 2 times a week. We measured tumor volume 2 times a week until reaching the study endpoint.

Statistical Analysis.

All quantitative data were analyzed using GraphPad Prism 7 (San Diego, CA). One-way ANOVA followed by the Dunnett's multiple comparison test was applied to all in vitro experiments and lung & liver metastasis quantification. Significance levels are defined as *p<0.05, p<0.01, *p<0.001, ****p<0.0001.

Example 6: X-Ray Crystallography (FIG. 6)

Special reagents. Porcine brain tubulin (Catalog #T-238P) was obtained from Cytoskeleton. Bis-Tris propane, tyrosine, DTT, MES and AMPPCP were purchased from Sigma. Glycerol and antiprotease cocktail were obtained from Sangon Biotech. β-Mercaptoethanol was obtained from XiYa Reagent.

Protein Expression and Purification. The stathmin-like domain of RB3 (RB3-SLD) gene was cloned by the group of Dr. Benoît Gigant (Université Paris-Saclay, in France). Purification followed the published protocol, Charbaut, et al., "Family Proteins Display Specific Molecular and Tubulin Binding Properties," J. Biol. Chem., 2001, 276 (19), 16146-16154; Dorleans, et al., "Variations in the colchicine-binding domain provide insight into the structural switch of tubulin," Proc. Natl. Acad. Sci., 2009, 106(33), 13775-13779. Briefly, the gene was transformed into E. coli and over-expressed and the bacterial cells were collected by centrifugation and resuspended with lysis buffer. The supernatant was collected by centrifugation and the RB3-SLD was purified by anion-exchange chromatography and gel filtration chromatography. The peak fractions of target protein were finally concentrated to 10 mg/mL and stored at −80° C. The plasmid of TTL was a kind gift from Dr Michel O. Steinmetz (Paul Scherrer Institut, PSI, Switzerland), and it was expressed and purified as described previously. Prota et al., "Molecular Mechanism of Action of Microtubule-Stabilizing Anticancer Agents," Science, 203, 339(6119), 587-590. Briefly, the transformed E. coli were induced in LB medium overnight at 25° C. with IPTG. Then the cells were collected and lysed by sonication in the lysis buffer. The lysate was subsequently clarified by centrifugation and the TLL was purified by Ni-NTA affinity chromatography and gel filtration chromatography to purify. The purified protein was finally concentrated to 20 mg/ml and stored at −80° C. until use. The purity of RB3 and TTL were examined by SDS-PAGE. Porcine brain tubulin (Catalog #T-238P, Cytoskeleton, Inc.) was supplied at 10 mg/ml in G-PEM (General tubulin buffer: 80 mM PIPES pH 6.9, 2 mM $MgCl_2$, 0.5 mM EGTA and 1 mM GTP) as a frozen liquid and saved at −80° C.

Crystallization and Crystal Soaking. Crystals were grown by the sitting-drop vapor diffusion method. Detailed steps for crystals of T2R-TTL was described as before. See Prota, Wang et al., "Mechanism of microtubule stabilization by taccalonolide AJ," Nat. Commun., 2017, 8, 15787. Briefly, the protein mixtures containing tubulin (10 mg/ml), TTL (20 mg/ml) and RB3 (10 mg/ml) at the molar ratio of 2:1.3:1.2 (Tubulin:RB3:TTL) was incubated on ice supplemented with 1 mM AMPPCP, 5 mM tyrosine and 10 mM DTT. It was then concentrated to 20 mg/ml at 4° C. and 1.0 µL of protein was used to mix with 1.0 µL crystallization buffer (4-8% PEG4K, 5% glycerol, 0.1 M MES, 30 mM $CaCl_2$, 30 mM $MgCl_2$, pH 6.7) to grow the crystals. Initial crystals were observed after two days and then the crystal could reach to the final size around a length of 200-300 µm within 3-5 days. After this, the compound of 5j, 5k, 5l, 5m, and 5t were dissolved in DMSO at 10 mM concentration, and then were soaked to the crystals at 20° C. for 12 h. The soaked crystals were quickly transferred into the cryo-protectant (30 mM $MgCl_2$, 30 mM $CaCl_2$, 0.1M MES, pH 6.7 contained 20% glycerol) and flash frozen at 100 K for synchrotron X-ray data collection.

X-Ray Data Collection and Structure Determination. The crystals of the T2R-TTL-compound complexes were mounted in nylon loops and flash-cooled in a cold nitrogen stream at 100K. The diffraction data were collected on beam-line BL19U1 at Shanghai Synchrotron Radiation Facility (SSRF), Shanghai, China. The data set was initially processed by the HKL2000 program package. The previously published T2R-TTL structure (PDB ID: 4I55) was used as the starting model to determine the structures by molecular replacement. The structures were built, optimized, and refined using Coot and PHENIX. See, Emsley et al., "Coot: model-building tools for molecular graphics," Acta Cryst., 2004, 60 (12 Part 1), 2126-2132; Terwilliger, et al., "PHENIX: building new software for automated crystallographic structure determination," Acta Cryst., 2002, 58(11), 1948-1954. The refined structures were validated using MolProbity. Data parameters and refinement statistics are summarized in Table 5.

TABLE 5

Data collection and refinement statistics

| Parameter | 5j | 5k | 5l | 5m | 5t |
|---|---|---|---|---|---|
| Data Collection[a] | | | | | |
| Wavelength (Å) | 0.97853 | 0.97853 | 0.97853 | 0.97853 | 1.0000 |
| Space group | $P2_12_12_1$ | $P2_12_12_1$ | $P2_12_12_1$ | $P2_12_12_1$ | $P2_12_12_1$ |
| Cell dimensions | | | | | |
| a (Å) | 105.3 | 105.2 | 105.4 | 105.5 | 104.6 |
| b (Å) | 158.3 | 158.0 | 157.7 | 157.9 | 155.0 |
| c (Å) | 181.9 | 182.1 | 182.2 | 182.2 | 182.3 |
| α (°) | 90.0 | 90.0 | 90.0 | 90.0 | 90.0 |
| β (°) | 90.0 | 90.0 | 90.0 | 90.0 | 90.0 |
| γ (°) | 90.0 | 90.0 | 90.0 | 90.0 | 90.0 |
| Resolution range (Å) | 50.0-2.90 | 50.0-2.80 | 50.0-2.90 | 50.0-2.70 | 50.0-2.90 |
| | (2.95-2.90) | (2.85-2.80) | (2.95-2.90) | (2.75-2.70) | (3.00-2.90) |
| $R_{merge}$[b] | 0.209 (1.310) | 0.187 (1.140) | 0.177 (1.137) | 0.106 (0.000) | 0.085 (0.869) |
| $R_{pim}$ | 0.060 (0.372) | 0.053 (0.339) | 0.050 (0.317) | 0.045 (0.480) | 0.048 (0.506) |
| CC1/2 | 0.992 (0.769) | 0.999 (0.749) | 0.996 (0.804) | 0.990 (0.592) | 0.994 (0.465) |
| Completeness (%) | 99.9 (100.0) | 100.0 (100.0) | 100.0 (99.8) | 99.9 (100.0) | 98.7 (98.7) |

TABLE 5-continued

Data collection and refinement statistics

| Parameter | 5j | 5k | 5l | 5m | 5t |
|---|---|---|---|---|---|
| Redundancy | 12.8 (12.9) | 13.3 (12.3) | 13.3 (13.6) | 6.8 (7.0) | 4.2 (4.2) |
| I/σ(I) | 13.1 (2.4) | 14.6 (2.5) | 15.7 (3.0) | 17.5 (2.0) | 16.2 (1.1) |
| Unique reflections | 69.598 (3,470) | 75,636 (3,739) | 67,407 (3,331) | 84,115 (4,130) | 64,109 (6,296) |
| Refinement | | | | | |
| Resolution range (Å) | 48.1-2.9 | 49.9-2.8 | 49.9-2.9 | 48.2-2.7 | 45.4-2.9 |
| No. of reflections | 67,675 | 74,550 | 66,958 | 80,919 | 64,032 |
| No. of atoms | | | | | |
| Protein | 17,173 | 17,191 | 17,202 | 17,166 | 16,533 |
| Ligand | 232 | 234 | 232 | 230 | 227 |
| Water | 104 | 135 | 109 | 280 | 37 |
| $R_{work}$ | 0.174 | 0.171 | 0.170 | 0.190 | 0.184 |
| $R_{free}$ | 0.216 | 0.211 | 0.224 | 0.241 | 0.228 |
| Average B factors | | | | | |
| Protein | 52.9 | 53.0 | 57.2 | 51.3 | 85.7 |
| Ligand | 47.2 | 52.9 | 52.0 | 44.0 | 79.3 |
| Water | 38.6 | 38.8 | 41.0 | 34.8 | 71.1 |
| Rmsd from ideal | | | | | |
| Bond lengths (Å) | 0.002 | 0.002 | 0.002 | 0.002 | 0.003 |
| Bond angles (°) | 0.527 | 0.554 | 0.545 | 0.532 | 0.617 |
| Ramachandran plot | | | | | |
| Favored (%) | 98.00 | 98.14 | 97.76 | 97.80 | 97.38 |
| Allowed (%) | 2.00 | 1.82 | 2.14 | 2.15 | 2.57 |
| Outliers (%) | 0.00 | 0.05 | 0.09 | 0.05 | 0.05 |
| PDB accession code | 6X1C | 7LZ7 | 6X1E | 6X1F | 7LZ8 |

[a] Values in parentheses refer to the highest resolution shell.
[b] $R_{merge} = \Sigma |(I - \langle I \rangle)|/\Sigma(I)$, where I is the observed intensity.

Example 7: Pancreatic Cancer Treatment

Cell Culture:

The human pancreatic cancer cell lines Mia PaCa-2 and PANC-1 cell lines were obtained from ATCC and were routinely cultured in DMEM supplemented with 10% fetal bovine serum (Atlanta Biologicals) and 1% antibiotic/antimycotic solution (Sigma-Aldrich) at 37° C. in a humidified atmosphere with 5% $CO_2$. Additional 2.5% horse serum were supplemented when culturing Mia PaCa-2 cell line. Mia PaCa-2-Luc cell lines was transfected in the lab using lentivirus gifted from Dr. Junming Yue's Lab, cultured with DMEM supplemented with 10% FBS, 2.5% horse serum and 0.5 μg/mL puromycin (Sigma). The medium was refreshed 2 times a week, and the cells were maintained to 80-90% confluency. Compound stocks of 20 mmol/L were dissolved in dimethyl sulfoxide (DMSO, ATCC) and further diluted into designated concentration in cell culture medium freshly before use.

Cytotoxicity Assay (FIG. 20):

Mia PaCa-2 and PANC-1 cells were seeded in 96-well plates at 4000 and 5000 cells per well, respectively. After overnight incubation, cells were treated with test compounds of increasing concentration range from 1 nmol/L to 1.25 μmol/L for 72 h in four replicates. The MTS reagent (Promega) was added and incubated for 1.5 h at 37° C. before measured under 490 nM absorbance in a plate reader (BioTek Instruments Inc.) $IC_{50}$ values were calculated by nonlinear regression analysis using GraphPad Prism 9 based on the normalized value to vehicle controls on log scale.

Colony Formation Assay (FIG. 21A):

Cells were seeded at 1000 cells per well in 6-well plates in triplicates and treated with vehicle control or 1-5 nmol/L test compounds for 11 to 14 days. The colonies were fixed with 100% methanol and stained with 0.5% crystal violet. Colony area was quantified with Image J software.

Scratch Migration Assay (FIG. 21B):

The Mia PaCa-2 cells (25,000 cells/well) were seeded in 96-well plates and allowed to adhere overnight. At 80-90% confluence, scratch was made with a wound maker. After washing off the debris, medium was replaced and tested compounds were added. Cells were live monitored with IncuCyte and pictures obtained every 2 h. Compared with the control, the wound width of cells under different treatment conditions was quantified according to the endpoint width over starting point.

Cell Cycle Analysis (FIG. 22A):

The cells were plated in 100-mm dishes at a concentration of $1-2\times10^6$ cells/dish in DMEM without serum. After serum starvation for 24 h, medium was replaced with complete culture medium containing tested compounds. For cell cycle analysis, the cells were trypsinized and fixed with 70% ethanol in −20° C. overnight. The fixed cells were incubated with 100 μg/mL of RNase A and 50 μg/mL propidium iodide for 30 min at room temperature. Stained cells were analyzed using Bio-Rad ZE5 and ModFit LT 5.0.9 software at Flow cytometry and cell sorting core at the University of Tennessee Health Science Center (UTHSC) and the proportion of G1, S, G2/M phases were determined.

Western Blot Analysis (FIG. 22B):

Cells ($1\times10^6$ cells/well) were seeded in 6-well plates overnight and treated with increasing concentrations of 5m and PTX for 24 hrs. Total cell lysates were collected in ice-cold RIPA buffer containing protease inhibitor cocktail for 30 min and centrifuged at 13000 rpm at 4° C. for 10 min. Total protein concentrations were quantified by the BCA Protein Assay Kit (Thermo Fisher Scientific). 20 μg protein samples were loaded and separated by TGX 4-15% gradient gels (Bio-Rad) and transferred onto activated PVDF membrane. Membranes were blocked with 5% non-fat milk for 1 h, followed by incubation of primary antibody (PARP #9542 (1:500); β-actin #4970 (1:1000), Cell Signaling Technology) at 4° C. overnight and blotted with secondary antibody for 1 h at room temperature. Protein was detected by Bio-Rad ChemiDoc Imager and analyzed by Image J software.

In Vivo Subcutaneous Mia PaCa-2-Luc and PANC-1-Luc Xenograft Models (FIGS. 23 and 24)

All animal procedures were performed in accordance with the protocols approved by the Institutional Animal Care and Use Committee (IACUC) at UTHSC. Two pancreatic cancer cell lines, Mia PaCa-2-Luc and PANC-1-Luc, were used in this study. 50 µL of Mia PaCa-2-Luc ($5\times10^6$ cells in HBSS) or PANC-1-Luc ($3\times10^6$ cells in HBSS) cell suspension was mixed with same volume of Matrigel (1:1 mixture) right before use. Cell mixture was subcutaneously injected to the right flank of each NSG mice (male, 6-8 weeks). 5m was dissolved in PEG300:saline (1:4 v/v). The control group received no treatment. Treatment started when the average tumor size reached 70-100 mm$^3$. For Mia PaCa-2-Luc tumor-bearing mice, we administered 5m via intravenous (i.v.) injection at the dose of 2 mg/kg, 1 dose/week for 6 weeks. For PANC-1-Luc tumor-bearing mice, we also administered 5m by i.v. injection at a dose of 1 mg/kg or 2 mg/kg, 1dose/week for 7 weeks. Tumor volume and body weight were measured twice per week. Tumor volume was calculated by the equation: volume (mm$^3$)=0.5×(length× width$^2$). All animals were euthanized at the end of the study. Tumors were excised, recorded for ex-vivo weight and size, and imaged.

Figure 20:
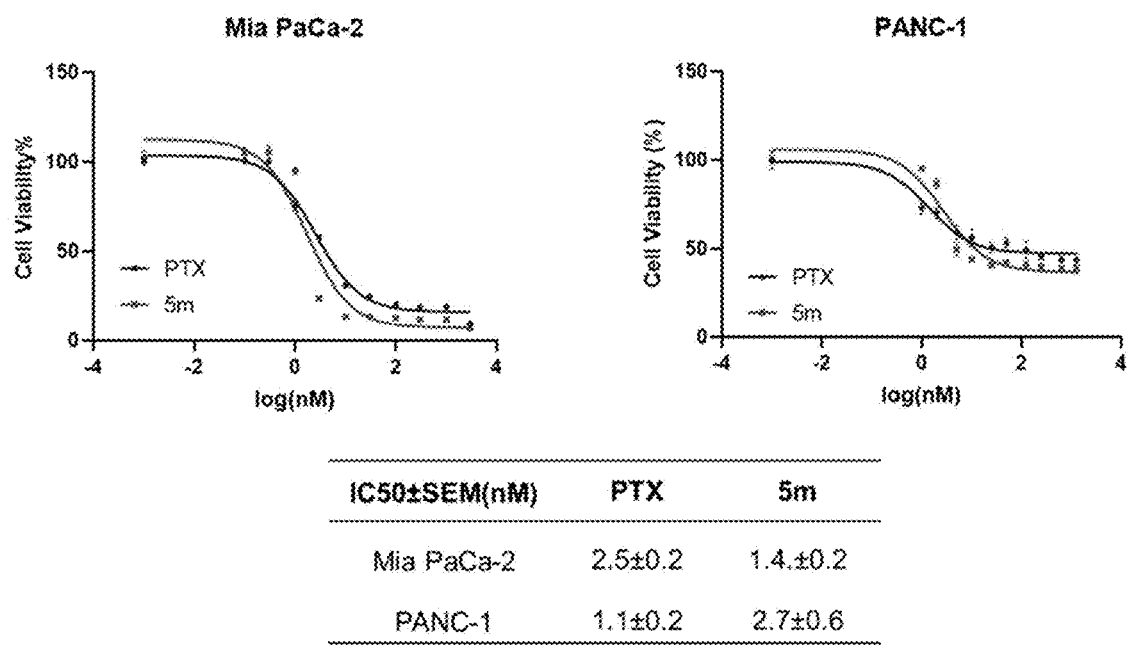
FIG. 20 illustrates graphically that 5m showed comparable cytotoxic potency in pancreatic ductal adenocarcinoma (PDAC) cells as paclitaxel (PTX) in Mia PaCa-2 and PANC-1 cell lines.
Figure 21A:
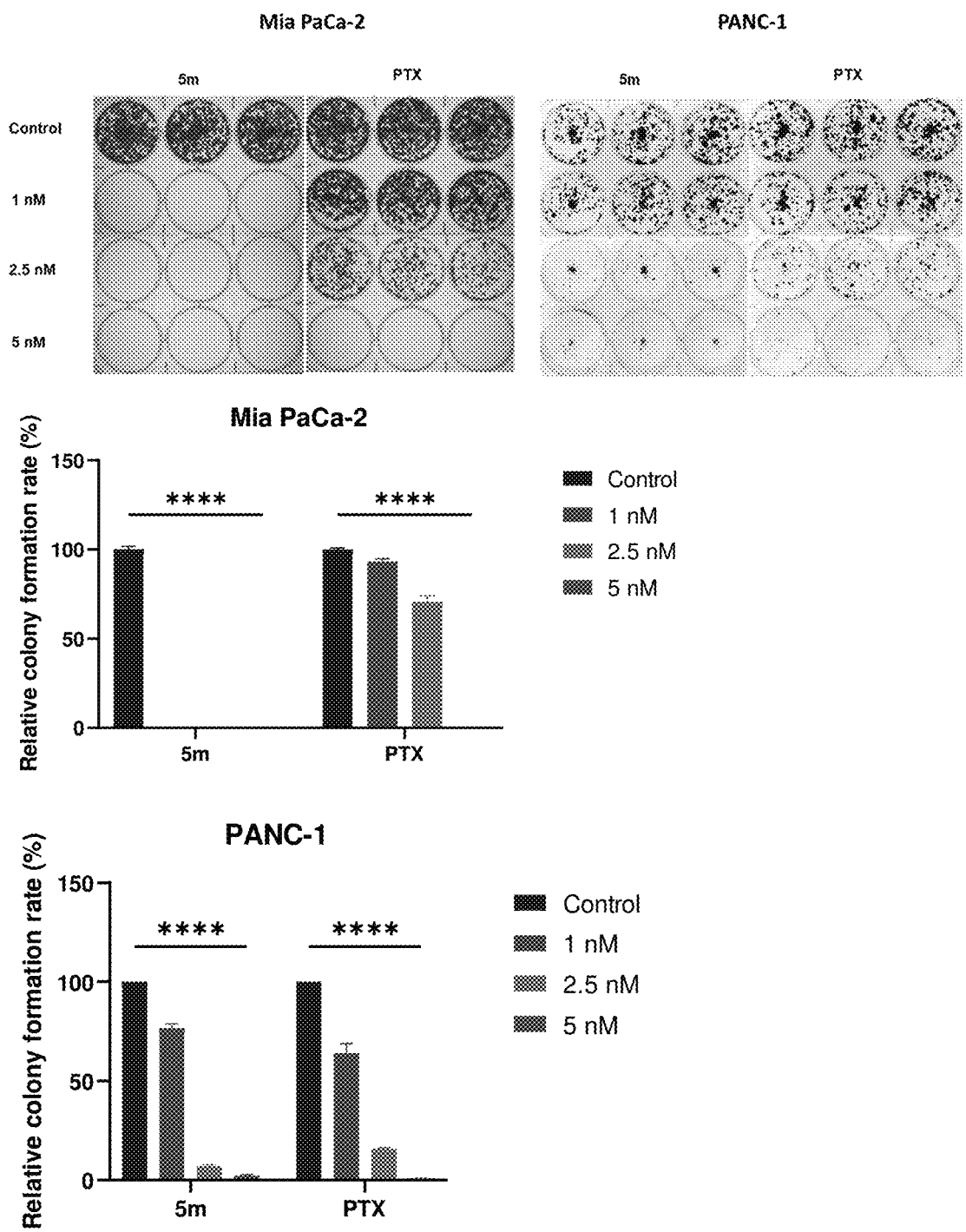
FIGS. 21A and 21B illustrate that 5m demonstrated dose-responsive inhibition of colony formation and cell migration that was more potent than paclitaxel (PTX) in the pancreatic ductal adenocarcinoma (PDAC) cell lines Mia PaCa-2 and PANC-1.
Figure 21B:
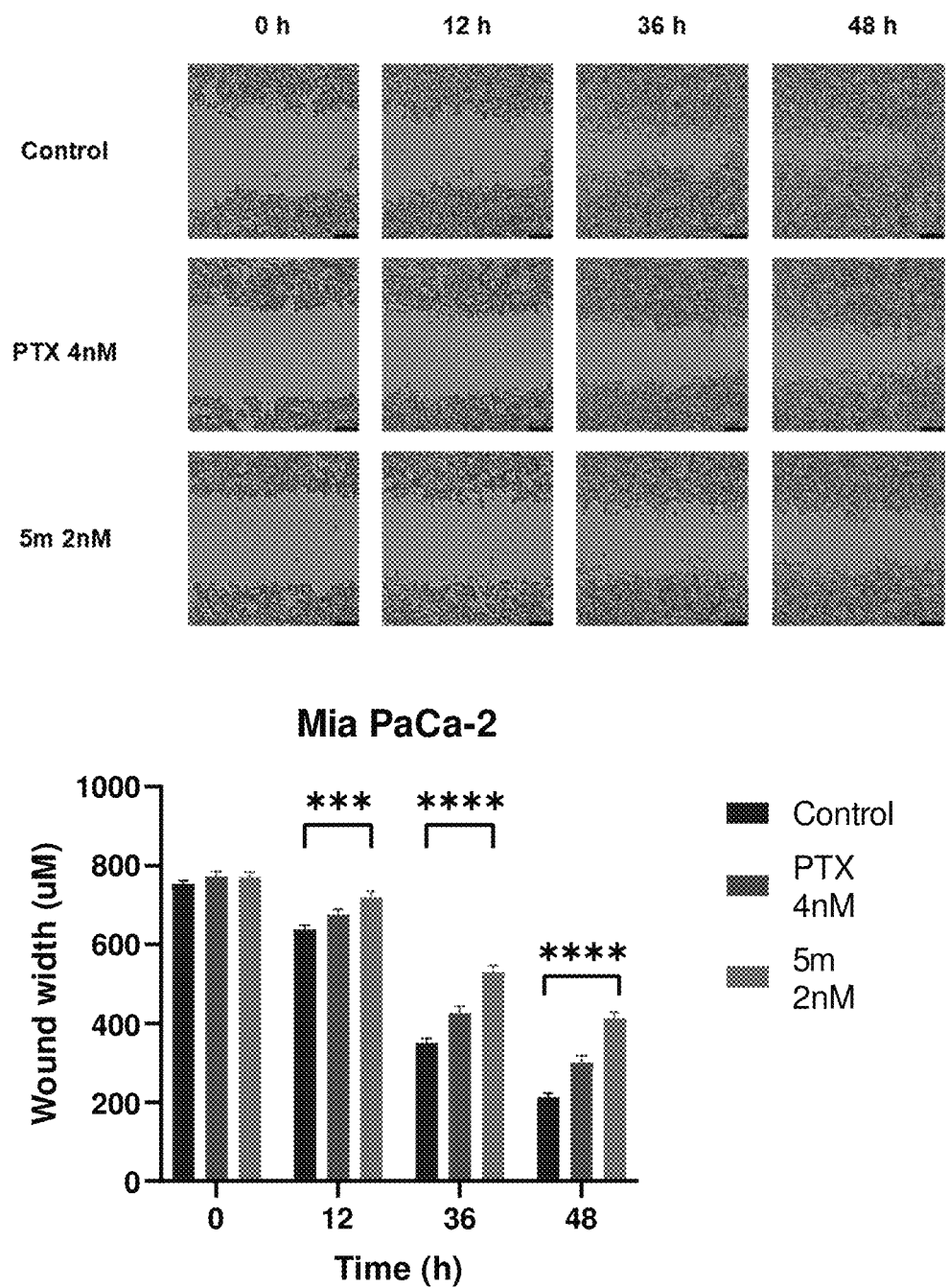

Results:

Compound 5m shows comparable cytotoxic potency in the pancreatic ductal adenocarcinoma (PDAC) cell lines Mia PaCa-2 and PANC-1 as compared to paclitaxel (PTX) as illustrated in FIG. 20. The calculated IC$_{50}$ values suggested that Compound 5m (1.4 nM) was slightly more potent that PTX (2.5 nM) in Mia PaCa-2 cells, whereas PTX (1.1 nM) was slightly more potent than Compound 5m (2.7 nM) in PANC-1 cells. Compound 5m inhibited colony formation and cell migration in vivo, as illustrated in FIGS. 21A and 21B. FIG. 21A illustrates the effect of Compound 5m on colony formation and cell migration in Mia PaCa-2 and Panc-1 cell lines where Compound 5m was compared to paclitaxel (PTX) at 1 nM, 2.5 nM, and 5 nM. The representative colony formation images shown illustrate that Compound 5m demonstrated inhibition of colony formation that was more potent than paclitaxel (PTX) in both PDAC cell lines, Mia PaCa-2 and PANC-1. Bar graphs demonstrate that for Mia PaCa-2, colony formation was completely inhibited by Compound 5m at the lowest dose (1 nM), whereas for PTX complete inhibition was only seen at 5 nM. Whereas for PANC-1 cells, the potency of inhibition of colony formation was comparable for 5m and PTX with only the 5 nM doses demonstrating nearly complete inhibition of colony formation. **p<0.0001. FIG. 21B graphically illustrates the effect of Compound 5m on cell migration in Mia PaCa-2 cells where compound 5m (2 nM) was compared to PTX (4 nM). The representative images illustrate the wound healing as captured by IncuCyte. Cells were live monitored with IncuCyte and pictures obtained every 2 h. Compared with the control, wound closure is shown as the wound width in microns (µm) at each time point, as summarized in the bar graph. 5m (2 nM) and PTX (4 nM) both inhibited cell migration over 48 h in Mia PaCa-2 cell cultures compared to control. As the bar graph demonstrated, 5m (2 nM) more effectively inhibited wound healing as compared to PTX (4 nM) at each time point. * p<0.001, and ****p<0.0001.

Figure 22A:
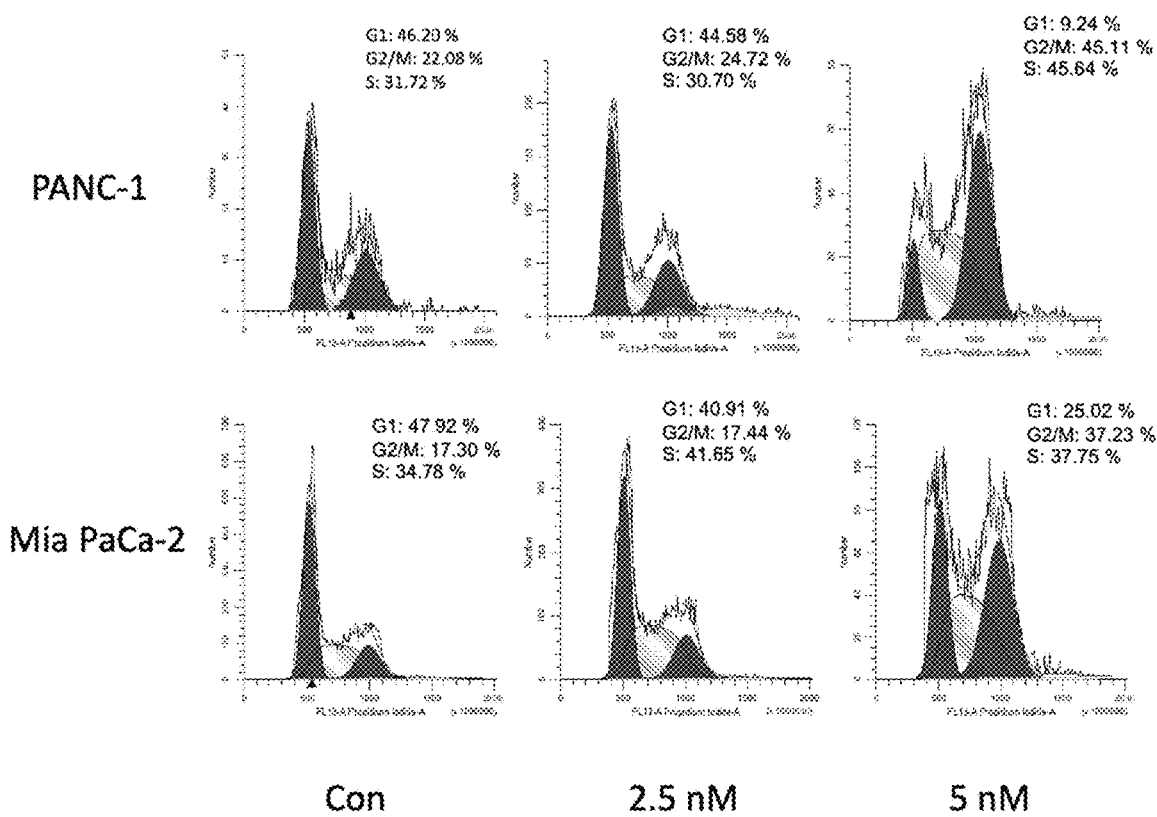
FIGS. 22A and 22B illustrate that compound 5m induced cell cycle arrest at G2/M phase and induced cell apoptosis in a dose dependent manner.
Figure 22B:
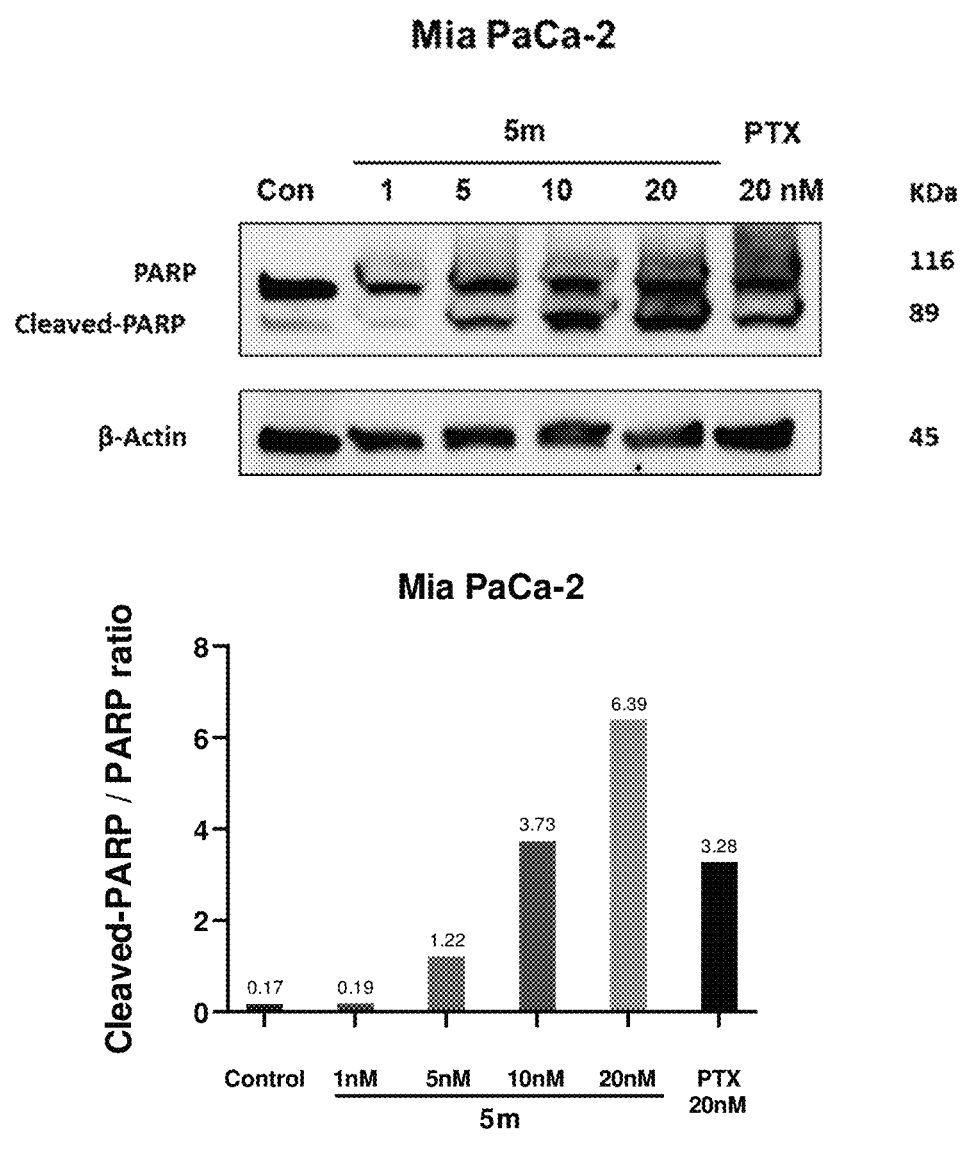

Compound 5m induced cell cycle arrest at G2/M phase and cell apoptosis in PDAC cell lines Mia PaCa-2 and PANC-1 in a dose dependent manner as illustrated in FIGS. 22A and 22B. FIG. 22A illustrates the ability of Compound 5m to dose dependently increase the proportion of cells in G2/M phase (relative to G1 or S phase) in PANC-1 and Mia PaCa-2 cell lines, suggesting mitotic arrest in these PDAC cell lines. FIG. 22B illustrates that Compound 5m and PTX induced apoptosis in Mia PaCa-2 cells as measured by Western blot which demonstrated an increased cleaved PARP to PARP ratio. R-actin was used as an internal standard to correct for total protein loaded. As demonstrated in the bar graph (FIG. 22B), induction of apoptosis by Compound 5m was dose-dependent and more potent as compared to PTX in the Mia PaCa-2 cell line. For example, this ratio was comparable for 10 nM of 5m as compared to 20 nM of PTX.

Figure 23A:
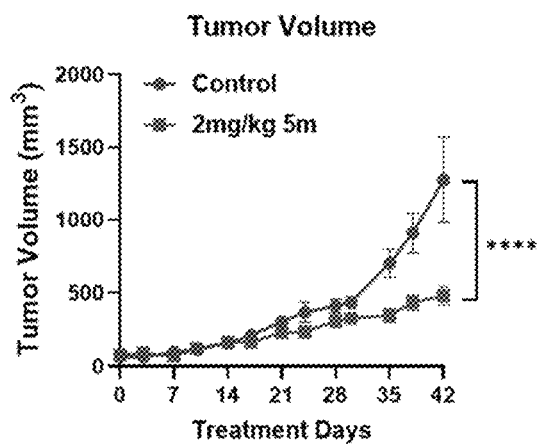
FIGS. 23A-23E illustrate that 5m inhibited PDAC tumor growth in Mia PaCa-2-Luc subcutaneous xenograft model with minimum signs of toxicity.
Figure 23B:
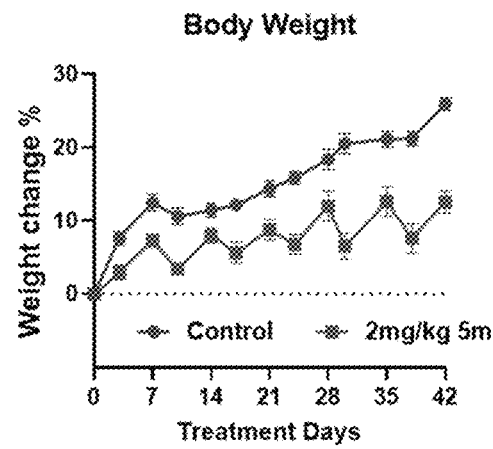
Figure 23C:
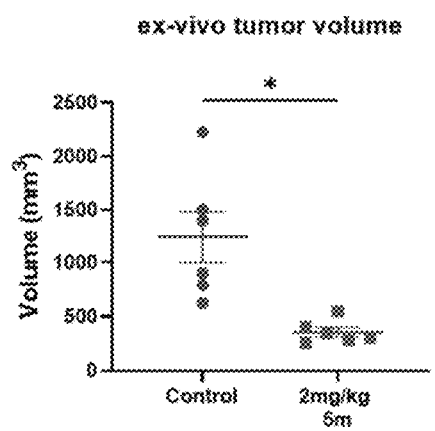
Figure 23D:
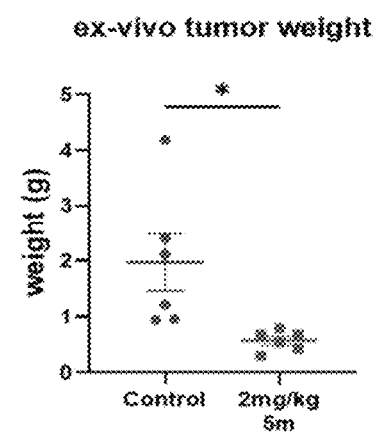
Figure 23E:
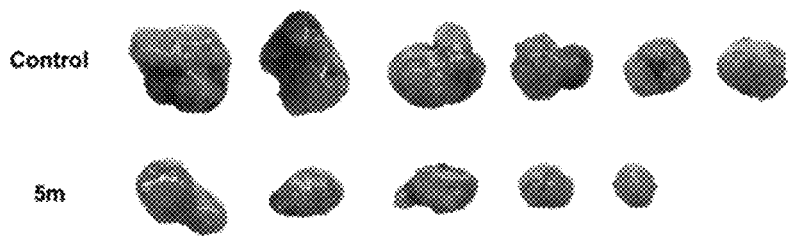

Compound 5m inhibited PDAC tumor growth in Mia PaCa-2-Luc subcutaneous xenograft model with minimum signs of toxicity as illustrated in FIGS. 23A-23E. Compound 5m inhibited PDAC tumor growth in Mia PaCa-2-Luc subcutaneous xenograft model with minimum signs of toxicity as illustrated in FIGS. 23A-23E. As can be seen, Compound 5m (2 mg/kg) significantly reduced tumor growth vs. control (untreated) by about 70-80%. FIG. 23B illustrates the effect of Compound 5m as compared to control on body weight over 42 days. The body weight was represented as weight change %. As can be seen, limited global toxicity was observed with Compound 5m as body weight trended toward slightly reduced values compared to control. FIG. 23C graphically illustrates the effect of Compound 5m (2 mg/kg) as compared to control on ex vivo tumor volume as measured over 42 days. FIG. 23D graphically illustrates the effect of Compound 5m (2 mg/kg) as compared to control on ex vivo tumor weight over 42 days. The images captured in FIG. 23E illustrate that excised tumor sizes after treatment with Compound 5m were smaller as compared to control treated tumors. Consistent with FIGS. 23A and 23E, tumor volumes (FIG. 23C) and tumor weights (FIG. 23D) were significantly reduced by the treatment of Compound 5m (2 mg/kg) over control for 42 days, which can also be appreciated in the pictures of the excised tumors. Data are presented as means±standard errors of the means (SEM). Significant differences related to control groups are presented by P values<0.05 (* p<0.05,  p<0.01, * p<0.001, **** p<0.001), as measured two tailed, unpaired Welch's t test or two-way ANOVA followed by Šidák's or Dunnett's multiple comparison. IC$_{50}$ were calculated by nonlinear regression. All data were analyzed using GraphPad Prism 9.

Figure 24A:
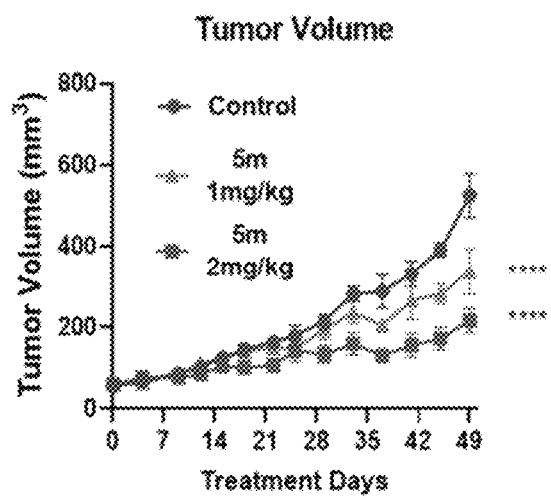
FIGS. 24A-24E illustrate that 5m inhibited PDAC tumor growth in PANC-1-Luc subcutaneous xenograft model with no signs of toxicity. 5m (1 mg/kg or 2 mg/kg; 1 dose/week for 7 weeks) or vehicle (control) was administered by i.v. injection into the right flank of each NSG mice (male, 6-8 weeks). Tumor volume and body weight was measured twice per week.
Figure 24B:
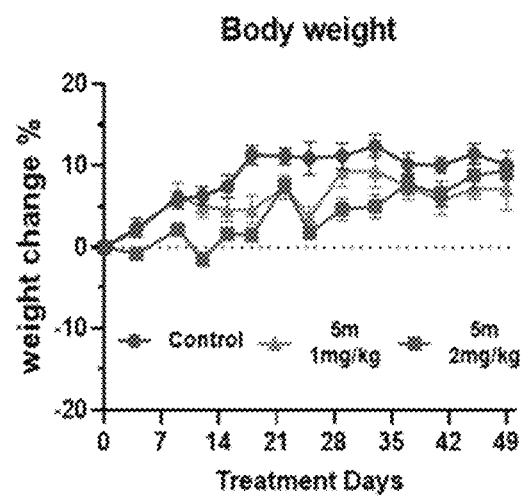
Figure 24C:
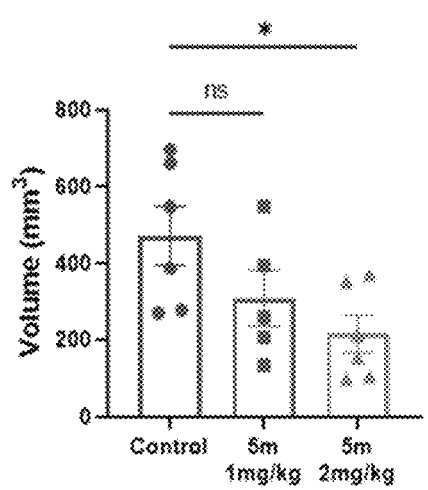
Figure 24D:
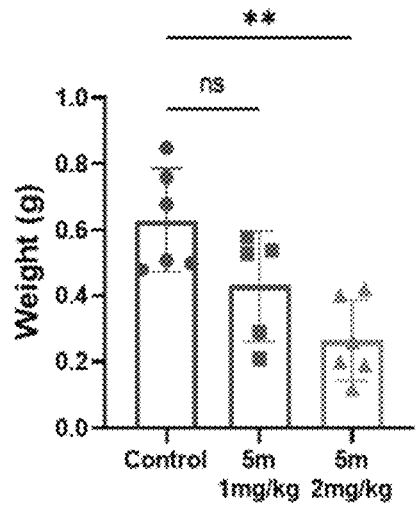
Figure 24E:
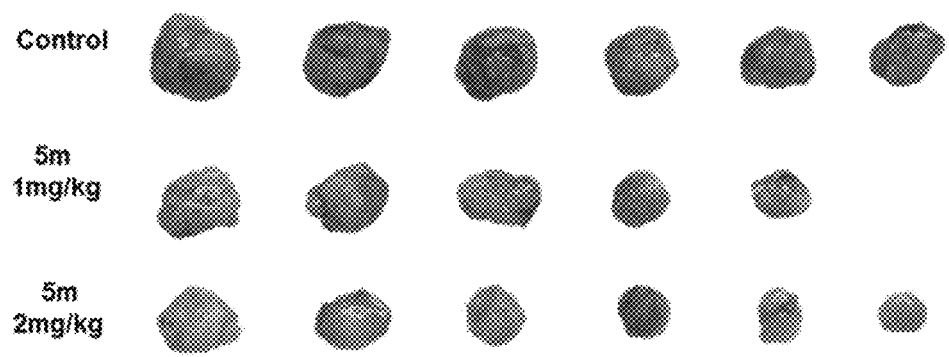

FIGS. 24A-24E illustrate that Compound 5m inhibited PDAC tumor growth in the PANC-1-Luc subcutaneous xenograft model with no signs of toxicity. Compound 5m (1 mg/kg or 2 mg/kg; 1dose/week for 7 weeks) was administered by i.v. injection into the right flank of each NSG mice (male, 6-8 weeks). Tumor volume and body weight were measured twice per week. FIG. 24A illustrates the effect of Compound 5m as compared to control (untreated) on tumor volume. Compound 5m demonstrated dose-dependent and significant inhibition of xenograft tumor growth compared to control. FIG. 24B illustrates the effect of Compound 5m as compared to control on body weight (weight change %). After 49 days of treatment with Compound 5m at two doses, there was no differences seen in body weight for the treated animals compared with control, indicating that Compound 5m does not demonstrate significant global toxicity. FIGS. 24C and 24D graphically illustrate the effect of Compound 5m as compared to control on ex vivo tumor volume (mm$^3$) and ex vivo tumor weight (g), respectively. Consistent with the results for tumor volume, Compound 5m dose-dependently inhibited xenograft tumor growth compared to control as measured by ex vivo tumor volume and ex vivo tumor weight. FIG. 24E photographically illustrates a comparison of the excised tumor sizes after treatment with compound 5m as compared to control. Tumor volume was calculated by the equation: volume (mm$^3$)=0.5×(length×width$^2$). All animals were euthanized at the end of the study. Tumors were excised, recorded with ex vivo weight and size and imaged. Data are presented as means±standard errors of the means (SEM). Significant differences related to control groups are presented by P values<0.05 (* p<0.05,  p<0.01, * p<0.001, **** p<0.001), as measured two tailed, unpaired Welch's t test, or one-way ANOVA followed by Dunnett's multiple comparison, or two-way ANOVA followed by Šidák's or Dunnett's multiple comparison. IC$_{50}$ were calculated by nonlinear regression. All data were analyzed using GraphPad Prism 9 (GraphPad Software Inc.).

Figure 25:
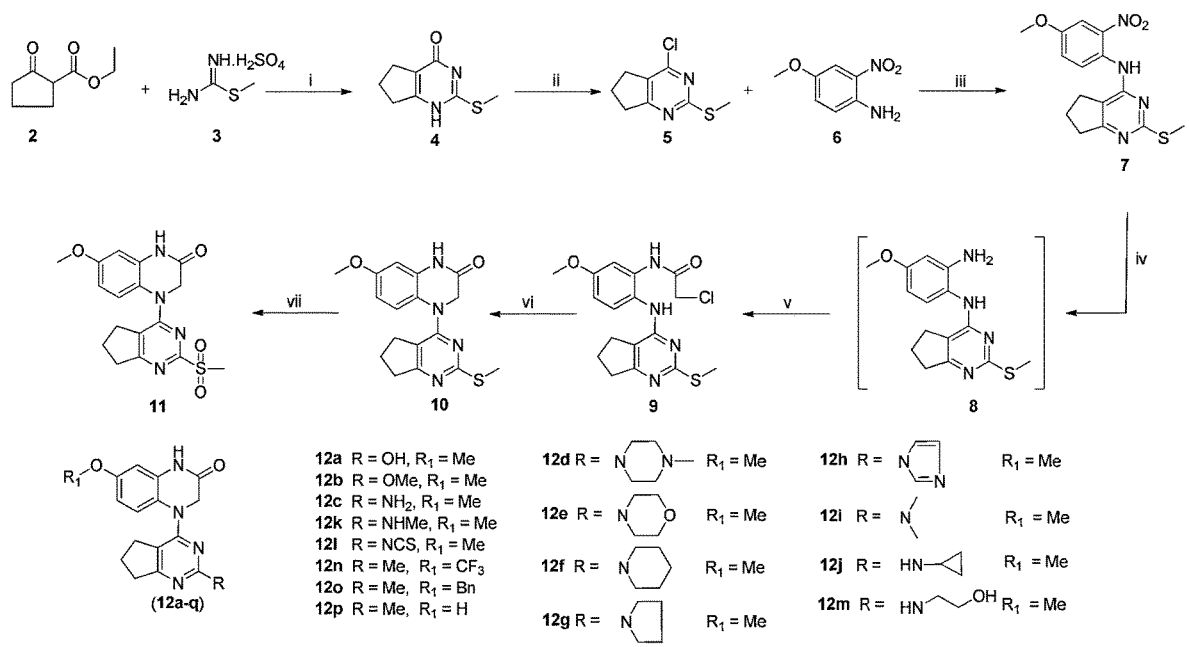
FIG. 25 illustrates the synthetic scheme for compounds 12a-n. $^a$ Reagents and conditions: (i) t-BuOK/t-BuOH; (ii) $POCl_3$, 90° C.; (iii) IPA/HCl, rt, 5-6 h; (iv) Zn/AcOH, $CH_2Cl_2$; (v) Chloroacetyl chloride/$K_2CO_3$, acetone, 0° C.; (vi) NaH, THF, 0° C. to rt; (vii) Oxone, methanol/water, rt.

Example 8: General Procedure for the Preparation of Dihydroquinaxolinone-Pyrimidine/Pyridine Analogues (12a-12m and 5v) and Preparation of 12o-12q General Methods All nonaqueous reactions were performed in oven-dried glassware under an inert atmosphere of dry nitrogen. All the reagents and solvents were purchased from Aldrich (St. Louis, MO), Alfa-Aesar (Ward Hill, MA), Combi-Blocks (San Diego, CA), Ark Pharm (Libertyville, IL) and used without further purification. Analytical thin layer chromatography was performed on silica gel GHLF 10 cm×20 cm Analtech TLC Uniplates (Analtech, Newark, DE) and were visualized by fluorescence quenching under UV light. Silica gel (60-120 or 100-200 mesh) was used to purify the compounds. $^1$H NMR and $^{13}$C NMR spectra were recorded on a Varian Inova-500 spectrometer (400 MHz) (Agilent Technologies, Santa Clara, CA) or a Bruker Ascend 400 (400 MHz) (Billerica, MA) spectrometer. Chemical shifts are reported in ppm on the δ scale and referenced to the appropriate solvent residual peaks (CDCl$_3$, 7.27 ppm for $^1$H and 77.23 ppm for $^{13}$C and DMSO-d$_6$, 2.50 ppm for $^1$H and 39.51 ppm for $^{13}$C) and all coupling constants (J) are given in hertz (Hz). Mass spectra were collected on a Bruker amazon SL electrospray/ion trap instrument in the positive and negative modes. High resolution mass spectrometer (HRMS) data were acquired on a Waters Xevo G2-S qTOF (Milford, MA) system equipped with an Acquity I class UPLC system. Porcine brain tubulin (catalog no. T-238P) was purchased from Cytoskeleton, Inc. The purity of all tested compounds was determined to be ≥95% by $^1$H NMR and HPLC. The HPLC method used to determine purity is as follows: Compound purity was analyzed using an Agilent 1100 HPLC system (Santa Clara, CA) with a Zorbax SB-C18 column, particle size 3.5 μm, 4.6 mm×150 mm, from Agilent. Mobile phases consist of water with 0.1% formic acid (A) and acetonitrile with 0.1% formic acid (B). A flow rate of 1 mL/min was used. The gradient elution started at 50% B. It reached 100% B from 0 to 9 min, was maintained at this from 9 to 12 min, and was then decreased to 50% B from 12 to 15 min and stopped. Compound purity was monitored with a DAD detector set at 254 nm. FIG. 25 illustrates the synthetic scheme for the compounds below.

Synthesis of N-(4-methoxy-2-nitrophenyl)-2-(methylthio)-6,7-dihydro-5H-cyclopenta[d]pyrimidin-4-amine (7). A mixture of compound 5 (10 g, 0.05 mol) and 4-methoxy-2-nitroaniline 6 (9.2 g, 0.055 mol) in anhydrous IPA (50 mL) with a catalytic amount of HCl (conc, 10 drops) was stirred at 50° C. for 8 h and monitored by TLC until the reaction was complete. The reaction mass was diluted with saturated aqueous NaHCO$_3$ solution (pH=7), filtered, washed with water, and dried to obtain 7 as an orange solid 15.0 g, 90.3% yield; $^1$H NMR (400 MHz, CDCl$_3$) δ 9.91 (s, 1H), 8.99 (d, J=7.4 Hz, 1H), 7.70 (d, J=6.3 Hz, 1H), 7.26 (s, 1H), 3.87 (s, 3H), 2.96 (t, J=7.8 Hz, 2H), 2.88 (t, J=7.1 Hz, 2H), 2.57 (s, 3H), 2.22 (dd, J=16.0, 9.1 Hz, 2H); $^{13}$C NMR (100 MHz, CDCl$_3$) δ 155.65, 154.30, 136.94, 128.59, 124.06, 123.68, 121.97, 115.43, 109.62, 108.23, 55.95, 33.81, 26.45, 21.70, 14.45; found LCMS [M+H] 333.2.

Synthesis of 2-chloro-N-(5-methoxy-2-((2-(methylthio)-6,7-dihydro-5H-cyclopenta[d]pyrimidin-4-yl)amino)phenyl)acetamide (9). A mixture of 7 (15.0 g, 0.045 mol) and zinc powder (6.0 g, 0.09 mol) in 100 mL of CH$_2$Cl$_2$ in the presence of 1.5 mL of AcOH was stirred at 0° C. for 0.5 h. After compilation of starting material, which was filtered through Celite® bed, the filtrate was concentrated to obtain the aniline derivative (8). It was immediately dissolved in acetone (100 mL), and powered K$_2$CO$_3$ (20.5 g, 0.15 mol) was added, and the mixture was cooled to 0° C. Chloroacetyl chloride (5 mL, excess) was dropped slowly into the mixture, which was stirred at 0° C. for another 2 h. Then the mixture was diluted with water, extracted with CH$_2$Cl$_2$, and washed with brine solution, dried over Na$_2$SO$_4$ and concentrated. Crude was purified by column chromatography to obtain 9 as a bright pink solid (12 g, 63.8% yield); $^1$H NMR (400 MHz, DMSO-d$_6$) δ 9.64 (s, 1H), 8.25 (s, 1H), 7.34-7.31 (m, 2H), 6.80-6.77 (m, 1H), 4.30 (s, 2H), 3.74 (s, 3H), 2.73 (t, J=7.4 Hz, 2H), 2.64 (t, J=7.6 Hz, 2H), 2.28 (s, 3H), 2.01-1.97 (m, 2H); $^{13}$C NMR (100 MHz, CDCl$_3$) δ 165.23, 158.20, 157.30, 132.71, 127.67, 122.83, 113.21, 112.02, 108.91, 55.63, 43.03, 33.32, 26.85, 21.70, 14.05; found LCMS [M+H] 379.81.

Synthesis of 7-methoxy-4-(2-(methylthio)-6,7-dihydro-5H-cyclopenta[d]pyrimidin-4-yl)-3,4-dihydroquinoxalin-2(1H)-one (10). Added 60% sodium hydride (1.258 g, 0.039 mol) as a portion wise to a compound of 9 (10.0 g, 0.026 mol) in anhydrous THF (100 mL) at 0° C. and slowly allowed to room temperature, which was stirred for until completed as judged by TLC monitoring. The mixture was poured into ice-water, and the solid product 10 was removed by filtration, washed with water, and dried to give 6.0 g in a 66.6% yield as an ash colored solid; $^1$H NMR (400 MHz, CDCl$_3$) δ 9.62 (s, 1H), 7.34 (d, J=9.1 Hz, 2H), 6.78 (dd, J=8.8, 2.8 Hz, 1H), 4.25 (s, 2H), 3.83 (s, 3H), 2.94 (t, J=7.8 Hz, 2H), 2.73 (s, 2H), 2.39 (s, 3H), 2.15 (dd, J=17.0, 9.6 Hz, 2H); $^{13}$C NMR (100 MHz, CDCl$_3$) δ 168.40, 156.73, 131.17, 122.96, 115.74, 108.16, 102.36, 55.78, 49.64, 30.99, 22.60, 14.21; HRMS [C$_{17}$H$_{18}$N$_4$O$_2$S$^+$] calcd. 343.1229, found 343.1233; HPLC purity 99.7%; Mp=170-171° C.

Synthesis of 7-methoxy-4-(2-(methylsulfonyl)-6,7-dihydro-5H-cyclopenta[d]pyrimidin-4-yl)-3,4-dihydroquinoxalin-2(1H) one (11). A mixture of 10 (5 g, 0.014 mol) and potassium peroxymonosulfate (also known as oxone) (11.1 g, 0.073 mol) in water/MeOH (1:1 vol) was stirred at rt for 5 h and then the reaction mixture was diluted with water, filtered and dried under vacuum to give 5.0 g, 92.6% of title compound 11 without further purification; $^1$H NMR (400 MHz, DMSO-d$_6$) δ 10.74 (s, 1H), 6.98 (d, J=9.3 Hz, 1H), 6.62-6.59 (m, 2H), 4.53 (s, 2H), 3.74 (s, 3H), 2.86 (d, J=13.5 Hz, 2H), 2.25 (d, J=7.1 Hz, 2H), 1.93-1.91 (m, 2H); $^{13}$C NMR (100 MHz, DMSO-d$_6$) δ 176.79, 167.87, 163.91, 157.57, 157.10, 133.16, 123.25, 122.89, 120.25, 107.32, 102.15, 55.82, 49.78, 33.97, 31.44, 22.46; HRMS [C$_{17}$H$_{19}$N$_4$O$_4$S$^+$] calcd. 375.1127, found 375.1130; HPLC purity 95.6%; Mp=156-157° C.

Synthesis of 4-(2-hydroxy-6,7-dihydro-5H-cyclopenta[d]pyrimidin-4-yl)-7-methoxy-3,4-dihydroquinoxalin-2(1H)-one (12a). A mixture of 11 (100 mg, 0.26 mmol) and 1 N NaOH (5 mL) in 1,4-dioxane was heated to 90° C. for 6 h. After completion of conversion, the mixture was poured into ice water and solid was collected, washed with water, and dried. The crude was purified by column chromatography to afford pure 12a as a light brown solid (80 mg, 96.3% yield); $^1$H NMR (400 MHz, DMSO-d$_6$) δ 10.67 (s, 1H), 6.90 (d, J=8.5 Hz, 1H), 6.60-6.57 (m, 2H), 4.40 (s, 2H), 3.72 (s, 3H), 2.61 (t, J=7.5 Hz, 2H), 1.99 (t, J=6.6 Hz, 2H), 1.80 (dd, J=14.3, 7.1 Hz, 2H): $^{13}$C NMR (100 MHz, DMSO-d$_6$) δ 168.44, 163.52, 160.99, 157.42, 133.18, 124.18, 120.80, 107.44, 105.49, 102.04, 72.63, 66.77, 60.66, 55.79, 49.30, 30.83, 22.44; HRMS [C$_{16}$H$_{17}$N$_4$O$_3$$^+$] calcd. 313.1310, found 313.1306; HPLC purity 98.7%; Mp=198-199° C.

Synthesis of 7-methoxy-4-(2-methoxy-6,7-dihydro-5H-cyclopenta[d]pyrimidin-4-yl)-3,4-dihydroquinoxalin-2(1H)-one (12b). A mixture of 11 (100 mg, 0.29 mmol) and 0.5 M CH$_3$ONa in MeOH (5 mL) was heated to 90° C. for 6 h in a sealed tube. The mixture was poured into ice-water, solid was separated out, washed with water, and dried. The crude was purified by column chromatography to afford pure 12b as a blood red solid (79 mg, 90.7% yield); $^1$H NMR (400 MHz, DMSO-d$_6$) δ 10.66 (s, 8H), 6.86 (d, J=8.3 Hz, 7H), 6.58 (t, J=5.6 Hz, 2H), 4.44 (s, 2H), 3.86 (s, 3H), 3.73 (s, 3H), 2.71 (t, J=7.6 Hz, 2H), 2.14 (t, J=7.1 Hz, 2H), 1.86 (dd, J=14.6, 7.2 Hz, 2H); $^{13}$C NMR (100 MHz, DMSO-d$_6$) δ 177.04, 168.20, 164.33, 158.09, 157.07, 132.88, 123.14, 121.00, 113.21, 107.41, 102.09, 55.78, 54.77, 49.57, 33.79, 30.51, 22.68; HRMS [C$_{17}$H$_{19}$N$_4$O$_3$$^+$] calcd. 327.1457, found 327.1459; HPLC purity 95.02%; Mp=163-164° C.

Synthesis of 4-(2-amino-6,7-dihydro-5H-cyclopenta[d]pyrimidin-4-yl)-7-methoxy-3,4-dihydroquinoxalin-2(1H)-one (12c). A mixture of 11 (100 mg, 0.26 mmol) and 0.5 M ammonia in 1,4-dioxane (5 mL) was heated to 90° C. for 8 h in a sealed tube. The mixture was poured into ice-water, solid was collected out through filtration, washed with water, and dried. The crude was purified by column chromatography to afford pure 12c as a light brown solid (70 mg, 84.2% yield); $^1$H NMR (400 MHz, DMSO-d$_6$) δ 10.61 (s, 1H), 6.76 (d, J=8.4 Hz, 1H), 6.59-6.54 (m, 2H), 6.23 (s, 2H), 4.34 (s, 2H), 3.72 (s, 3H), 2.58 (t, J=7.6 Hz, 2H), 2.08-2.04 (m, 2H), 1.79-1.75 (m, 2H); $^{13}$C NMR (100 MHz, DMSO-d$_6$) δ 167.78, 157.83, 156.73, 156.30, 155.58, 150.40, 133.05, 122.97, 120.44, 119.08, 107.36, 102.30, 55.85, 50.51, 32.35, 29.74, 23.09, 21.22, 14.54; HRMS [C$_{16}$H$_{18}$N$_5$O$_2$$^+$] calcd. 312.1460, found 312.1461; HPLC purity 95.26%; Mp=208-209° C.

Synthesis of 7-methoxy-4-(2-(4-methylpiperazin-1-yl)-6,7-dihydro-5H-cyclopenta[d]pyrimidin-4-yl)-3,4-dihydroquinoxalin-2(1H)-one (12d). A mixture of 11 (100 mg, 0.29 mmol) and methyl piperazine (80 mg, 0.8 mmol) in 1,4-dioxane was heated to 110° C. for 10 h in a sealed tube. The mixture was poured into ice-water, solid was collected through filtration, washed with water, and dried. The crude was purified by column chromatography to afford pure 12d as a pale yellow solid (68 mg, 64.5% yield); $^1$H NMR (400 MHz, DMSO-d$_6$) δ 10.61 (s, 1H), 6.78 (d, J=8.2 Hz, 1H), 6.58 (d, J=7.7 Hz, 2H), 4.37 (s, 2H), 3.72 (s, 3H), 3.68 (s, 4H), 2.63 (t, J=7.6 Hz, 2H), 2.35-2.32 (m, 4H), 2.20 (s, 3H), 2.10 (t, J=7.1 Hz, 2H), 1.87-1.71 (m, 2H); $^{13}$C NMR (100 MHz, DMSO-d$_6$) δ 179.49, 176.51, 169.60, 168.51, 161.53, 157.13, 156.42, 156.29, 152.28, 151.73, 132.41, 130.50, 124.22, 122.49, 121.87, 112.39, 108.47, 107.39, 107.24, 102.06, 96.24, 55.96, 55.73, 54.92, 49.40, 46.28, 34.40, 34.30, 30.41, 29.22, 22.52, 22.36; HRMS [C$_{21}$H$_{27}$N$_6$O$_2$$^+$] calcd. 395.2195, found 395.2209; Mp=187-188° C.

Synthesis of 7-methoxy-4-(2-morpholino-6,7-dihydro-5H-cyclopenta[d]pyrimidin-4-yl)-3,4-dihydroquinoxalin-2(1H)-one (12e). A mixture of 11 (100 mg, 0.26 mmol) and morpholine (69.8 mg, 0.8 mmol) in 1,4-dioxane was heated to 110° C. for 10 h in a sealed tube. The mixture was poured into ice-water, solid was collected out through filtration, washed with water, and dried. The crude was purified by column chromatography to afford pure 12e as a pale yellow solid (101 mg, 79.2% yield); $^1$H NMR (400 MHz, DMSO-d$_6$) δ 10.60 (s, 1H), 6.77 (d, J=8.2 Hz, 1H), 6.60-6.53 (m, 2H), 4.36 (s, 2H), 3.71 (s, 3H), 3.64 (s, 8H), 2.63 (dd, J=16.6, 9.1 Hz, 2H), 2.10 (dd, J=18.6, 11.6 Hz, 2H), 1.84-1.71 (m, 2H): $^{13}$C NMR (100 MHz, DMSO-d$_6$) δ 175.49, 167.39, 160.54, 156.08, 155.40, 131.42, 121.41, 120.76, 107.81, 106.28, 101.00, 65.47, 54.67, 48.35, 43.64, 33.26, 29.37, 21.58; HRMS [C$_{20}$H$_{24}$N$_5$O$_3$$^+$] calcd. 382.1879, found 382.1883; decomposes at ≈266° C.

Synthesis of 7-methoxy-4-(2-(piperidin-1-yl)-6,7-dihydro-5H-cyclopenta[d]pyrimidin-4-yl)-3,4-dihydroquinoxalin-2(1H)-one (12f). A mixture of 11 (100 mg, 0.26 mmol) and piperidine (68 mg, 0.8 mmol) in 1,4-dioxane was heated to 110° C. for 9 h in a sealed tube. The mixture was poured into ice-water, solid was collected out through filtration, washed with water, and dried. The crude was purified by column chromatography to afford pure 12f as an off white solid (80 mg, 78.9% yield); $^1$H NMR (400 MHz, CDCl$_3$) δ 8.12 (s, 1H), 6.75 (d, J=8.8 Hz, 1H), 6.58 (dd, J=8.8, 2.3 Hz, 1H), 6.44 (d, J=2.0 Hz, 1H), 4.56 (s, 2H), 3.80 (s, 3H), 3.77 (t, J=5.3 Hz, 4H), 2.75 (t, J=7.6 Hz, 2H), 2.18 (t, J=7.1 Hz, 2H), 1.94-1.83 (m, 2H), 1.63 (bs, 6H); $^{13}$C NMR (100 MHz, DMSO-d$_6$) δ 176.49, 168.53, 161.43, 157.17, 156.35, 122.46, 121.97, 107.77, 107.39, 102.05, 66.78, 55.72, 49.40, 44.89, 34.34, 30.37, 25.75, 24.90, 22.52; HRMS [C$_{21}$H$_{26}$N$_5$O$_2$$^+$] calcd. 380.2087, found 380.2096; HPLC purity 95.88%; Mp=248-249° C.

Synthesis of 7-methoxy-4-(2-(pyrrolidin-1-yl)-6,7-dihydro-5H-cyclopenta[d]pyrimidin-4-yl)-3,4-dihydroquinoxalin-2(1H)-one (12g). A mixture of 11 (100 mg, 0.26 mmol) and pyrrolidine (57 mg, 0.8 mmol) in 1,4-dioxane was heated to 110° C. for 10 h in a sealed tube. The mixture was poured into ice-water, solid was collected out through filtration, washed with water, and dried. The crude was purified by column chromatography to afford pure 12g as a light yellow solid (82 mg, 84% yield); $^1$H NMR (400 MHz, CDCl$_3$) δ 8.20 (s, 1H), 6.76 (d, J=8.8 Hz, 1H), 6.58 (dd, J=8.8, 2.6 Hz, 1H), 6.44 (d, J=2.6 Hz, 1H), 4.58 (s, 2H), 3.80 (s, 3H), 3.59 (bs, 4H), 2.77-2.71 (m, 2H), 2.18 (t, J=3.5 Hz, 2H), 1.98-1.95 (m, 4H), 1.89-1.83 (m, 2H); $^{13}$C NMR (100 MHz, DMSO-d$_6$) δ 175.22, 167.48, 159.32, 156.04, 155.22, 141.67, 131.35, 122.53, 121.13, 106.31 100.99, 54.65, 54.39, 48.33, 45.67, 33.24, 29.31, 24.43, 21.52; HRMS [C$_{20}$H$_{24}$N$_5$O$_2$$^+$] calcd. 366.1930, found 366.1930; Mp=144-145° C.

Synthesis of 4-(2-(1H-imidazol-1-yl)-6,7-dihydro-5H-cyclopenta[d]pyrimidin-4-yl)-7-methoxy-3,4-dihydroquinoxalin-2(1H)-one (12h). A mixture of 11 (100 mg, 0.29 mmol), imidazole (54 mg, 0.8 mmol) and DIPA (71 mg, 0.5 mmol) in 1,4-dioxane was heated to 110° C. for 12 h in a sealed tube. The mixture was poured into ice-water, solid was collected out through, washed with water, and dried. The crude was purified by column chromatography to afford pure 12h as a light yellow solid (78 mg, 80.6% yield); $^1$H NMR (400 MHz, DMSO-d$_6$) δ 10.69 (s, 1H), 8.54 (s, 1H), 7.92 (s, 1H), 7.08 (s, 1H), 6.95 (d, J=8.3 Hz, 1H), 6.61 (d, J=9.1 Hz, 2H), 4.55 (s, 2H), 3.74 (s, 3H), 2.83 (t, J=7.6 Hz, 2H), 2.23 (t, J=7.1 Hz, 2H), 1.92-1.88 (m, 2H); $^{13}$C NMR (100 MHz, DMSO-d$_6$) δ 177.38 (s), 168.13, 157.62, 157.28, 153.13, 136.08, 133.09, 130.34, 123.25, 120.74, 117.57, 117.22, 107.30, 102.11, 66.79, 55.79, 49.74, 34.12, 31.00, 22.52; HRMS [C$_{19}$H$_{19}$N$_6$O$_2$$^+$] calcd. 363.1569, found 363.1577; Mp=242-243° C.

Synthesis of 4-(2-(dimethylamino)-6,7-dihydro-5H-cyclopenta[d]pyrimidin-4-yl)-7-methoxy-3,4-dihydroquinoxalin-2(1H)-one (12i). A mixture of 11 (100 mg, 0.26 mmol), dimethylamine salt (65 mg, 0.8 mmol) and DIPA (2 mL) in 1,4-dioxane was heated to 110° C. for 10 h in a sealed tube. The mixture was poured into ice-water, solid was collected out through filtration, washed with water, and dried. The crude was purified by column chromatography to afford pure 12i as a light yellow solid (70 mg, 77.2% yield); $^1$H NMR (400 MHz, DMSO-d$_6$) δ 10.59 (s, 1H), 6.77 (d, J=8.2 Hz, 1H), 6.59-6.56 (m, 2H), 4.38 (s, 2H), 3.72 (s, 3H), 3.08 (s, 6H), 2.63 (t, J=7.4 Hz, 2H), 2.09 (t, J=6.7 Hz, 2H), 1.80-1.77 (m, 2H); $^{13}$C NMR (100 MHz, DMSO-d$_6$) δ 176.35, 168.51, 162.22, 157.07, 156.32, 132.43, 122.36, 122.04, 107.44, 107.31, 102.05, 55.71, 49.41, 37.20, 34.36, 30.34, 22.56; HRMS [C$_{18}$H$_{22}$N$_5$O$_2$$^+$] calcd. 340.1773, found 340.1787; HPLC purity 96.92%; Mp=198-199° C.

Synthesis of 4-(2-(cyclopropylamino)-6,7-dihydro-5H-cyclopenta[d]pyrimidin-4-yl)-7-methoxy-3,4-dihydroquinoxalin-2(1H)-one (12j). A mixture of 11 (100 mg, 0.26 mmol) and cyclopropyl amine (45 mg, 0.8 mmol) in 1,4-dioxane was heated to 80° C. for 10 h in a sealed tube. The mixture was poured into ice-water, solid was collected removed through filtration, washed with water, and dried. The crude was purified by column chromatography to afford pure 12j as a pale yellow solid (62 mg, 61% yield); $^1$H NMR (400 MHz, DMSO-d$_6$) δ 10.60 (bs, 1H), 6.95 (d, J=3.3 Hz, 1H), 6.79 (d, J=8.5 Hz, 1H), 6.59-6.55 (m, 2H), 4.38 (s, 2H), 3.75 (s, 3H), 2.69 (dq, J=10.6, 3.6 Hz, 1H), 2.61 (t, J=7.5 Hz, 2H), 2.08 (t, J=7.1 Hz, 2H), 1.79 (dd, J=14.5, 7.3 Hz, 2H), 0.62 (dt, J=6.5, 3.1 Hz, 2H), 0.44-0.43 (m, 2H); $^{13}$C NMR (100 MHz, DMSO-d$_6$) δ 176.31, 168.54, 163.27, 157.23, 156.35, 132.49, 122.50, 122.08, 107.31, 102.03, 66.79, 55.72, 49.43, 34.12, 30.45, 24.38, 22.55, 6.89; HRMS [C$_{19}$H22N$_5$O$_2$$^+$] calcd. 352.1773, found 352.1782; HPLC purity 95.9%; Mp=171-172° C.

Synthesis of 7-methoxy-4-(2-(methylamino)-6,7-dihydro-5H-cyclopenta[d]pyrimidin-4-yl)-3,4-dihydroquinoxalin-2(1H)-one (12k). A mixture of 11 (100 mg, 0.26 mmol) and 2M methyl amine in THF (0.4 mL, 8 mmol) in 1,4-dioxane was heated to 110° C. for 7 h in a sealed tube. The mixture was poured into ice-water, solid was collected through filtration, washed with water, and dried. The crude was purified by column chromatography to afford pure 12k as an off white solid (70 mg, 80.6% yield); $^1$H NMR (400 MHz, DMSO-d$_6$) δ 10.58 (s, 1H), 6.75 (d, J=8.4 Hz, 1H), 6.65 (q, J=4.7 Hz, 1H), 6.56 (dd, J=12.2, 2.7 Hz, 2H), 4.36 (s, 2H), 3.71 (s, 3H), 2.77 (d, J=4.8 Hz, 3H), 2.59 (t, J=7.4 Hz, 2H), 2.06 (t, J=7.1 Hz, 2H), 1.78-1.75 (m, 2H); $^{13}$C NMR (100 MHz, DMSO-d$_6$) δ 176.36, 168.53, 162.94, 157.29, 156.30, 132.43, 122.11, 107.32, 102.05, 55.72, 49.40, 30.40, 28.49, 22.54; HRMS [C$_{17}$H$_{20}$N$_5$O$_2$$^+$] calcd. 326.1617, found 326.1624; HPLC purity 96.7%; Mp=201-202° C.

Synthesis of 4-(2-isothiocyanato-6,7-dihydro-5H-cyclopenta[d]pyrimidin-4-yl)-7-methoxy-3,4-dihydroquinoxalin-2(1H)-one (12l). 0.50 M solution of thiophosgene (0.55 mL, 0.4 mmol) in anhydrous CH$_2$Cl$_2$ was cooled to 0° C. under argon. A solution of the 12c (100 mg, 0.3 mmol) in anhydrous CH$_2$Cl$_2$ and DIPA (0.7 mL) was added. The resulting solution was allowed to warm to ambient temperature over 8 h. The reaction mass was quenched with 1N HCl (5 mL) and extracted with CH$_2$Cl$_2$ (20 mL×2). The combined organic layers were dried over Na$_2$SO$_4$ and concentrated. The crude was purified by column chromatography to afford isothiocyanate pale-yellow solid (50 mg, 44.2% yield); $^1$H NMR (400 MHz, DMSO-d$_6$) δ 10.72 (s, 1H), 6.91 (d, J=8.5 Hz, 1H), 6.60 (d, J=7.8 Hz, 2H), 4.43 (s, 2H), 3.74 (s, 3H), 2.78 (t, J=7.6 Hz, 2H), 2.20 (t, J=7.2 Hz, 2H), 1.90-1.86 (m, 2H); $^{13}$C NMR (100 MHz, DMSO-d$_6$) δ 182.66, 166.12, 156.44, 154.36, 153.29, 153.26, 127.11, 126.48, 119.80, 116.90, 109.81, 55.90, 55.54, 34.45, 26.89, 22.32; HRMS [C$_{17}$H$_{16}$N$_5$O$_2$S$^+$] calcd. 354.1025, found 354.1031; HPLC purity 96.4%; decomposes at 139° C.

Synthesis of 4-(2-((2-hydroxyethyl)amino)-6,7-dihydro-5H-cyclopenta[d]pyrimidin-4-yl)-7-methoxy-3,4-dihydroquinoxalin-2(1H)-one (12m). A mixture of 11 (100 mg, 0.26 mmol), 2-aminoethanol (500 mg, 0.80 mmol) and DIPA (2 mL) in 1,4-dioxane was heated to 110° C. for 12 h in a sealed tube. The mixture was poured into ice-water, then extracted with CH$_2$Cl$_2$ (30 mL×2). The combined organic layer was washed with brine, dried over anhydrous Na$_2$SO$_4$, concentrated, and then purified through silica gel column chromatography to afford pure 12m as an white solid (75 mg, 79% yield); $^1$H NMR (400 MHz, DMSO-d$_6$) δ 10.60 (s, 1H), 6.77 (d, J=8.4 Hz, 1H), 6.60 (s, 1H), 6.59 (dt, J=11.6, 4.1 Hz, 2H), 4.68 (bs, 1H), 4.35 (s, 2H), 3.72 (s, 3H), 3.51-3.48 (m, 2H), 3.35-3.30 (m, 2H), 2.50 (t, J=7.5 Hz, 2H), 2.07 (t, J=6.8 Hz, 2H), 1.79 1.76 (m, 2H); $^{13}$C NMR (100 MHz, DMSO-d$_6$) δ 168.51, 162.39, 157.31, 156.34, 132.45, 122.43, 122.04, 107.32, 102.05, 60.56, 55.72, 55.37, 49.41, 34.13, 30.43, 22.53; HRMS [C$_{18}$H$_{22}$N$_5$O$_3$$^+$] calcd. 340.1773, found 340.1789; HPLC purity 99.73%; Mp=143-144° C.

Synthesis of 4-(2-(ethylamino)-6,7-dihydro-5H-cyclopenta[d]pyrimidin-4-yl)-7-methoxy-3,4-dihydroquinoxalin-2(1H)-one (5v) (alternative method listed in Example 4). A mixture of 11 (100 mg, 0.26 mmol), ethylamine (36 mg 0.80 mmol) in 1,4-dioxane was heated to 110° C. for 6 h in a sealed tube. The mixture was poured into ice-water, solid was collected out through filtration washed with water, and dried. The crude was purified by column chromatography to afford pure salt free 5v as an off white solid (50 mg, 50% yield); $^1$H NMR (400 MHz, DMSO-d$_6$) δ 10.84 (s, 1H), 8.04 (bs, 2H), 7.08 (d, J=8.1 Hz, 1H), 6.65-6.63 (m, 2H), 3.88 (bs, 1H), 3.76-3.72 (m, 4H), 3.44-3.41 (m, 2H), 2.83 (bs, 1H), 2.08 (bs, 1H), 1.88 (bs, 2H), 1.18 (t, J=6 Hz, 2H); $^{13}$C NMR (100 MHz, DMSO-d$_6$) δ 167.56, 158.48, 133.92, 125.18, 119.29, 107.38, 102.11, 55.90, 49.70, 36.50, 31.18, 22.44, 14.75; HRMS [C$_{18}$H$_{22}$N$_5$O$_2$$^+$] calcd. 340.1773, found 340.1789; HPLC purity 97.3%; decomposes at 210-211° C.

Synthesis of 4-(2-methyl-6,7-dihydro-5H-cyclopenta[d]pyrimidin-4-yl)-7-(trifluoromethoxy)-3,4-dihydroquinoxalin-2(1H)-one (12o). Added sodium hydride (15 mg, 0.3 mmol) to 2-chloro-N-(2-((2-methyl-6,7-dihydro-5H-cyclopenta[d]pyrimidin-4-yl)amine)-2-((4-trifluoromethoxy)phenyl)acetamide (100 mg, 0.25 mmol) in anhydrous THF (5 mL) at 0° C. and mixture was stirred at room temperature for until completed, as determined by TLC monitoring. The mixture was poured into ice-water, and the solid was removed by filtration, washed with water, and dried. The crude was purified by column chromatography to afford 12o off-white solid (50 mg, 55% yield); $^1$H NMR (400 MHz, DMSO-d$_6$) δ 10.87 (s, 1H), 6.96 (d, J=7.6 Hz, 1H), 6.86 (d, J=9.1 Hz, 2H), 4.44 (s, 2H), 2.79 (t, J=7.6 Hz, 2H), 2.49 (s, 3H), 2.21 (t, J=7.1 Hz, 2H), 1.89-1.86 (m, 4H); $^{13}$C NMR (100 MHz, DMSO-d$_6$) δ 176.30, 167.83, 165.81, 156.41, 144.28, 132.31, 127.44, 121.44, 118.13, 114.62, 108.88, 49.36, 34.06, 30.73, 25.77, 22.48; HRMS [C$_{17}$H$_{15}$F$_3$N$_4$O$_2$$^+$] calcd. 365.1225, found 365.1236; HPLC purity 98.7%; Mp=188-189° C.

Synthesis of 7-(benzyloxy)-4-(2-methyl-6,7-dihydro-5H-cyclopenta[d]pyrimidin-4-yl)-3,4-dihydroquinoxalin-2(1H)-one (12p). Added sodium hydride (71 mg, 1.7 mmol) as a portion wise to N-(5-(benzyloxy)-2-((2-methyl-6,7-dihydro-5H-cyclopenta[d]pyrimidin-4-yl)amino)phenyl)-2-chloroacetamide (500 mg, 1.1 mmol) in anhydrous THF (20 mL) at 0° C. and mixture was stirred at room temperature for until completed, as mediated by TLC monitoring. The mixture was poured into ice-water, and the solid was removed by filtration, washed with water, and dried. The crude was purified by column chromatography to afford 12p brown solid (300 mg, 65.6% yield); $^1$H NMR (400 MHz, DMSO-d$_6$) δ 10.69 (s, 1H), 7.46-7.34 (m, 5H), 6.79 (d, J=8.4 Hz, 1H), 6.67-6.65 (m, 2H), 5.06 (s, 2H), 4.43 (s, 2H), 2.75 (t, J=7.6 Hz, 2H), 2.47 (s, 3H), 2.17 (t, J=7.1 Hz, 2H), 1.85-1.82 (m, 2H); $^{13}$C NMR (100 MHz, DMSO-d$_6$) δ 175.58, 168.26, 165.53, 156.81, 155.79, 137.33, 132.71, 128.90, 128.36, 128.25, 122.27, 121.75, 116.88, 108.09, 103.10, 69.98, 49.57, 33.98, 30.92, 25.76, 22.37; HRMS [C$_{23}$H$_{23}$N$_4$O$_2$$^+$] calcd. 387.1821, found 387.1833; HPLC purity 99.4%; Mp=150-151° C.

Synthesis of 7-hydroxy-4-(2-methyl-6,7-dihydro-5H-cyclopenta[d]pyrimidin-4-yl)-3,4-dihydroquinoxalin-2(1H)-one (12q). A solution of 12p (200 mg, 0.5 mmol) was prepared in a mixture of dry MeOH/EtOAc (1:1 vol) under nitrogen and 5% Pd/C (10 wt %) was added. The nitrogen atmosphere was then removed under vacuum, and the mass was stirred at room temperature for 2 h under 1 atm of H$_2$ (hydrogen balloon), until complete consumption of starting material was indicated by TLC. The hydrogen atmosphere was then removed under vacuum, and the reaction mixture was flushed generously with nitrogen. The suspended Pd/C was removed by filtration through Celite®, and the solvent was evaporated and purified by column chromatography to afford 12q white solid (100 mg, 65.3% yield); $^1$H NMR (400 MHz, DMSO-d$_6$) δ 10.58 (s, 1H), 9.47 (s, 1H), 6.68 (d, J=8.5 Hz, 1H), 6.47 (d, J=2.6 Hz, 1H), 6.40 (dd, J=8.6, 2.6 Hz, 1H), 4.42 (s, 2H), 2.73 (d, J=7.7 Hz, 2H), 2.45 (s, 3H), 2.16 (t, J=7.1 Hz, 2H), 1.84-1.80 (m, 2H); $^{13}$C NMR (100 MHz, DMSO-d$_6$) δ 175.45, 168.38, 165.48, 156.95, 155.04, 132.80, 122.65, 120.06, 116.49, 108.93, 103.25, 49.63, 33.97, 30.91, 25.78, 22.33; HRMS [C$_{16}$H$_{17}$N$_4$O$_2$$^+$] calcd. 297.1352, found 297.1353; HPLC purity 96.9%; Mp=161-162° C.

Synthesis of ethyl 2-((5-methoxy-2-((2-(methylthio)-6,7-dihydro-5H-cyclopenta[d]pyrimidin-4-yl)amino)phenyl)amino)-2-oxoacetate (13). An aniline derivative 8 (

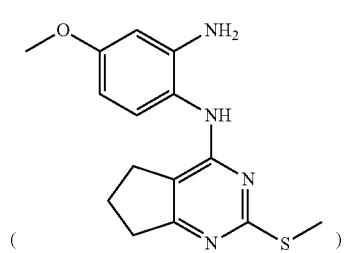

8

(3 g, 9 mmol) dissolved in acetone (40 mL), added powered K$_2$CO$_3$ (5.4 g, 4 mmol) and the mixture was cooled to 0° C. Ethyl oxalyl chloride (2 mL, excess) was added slowly into the mixture, which was stirred at 0° C. for another 1 h. Then the mixture was diluted with water, extracted with CH$_2$Cl$_2$, and washed with brine solution, dried over Na$_2$SO$_4$ concentrated. The crude was purified by column chromatography to afford pure bright brown solid (2.50 g, 62.6% yield); $^1$H NMR (400 MHz, DMSO-d$_6$) δ 9.99 (s, 1H), 8.53 (s, 1H), 7.39 (d, J=2.8 Hz, 1H), 7.33 (d, J=8.8 Hz, 1H), 6.85 (dd, J=8.8, 2.8 Hz, 1H), 4.23 (q, J=7.1 Hz, 2H), 3.76 (s, 3H), 2.75 (t, J=7.7 Hz, 2H), 2.68 (t, J=7.1 Hz, 2H), 2.07-1.96 (m, 2H), 1.23 (t, J=7.1 Hz, 3H); $^{13}$C NMR (100 MHz, CDCl$_3$) δ 177.41, 173.72, 165.18, 162.20, 162.02, 159.86, 137.43, 133.13, 128.90, 117.71, 116.20, 114.19, 67.86, 60.56, 38.77, 32.01, 26.35, 18.86, 18.47; found LCMS [M+H] 403.

Synthesis of 6-methoxy-1-(2-(methylthio)-6,7-dihydro-5H-cyclopenta[d]pyrimidin-4-yl)quinoxaline-2,3(1H,4H)-dione (14). To a stirred solution of compound 13 (1 g, 2.4 mmol) in THF (20 mL) and 60% sodium hydride (0.86 g, 5.0 mmol) was added at 0° C. The mixture was stirred at rt for 12 h and monitored by TLC. After completion of reaction, mixture was diluted with water, extracted with CH$_2$Cl$_2$ (30 mL×2), and combined organic layer was washed with 0.5N HCl (2×5 mL) dried over Na$_2$SO$_4$ concentrated. The crude was purified by column chromatography to afford pure bright brown solid 14 (0.75 g, 79% yield): $^1$H NMR (400 MHz, DMSO-d$_6$) δ 12.18 (s, 1H), 6.80 (d, J=2.4 Hz, 1H), 6.65 (dd, J=9.1, 2.5 Hz, 1H), 6.54 (d, J=9.1 Hz, 1H), 3.74 (s, 3H), 3.05 (d, J=7.0 Hz, 2H), 2.68-2.66 (m, 2H), 2.49 (s, 3H), 2.08-2.05 (m, 2H); $^{13}$C NMR (100 MHz, DMSO-d$_6$) δ 180.80, 171.27, 156.46, 154.33, 153.35, 152.57, 128.95, 127.16, 119.80, 116.87, 109.78, 01.17, 55.91, 34.39, 27.32, 21.99, 14.22; HRMS [C$_{17}$H$_{17}$N$_4$O$_3$S$^+$] calcd. 357.1021, found 357.1034; HPLC purity 97.6%; Mp=210-211° C.

Synthesis of 6-methoxy-1-(2-(methylsulfone)-6,7-dihydro-5H-cyclopenta[d]pyrimidin-4-yl)quinoxaline-2,3(1H,4H)-dione (15). A mixture of 14 (500 mg, 1.4 mmol) and potassium peroxymonosulfate (0.65 g, 4.2 mmol) in water/MeOH (1:1 vol) was stirred at rt for 12 h and then the reaction mixture was diluted with water, filtered and dried under vacuum to give (0.5 g, 92.5%) of title compound 15 without further purification; $^1$H NMR (400 MHz, DMSO-d$_6$) δ 12.19 (s, 1H), 6.81 (d, J=2.0 Hz, 1H), 6.65-6.63 (m, 2H), 3.75 (s, 3H), 3.40 (s, 3H), 3.22 (s, 2H), 2.84 (s, 2H), 2.17 (s, 2H); $^{13}$C NMR (100 MHz, DMSO-d$_6$) δ 182.85, 165.17, 156.65, 154.15, 153.55, 152.80, 138.21, 127.36, 119.81, 117.21, 109.57, 101.23, 55.94, 34.54, 28.31, 22.25; HRMS [C$_{17}$H$_{17}$N$_4$O$_5$S$^+$] calcd. 389.0920, found 389.0927; Mp=178-179° C.

Synthesis of 6-methoxy-1-(2-methoxy-6,7-dihydro-5H-cyclopenta[d]pyrimidin-4-yl)quinoxaline-2,3(1H,4H)-dione (16). A mixture of 15 (100 mg, 0.25 mmol) and 5N sodium methoxide in methanol (2.2 mL) was stirred at rt for 48 h in closed seal tube. After completion of reaction, mixture was diluted with water, filtered and dried under vacuum to give off white solid 16 (50 mg, 57.4%); $^1$H NMR (400 MHz, DMSO-d$_6$) δ 12.16 (s, 1H), 6.79 (d, J=2.4 Hz, 1H), 6.63 (dd, J=9.1, 2.4 Hz, 1H), 6.57 (d, J=9.1 Hz, 1H), 3.89 (s, 3H), 3.73 (s, 3H), 3.02 (dd, J=13.6, 6.8 Hz, 2H), 2.63-2.57 (m, 2H), 2.07-2.03 (m, 2H); $^{13}$C NMR (100 MHz, DMSO-d$_6$) δ 182.87, 166.12, 156.44, 154.36, 153.29, 153.27, 127.11, 126.48, 119.80, 116.98, 109.81, 101.11, 55.90, 55.54, 34.44, 26.89, 22.31; HRMS [C$_{17}$H$_{17}$N$_4$O$_4$$^+$] calcd. 341.1250, found 341.1257; HPLC purity 98.3%; Mp=126-127° C.

Synthesis of 5-methoxy-1-(2-(methylthio)-6,7-dihydro-5H-cyclopenta[d]pyrimidin-4-yl)-1H-benzo[d]imidazol-2(3H)-one (18). Compound 8

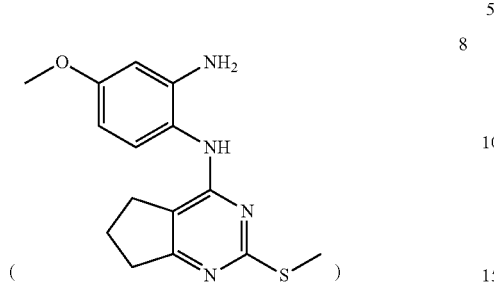

(200 mg, 0.06 mmol) dissolved in acetone (25 mL), powered K₂CO₃ (0.45 mg, 3.3 mmol) was added, and the mixture was cooled to 0° C. Ethyl chloroformate (0.4 mL, excess) was dropped slowly into the mixture, which was stirred at 0° C. for another 2 h. Then the mixture was diluted with water, extracted with CH$_2$Cl$_2$ (20 mL×2), and washed with brine solution, dried over Na$_2$SO$_4$ concentrated and crude 17 was dissolved in anhydrous in THF (5 mL), cooled to 0° C. and added sodium hydride (41 mg, 1.06 mmol), allowed to room temperature until completed. The mixture was poured into ice-water, and the solid product was removed by filtration, washed with water, and dried to give as an off white solid 18 (98 mg, 56%); $^1$H NMR (400 MHz, CDCl$_3$) δ 8.96 (bs, 1H), 7.40 (d, J=8.6 Hz, 1H), 6.69-6.66 (m, 2H), 3.82 (s, 3H), 3.06 (td, J=7.5, 4.1 Hz, 4H), 2.58 (s, 3H), 2.21-2.09 (m, 2H); $^{13}$C NMR (100 MHz, CDCl$_3$) δ 178.41, 169.49, 156.71, 153.04, 151.84, 129.49, 124.51, 122.25, 112.67, 107.79, 96.42, 55.91, 34.23, 29.50, 22.57, 14.34; HRMS [C$_{16}$H$_{17}$N$_4$O$_2$S$^+$] calcd. 329.1072, found 329.1076; HPLC purity 95%; Mp=167-168° C.

Synthesis of 1-(2-methyl-6,7-dihydro-5H-cyclopenta[d]pyrimidin-4-yl)-5-(trifluoromethoxy)-1H-benzo[d]imidazol-2-one (18a). Compound of N1-(2-methyl-6,7-dihydro-5H-cyclopenta[d]pyrimidin-4-yl)-4-(trifluoromethoxy)benzene-1,2-diamine (500 mg, 1.5 mmol) dissolved in acetone (20 mL), added powered K$_2$CO$_3$ (850 mg, 6.1 mmol), and the mixture was cooled to 0° C. Ethyl chloroformate (1.0 mL, excess) was dropped slowly into the mixture, which was stirred at 0° C. for another 2 h. Then the mixture was diluted with water, extracted with CH$_2$Cl$_2$ (20 mL×2) and washed with brine solution, dried over Na$_2$SO$_4$ concentrated and crude was dissolved in in anhydrous in THF (5 mL), cooled to 0° C. and added 60% sodium hydride (71 mg, 1.7 mmol), allowed to room temperature until completed. The mixture was poured into ice-water, and the solid product was removed by filtration, washed with water, and dried to give as an off-white solid 18a (180 mg, 43.6%); $^1$H NMR (400 MHz, DMSO-d$_6$) δ 11.55 (s, 1H), 7.44 (d, J=8.6 Hz, 1H), 7.15-6.97 (m, 2H), 3.03-2.89 (m, 4H), 2.61 (s, 3H), 2.09-1.98 (m, 2H); $^{13}$C NMR (100 MHz, DMSO-d$_6$) δ 179.19, 166.25, 152.26, 151.00, 144.15, 130.35, 127.77, 126.19, 121.93, 119.39, 114.37, 112.32, 103.53, 34.41, 29.15, 25.54, 22.32; HRMS [C$_{16}$H$_{14}$F$_3$N$_4$O$_2$$^+$] calcd. 351.1069, found 351.1080; HPLC purity 95.2%; Mp=136-137° C.

Synthesis of 5-methoxy-1-(2-(methylthio)-6,7-dihydro-5H-cyclopenta[d]pyrimidin-4-yl)-2-(2,3,4-trimethoxyphenyl)-1H-benzo[d]imidazole (19). A mixture of compound 8

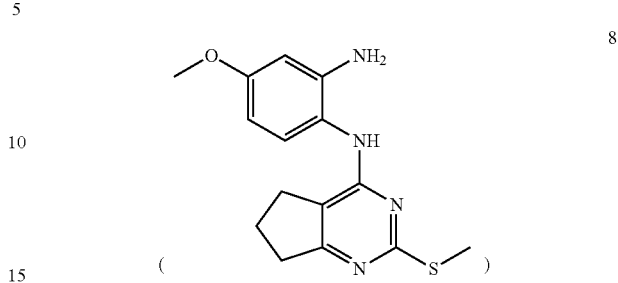

(200 mg, 0.6 mmol) and the corresponding 2,3,4-trimethoxybenzaldehyde (142 mg, 0.7 mmol) in EtOH (6 mL) was refluxed for 1 h. Then the solvent was evaporated under reduced pressure to give the crude imine, which was redissolved in CH$_2$Cl$_2$ (6 mL), followed by the sequential addition of iodine (75 mg, 0.45 mmol) and K$_2$CO$_3$ (115 mg, 0.8 mmol). The reaction mixture was stirred at room temperature upon completion of the reaction, it was quenched with 5% Na$_2$S$_2$O$_3$ (15 mL) and then extracted with CH$_2$Cl$_2$ (30 mL×2). The combined organic layer was washed with brine, dried over anhydrous Na$_2$SO$_4$, concentrated, and then purified through silica gel column chromatography to afford as an off white solid 19 (99 mg, 49.7%); $^1$H NMR (400 MHz, CDCl$_3$) δ 7.47 (d, J=8.6 Hz, 1H), 7.36 (d, J=1.9 Hz, 1H), 7.32 (d, J=8.9 Hz, 1H), 6.96 (dd, J=8.9, 2.1 Hz, 1H), 6.79 (d, J=8.7 Hz, 1H), 3.91 (s, 3H), 3.90 (s, 3H), 3.68 (s, 3H), 3.49 (s, 3H), 2.95 (t, J=7.4 Hz, 2H), 2.32 (s, 3H), 2.09-1.97 (m, 2H); $^{13}$C NMR (100 MHz, CDCl$_3$) δ 179.88, 171.57, 151.42, 141.66, 127.14, 123.45, 112.67, 107.85, 77.35, 77.04, 76.72, 61.19, 61.11, 56.22, 56.06, 34.46, 28.45, 23.01, 14.16; HRMS [C$_{25}$H$_{27}$N$_4$O$_4$S$^+$] calcd. 479.1753, found 479.1755; HPLC purity 95.8%; Mp=127-128° C.

Synthesis of 4-methoxy-N1-(2-methoxy-6,7-dihydro-5H-cyclopenta[d]pyrimidin-4-yl)benzene-1,2-diamine (20). A mixture of 15

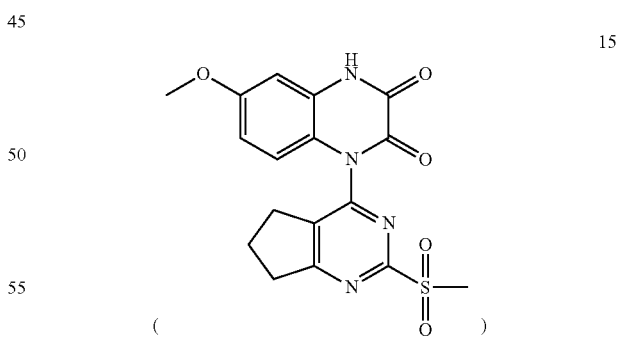

(100 mg, 0.25 mmol) and 5N sodium methoxide in methanol (3.0 mL) was stirred at 70° C. for 2 h in closed seal tube. After completion of reaction, mixture was diluted with water, filtered and dried under vacuum to give white solid 20 (60 mg, 81%); $^1$H NMR (400 MHz, DMSO-d$_6$) δ 7.98 (bs, 1H), 6.90 (d, J=2.8 Hz, 1H), 6.30 (d, J=9.1 Hz, 1H), 6.12 (dd, J=9.2, 2.5 Hz, 1H), 4.85 (bs, 2H), 3.68 (s, 3H), 3.67 (s, 3H), 2.66 (t, J=7.1 Hz, 2H), 2.55-2.50 (bs, 2H), 1.97-1.93 (m, 2H); $^{13}$C NMR (100 MHz, DMSO-d$_6$) δ 165.29, 160.13, 158.61, 146.06, 129.37, 117.54, 110.31, 101.93, 100.59, 55.24, 53.97, 33.96, 27.06, 21.92; HRMS [$C_{15}H_{19}N_4O_2^+$] calcd. 287.1508, found 287.1519; HPLC purity 98.2%; Mp=189-190° C.

Synthesis of N1-(5-methoxy-2-((2-(methylthio)-6,7-dihydro-5H-cyclopenta[d]pyrimidin-4-yl)amino)phenyl)-N2-methyloxalamide (21). To a stirred solution of compound 17

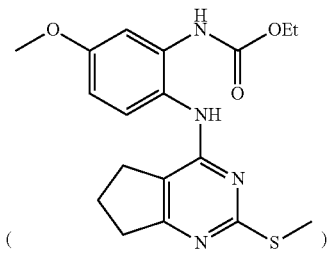

(0.2 g, 0.49 mmol) methyl amine in THF (2 mL, excess) was added at 0° C. The mixture was stirred at rt for 12 h in a sealed tube and monitored by TLC. After completion of reaction, mixture was diluted with water, filtered, and dried under vacuum to give off white solid 21 (100 mg, 52%); $^1$H NMR (400 MHz, DMSO-$d_6$) δ 9.96 (s, 1H), 9.02 (d, J=2.6 Hz, 1H), 8.59 (s, 1H), 7.55 (d, J=9.3 Hz, 1H), 7.27 (d, J=9.1 Hz, 1H), 6.81 (dd, J=8.9, 2.1 Hz, 1H), 3.77 (s, 3H), 2.77-2.73 (m, 2H), 2.69-2.66 (m, 5H), 2.27 (s, 3H), 2.03-1.99 (m, 2H); $^{13}$C NMR (100 MHz, DMSO-$d_6$) δ 172.75, 169.0, 160.44, 158.11, 157.77, 157.56, 133.51, 128.77, 123.46, 112.74, 110.72, 108.31, 55.77, 33.98, 27.28, 26.59, 21.61, 13.70; HRMS [$C_{18}H_{22}N_5O_3S^+$] calcd. 388.1443, found 388.1457; HPLC purity 99.2%; Mp=165-166° C.

Example 9: Biological Characterization of Cyclopentano-Pyrimidine Dihydroquinoxalinones (12a-12m, 12o-12., 5v, Etc.)

Biology. Cell culture and Reagents. Human melanoma cell lines A375 and M14; human breast cancer cell lines MDA-MB-231 and MDA-MB-453; human pancreatic cancer cell lines MIA Paca-2 and PANC-1; and prostate cancer cell lines PC-3 were purchased from American Type Culture Collection (ATCC, Manassas, VA). A375, M14, MDA-MB-231, MDA-MB-453, and MIA Paca-2 were cultured in Dulbecco's modified Eagle's medium (Corning, Manassas, VA) supplemented with 10% fetal bovine serum (FBS, Atlanta Biologicals, Lawrenceville, GA) and 1% antibiotic/antimycotic solution (Sigma-Aldrich, St. Louis, MO). MIA Paca-2 pancreatic cancer cells were cultured in media also supplemented with 2.5% horse serum. PANC-1 and PC-3 were cultured in RPMI 1640 medium (Gibco, Carlsbad, CA) supplemented with 10% FBS and 1% antibiotic/antimycotic mixture. Paclitaxel-resistant PC-3 cells (PC3/TxR) cells were developed by the sequential treatment with paclitaxel and maintained in the medium with 10 nM paclitaxel at 37° C. in a humidified atmosphere with 5% $CO_2$. For biological experiments, pyrimidine dihydroquinoxalinone derivatives were dissolved in DMSO to create 20 mM stock solutions and stored at −20° C. until use.

The compounds synthesized in Example 8 were tested for their cytotoxicity activity against a panel of cancer cell lines such as melanoma (A375, M14), breast (MDA-MB-231, MDA-MB-453), pancreatic (Mia PaCa-2, PANC-1), and prostate (PC3, PC3/TxR) cancers. Half-maximal inhibitory concentration values ($IC_{50}$) for cell growth inhibition are summarized in Table 6.

TABLE 6

Antiproliferative Potency of Pyrimidine Analogues of Example 8 Against Melanoma, Breast, Pancreatic and Prostate Cancer Cell lines

| | $IC_{50}$ (nM) | | | | | | | |
|---|---|---|---|---|---|---|---|---|
| | Melanoma Cancer | | Breast Cancer | | Pancreatic cancer | | Prostate cancer | |
| ID | A375 | M14 | MDA-MB-231 | MDA-MB-453 | Mia PaCa-2 | PANC-1 | PC3 | PC3/TxR |
| 10 | 3.4 ± 0.5 | 3.2 ± 0.5 | 4.3 ± 0.7 | 1.4 ± 0.6 | 3.9 ± 0.6 | 3.4 ± 0.6 | 2.4 ± 0.4 | 1.6 ± 0.2 |
| 11 | 84.9 ± 17.0 | 62.2 ± 10.8 | 190.7 ± 32 | 58.8 ± 16.3 | >1.25 μM | >1.25 μM | ND | ND |
| 12a | 646.5 ± 124.2 | 661.6 ± 126 | 1198 ± 346 | 687.6 ± 186 | >1.25 μM | >1.25 μM | ND | ND |
| 12b | 3.2 ± 0.5 | 5.3 ± 1.1 | 7.5 ± 1.5 | 3.4 ± 0.8 | 9.0 ± 1.3 | 9.4 ± 1.5 | 7.2 ± 1.2 | 4.7 ± 0.7 |
| 12c | 2.01 ± 0.4 | 1.7 ± 0.3 | 2.3 ± 0.5 | 1.4 ± 0.4 | 5.0 ± 0.7 | 5.5 ± 1.0 | 3.8 ± 0.6 | 2.3 ± 0.3 |
| 12d | 542.8 ± 111 | 574.3 ± 124 | 1858 ± 650 | 416.1 ± 107 | >1.25 μM | >1.25 μM | ND | ND |
| 12e | 13.6 ± 2.0 | 18.3 ± 3.7 | 25.8 ± 4.6 | 17.6 ± 4 | 44.4 ± 7.1 | 56.2 ± 9.0 | 23.9 ± 3.6 | 14.4 ± 2.2 |
| 12f | 436.1 ± 76 | 600.6 ± 117 | 689.6 ± 147 | 498.8 ± 126 | >1.25 μM | >1.25 μM | ND | ND |
| 12g | 82.2 ± 12.9 | 84.7 ± 17.6 | 118.9 ± 20.5 | 98.1 ± 23.3 | 507.5 ± 59.1 | 212.8 ± 47.6 | ND | ND |
| 12h | 5.7 ± 0.9 | 5.8 ± 1.2 | 8.4 ± 1.5 | 4.5 ± 1.2 | 15.5 ± 2.5 | 11.5 ± 2.3 | 8.2 ± 1.4 | 4.7 ± 0.7 |
| 12i | 22.0 ± 4.5 | 21.1 ± 4.1 | 36.9 ± 6.1 | 16.1 ± 4.7 | >1.25 μM | >1.25 μM | ND | ND |
| 12j | 1.4 ± 0.3 | 1.2 ± 0.3 | 2.2 ± 0.4 | 1.1 ± 0.3 | 3.9 ± 0.6 | 3.4 ± 0.6 | 0.6 ± 0.0 | 0.2 ± 0.0 |
| 12k | 1.2 ± 0.2 | 0.7 ± 0.1 | 2.2 ± 1.5 | 0.9 ± 0.2 | 2.9 ± 0.5 | 2.8 ± 0.5 | 0.5 ± 0.1 | 0.2 ± 0.0 |
| 12l | 3.3 ± 0.5 | 2.6 ± 0.4 | 4.9 ± 0.8 | 2.9 ± 0.6 | 7.3 ± 1.2 | 10.7 ± 2.3 | 6.3 ± 0.8 | 4.8 ± 0.7 |
| 12m | 8.6 ± 0.2 | 7.0 ± 1.0 | 8.6 ± 1.2 | 6.4 ± 1.6 | 23.6 ± 3.5 | 43.1 ± 8.2 | 14.8 ± 1.8 | 15 ± 1.6 |
| 5v | 1.6 ± 0.3 | 1.5 ± 0.3 | 2.6 ± 0.5 | 1.3 ± 0.5 | 3.4 ± 0.4 | 3.7 ± 0.7 | 1.7 ± 0.1 | 0.8 ± 0.1 |
| 12o | 43.1 ± 6.9 | 41.9 ± 5.6 | 75.8 ± 13.1 | 34.9 ± 6.4 | 83.5 ± 12.8 | 42.4 ± 8.5 | ND | ND |
| 12p | ND | ND | 422.7 ± 110 | ND | >1.25 μM | >1.2 μM | ND | ND |
| 12q | 19.0 ± 2.9 | 21.8 ± 4.5 | 25.9 ± 4.9 | 13.5 ± 3.3 | 34.3 ± 5.3 | ND | ND | ND |
| 14 | ND | ND | ND | ND | ND | ND | ND | ND |
| 15 | >3 μM | >3 μM | >3 μM | >3 μM | ND | ND | ND | ND |
| 16 | >3 μM | >3 μM | >3 μM | >3 μM | >1.25 μM | >1.25 μM | ND | ND |
| 18 | 1182 ± 339 | 1111 ± 306 | 1340 ± 409 | 2184 ± 861 | >1.25 μM | >1.25 μM | ND | ND |

TABLE 6-continued

Antiproliferative Potency of Pyrimidine Analogues of Example 8 Against
Melanoma, Breast, Pancreatic and Prostate Cancer Cell lines

| | IC$_{50}$ (nM) | | | | | | | |
|---|---|---|---|---|---|---|---|---|
| | Melanoma Cancer | | Breast Cancer | | Pancreatic cancer | | Prostate cancer | |
| ID | A375 | M14 | MDA-MB-231 | MDA-MB-453 | Mia PaCa-2 | PANC-1 | PC3 | PC3/TxR |
| 18a | 238.1 ± 126 | 1078.0 ± 682 | 919.4 ± 722 | ND | 666.7 ± 651.7 | 164.4 ± 98.2 | ND | ND |
| 19 | >3 µM | >3 µM | >3 µM | >3 µM | >1.25 MM | >1.25 µM | ND | ND |
| 20 | ND | ND | ND | ND | ND | ND | ND | ND |
| 21 | ND | ND | ND | ND | ND | ND | ND | ND |

The study revealed that the size of the heteroatom has significant impact on the cytotoxic potency with decreasing size of the heteroatom tending to increase the potency. For example, the thioether 10 (IC$_{50}$≈3.4±0.5 nM, A375 cell lines, Table 6), ether 12b (IC$_{50}$≈3.2±0.5 nM), and secondary amine 12k (IC$_{50}$≈1.2±0.2 nM) were relatively small and possessed single digit nM potencies. Substitution of cyclic derivatives such as N-methyl piperazine 12d (IC$_{50}$≈542.8±111.0 nM), morpholine 12e (IC$_{50}$≈13.6±2.0 nM, Table 6), piperidine 12f (IC$_{50}$ 436.1±76.2 nM), and pyrrolidine 12g (IC$_{50}$≈82.1±12.9 nM) had relatively low in potency except the morpholine derivative which showed moderate to high potency. An aromatic heterocycle, i.e., imidazole 12h (IC$_{50}$≈5.7±0.9 nM) showed good potency. The tertiary amine 12i (IC$_{50}$≈22.6±4.5 nM) derivative showed moderate potency. The results obtained with compound 12k paved the way to study the pharmacological potency of secondary amines such as N-ethyl 5v (IC$_{50}$≈1.6±0.3 nM) and N-cyclopropyl 12j (IC$_{50}$≈1.4±0.3 nM) which were high potency. Adding on an extra hydrogen bonding donor such as a —OH group in the ethanolamine moiety of 12m (IC$_{50}$≈8.6±0.2 nM) decreased potency slightly when compared with 5v (the ethylamine version) and the isothiocyanate derivative 12l (IC$_{50}$≈3.3±0.5 nM) has also shown very good potency. The unprotected phenolic OH at C2 position on the pyrimidine (2-Py) ring 12a (IC$_{50}$≈646.5±124.2 nM) drastically reduced potency as do other electron withdrawing groups such as sulfone derivative 11 (IC$_{50}$≈84.9±17 nM). On the other hand, a free amine 12c at the same position resulted in improved potency (IC$_{50}$≈2.01±0.4 nM).

Compounds 12o-p (i.e., OCF$_3$, OBn and OH) as replacements of the OMe group had a decreased potency. A general trend with the aryl substituent was that 4-OMe compounds had the highest affinity, those with 4-OCF$_3$ (12o, IC$_{50}$≈43.1±6.9), OH (12q, IC$_{50}$≈19.0±2.9, Table 6) were intermediate in potency, and compounds with OBn (12p) substitution had the least potency. In addition, C-ring structural modifications resulted no potency improvements. Both closed ring systems, such as the benzimidazole 19 (IC$_{50}$>3 µM) and the 2-imidazolone derivatives 18a-b (IC$_{50}$≈1182±339, 238.1±126.5 nM), respectively, the various quinoxalinedione derivatives 14, 15, 16 (IC$_{50}$>3 µM), and the open systems such as amine 20 (Table 6) and amide 21 were negatively impacted leading to little to no cytotoxic activity.

Pharmacokinetic Evaluation.

Figure 27:
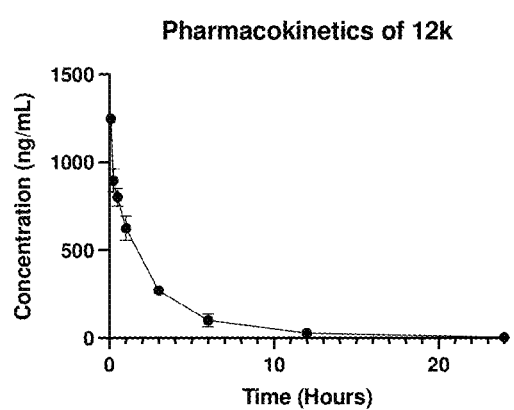
FIG. 27 illustrates the plasma concentration-time profile (mean±SEM) of 12k in mice (n=3) after intravenous administration of 4 mg/kg.

Female NSG mice at 7 to 9 weeks of age were used in pharmacokinetic studies. Mice received a single dose of 4 mg/kg 12k intravenously (50% PEG300:50% saline) or 10 mg/kg orally (90% PEG300:10% saline). Blood of animals (n=3) was collected in heparinized tubes via terminal intracardiac blood collection at predefined time points (0.08, 0.25, 0.5, 1, 3, 6, 12, 24 h) and plasma was immediately separated by centrifugation (10,000 rpm for 10 min at 4° C.) and stored at −80° C. until analysis. The concentration-time curve from this experiment is shown in FIG. 27.

Metabolic Stability of Compounds 12j, 12k, and 5v in human and mouse liver microsomes. Liver microsomal incubations (1 mg microsomal protein/mL) with human (Corning Life Sciences, Oneonta, NY) and mouse microsomes (Sekisui XenoTech, Kansas City, KS) were assessed for compounds 12j, 12k, 5v, and verapamil (1 µg/mL), in presence of NADPH (Acros Organics, Fair Lawn, NJ) (1 mM). At predefined times (0, 5, 15, and 60 min), aliquots (50 µL) were removed, and the reaction was quenched by addition of 200 µL ice-cold methanol containing internal standard. Samples were briefly vortexed and centrifuged at 3200×g for 5 min at 4° C. Supernatants were collected and analyzed by LC-MS/MS. In vitro half-life (t$_{1/2}$) and intrinsic clearance (CL$_{int}$) were assessed per standard procedures. Obach, R. S., *Cytochrome P450-catalyzed metabolism of ezlopitant alkene (CJ-12,458), a pharmacologically active metabolite of ezlopitant: enzyme kinetics and mechanism of an alkene hydration reaction.* Drug metabolism and disposition, 2001, 29(7), 1057-1067.

The in vitro microsomal stability of compounds 12j, 12k, and 5v in human and mouse liver microsomes were determined and the results are summarized in Table 7. Compounds 12j and 5v exhibited limited stability, and in the mouse microsomal preparations, compound 12k showed good stability in both species, with half-lives exceeding 300 min.

TABLE 7

In vitro metabolic stability of compounds 12j,
12k, and 5v in human and mouse liver microsomes

| ID | Human microsomes | | Mouse microsomes | |
|---|---|---|---|---|
| | $t_{1/2}$ (min) | $CL_{int}$ (µL/min/mg) | $t_{1/2}$ (min) | $CL_{int}$ (µL/min/mg) |
| 12j | 80.3 (9.22) | 8.68 (9.31) | 13.6 (4.09) | 51.0 (4.19) |
| 12k | >300* | <2.31* | >300* | <2.31* |
| 5v | 24.7 (1.86) | 28.1 (1.88) | 6.33 (0.608) | 109 (0.607) |
| Verapamil | 7.73 (2.97) | 89.6 (2.94) | 7.61 (6.23) | 91.3 (18.7) |

Compound 12k was carried forward into in vivo studies that are graphically illustrated in FIG. 28. The in vivo pharmacokinetic study for compound 12k in NSG mice after intravenous 4 mg/kg (FIG. 27) or oral administration 10 mg/kg. The in vivo half-life was 238 minutes (3.97 hr). Oral bioavailability remained limited at 2.02% as demonstrated in Table 8.

TABLE 8

Pharmacokinetic Parameters of Compound 12k after
Intravenous and Oral Administration to NSG mice $^a$

| parameters | intravenous (4 mg/kg) | oral (10 mg/kg) |
|---|---|---|
| $C_{max}$ (ng/ml) | 1247 | 78.3 |
| $t_{max}$ (min) | 5.0 | 10.0 |
| AUC (ng/mL · min) | 173476 | 8161 |
| $t_{1/2}$ (hr) | 238 | 358 |
| bioavailability (%) | | 2.02 |

$^a$ Data are presented as the mean (% CV)

Cytotoxicity Assay. Cancer cells were seeded at a concentration of 3,500-5,000 cells per well in a 96-well plate. After 24 hours, the media was replaced with test compounds in fresh media at concentrations ranging from 0.1 nmol/L to 3 µmol/L in A375, M14, MDA-MB-231, and MDA-MB-453 cancer cells. A concentration range of 1 nmol/L to 1.25 µmol/L was used for Mia Paca-2, PANC-1, PC3, and PC3/TxR cancer cells. Each experiment consisted of four replicates. Cancer cells were treated for 72 h before adding the MTS reagent (Promega, Madison, WI) to each well and incubating in the dark for 1-2 h at 37° C., depending on the cell type. A microplate reader was used to record the absorbance at 490 nm (BioTek Instruments Inc., Winooski, VT). $IC_{50}$ values were calculated by GraphPad Prism software (San Diego, CA).

In vivo subcutaneous PC-3/TxR xenograft model. Compound 12k antitumor efficacy in vivo in a subcutaneous human prostate cancer drug-resistant cell line PC-3/TxR xenograft model in mice was evaluated. All animal procedures were performed following the protocols approved by the Institutional Animal Care and Use Committee (IACUC) at UTHSC (protocol #20-0166). Male Nod-Skid-Gamma (NSG) mice (n=8 per group) at 7-10 weeks of age were housed under 12/12 lighting in the animal facility. PC-3/TxR prostate cancer tumors were tested *mycoplasma* free and verified for in vivo resistance to paclitaxel prior to the study. $3 \times 10^6$ cells were suspended in 75 µL of HBSS and Matrigel mixture (2:1) and subcutaneously injected to the right flank of each mouse using the 28G ½ insulin syringe. Mice were anesthetized at 5% isoflurane and maintained under 2% isoflurane while performing the cell injection. Mice were randomly divided into groups of control, paclitaxel treatment, and 12k treatment when the average tumor size reached 70-100 mm$^3$ around two weeks after inoculation. Paclitaxel was dissolved in ethanol first and diluted in Cremophor EL/Saline solution (1:1:18 ratio). Compound 12k was dissolved in PEG 300 and diluted with saline solution (1:4 ratio) before use. Both paclitaxel (10 mg/kg 1 dose/week) and compound 12k (2.5 mg/kg, 2 doses/week) were administered intravenously (i.v.) until the endpoint. Tumor volumes were measured twice per week with the caliper and calculated by the equation: volume=0.5× (length×width 2). All animals were euthanized at the endpoint after 2 weeks of treatment. Tumors were excised and recorded for weight and size ex vivo, and imaged in petri dishes as size reference.

Figure 28A:
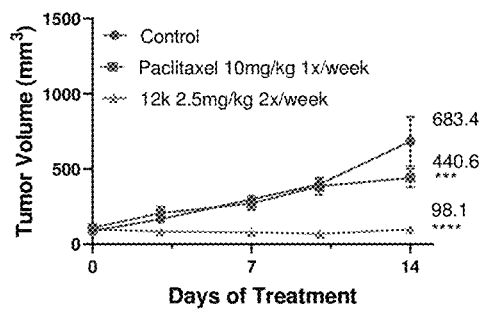
FIGS. 28A-E illustrate the antitumor efficacy of compound 12k against growth of PC3/TxR xenograft tumors in NSG male mice. PC3/TxR cells ($3×10^6$ cells/mice) were subcutaneously inoculated into the right flank of NSG mice (n=8).
Figure 28B:
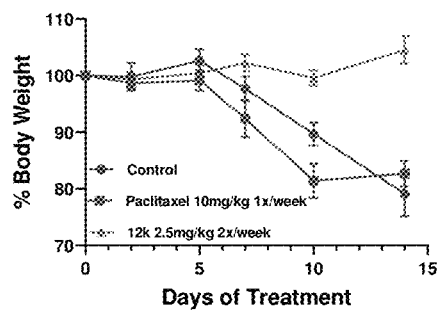
Figure 28C:
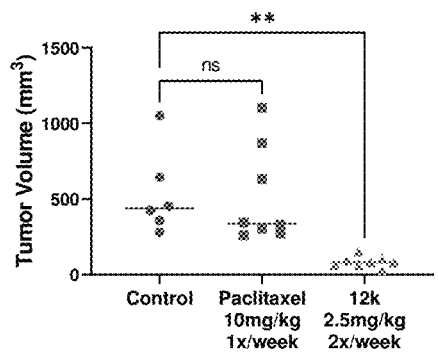
Figure 28D:
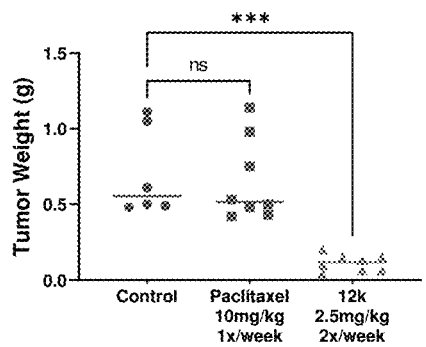
Figure 28E:
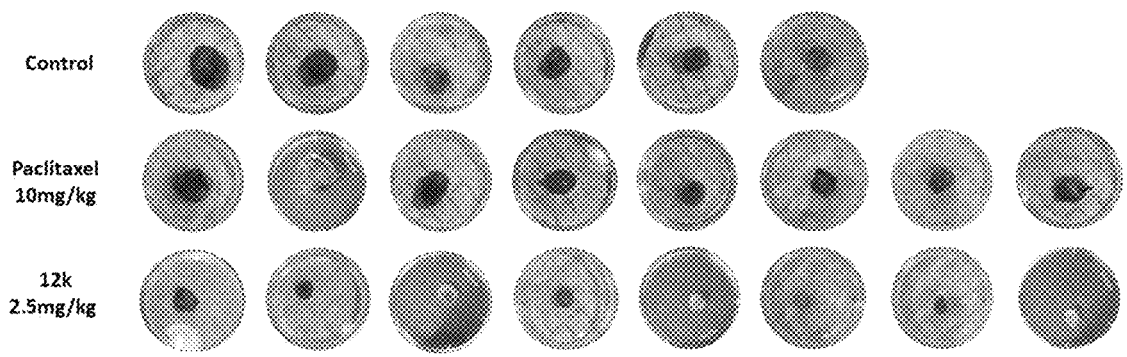

As illustrated in FIGS. 28A-E, compound 12k significantly inhibited tumor growth in the treatment group compared with paclitaxel treatment group and control group. FIG. 28A illustrates the tumor growth curve for the control, paclitaxel, and compound 12k treated groups (two-way ANOVA followed by multiple comparisons test). All mice were stable and there was no significant weight loss in the compound 12k treatment, indicating the treatment dose of 2.5 mg/kg twice per week was well tolerated, while both the control group and paclitaxel treated group experienced steady weight loss until the end of the study, as illustrated in FIG. 28B. At the endpoint of the study, all mice were euthanized and tumors and major organs were harvested. Tumors were weighed and tumor volume was measured ex vivo. Compared to the control, treatment with compound 12k inhibited the tumor growth in volume by approximately 85.6% (FIG. 28C) and the tumor weight was reduced by 84.5% (FIG. 28D), respectively. A higher dose of paclitaxel showed an insignificant tumor weight reduction. The results demonstrated that compound 12k was able to attenuate the progression of prostate cancer tumors and overcome taxane resistance at a low and safe, but potent dose in vivo. FIG. 28E is the comparison of isolated tumors in 35 mm petri dishes for the control, paclitaxel, and compound 12k treatment groups. The data were presented as the mean+/−SEM. (FIGS. 28C-D) Significant differences between groups were determined by one-way ANOVA, followed by Dunnett's multiple comparison test (p<0.005, *p<0.0005, ****p<0.0001).

Example 10: 5v Inhibits of Tubulin Polymerization,
Taxol-Resistant Melanoma Growth and
Spontaneous Metastasis X-ray crystal structure and tubulin polymerization assay confirmed that 5v is a colchicine binding site inhibitor (CBSI) that could disrupt the microtubule dynamics and interfere with microtubule assembly. In vitro studies showed that 5v possessed sub-nanomolar anti-proliferative activities against a panel of cancer cell lines and some of their paclitaxel-resistant cell lines (TxR). 5v inhibited the colony formation and migration of A375/TxR cells, and induced apoptosis and G2/M phase arrest of A375/TxR cells. The following in vivo studies confirmed that 5v strongly inhibited the tumor growth of A375/TxR melanoma xenografts and induced necrosis, anti-angiogenesis, and apoptosis in tumors. Moreover, 5v treatment significantly inhibited the spontaneous axillary lymph node, lung, and liver metastases originating from subcutaneous tumors and had no obvious toxicity to major organs of mice, demonstrating the therapeutic potential of 5v as a novel anticancer agent for cancer therapy.

Microtubules are the key elements of polymerized α- and β-tubulin heterodimers arranged in a head-to-tail manner, in which the α-subunit in one dimer is binding with the β-subunit in the next dimer. The non-covalent binding of these subunits forms the protofilament. The protofilaments are assembled longitudinally into a cylindrical structure, usually, there are 13 pieces, constituting 22 nm microtubules. The microtubules undergo two stages of alternation, growth and shrinkage, a behavior called dynamic instability. The continuous alterations of slow polymerization and fast depolymerization dynamics make microtubules play a fundamental and essential role in many cellular processes including cell division, cell structure maintenance, intracellular transport, and movement regulation.

Microtubule-targeting agents (MTAs) affect microtubule dynamics by binding to the microtubules through different mechanisms. In the intercellular phase, MTAs have a great influence on the microtubules that are involved in the intracellular transport of proteins, vesicles and organelles, and interphase cytoskeleton. In mitosis, the structure required to separate duplicated chromosomes, that is, the mitotic spindle composed of the cytoskeleton of rearranged microtubules, is also greatly affected by MTAs. The destruction of microtubule dynamics causes the cell cycle to stagnate in the G2/M phase, leading to mitotic arrest. Given the important role of microtubules in cell growth, microtubules have become attractive targets for the development of anticancer drugs.

Colchicine-binding site inhibitors (CBSIs) target the binding domain of microtubules located at the interface between the α and β subunits of tubulin heterodimers. Compared to other MTAs or colchicine itself, CBSIs have several advantages, including overcoming ABC-transporter-mediated multidrug resistance and β3-tubulin overexpression, and vascular disrupting activity. Several of CBSIs are currently in the clinical trials, such as CA-4P, OXi4503, ABT-751, and 17ya, however, there are currently no FDA-approved CBSI available for cancer therapy mainly due to undesired adverse events (e.g. haematological toxicities, neurological toxicity), lack of bioavailability or low aqueous solubility. Therefore, extensive efforts are still needed to find more CBSIs that can avoid multidrug resistance (MDR) or are non-MDR substrates, and these promising CBSIs should have a wider therapeutic window, excellent pharmacokinetic/pharmacodynamic properties, and better efficacies.

All CBSIs that we have generated had different chemical structures, but they were potent and were able to overcome MDR, and some of them even had good bioavailability. Among them, CBSIs of this invention having pyridopyrimidine and dihydroquinoxalinone structures, represented by 5m and 5t showed the most potent anti-proliferative activities against a panel of human cancer cell lines, including melanoma, lung, and breast cancer, with single-digit $IC_{50}$ values (Example 9). And the in vivo studies confirmed the potent efficacies of 5m (4 mg/kg) and 5t (5 mg/kg) against tumor growth and spontaneous metastasis of subcutaneous melanoma to lung and liver using paclitaxel-resistant A375/TxR xenograft model (e.g., FIGS. 10 and 11). We hypothesized that by combining the structures of 5m and 5t we could acquire a new dihydroquinoxalinone analogue that would be more efficacious than either 5m or 5t Herein, in this report, we designed and synthesized a new analogue, 5v, and evaluated its potency in vitro and in vivo. Through X-ray crystal structure study and a panel of in vitro techniques, we confirmed that 5v is a potent CBSI that could inhibit cancer cell growth at sub-nanomolar concentration ranges. We also confirmed the in vivo efficacy of 5v in inhibiting tumor growth and spontaneous metastasis using A375/TxR xenograft model without causing toxicity to major organs in mice. Together, the results we report here demonstrate that 5v is a promising CBSI with comparable antiproliferative activity to paclitaxel, and can be used for the treatment of paclitaxel-sensitive or -resistant cancers. Further, 5v possesses the same biological profile as other CBSI's of this invention that are able to overcome 17ya resistance. Hence, it is reasonable to expect that 5v can also overcome 17ya resistance.

Cell Culture: Colchicine, paclitaxel, and Azixa

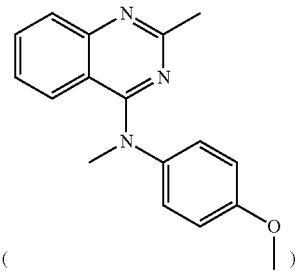 [SMILES: COc1ccc(N(C)c2nc(C)nc3ccccc23)cc1]

were purchased from Sigma-Aldrich, LC Laboratories, and APExBIO Technology LLC, respectively. Human melanoma cell lines A375 and RPMI-7951, and human breast cancer cell lines MDA-MB-231, MDA-MB-453, and MDA-MB-468 were purchased from the American Type Culture Collection (ATCC). Melanoma cell line M14 and M14 multi-drug resistant daughter line M14/LCC6MDR1 are gifts from Dr. Robert Clarke of Georgetown University. Prostate cancer cell lines PC-3, PC-3/TxR, DU-145, and DU145/TxR are gifts from Dr. Evan Keller from the University of Michigan. Melanoma and breast cancer cells were cultured in Dulbecco's modified Eagle medium (Corning) supplemented with 10% fetal bovine serum (FBS, Atlanta Biologicals) and 1% antibiotic-antimycotic solution (Sigma-Aldrich). Paclitaxel-resistant A375/TxR and MDA-MB-231/TxR cells were produced by culturing in medium containing paclitaxel gradually and continuously. All the cells were cultured at 37° C. in a 5% $CO_2$ atmosphere. A375/TxR and MDA-MB-231/TxR cells were maintained in medium containing 100 nM paclitaxel. PC-3/TxR and DU-145/TxR cells were stored in medium containing 10 nM paclitaxel or docetaxel, respectively. Taxanes were removed from the culture medium one week before the experiment.

Cell proliferation inhibition assay: The cell proliferation inhibitory effects of tested compounds were first determined through MTS assay as previously described. In short, 3000 to 7500 cells were added to a 96-well cell culture plate followed by the treatment of the test compounds (0.1 nM to 3 μM) in quadruplicate after seeding and overnight incubation. After 72 hours of treatment, MTS (Promega) was added to the wells and the absorbance was measured at 590 nm after incubating for 1.5 to 2 h. The $IC_{50}$ values were calculated by GraphPad Prism 8 (GraphPad Software). The colony formation inhibition of 5v was assayed on A375/TxR cells as described before. Briefly, A375/TxR cells (1000 cells/well) were treated with growth medium containing 0.5 nM, 1 nM, or 2 nM of 5v and incubated for over 7 days (the incubation medium was changed every 3 days). After fixing and staining with 0.5% crystal violet, the cell colonies were quantified by the Hybrid Counting module of the Keyence BZ-X700 microscope. The assay was performed in triplicate.

Tubulin polymerization inhibitory assay: In vitro tubulin polymerization assay was carried out according to the manufacturers' instructions (Cytoskeleton). Briefly, 10 μM of 5v was added into tubulin protein (3 mg/mL, purity>99%), and the mixture was transferred into a microplate reader and incubated at 37° C. The absorbance of the mixture was recorded at 350 nm every 30 s for 1 h. Colchicine and paclitaxel were used as positive controls. The immunofluorescence staining of α-tubulin in 5v treated A375/TxR cells was performed as previously described. In brief, A375/TxR cells seeded on glass coverslips were treated with 2 nM of colchicine, 2 nM of paclitaxel, 1 nM of 5v, or 2 nM of 5v for 24 h. Then the cells were incubated with α-tubulin antibody (Thermo Scientific, #62240) and subsequent Alexa Fluor 647 conjugated goat anti-mouse IgG (Molecular Probes) after fix and permeabilization. The stained microtubules were observed and imaged with a Keyence BZ-X700 microscope. The assay was carried out in duplicate.

X-ray crystallography: was performed as described Example 5 to determine the crystal structures of 5m, 12e, 12j, 12k, and 5v, as shown in FIG. 26.

Scratch-wound assay: The anti-migration effect of 5v was determined by a scratch-wound assay using an IncuCyte S3 live-cell imager as previously reported. After overnight incubation, the monolayers of A375/TxR cells were scratched by a WoundMaker (Essen BioScience) and the cells were treated with 5v (0.5 nM, 1 nM, 2 nM, and 5 nM) for 48 h. The wounds were imaged every 2 h by IncuCyte and the relative wound density was calculated by IncuCyte Scratch Wound Software Module. The assay was performed in quadruplicate.

Flow cytometric analysis of the cell cycle distribution and cell apoptosis: The cell cycle distribution of A375/TxR treated with 1 nM, 2 nM, and 5 nM 5v for 24 h was determined by propidium iodide staining after fix in ice-cold 70% ethanol overnight and incubation with 100 μg/mL RNase A for 1 h. Then the distribution of cell cycle was analyzed by a ZE5 Cell Analyzer (Bio-Rad) in the University of Tennessee Health Science Center (UTHSC) Flow Cytometry and Cell Sorting core and the results were processed by ModFit LT software (Verity Software House). The cell apoptosis of A375/TxR cells with the same treatments of cell cycle analysis was determined by a FITC Annexin V apoptosis detection kit (eBioscience) as previously described. Data were analyzed by FlowJo software (Becton, Dickinson, and Co.).

In vivo antitumor study: All animal studies were approved by the UTHSC Animal Care and Use Committee (ACUC) and performed according to the rules of the NIH Principles of Laboratory Animal Care under a protocol (protocol #17-056). NOD scid gamma (NSG) mice (5-6 weeks old) purchased from Jackson Laboratories were kept in a controlled animal facility with a 12:12 h light-dark cycle. The tolerability of 5v was tested by intraperitoneal injection (IP) or intravenous injection (IV) using 5 mg/kg or 10 mg/kg in NSG mice daily for at least 5 consecutive days. For IP groups, 3 NSG mice were used in each group. And for IV groups, 4 NSG mice were included in each group. The physical activity, breathing, feeding, fur condition, and body weight of the mice were observed daily to monitor the possible signs of toxicity. For the xenograft model, $2\times10^6$ A375/TxR cells suspended in the FBS and phenol red-free medium and Matrigel (50%/50%) were inoculated subcutaneously into the right flank of the NSG mice. When the tumors grew to 100 $mm^3$, the mice were randomly divided into 4 groups (6 mice in each group): vehicle (DMSO: PEG300:Tween 80:saline=2:20:5:73), 5v (2 mg/kg), 5v (4 mg/kg) and paclitaxel (4 mg/kg) treatment groups. 5v and paclitaxel were given to mice twice a week intravenously for 3 consecutive weeks. Tumor volume calculated by the formula volume=($width^2\times length$)/2 and the body weight of mice were measured 2 times a week. The study was terminated when the tumor volume in the vehicle group exceeded 1500 $mm^3$. Mice were euthanized and the tumors and major organs were quickly dissected and fixed in 10% buffered formalin for further experiment.

Histology and immunohistochemistry (IHC) analysis: Fixed tumor tissues and major organs (lung, liver, kidney, heart, and spleen) were embedded in paraffin and sectioned with a thickness of 4 m by UTHSC Research Histology Core. Hematoxylin-eosin (H&E) staining of major organs was carried out on all tumors and major organs for histology examination. Representative images were acquired by the Keyence BZ-X700 microscope. IHC staining and anti-human mitochondria staining were performed with primary antibodies including rabbit anti-Ki67 (1:400, #9027, Cell Signaling Technology), rabbit anti-CD31 (1:100, #77699, CST), rabbit anti-cleaved caspase-3 (1:200, #9661, CST) and mouse anti-human-specific mitochondria (1:1000, #ab92824, Abcam) as described previously. IHC slides were imaged by Keyence BZ-X700 microscope, and quantification of Ki67, CD31, cleaved caspase-3, and human-mitochondria stained area was quantified by 7 or 8 representative fields per group via IHC Profiler module in ImageJ.

Statistical analysis: We used one-way ANOVA followed by pairwise, two-tailed Student t-tests or Dunnett multiple comparison test for analysis of independent groups for the in vitro assays. Two-way ANOVA followed by Dunnett multiple comparison tests was used to compare the treatment group with the control group for the in vivo xenograft model. Significance levels are expressed as *, $P<0.05$; , $P<0.01$; *, $P<0.001$; ****, $P<0.0001$.

5v (synthesized as described in Example 4) targeted colchicine-binding site and inhibited tubulin polymerization: Based on the X-ray crystal structures of 5m and 5t (FIG. 6E-6G), we found that the large pocket near the pyrimidine B ring could accommodate both ethylamine moiety and saturated cycloalkane. Thus, 5v was synthesized according to the procedure in Example 4 for 5m and 5t which were proven to be potent tubulin polymerization inhibitors targeting the colchicine-binding site. To determine the effect of 5v on microtubules, we first characterized the molecular interactions between 5v and the colchicine-binding site (FIG. 26E).

To confirm the tubulin polymerization inhibition effects of 5v on the microtubule network, the tubulin polymerization assay was performed in vitro. After adding the DMSO into the tubulin mixture at 37° C., the control group showed an increase of absorbance at 340 nm within 40 min due to the tubulin assembly and stabilized at A340 of 0.3 (FIG. 29A). Paclitaxel induced rapid tubulin polymerization within 20 min as expected and stabilized the tubulin assembly at A340 of approximately 0.4. Similar to the effect of colchicine, which is a known tubulin polymerization inhibitor, 5v inhibited and stabilized the tubulin assembly at A340 of approximately 0.05 in vitro, suggesting that 5v is a tubulin polymerization inhibitor. We also characterized the effect of 5v on the microtubule system using A375/TxR cells. Since A375/TxR cells are a paclitaxel-resistant subline of A375 cells and were reported to have an overexpression of p-glycoprotein (P-gp), and colchicine and paclitaxel are the substrates of P-gp, 2 nM of colchicine or paclitaxel treated A375/TxR cells showed similar intact microtubule network either in interphase or mitotic phase as the untreated control group (FIG. 29B). However, in the single-digit nanomolar concentration, 5v disrupted the organization of intact microtubules and induced disorganized and diffused microtubules. Even at the concentration of 1 nM, 5v could induce the formation of multipolar spindles (FIG. 29B). While 2 nM 5v seemed to inhibit all the A375/TxR cells going to the mitotic phase, and we could not find a mitotic cell under the microscope (FIG. 29B).

Figure 30A:
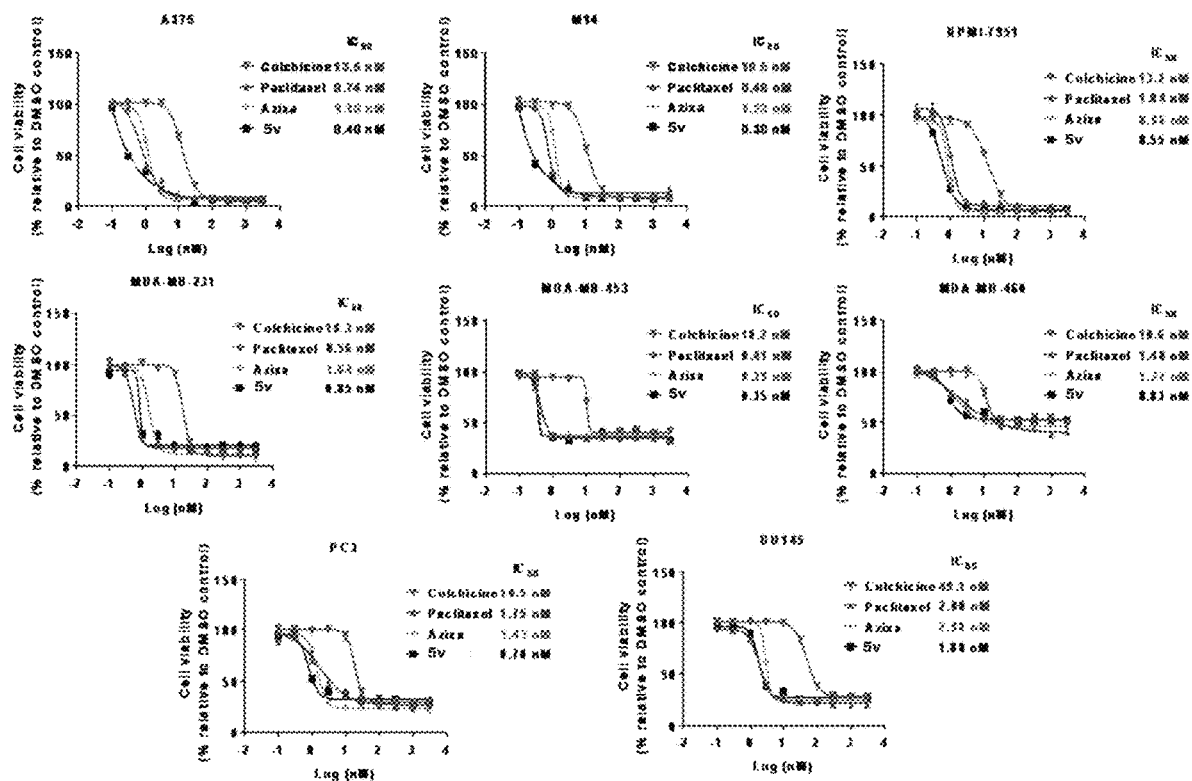
FIGS. 30A-C illustrates that 5v exhibited growth inhibitory effects on a panel of Taxol-sensitive and Taxol-resistant cancer cells.
Figure 30B:
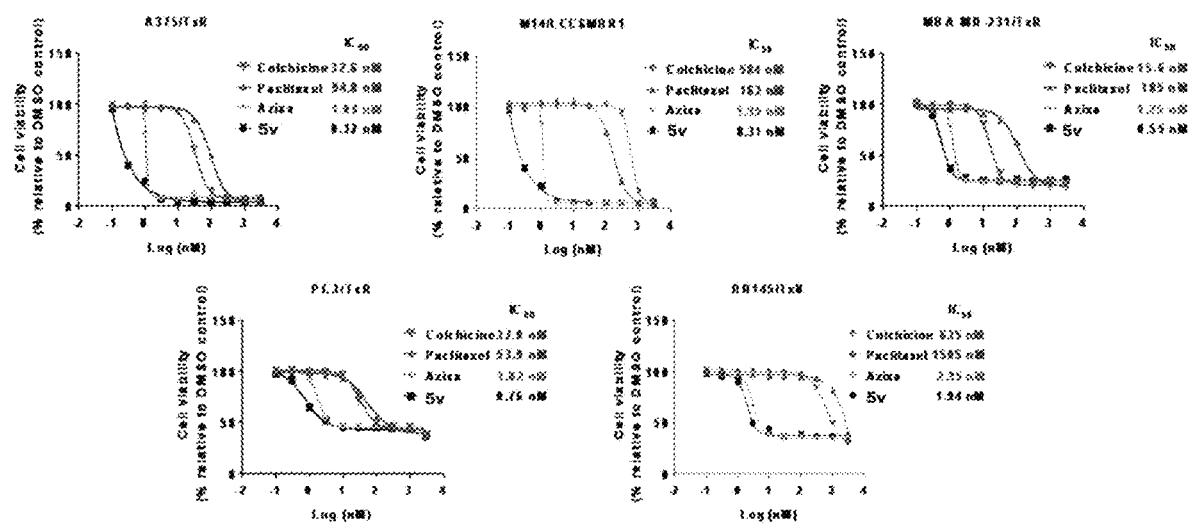
Figure 30C:
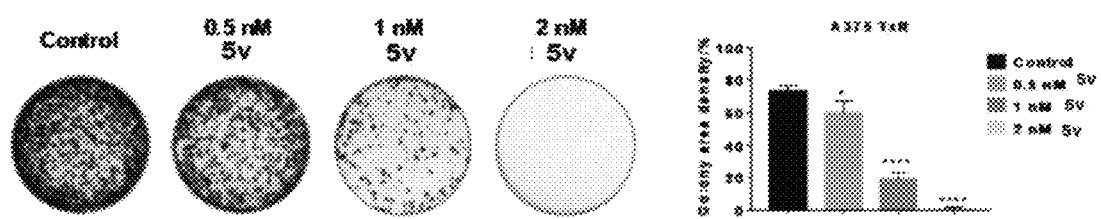

The anti-proliferative effect of 5v on paclitaxel-sensitive and paclitaxel-resistant cancers cell lines: The growth inhibitory effect of 5v was first evaluated on a panel of human cancer cell lines, including melanoma cell lines A375, M14, and RPMI-7951, breast cancer cell lines MDA-MB-231, MDA-MB-453 and MDA-MB-468, and prostate cancer cell lines PC3 and DU145 as shown in FIG. 30A. We used colchicine, paclitaxel, and Azixa (N-(4-methoxyphenyl)-N,2-dimethylquinazolin-4-amine), which is currently in clinical trials, as controls. 5v showed very high anti-proliferative efficacy on all cancer cell lines tested with an average $IC_{50}$ value of 0.5 nM. Its cytotoxic effect was stronger than colchicine and Azixa and was comparable to paclitaxel, which is a cytotoxic anticancer drug used to treat solid tumors. Then we further determined the efficacy of 5v on paclitaxel-resistant cancer cell lines (A375/TxR, M14/LCC6MDR1, MDA-MB-231/TxR, PC3/TxR, and DU145/TxR). While the potency of colchicine or paclitaxel is limited, 5v still maintained highly efficacious cytotoxicity in inhibiting the growth of all paclitaxel-resistant cancer cells tested with $IC_{50}$ value at sub-nanomolar level, and it was more potent than Azixa (FIG. 30B). Altogether, our results showed that 5v could inhibit the growth of all paclitaxel-sensitive and paclitaxel-resistant cancer cells tested, and its cytotoxicity to paclitaxel-sensitive cells was similar to paclitaxel. We also determined the anti-colony formation effect of 5v using one paclitaxel-resistant cell line, A375/TxR. As shown in FIG. 30C, the number and size of colonies in 5v-treated A375/TxR cells were significantly smaller than that of the control cells. And 5v could inhibit the proliferation of A375/TxR cell colonies in a concentration-dependent manner.

Figure 31A:
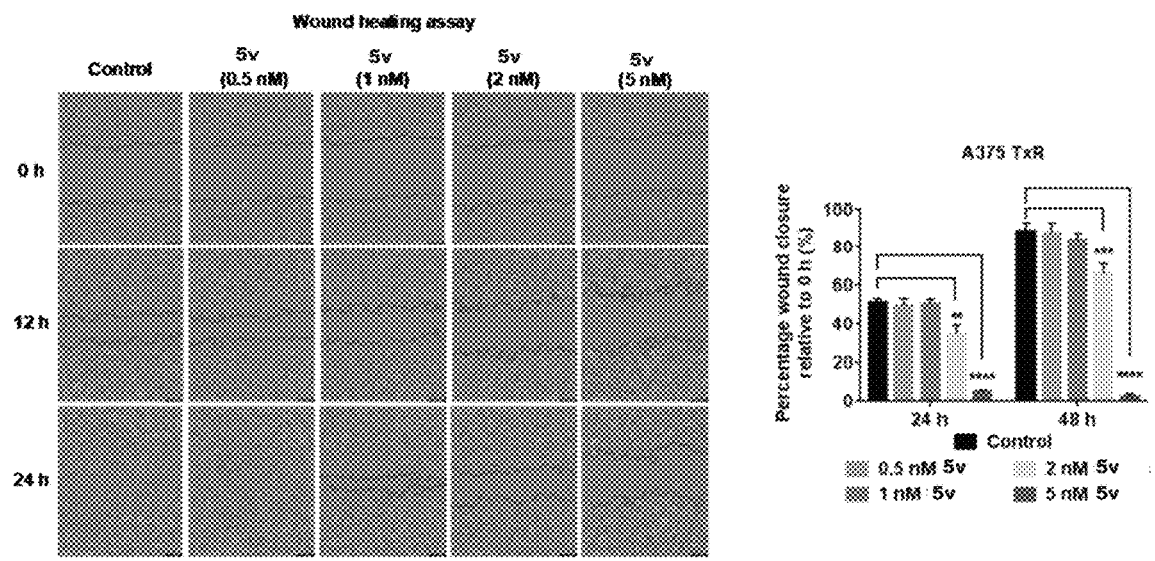
FIGS. 31A-C illustrates that 5v induces the inhibition of cell migration, cell apoptosis, and mitotic arrest in A375/TxR cells.
Figure 31B:
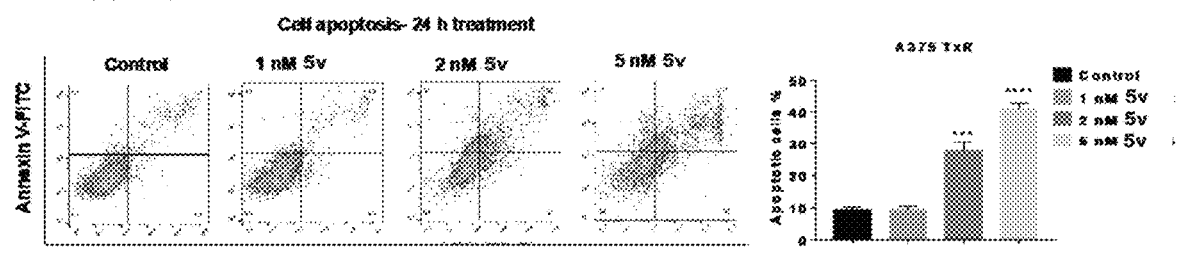
Figure 31C:
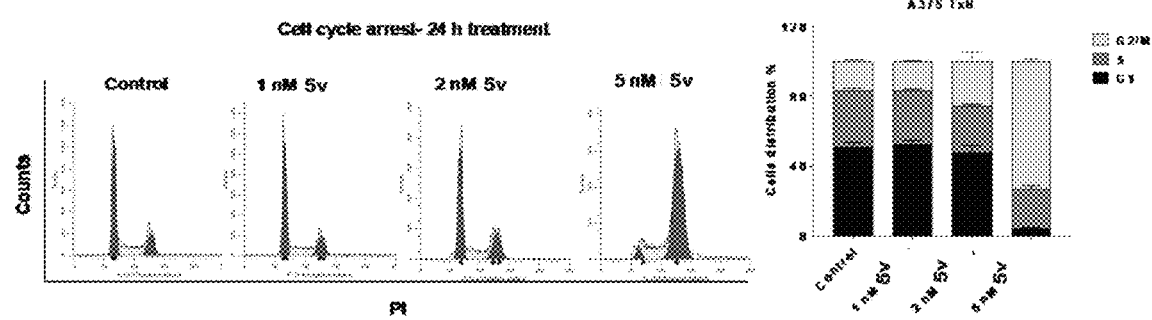

5v led to the inhibition of cell migration, cell cycle arrest, and ultimately cell death on A375/TxR cells: Since cell motility is dependent on microtubule structure and microtubule-targeting agents are reported to always cause G2/M cycle arrest and ultimately cell death in cancer cells, and 5v showed very strong cytotoxicity in inhibiting the colony formation of A375/TxR cells, we continued to evaluate the effect of 5v on cell migration, cell cycle distribution, and cell apoptosis induction using A375/TxR cells. As displayed in FIG. 31A, 5v showed remarkable potency in inhibiting the cell migration of A375/TxR cells at a single-digit nanomolar range. And it slowed the wound healing of A375/TxR cells in a concentration-dependent manner and showed maximum inhibitory effect after 5v treatment for 48 h. Moreover, flow cytometry analysis using Annexin V-FITC/PI staining showed that compared with the untreated control group, 5v incubation groups had significantly increased the number of apoptotic percentage of A375/TxR cells, increasing from 28% to 42% in a dose-dependent manner starting from the concentration of 2 nM (FIG. 31B). Furthermore, cell cycle analysis by single PI staining showed that even without serum starvation, 5v treatment induced the number of A375/TxR cells arrested in the G2/M phase to increase dramatically with maximum strength at the concentration of 5 nM (FIG. 31C). Together, 5v showed potent anti-migration, pro-apoptotic, and G2/M phase arrest effects against A375/TxR cells at single-digit nanomolar concentration.

Figure 32A:
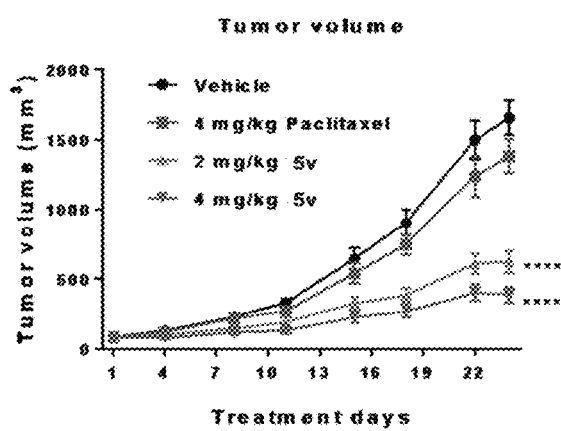
FIGS. 32A-D illustrates that 5v demonstrated antitumor efficacy in A375/TxR xenograft model.
Figure 32B:
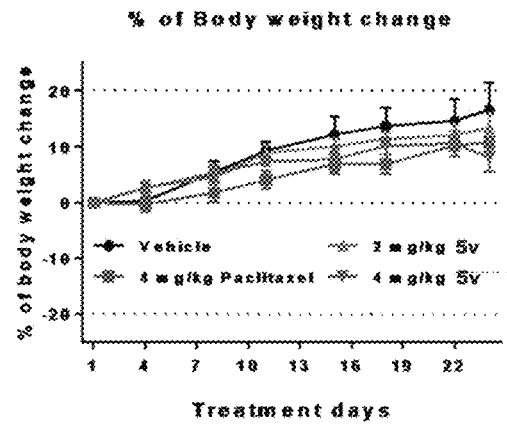
Figure 32C:
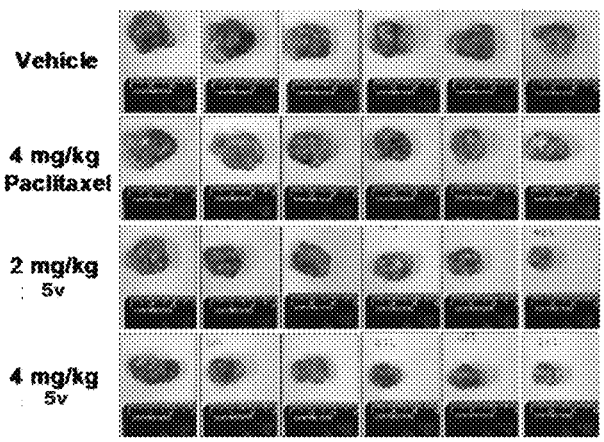
Figure 32D:
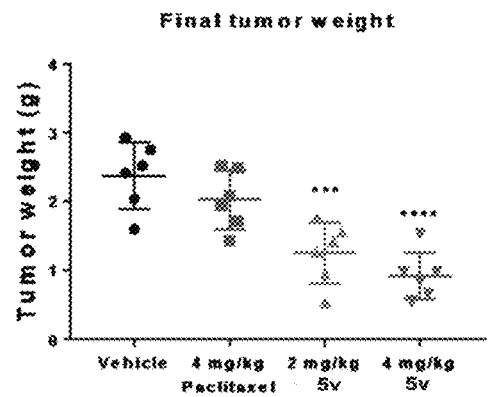
Figure 36A:
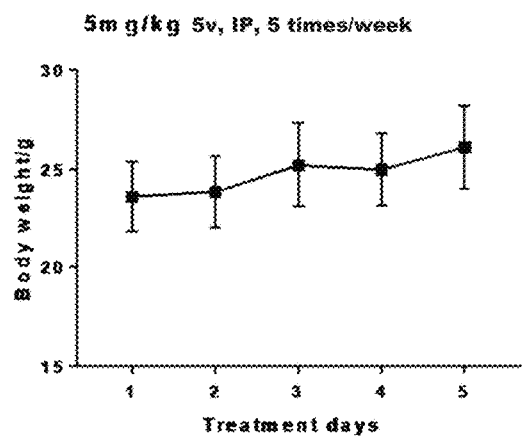
FIGS. 36A-D illustrates a tolerability assessment of 5v in healthy NSG mice. E.g., 5v was tolerated at 5 mg/kg IP but not 10 mg/kg IP.
Figure 36B:
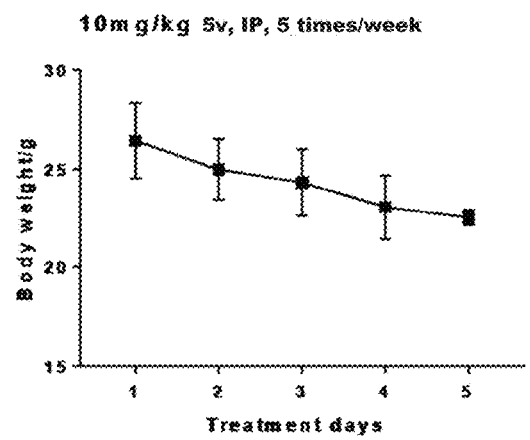
Figure 36C:
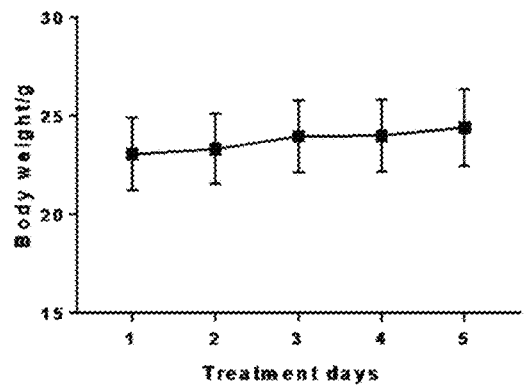
Figure 36D:
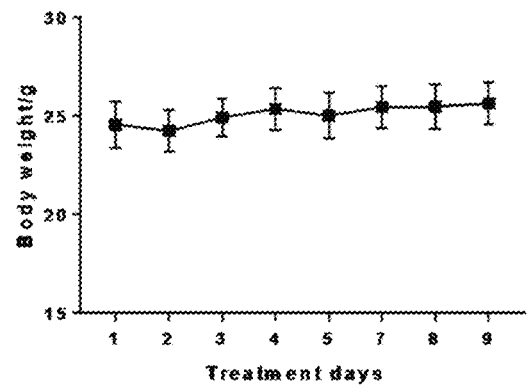

5v strongly suppressed the melanoma tumor growth in vivo: Before assessing the efficacy of 5v in xenograft models, we did a simple tolerability study to find a safe dose of 5v for in vivo studies. We first used the dose of 5 mg/kg and 10 mg/kg in treating healthy NSG mice intraperitoneally with a dose frequency of five times a week (FIGS. 36A-36B). During the treatment, mice in the 5 mg/kg 5v treatment group were still healthy but those in the 10 mg/kg 5v treatment group had fuzzy fur and weight loss. On the fifth day, the mice in the 10 mg/kg 5v treatment group were either dead or euthanized due to the bad condition, so 10 mg/kg of 5v treatment with five times a week IP injection is toxic to mice. Then we selected 5 mg/kg and 10 mg/kg of 5v as doses to determine the potential toxicity of IV injections and 2 times a week as dose frequency. The results showed that both 5 mg/kg and 10 mg/kg are safe via IV injections by 2 times a week (FIG. 36C-36D). Our previous studies showed that the parent compounds of 5v, 5m, and 5t were very potent in inhibiting the growth of paclitaxel-resistant A375/TxR xenografts. To compare the effect of 5v with 5m and 5t we also used A375/TxR xenograft model to evaluate the antitumor effect of 5v. When the mean tumor volume reached 100 mm$^3$, mice were randomized according to tumor volume and body weight and were administered intravenously with vehicle, 2 mg/kg 5v, 4 mg/kg 5v, or the reference compound paclitaxel (4 mg/kg) twice a week until three weeks of treatment. As displayed in FIG. 32A, the paclitaxel-treated group had no significant tumor-suppressive effect, while 5v treatment significantly reduced the tumor volume, especially at a dose of 4 mg/kg. The tumor growth inhibition values of 2 mg/kg and 4 mg/kg 5v treatment reached 62.3% and 76.6%, respectively. And there was no body weight loss observed in all treatment groups, suggesting that two doses of 5v were tolerated for the mice in this A275/TxR xenograft model (FIG. 32B). In addition, compared to the vehicle group, mice treated with 2 mg/kg 5v had a 47.4% decrease in tumor weight, while 4 mg/kg 5v-treated mice had tumor weight decreased by 59.9%, indicating that the high-dose of 5v had a better inhibitory effect on tumor growth (FIG. 32C-32D).

Figure 33A:
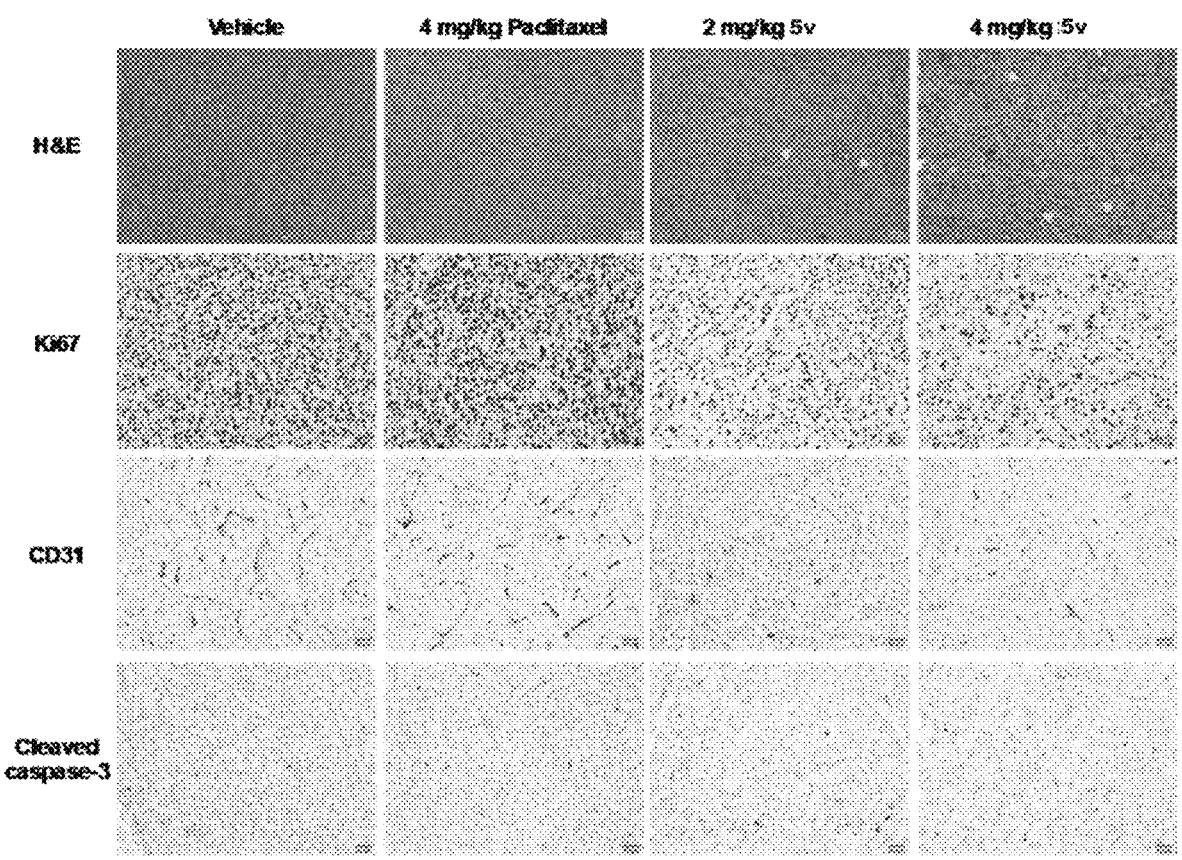
FIGS. 33A-B illustrates demonstrated H&E and IHC staining of A375/TxR tumors showing the effect of that 5v on tumor apoptosis, proliferation, and angiogenesis in vivo.
Figure 33B:
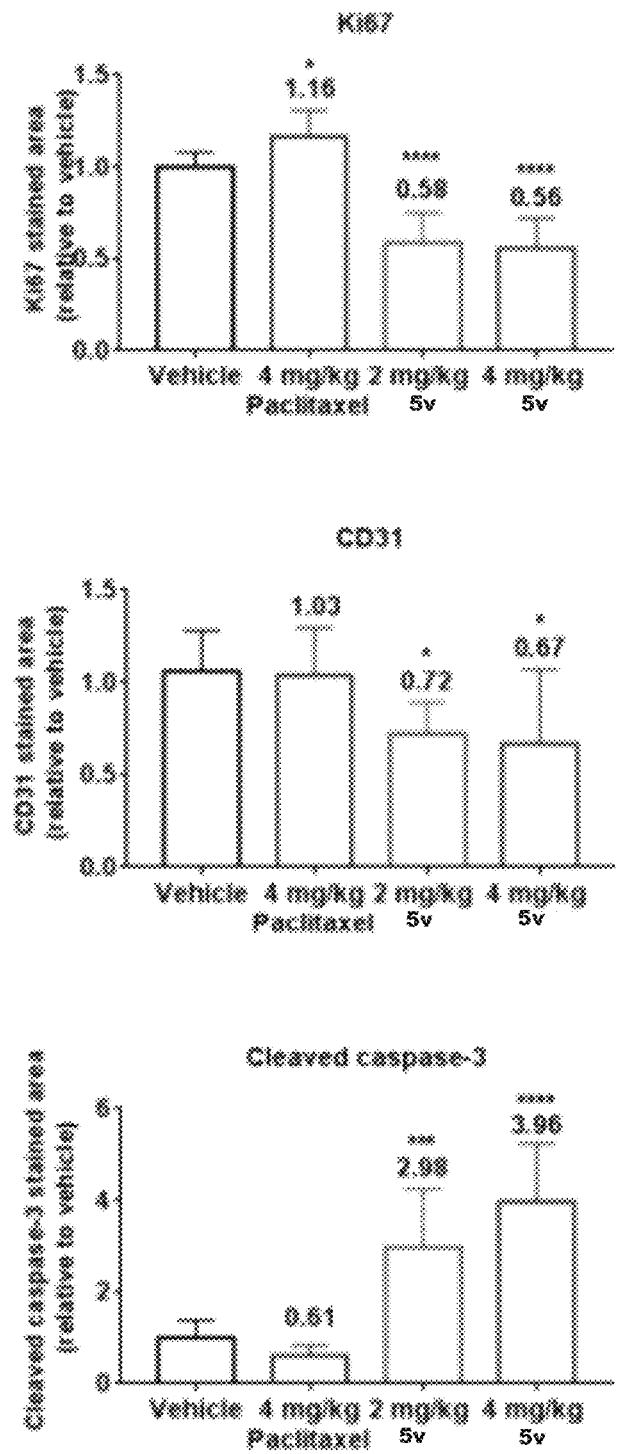

We further excised the tumors from the A375/TxR xenograft study and performed H&E staining to see the extent of tumor necrosis. As shown in FIG. 33A, images of H&E-stained tissues showed more necrotic cells in 5v-treated tumors compared to vehicle-treated or paclitaxel-treated tumors, suggesting that 5v could induce A375/TxR tumor necrosis. To further confirm the effect of 5v on tumor cell proliferation, angiogenesis, and apoptosis in vivo, we performed IHC staining to detect the expression of Ki67, CD31, and cleaved caspase-3 in tumors acquired in A375/TxR xenograft model. Ki67 and CD31 expressions were significantly decreased in 5v-treated tumors compared to those treated with vehicle or paclitaxel, indicating that 5v inhibited tumor proliferation and angiogenesis significantly in mice bearing tumors (FIG. 33A-B). However, paclitaxel-treated tumors had slightly elevated Ki67 expression relative to the vehicle group, while having no significant change in CD31 expression (FIG. 33B). Additionally, the IHC staining results of cleaved caspase-3 showed that 5v (2 mg/kg, 4 mg/kg) significantly increased the proportion of cleaved caspase-3 positive cells in 5v-treated tumors in a dose-dependent manner, suggesting that 5v had the proapoptotic effect in vivo (FIG. 33A-B). Collectively, these data demonstrate that 5v, as a microtubule polymerization inhibitor, inhibits tumor growth by inhibiting tumor proliferation, targeting tumor angiogenesis, and inducing apoptosis.

Figure 37:
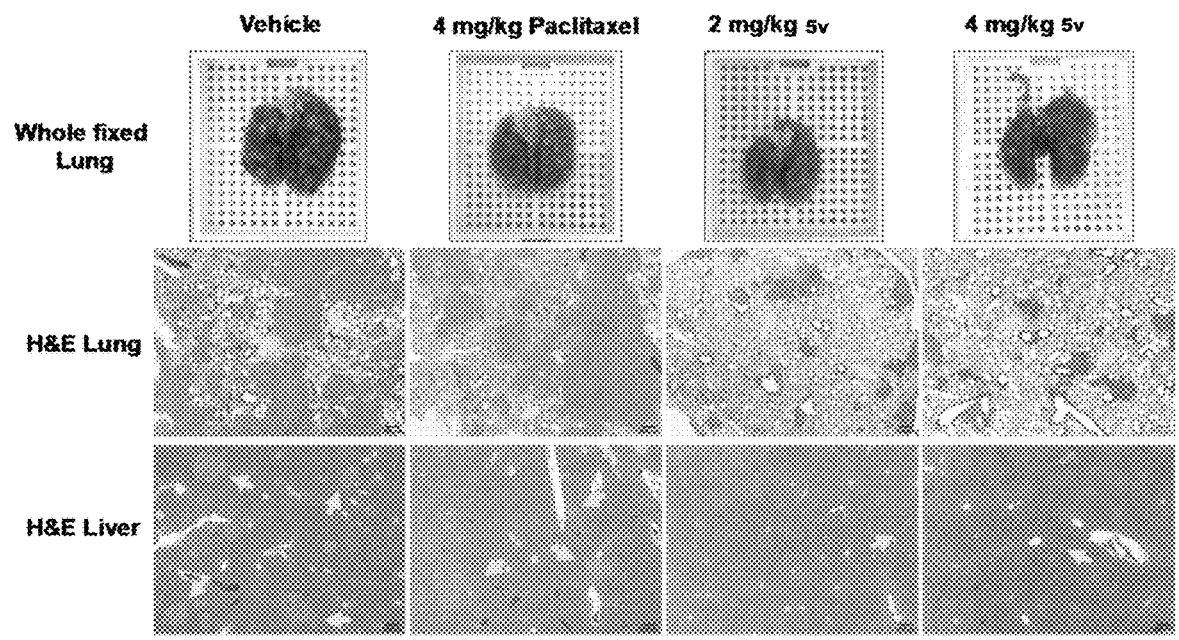
FIG. 37 illustrates that 5v suppressed the spontaneous metastasis of A375/TxR tumors. Representative images of whole lungs (top), H&E stained lungs (middle) and H&E stained livers (bottom) treated with vehicle, 4 mg/kg paclitaxel, 2 mg/kg 5v, or 4 mg/kg 5v for 23 days. Lung or liver metastases in H&E stained slides are indicated by yellow arrows.

5v inhibited the spontaneous metastasis of A375/TxR xenografts without obvious toxicity to major organs: Our newly established A375/TxR xenograft model was shown to have spontaneous metastasis to the lung and liver. Thus, in the current study, we also looked at the efficacy of 5v in inhibiting spontaneous metastasis. When dissecting the mice, we found almost all mice had growths in axillary lymph nodes. So we collected all the axillary lymph nodes and imaged them (FIG. 34A). Visually, 5v could potentially inhibit the tumor metastasis into axillary lymph nodes. Moreover, metastases were widely detected in the whole lungs of the vehicle or paclitaxel-treated groups, while 5v (2 mg/kg or 4 mg/kg) treatment groups had significantly reduced the number and size of tumor nodules in the lungs (FIG. 37). Furthermore, H&E staining of mouse lungs or livers indicated that 5v significantly inhibited spontaneous lung metastases or liver metastases as indicated by yellow arrows in representative images (FIG. 37). As shown in FIGS. 34B-34C and the representative anti-mitochondrial stained lung or liver images (FIG. 34D), both 2 mg/kg 5v and 4 mg/kg 5v resulted in significant inhibition of lung or liver metastasis compared to vehicle, indicating that 5v is not only effective against the growth of A375/TxR tumors but also significantly inhibited the tumor metastasis to lymph node, lung, and liver.

Figure 35:
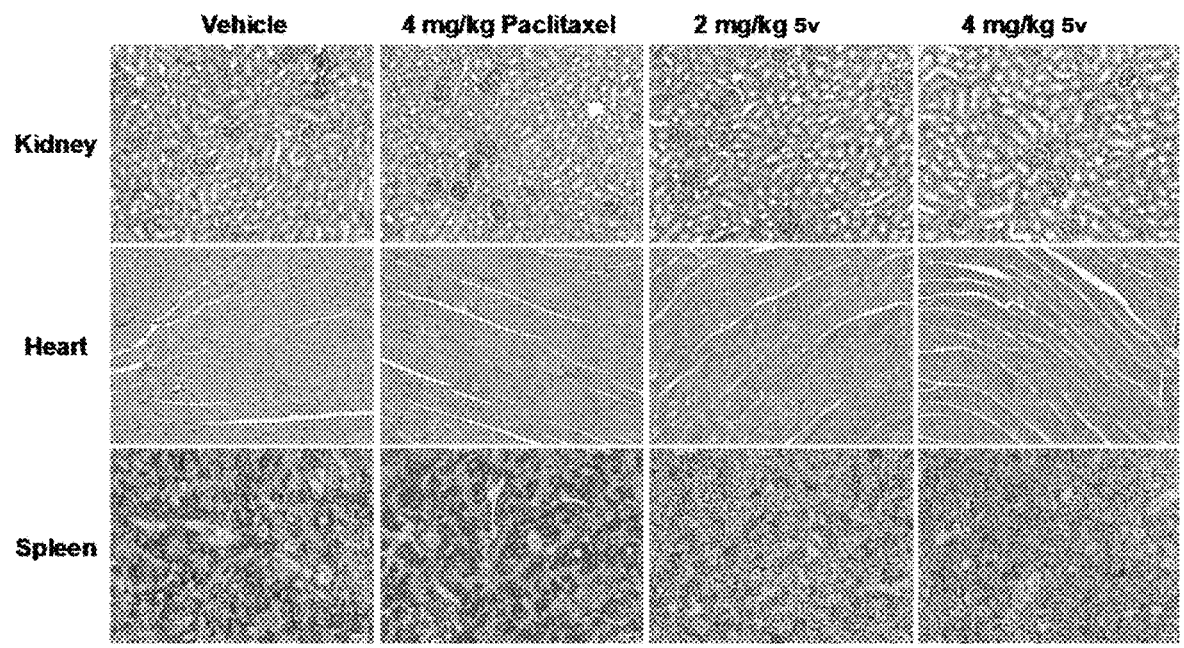
FIG. 35 illustrates that 5v demonstrated a lack of acute toxicity. H&E staining of kidney, heart, and spleen of mice in each group. After 3 weeks of treatment, the major organs (kidney, heart, and spleen) were harvested from mice and stained with H&E. Keyence microscope magnification, 20×. Scale bar, 50 µm.

We have shown that 5v at the dose of 2 mg/kg or 4 mg/kg had no acute toxicity (FIG. 32B). To determine if 5v had toxicity to the major organs, we further investigated the toxicity of 5v by staining the major organs (heart, kidney, and spleen) with H&E because both the lungs and livers of the mice in the study had A375/TxR tumor mass, and it is hard to exclude the influence of metastasis on the damage of organs. The results showed that after three weeks of 5v (2 mg/kg or 4 mg/kg) treatment, there was no obvious damage to the major organs of the mice, and the organs treated by 5v was similar to the H&E staining results of the vehicle and paclitaxel-treated organs (FIG. 35). In conclusion, 5v exhibited potent antitumor efficacy, anti-spontaneous metastasis activity, and low toxicity both in vitro and in vivo, and deserves further study.

Discussion: In our efforts to discover novel CBSIs, we identified 5v as a novel tubulin polymerization inhibitor. In our previous study (Example 5), we reported that both 5m and 5t had very strong anti-proliferative efficacies in vitro and in vivo. Therefore, we hypothesized that a new analogue of 5m and 5t designed by replacing the methyl moiety of 5m with the ethylamine moiety of 5t could obtain higher cytotoxicity and potency than 5m or 5t Before carrying out any in vitro or in vivo experiments, we used X-ray crystallography, tubulin polymerization assay, and immunofluorescence assay to verify whether the newly synthesized 5v was a CBSI. As expected, 5v could target the colchicine-binding site and inhibit tubulin polymerization (FIG. 29A). The following MTS and colony formation assays demonstrated that 5v had more cytotoxic anti-proliferative activity than 5m or 5t with $IC_{50}$ values at sub-nanomolar levels against a panel of cancer cells and paclitaxel-resistant sublines as we hypothesized (FIG. 30), and its potency was similar to paclitaxel, an anticancer drug used to treat solid tumors in the clinic. We then conducted the scratch assay, Annexin V/PI staining, and cell cycle analysis experiments to further confirm the effect of 5v as a CBSI on other aspects of cell growth inhibition, such as cell migration, cell apoptosis, and cell cycle arrest. Indeed, 5v induced cell migration inhibition, cell cycle arrest, and apoptosis in taxane-resistant A375/TxR cells (FIG. 31).

Our further in vivo studies showed that 5v was able to inhibit the growth of A375/TxR xenografts in a dose-dependent manner without causing acute toxicity, and H&E staining of tumors in this study demonstrated that 5v (2 mg/kg or 4 mg/kg) induced the tumor necrosis in vivo (FIG. 32 and FIG. 33A). Moreover, the IHC staining using the cell proliferation marker Ki67, the prognostic angiogenic marker CD31, and the apoptosis marker cleaved caspase-3 showed that relative to vehicle or paclitaxel-treated tumors, all doses of 5v treatment significantly reduced the percentage of Ki67-positive area and CD31-positive area, and increased the percentage of cleaved caspase-3-positive area in a dose-dependent manner in 5v-treated tumors (FIG. 33). However, different from its in vitro cytotoxicity, 5v showed weaker in vivo efficacy than 5m (2 mg/kg: 62.3% of tumor growth inhibition vs. 70.5% of 5m; 4 mg/kg: 76.6% of tumor growth inhibition vs. 88.2% of 5m), and similar potency as 5t (2 mg/kg: 62.3% of tumor growth inhibition vs. 64.6% of 5m; 4 mg/kg: 76.6% of tumor growth inhibition vs. 78.4% of 5t), which is different than we expected. One reason for causing reduced efficacy of 5v in vivo might be the low metabolic stability.

As displayed in Table 7, compared to 5m, which had a half-life time of 53.6 min in human liver microsomes, 8.0 min in rat liver microsomes, and 14.4 min in mouse liver microsomes, 5v did not show improved metabolic stability but rather had decreased half-life time in human liver microsomes (24.7 min), rat liver microsomes (3.6 min; not shown) and mouse liver microsomes (6.33 min).

In addition, the clearance rate of 5v was higher than 5m in human, rat, and mouse liver microsomes, further muting the metabolic stability of 5v. Despite the low metabolic stability in vivo, 5v is still a promising CBSI with sub-nanomolar efficacy that could be used as payloads for antibody-drug conjugate or loading drugs for nanoparticles through its ethylamine moiety.

Figure 38:
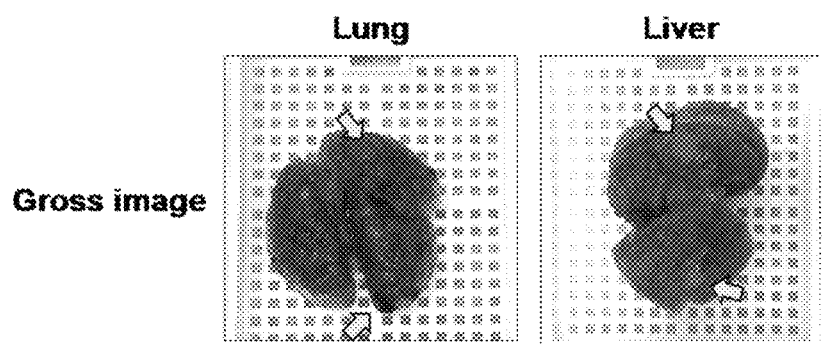
FIG. 38 illustrates that 5v suppressed the spontaneous metastasis of A375/TxR tumors to lung and liver. Representative images of whole lung (left) and whole liver (right) of the mouse in vehicle group that had none (zero) observed axillary lymph node.

At the same time, we also proved that 5v could inhibit the spontaneous axillary lymph node, lung, and liver metastases originating from subcutaneous tumors (FIG. 34 and FIG. 37). However, as shown in FIG. 34A, there was one mouse in the vehicle group that had no growth in its axillary lymph nodes. When we collected the lung and liver of that mouse, we found that the number and size of tumor nodules present on the lung or liver were bigger than those in other mice in the vehicle group, suggesting that this specific mouse might have a deficiency in spontaneous metastasis going into the axillary lymph node, but preferring to migrate to lung or liver (FIG. 38). And thus, when assessing the area of spontaneous metastases present in the lung or liver in the vehicle group, we excluded this mouse. Therefore, 5v was not only efficacious in suppressing the growth of primary tumors, but it was also potent in inhibiting the metastasis at a dose of 2 or 4 mg/kg. And 5v deserves further investigations on many other solid tumor types, such as prostate cancer, lung cancer, and ovarian cancer. Our previous studies have shown that CBSIs, represented by 17ya, 5m and 5t and 5v, could efficiently suppress the tumor metastasis to the liver, suggesting the potential role of CBSIs in inhibiting the liver metastasis, which deserves further investigations. Our further evaluation of toxicity of 5v using H&E staining demonstrated that 5v had no toxicity to major organs at the dose of 2 mg/kg and 4 mg/kg intravenously for 2 times/week (FIG. 35). And from its tolerability study, we showed that 5v had no acute toxicity when administering 10 mg/kg twice a week intravenously (FIG. 36). Although 5v was not more efficacious than 5m at the same dose levels in vivo, it was safer than 5m, which had toxicity when applying for a higher dose (5 mg/kg), further supporting the development of new CBSIs based on the findings of 5v.

In conclusion, we synthesized an analogue of our previously reported CBSIs 5m and 5t and termed it 5v. Then we obtained the high-resolution X-ray crystal structure of 5v and identified it as a CBSI, which could inhibit the tubulin polymerization. We also showed that 5v effectively inhibited the growth of various cancer cell lines, overcame paclitaxel resistance, and had the effects of inhibiting cancer cell migration, inducing cell apoptosis and G2/M cell cycle arrest in vitro. Moreover, in vivo studies showed that 5v had strong antitumor and anti-spontaneous metastasis efficacy in A375/TxR xenograft mouse model without causing toxicity to major organs in mice. Therefore, the preclinical evaluation of 5v strongly supports the development of 5v as a next-generation tubule inhibitor and deserves further investigation.

Example 11: Treatment of Head and Neck Cancers with Dihydroquinoxalinones of the Invention A panel of dihydroquinoxalinones were tested in two head and neck cancer cell lines, A-253 and Detroit 562. A-253 cells are a human salivary epidermoid carcinoma cell line, whereas Detroit 562 is a head and neck squamous cell carcinoma (HNSCC). Oral cancer is the most common type of head and neck cancer and more than 90% of oral cancers are either oral or oropharyngeal squamous cell carcinoma (SCC). A major clinical dilemma is chemotherapy efficiency targeted for head and neck squamous cell carcinoma (HNSCC). The inability to successfully complete cancer treatment utilizing a standard surgical approach due to an advanced stage of HNSCC and/or resistance of SCC cells to conventional chemotherapy and/or radiotherapy leads to a continuous search for new compounds with cytostatic activity and minor side effects.

Figure 39A:
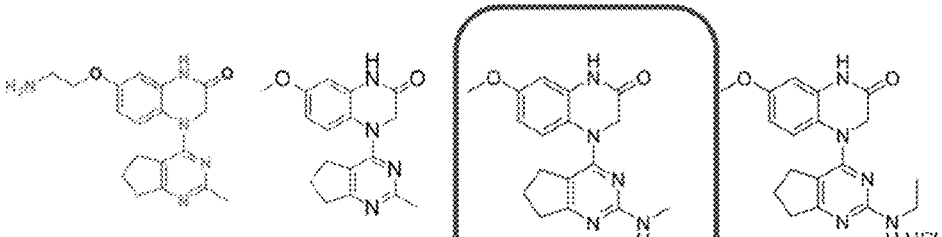
FIGS. 39A-C illustrate that 5m, 12k, and 5v HC possessed low nM to pM potency cytotoxicity in two different cell lines of head and neck cancer, A-253 and Detroit 562.
Figure 39B:
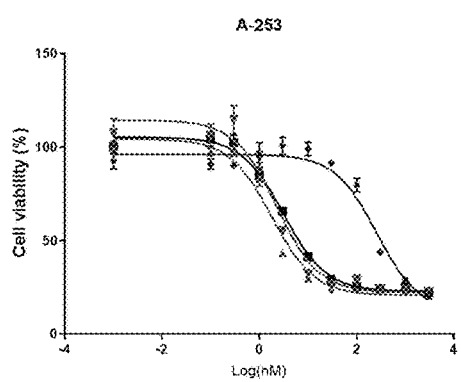
Figure 39C:
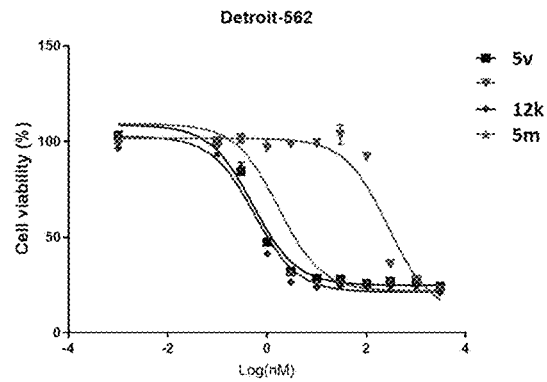
Figure 40A:
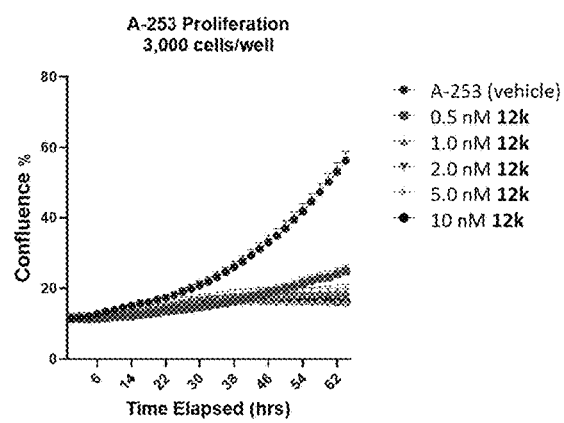
FIGS. 40A-D illustrate a dose-responsive decrease in head and neck cancer cell proliferation (Confluence %) over time elapsed (hrs).
Figure 40B:
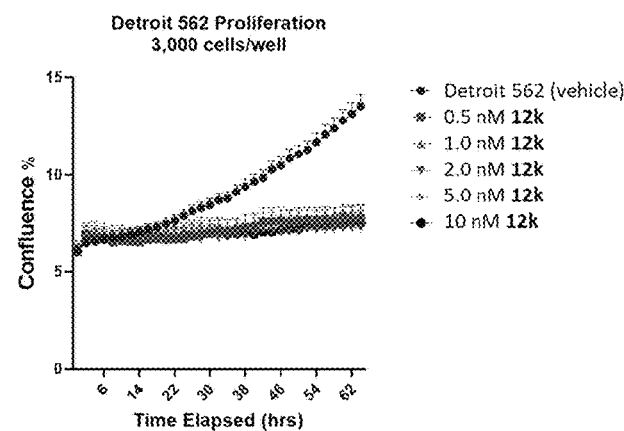
Figure 40C:
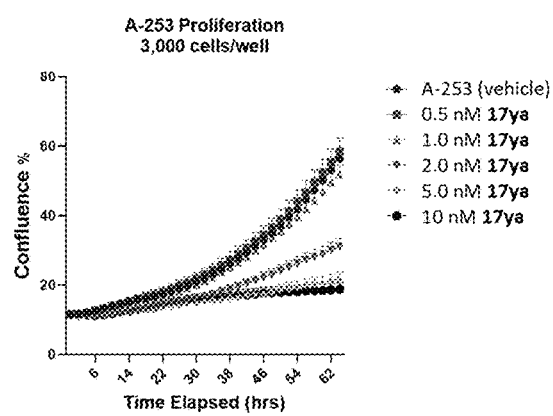
Figure 40D:
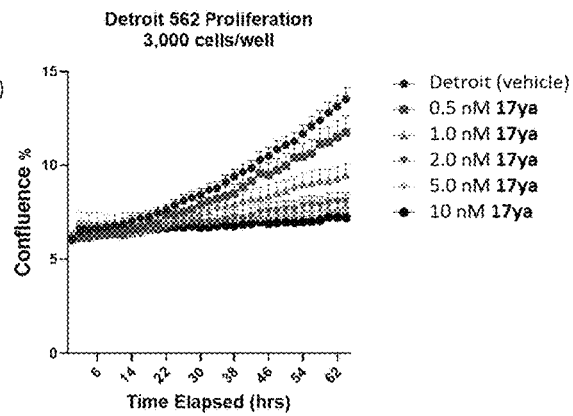
Figure 41A:
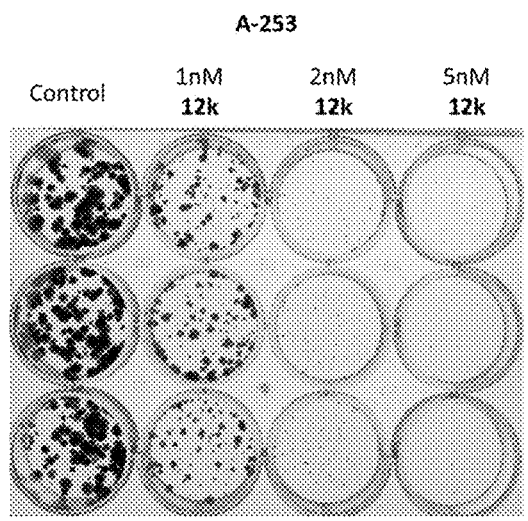
FIG. 41A and FIG. 41B illustrate that colony formation of A-253 and Detroit 562 cells was also potently inhibited by 12k.
Figure 41B:
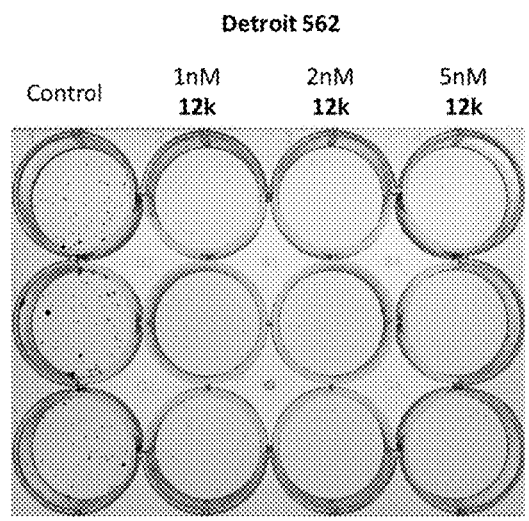

In the current experiment, four compounds (SP-I-104, 5m, 12k, and 5v HCl) were tested across two head and neck cell lines A-253 and Detroit 562 for cytotoxicity in vitro. As can be seen in FIG. 39A, three of four compounds (5m, 12k, and 5v HCl) produced low nM to high pM level $IC_{50}$ cytotoxicity values suggesting the ability to potently inhibit the growth of head and neck cancers. For example, the $IC_{50}$ values ranged from 0.52 nM to 3.2 nM for these three compounds. FIGS. 39B and 39C illustrate the graphical representation of the data. From these preliminary screening experiments, 12k was chosen as a lead for further investigation and was compared to a structurally unrelated CBSI compound 17ya. In these experiments, 12k unexpectedly possessed ~10-fold superior potencies (FIGS. 40A and 40B) as compared to compound 17ya (FIGS. 40C and 40D) in both A-253 and Detroit 562 cell lines. For example, at treatment levels as low of 0.5 nM, 12k was able to prevent head and neck cancer cell proliferation almost completely, whereas it required 5 nM of 17ya to achieve similar anti-proliferation. The results are graphically represented in FIGS. 40A-D. Similarly, 12k also demonstrated potent ability to prevent colony formation with near complete inhibition seen at 1 nM in A-253 cells vs. 2 nM in Detroit 562 cells as illustrated in FIG. 41A and FIG. 41B, respectively.

Figure 42A:
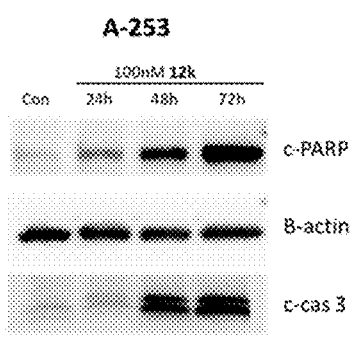
FIG. 42A and FIG. 42B illustrate that 12k induces apoptosis in the head and neck cancer cell lines A-253 and Detroit 562 as demonstrated by elevation of the apoptosis markers cleaved PARP (c-PARP) and cleaved cas 3 (c-cas 3) as revealed by Western blot analysis (performed as described elsewhere herein).
Figure 42B:
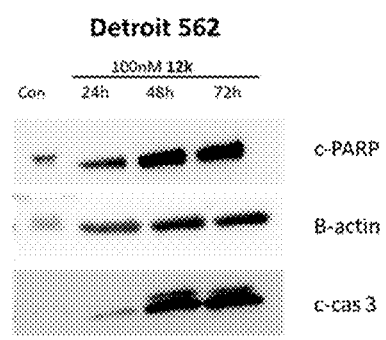

Further, the anti-mitotic mechanism of action was confirmed by Western blot analysis that demonstrated apoptosis was induced over time in the head and neck cancer cell types tested. By 72 hours of treatment of these cell lines with 100 nM of 12k elevated levels of apoptotic markers such as the cleavage of PARP (c-PARP) and cas 3 (c-cas 3). FIG. 42A and FIG. 42B graphically illustrate these results for cell lines A-253 and Detroit 562, respectively. This data suggested that the anticancer activity in head and neck cancers operates via induced apoptosis consistent with the known colchicine binding site inhibitor mechanism of action of these compounds.

Example 12: Synthesis of 5v and 5v HC

Figure 43:
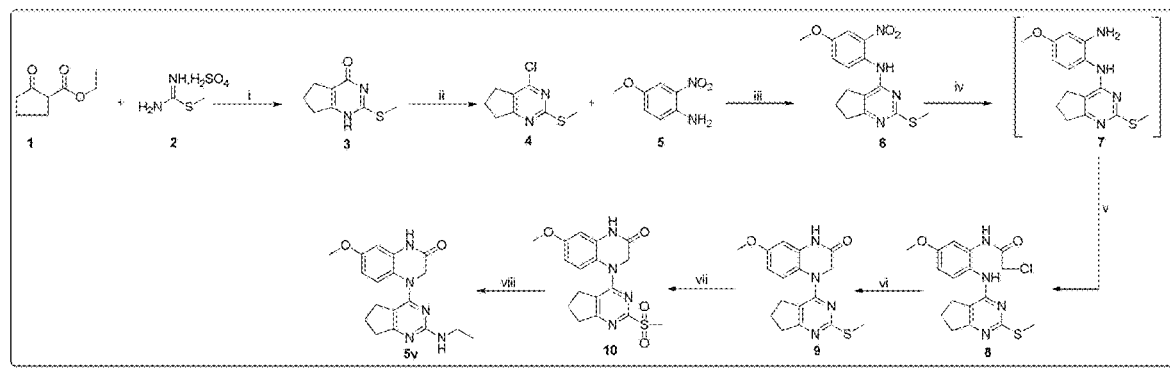
FIG. 43 illustrates that 5v can be synthesized according to the scheme in the figure.

The compound 5v (4-(2-(ethylamino)-6,7-dihydro-5H-cyclopenta[d]pyrimidin-4-yl)-7-methoxy-3,4-dihydroquinoxalin-2(1H)-one) was synthesized by the scheme shown in FIG. 43.

Chemistry: 4-Chloro-2-(methylthio)-6,7-dihydro-5H-cyclopenta[d]pyrimidinel (4) (Aware, et al., "Cyclopentyl-pyrimidine based analogues as novel and potent IGF-1R inhibitor," European Journal of Medicinal Chemistry, 2015, 92, 246-256) was obtained from hydroxy pyrimidine (3) and ethyl 2-oxocyclopentanecarboxylate (1) and which (4) was coupled with 4-methoxy-2-nitroaniline (5) in dry IPA in the presence of a catalytic amount of HCl (3-4 drops) to get 2-methylthio4-(4-methoxy-2-nitrophenyl) amino pyrimidine (6) in good yield. (Cui et al, "In vivo and mechanistic studies on antitumor lead 7-methoxy-4-(2-methylquinazolin-4-yl)-3, 4-dihydroquinoxalin-2 (1H)-one and its modification as a novel class of tubulin-binding tumor-vascular disrupting agents," J. Med. Chem., 2017, 60, 5586-5598.) Then the nitro group was reduced into amine (7) with the help of zinc powder in catalytic AcOH at 0° C. Immediately, the resulting amine was coupled with chloroacetyl chloride to produce 8. Next, compound 8 underwent an intra-molecular cyclization in presence of NaH in anhydrous THF to yield intermediate 9 which was oxidized in the presence of oxone in methanol and water to afford 10. Finally, sulfone group on the pyrimidine ring of 10 was replaced with ethyl amine in the presence anhydrous 1,4-dioxane at 100-110° C. to afford 5v.

General Methods

All nonaqueous reactions were performed in oven-dried glassware under an inert atmosphere of dry nitrogen. All the reagents and solvents were purchased from Aldrich (St. Louis, MO), Alfa-Aesar (Ward Hill, MA), Combi-Blocks (San Diego, CA), Ark Pharm (Libertyville, IL) and used without further purification. Analytical thin layer chromatography was performed on silica gel GHLF 10 cm×20 cm Analtech TLC Uniplates (Analtech, Newark, DE) and were visualized by fluorescence quenching under UV light. Silica gel (60-120 or 100-200 mesh) was used to purify the compounds. $^1$H NMR and $^{13}$C NMR spectra were recorded on a Varian Inova-500 spectrometer (400 MHz) (Agilent Technologies, Santa Clara, CA) or a Bruker Ascend 400 (400 MHz) (Billerica, MA) spectrometer. Chemical shifts are reported in ppm on the δ scale and referenced to the appropriate solvent residual peaks (CDCl$_3$, 7.27 ppm for $^1$H and 77.23 ppm for $^{13}$C and DMSO-d$_6$, 2.50 ppm for $^1$H and 39.51 ppm for $^{13}$C) and all coupling constants (J) are given in hertz (Hz). Mass spectra were collected on a Bruker amazon SL electrospray/ion trap instrument in the positive and negative modes. High resolution mass spectrometer (HRMS) data were acquired on a Waters Xevo G2-S qTOF (Milford, MA) system equipped with an Acquity I class UPLC system. Porcine brain tubulin (catalog no. T-238P) was purchased from Cytoskeleton, Inc. The purity of all tested compounds was determined to be ≥95% by 1H NMR and HPLC. The HPLC method used to determine purity is as follows: Compound purity was analyzed using an Agilent 1100 HPLC system (Santa Clara, CA) with a Zorbax SB-C18 column, particle size 3.5 μm, 4.6 mm×150 mm, from Agilent. Mobile phases consist of water with 0.1% formic acid (A) and acetonitrile with 0.1% formic acid (B). A flow rate of 1 mL/min was used. The gradient elution started at 50% B. It reached 100% B from 0 to 9 min, was maintained at this from 9 to 12 min, and was then decreased to 50% B from 12 to 15 min and stopped. Compound purity was monitored with a DAD detector set at 254 nm.

Chemical Synthesis:

Synthesis of 4-(2-(ethylamino)-6,7-dihydro-5H-cyclopenta[d]pyrimidin-4-yl)-7-methoxy-3,4-dihydroquinoxalin-2(1H)-one (5v-HCl). A mixture of 10 (100 mg, 0.26 mmol), ethylamine (36 mg 0.80 mmol) in 1,4-dioxane was heated to 110° C. for 6 h in seal tube. The mixture was poured into ice-water, solid was collected out through filtration washed with water (5×10 mL), and dried. The crude was purified by column chromatography to afford pure salt free 5v (80 mg) as an off white solid. Ether HCl (0.5 M HCl in ether) 0.52 mL (1.1 mol) was added to the solution of secondary amine 5v in $CH_2Cl_2$ and stirred at room temperature for 5 h under $N_2$ atmosphere. Then, the solvent was removed, and the resulted hydrochloride salt of amine (5v-HCl) was dried under high vacuum (50 mg, 56% yield); $^1$H NMR (400 MHz, DMSO-$d_6$) δ 10.84 (s, 1H), 8.04 (bs, 2H), 7.08 (d, J=8.1 Hz, 1H), 6.65-6.63 (m, 2H), 3.88 (bs, 1H), 3.76-3.72 (m, 4H), 3.44-3.41 (m, 2H), 2.83 (bs, 1H), 2.08 (bs, 1H), 1.88 (bs, 2H), 1.18 (t, J=6 Hz, 2H); $^{13}$C NMR (100 MHz, DMSO-$d_6$) δ 167.56, 158.48, 133.92, 125.18, 119.29, 107.38, 102.11, 55.90, 49.70, 36.50, 31.18, 22.44, 14.75; HRMS [$C_{18}H_{22}N_5O_2^+$] calcd. 340.1773, found 340.1777; HPLC purity 97.0%; decomposes at 210-211° C.

Example 13: Treatment of Metastatic Breast Cancer (MBC) that has Metastasized to the Brain (BrnMets) with Brain Penetrant Compounds of the Invention Challenges in MBC treatment and limitations of FDA-approved tubulin inhibitors: Despite the significant advancements in breast cancer therapy, effective treatment of metastatic breast cancer (MBC) remains challenging. Major metastasis sites in MBC overall include the bone (41%), lung (22%), liver (8%) and brain (7%). While exact distribution in these major metastasis sites depends on specific breast cancer molecular subtypes, the most frequent site is to the bone, and the most difficult site to treat is the brain. Overall, ~70% of women with ER-negative MBC (TNBC or HER2-positive) will develop brain metastases (BrnMets) within 5 years of diagnosis with metastases at any other site, whereas ER-positive MBC is a much larger patient population whose metastatic burden can eventually lead to BrnMets. Patients with bone-destroying lesions (osteolytic) are particularly susceptible to fractures and chronic pain. Except for liver metastasis where surgical resection is the standard treatment, systemic therapy is the main treatment option for stage IV patients, with limited efficacy. Therefore, there are significant unmet medical needs in developing new systemic/targeted therapies for effective treatment of MBC metastasis, especially for brain metastases (BrnMets) and bone metastases.

Tubulin inhibitors such as paclitaxel (Taxol) and docetaxel (Taxotere) are classical systemic drugs and are widely used to treat patients with metastatic disease. The three most characterized binding sites in tubulin are the taxane site, the vinca site and the colchicine site. Currently, all FDA-approved tubulin inhibitors for cancer therapy bind to either the taxane site (e.g. Taxol) or the vinca site (e.g. vinblastine). However, their clinical use is associated with several limitations. First, they are usually good substrates for drug efflux pumps, including P-glycoprotein (P-gp), breast cancer resistant protein (BCRP), or multidrug resistant proteins (MRPs). They are also susceptible to β3-tubulin overexpression mediated resistance. Thus, multidrug resistance (MDR) often develops upon extended periods of drug administration. While newer taxanes (e.g., cabazitaxel) are less susceptible to P-gp mediated drug efflux, they remain susceptible to β3-tubulin mediated drug resistance. Second, approved tubulin inhibitors have dose-limiting hematopoietic toxicity and cumulative neurotoxicity, including peripheral neuropathy, resulting in narrow therapeutic windows. Third, these approved drugs have poor aqueous solubility, which requires the use of surfactants (e.g., Cremophor EL) in their formulations. Surfactants may result in additional side effects and require pre-medication with corticosteroids/anti-histamines. Emerging data suggest that corticosteroids activate tumor-promoting stress response pathways in triple negative breast cancer (TNBC) and enrich for cancer stem cell-like activities. Efforts have been made to develop new generations of taxane drugs, including an oral formulation of paclitaxel (Oraxol) and a chemically modified paclitaxel (tesetaxel), but both failed FDA approval in early 2021, probably due to the inherent limitations of the taxane scaffold. Since tubulin inhibitors are first-line drugs for stage IV breast cancers, there is a strong clinical need to develop novel tubulin inhibitors for more effective treatment. The compounds of this invention of colchicine binding site inhibitors (CBSI) that potently act as antitubulin agents that lack the therapy limitations of taxanes and vincas, and variants thereof.

The research presented herein focused on structural optimization to produce a potent and high brain penetrable tubulin inhibitors that can also overcome taxane resistance for MBC brain metastasis (BrnMets) treatment. This ability will prolong survival and improve QOL for not only MBC patients, but also for patients with other cancer types for which tubulin inhibitors are currently used. We screened new analogs in vitro using a panel of TNBC and HER2+ conventional cell lines, including taxane-sensitive and taxane-resistant cell lines, and early passage cells derived from taxane-sensitive and taxane-resistant PDX models, as well as normal cells. We also determined brain penetration for the most active compounds in this series, the maximum tolerable dose (none shown), and optimal pharmacokinetics (PK) to select the best compounds for downstream in vivo efficacy studies. We selected 5m from the compounds of other examples as the overall best compound for in vivo evaluation. In vivo evaluation involved using a taxane-sensitive, well-characterized pre-clinical model that develops BrnMets following intracardiac injection (MDA-MB-2.31 BrM2 subline) to score for delay of metastatic progression and increased overall survival (OS) in response to treatment. Reducing BrnMets burden and progression is highly likely to significantly improve MBC patient PFS, OS and QOL. In addition, patients diagnosed with other types of metastatic solid tumors in which tubulin inhibitors are currently the standard of care (SOC) could also benefit from this invention.

The BrnMets data presented here are separated into three types of experiments: 1) determination of brain penetration of 5m as measured by the brain to plasma concentration ratio (B/P), 2) as measured the delay in metastatic progression with 5m compared to vehicle (all animals euthanized at the same time point), and 3) comparison of OS with 5m compared to vehicle (animals euthanized when moribund due to metastasis).

Figure 44:
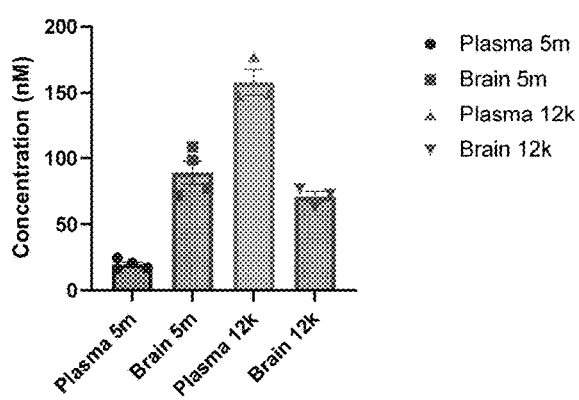
FIG. 44 illustrates the plasma and brain concentrations of 5m and 12k in mice treated as described in Example 13.

Increased B/P ratio for compounds of this invention. In the blood brain barrier penetration study, male NSG mice were dosed with 4 mg/kg of either 5m (four mice) or 12k (three mice) intravenously through tail vein injection. After one hour, mice were anesthetized, blood was collected via cardiac puncture, and brain samples were collected after perfusion with saline to remove all blood in the brain. Blood samples were processed for plasma by centrifugation. Brain samples were homogenized using a homogenizing buffer (1:2 methanol:PBS) at the ratio of 1:9 (1 gram of brain tissue to 9 mL of buffer). Tissue samples were kept at −80° C. until LC-MS/MS analysis, following established protocols [PMID: 22760659]. The concentration (nM) ratios of 5m or 12k in the brain (B) over plasma (P) is defined as the B/P distribution was determined as 4.56 for 5m and 0.45 for 12k (FIG. 44). As a comparison, compound 17ya (evaluated in nude mice) has a much lower brain penetration (B/P ratio of 17ya is only 0.054 at 1 h and 0.089 at 4 hr, [PMID: 22760659]).

Figure 45:
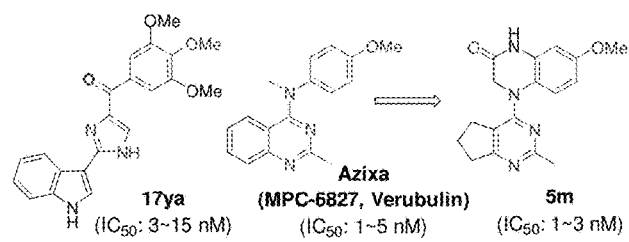
FIG. 45 illustrates 5m is a potent, stable, and high brain penetrable compound, having features in common with Azixa and 17ya, maintains the ability to overcome taxane resistance and hence may be useful in the treatment of late stage breast cancers even when the subjects were previously treated with taxanes or 17ya and subsequently have metastasized to the brain. This is currently an unmet clinical need.

Most breast cancer patients die from tumor metastases, therefore, durable treatments for metastatic breast cancer (MBC) must have good efficacy in treating metastases. Among the four major sites of MBC metastases (bone, lung, liver, and brain), brain metastases (BrnMets) are the most challenging site for treatment due to the requirement for drug availability across the blood:brain barrier (BBB). Compound 17ya has limited BBB penetration, and thus it is unlikely to be optimal for treating BrnMets. Interestingly, Azixa, a potent CBSI, distributes rapidly and extensively into the brain, exhibiting 14-fold higher brain exposure relative to plasma and elimination half-life similar to plasma [PMID: 19296653]. Even though Azixa failed as a cancer therapeutic drug due to its toxic metabolites, its radiolabeled version with Carbon-11 is currently under clinical trials as a PET imaging agent for neurodegenerative disease applications (e.g., NCT04575727), because of its very high brain penetration capability. We hypothesized that a proper hybridization of 17ya (metabolically stable, good safety profile, but low brain penetration) and Azixa (potent, excellent brain penetration, but metabolically unstable and high toxicity to heart and liver) would "dial-out" their respective limitations to produce a metabolically stable, low toxic, and brain penetrable CBSI. With extensive medicinal chemistry, we discovered a scaffold of dihydroquinoxalinones as exemplified throughout the examples, with 5m as the current lead (FIG. 45) for treatment of BrnMets. 5m maintains the ability to overcome taxane resistance (see FIGS. 10A-10D, 13A-13D, 19A, 19B, 19E, etc.), and has a high brain to plasma (B/P) distribution ratio of 4.56 (NSG mice, 4 mg/kg, IV bolus, n=4, see the previous paragraph for details). Further, FIG. 19C demonstrates that 5m is able to overcome resistance to 17ya in the TNBC cell line MDA-MB-231/VxR.

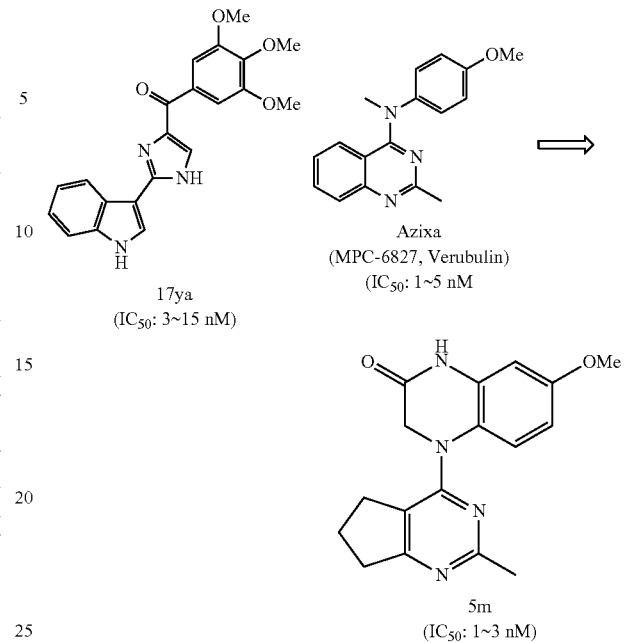

17ya
($IC_{50}$: 3~15 nM)

Azixa
(MPC-6827, Verubulin)
($IC_{50}$: 1~5 nM)

5m
($IC_{50}$: 1~3 nM)

These results indicated that 5m and other compounds of the invention, unlike the standard of care chemotherapies, were able to reach the site of action in the brain which is prerequisite to effectively treating MBC BrnMets. Further, due to their lack of susceptibility to taxane/vinca resistance mechanisms and 17ya resistance mechanisms, the compounds of the invention would be able to treat BrnMets patients in a heavily pretreated patient, even if these patients had already failed taxane, vinca and/or 17ya therapies.

Effects of Compounds of this Invention on the Growth of Breast Cancer Metastases to the Brain in Mice Following the demonstration of brain penetration by 5m, we tested the ability to prevent MBC metastasis to the brain and treat BrnMets progression using the widely used MDA-MB-231 BrM2 (BrM2) cell line following intracardiac (IC) injection to preferentially induce BrnMets (PMID: 19421193). The most efficient method to enrich for breast cancer BrnMets in mice is through intracardiac (IC) injection of single cell suspensions of tumor cells into highly immunocompromised NSG mice. As shown throughout the examples, 5m and its analogs have broad anticancer activity including in many taxane resistant models. For example, a commonly used model of TNBC is the MDA-MB-231 cell line (see FIG. 30A) and its taxane-resistant subline MDA-MB-231/TxR (see FIG. 30B).

Consistent with clinical observations that ~95% of MBC patients diagnosed with BrnMets have metastases in at least one other site, often in multiple extracranial sites (such as bone, liver and lung), the BrM2 model quickly generates BrnMets but, over time, will also develop other metastatic sites. Mortality is primarily driven by BrnMets in the BrM2 model. Importantly, the BrM2 model expresses a luciferase reporter to enable longitudinal bio-imaging and tracking of metastatic patterns over time using methods in PMID: 31645441. All bioimaging data are shown as total flux (photons/s), calculated using Living Image software. At harvest, all organs were collected and bioimaged ex vivo to confirm location of metastatic signals observed in intact mice and to quantitate metastatic burden specific to that organ.

Figure 46A:
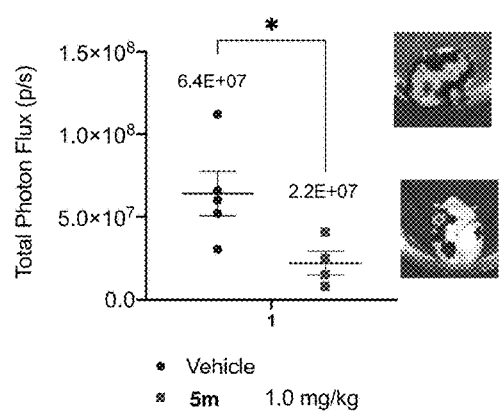
FIG. 46A and FIG. 46B illustrate that 5m represses BrnMets and increases OS.

Excitingly, in a pilot study, 5m reduced 231-BrM2 Brn-Met burden (bio-imaging of total photon flux shown; all mice were harvested after 28 days of therapy) (see FIG. 46A).

Procedures: In Experiment 1, the MDA-MB-231-BrM2 (BrM2) brain metastasis enriched subline was obtained from Memorial Sloan Kettering Cancer Care (MSKCC). A total of 200,000 cells were injected IC into 8-9 week old NSG female mice. Therapy was started 48 h later with IV administration 2×/week. The initial dose was 1.5 mg/kg, but mice lost weight and had diarrhea, so the dose was decreased to 1.0 mg/kg. All mice were harvested at same time on Day 24 of treatment.

Figure 47:
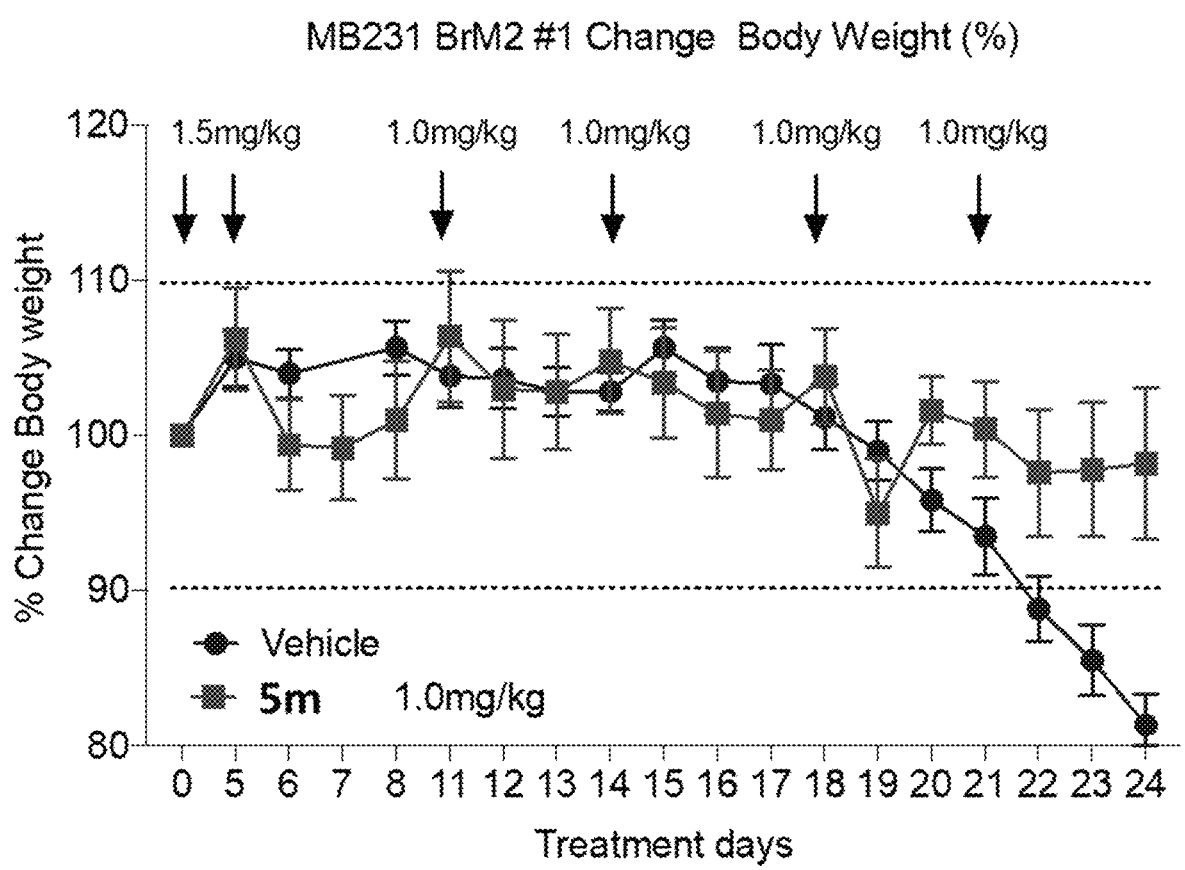
FIG. 47 illustrates that 5m treatment allowed mice to maintain body weight through day 24, whereas the body weight of vehicle treated mice decreased steadily from day 15 to day 24. Decreases in body weight are common as mice become sick due to metastatic burden. Further, the decrease in body weight was associated with signs and symptoms of brain metastasis including lethargy, difficulty walking, head tilt, etc.

FIG. 47 demonstrates that 5m treatment allowed mice to maintain body weight through day 24, whereas the body weight of vehicle treated mice decreased steadily from day 15 to day 24. Decreases in body weight are common as mice become sick due to metastatic burden. Further, the decrease in body weight was associated with signs and symptoms of brain metastasis including lethargy, difficulty walking, head tilt, etc.

Figure 48:
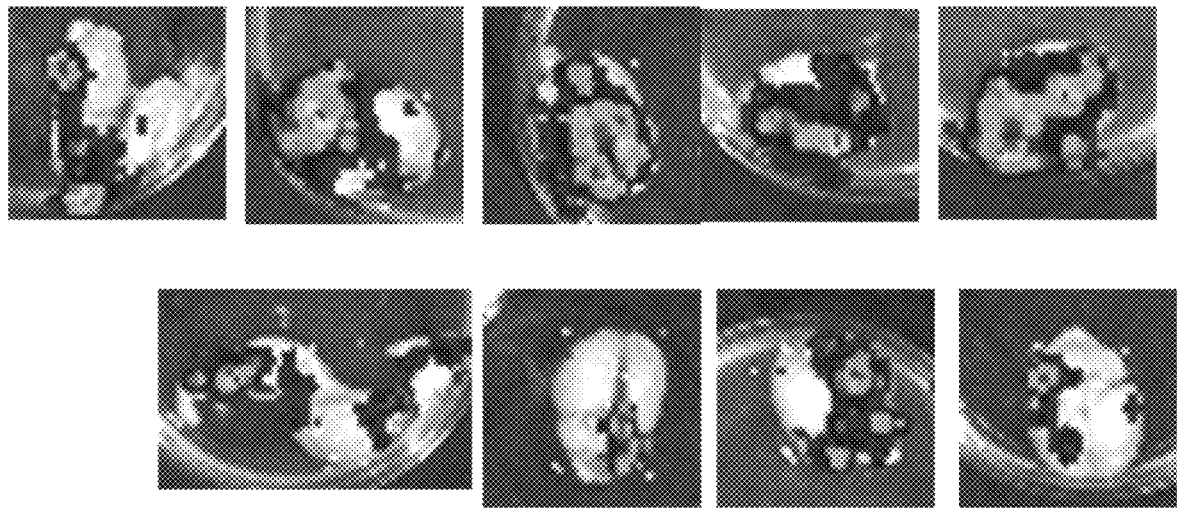
FIG. 48 illustrates that the excised brains of vehicle treated (top) and 5m treated (bottom) mice harvested on day 24 are shown following ex vivo bio-imaging. Quantitative analysis demonstrated that 5m treatment reduced total photon flux compared to vehicle treatment from a mean of $6.4 \times 10^7$ p/s to $2.2 \times 10^7$ p/s, and this difference was statistically significant (p=0.044).
Figure 49A:
FIG. 49A and FIG. 49B illustrate a comparison of the head imaged in vivo of intact mice (right side panel of each treatment) and then ex vivo (left side panel of each treatment) for the same animal is shown for a vehicle and 5m treated animal.
Figure 49B:
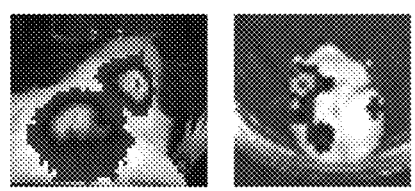

In FIG. 48, the excised brains of vehicle treated (top) and 5m treated (bottom) mice harvested on day 24 are shown following ex vivo bio-imaging. Quantitative analysis demonstrated that 5m treatment reduced total photon flux compared to vehicle treatment from a mean of $6.4 \times 10^7$ p/s to $2.2 \times 10^7$ p/s, and this difference was statistically significant (p=0.044). In FIG. 49A and FIG. 49B, a comparison of the head imaged in vivo of intact mice (right side panel of each figure treatment) and then ex vivo (left side panel of each figure treatment) for the same animal is shown for a vehicle and 5m treated animal. Using identical capture times (1 minute), the reduction in photon flux in the ex vivo brains can be further appreciated; the observed photon flux in the 5m treated ex vivo brain (see far right image; $1.51 \times 10^7$ p/s) is reduced compared to the vehicle treated brain (panel second from left; $6.01 \times 10^7$ p/s). Animals were imaged using a Perkin Elmer XMRS instrument.

Figure 50A:
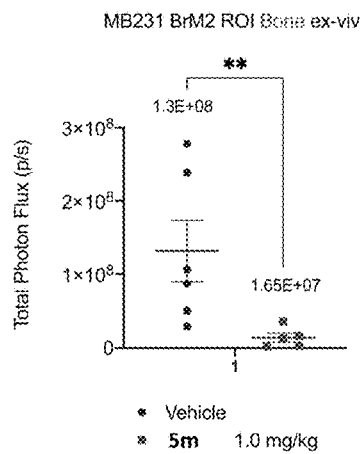
FIGS. 50A-C illustrate that the BrM2 cells will metastasize to bone, lungs, and spleen. Extracranial metastasis is observed in both treatment groups, but treatment with 5m reduced or delayed the metastatic growth of MBC, not just to brain (as demonstrated above), but also statistically reduced metastasis to bone, lungs, and spleen as determined by reduced total photon flux measured ex vivo in these organs in the same experiment.
Figure 50B:
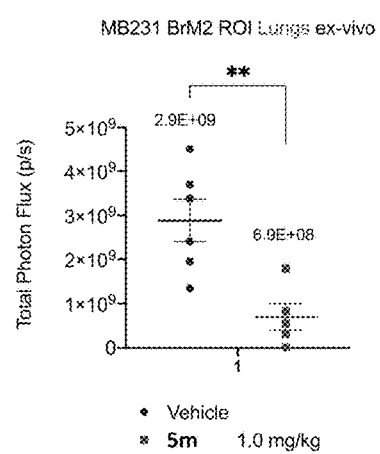
Figure 50C:
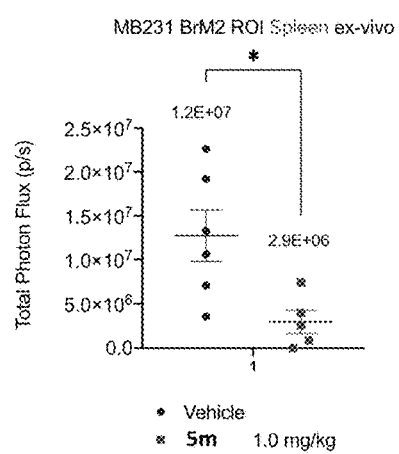

FIGS. 50A-C panels also demonstrate the BrM2 cells will metastasize to bone, lungs, and spleen. (FIGS. 50A, 50B, and 50C, respectively). Extracranial metastasis is observed in both treatment groups, but treatment with 5m reduced or delayed the metastatic growth of MBC, not just to brain (as demonstrated above), but also statistically reduced metastasis to bone, lungs, and spleen as determined by reduced total photon flux measured ex vivo in these organs in the same experiment.

Effects of Compounds of this Invention on the Overall Survival in Mice with Breast Cancer Metastases to the Brain (Animal Euthanized Only when Moribund)

Figure 46B:
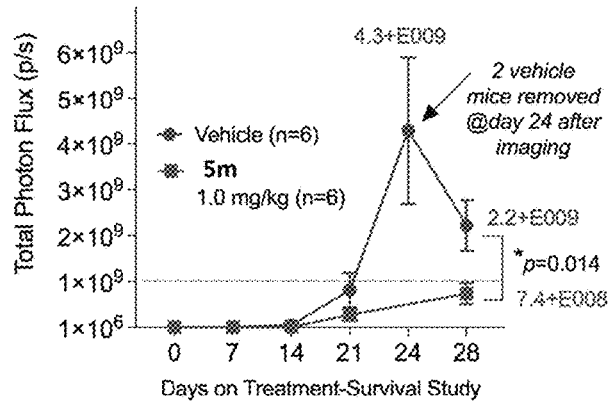
Figure 51:
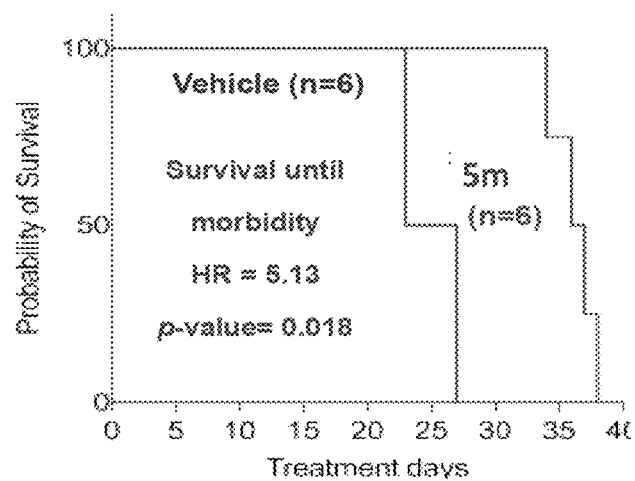
FIG. 51 illustrates that 5m significantly improves overall survival (OS) of mice bearing 231 BrM2 BrnMets. The survival data was only generated in Experiment #2 with 5m. 100,000 cells input, therapy started 24 h later, mice censored once moribund. Brains imaged in vivo until day of harvest, when also ex vivo imaged. The last data including all vehicle mice was Day 24, and the last imaging day in vivo including all 5m treated was Day 28.

In an independent study to measure survival, BrM2 cells (100,000) were injected IC into 8-9 week old mice and therapy initiated 24 h later. Therapy started 24 h later with dosing was 1.0 mg/kg given twice per week via IV route. The decreased cell number injected was selected to try to increase duration of treatment. In this study, mice were harvested only as they met the euthanasia criteria in order to develop a Kaplan-Meier survival curve. 5m not only dramatically reduced brain signals in vivo over time, similar to data from Experiment #1 shown in FIGS. 46A-B above, but also significantly improved overall survival (OS) with an impressive hazard ratio (HR=5.13) (p=0.018) as shown in FIG. 51.

Figure 52:
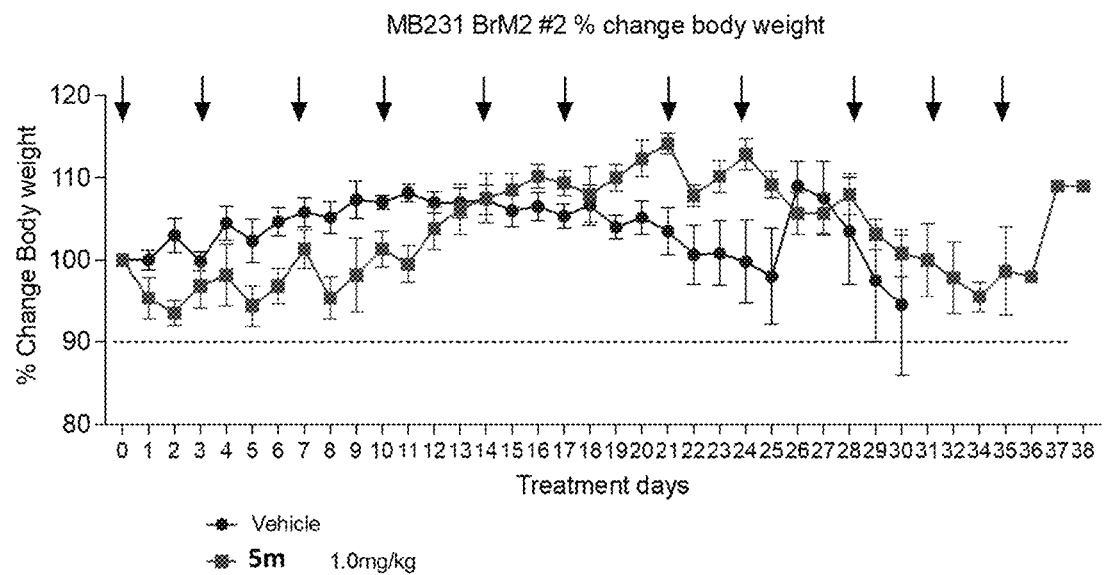
FIG. 52 illustrates that mice treated with 5m lived longer as is also apparent by the % change in body weight over time (see survival study (Experiment #2)). Further, the 5m cohort gained weight through day 21 of dosing, whereas vehicle treated mice began to lose weight by day 11. The % change in body weight in both cohorts seems to change in the latter stages of the experiment because the mean reflects the animals only still alive on those days and since extreme body weight loss (15-20%) is a primary euthanasia criterion. The arrows indicate the days on which 5m or vehicle were administered.

In this survival study (Experiment #2), mice treated with 5m lived longer as is also apparent by the % change in body weight over time in FIG. 52. Further, the 5m cohort gained weight through day 21 of dosing, whereas vehicle treated mice began to lose weight by day 11. The % change in body weight in both cohorts seems to change in the latter stages of the experiment because the mean reflects the animals only still alive on those days and since extreme body weight loss (15-20%) is a primary euthanasia criterion. The arrows indicate the days on which 5m or vehicle were administered.

Figure 53:
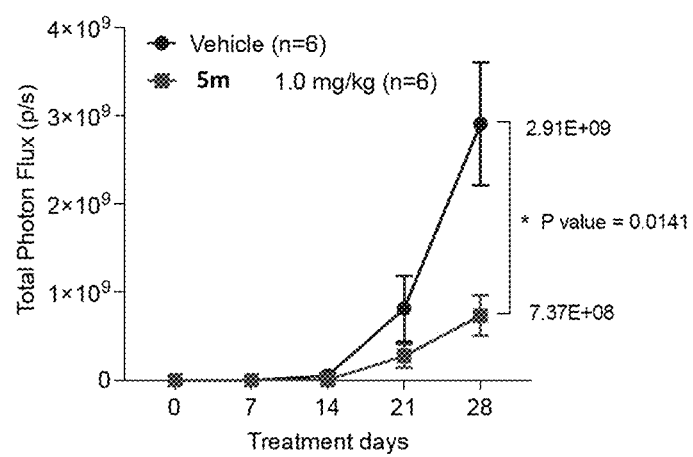
FIG. 53 illustrates that 5m treatment delayed metastatic progression in the brain as observed by decreased mean total photon flux at each time point greater than 14 days (signal traced in the figure is from the brain only). Despite high variability in the data, the effect of 5m treatment was statistically significant (p-value of 0.0141) on day 28.

Consistent with the previous study in which mice were harvested on the same day, mice in the survival study developed brain tumors measured over time as increased total photon flux in the brain. FIG. 53 demonstrated that 5m treatment delayed metastatic progression in the brain as observed by decreased mean total photon flux at each time point greater than 14 days (signal traced in the figure is from the brain only). Despite high variability in the data, the effect of 5m treatment was statistically significant (p-value of 0.0141) on day 28.

Figure 54A:
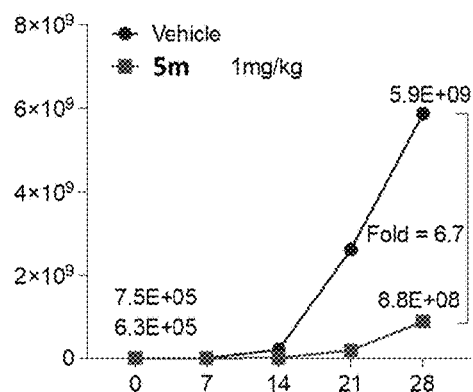
FIG. 54A and FIG. 54B illustrate that in vivo imaging of a single representative mouse (n=1 so no error bars) from each cohort revealed the same trends as ex vivo imaging.
Figure 54B:
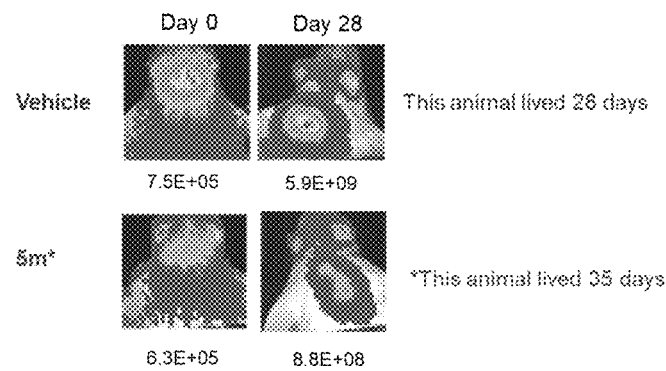

In FIG. 54, in vivo imaging of a single representative mouse (n=1 so no error bars) from each cohort was tracked over time (using identical bio-imaging capture times). Again, by day 14, the difference in total photon flux between vehicle-treated compared to 5m treated mouse started to diverge, again indicating that 5m delayed metastatic progression, with a 6.7 fold increased metastasis on day 28, despite each mouse showing similar starting values for BrnMets photon flux ($7.5 \times 10^5$ vs. $6.3 \times 10^5$). Further, the representative vehicle treated mouse died on day 28 whereas the 5m treated mouse lived until day 35. Animals were imaged using a Perkin Elmer XMRS instrument.

Figure 55:
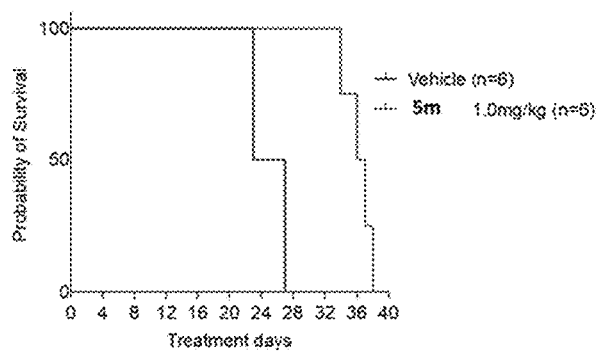
FIG. 55 (includes the table) illustrates that 5m increased survival. The survival of each cohort was tracked over time and plotted on a Kaplain-Meier survival curve. The table shows the euthanasia day of each of the six mice in each cohort. All the vehicle treated mice were deceased by 30 days whereas all the 5m treated mice lived longer than 30 days. Median survival of 5m treated mice was 36.5 days vs. 25 days for vehicle treated mice. Lastly, the Kaplain-Meier curve demonstrated a statistically significant increase in survival until morbidity for the 5m treated cohort with a hazard ratio of 5.13 and p-value of 0.018.

In the survival study, other sites of extracranial metastasis were not significantly repressed by 5m, as would be expected since euthanasia criteria was based on morbidity/survival and the cause of death is metastasis. In FIG. 55 which includes a table, the survival of each cohort was tracked over time and plotted on a Kaplain-Meier survival curve. The table shows the euthanasia day of each of the six mice in each cohort. All the vehicle treated mice were deceased by 30 days whereas all the 5m treated mice lived longer than 30 days. Median survival of 5m treated mice was 36.5 days vs. 25 days for vehicle treated mice. Lastly, the Kaplain-Meier curve demonstrated a statistically significant increase in survival until morbidity for the 5m treated cohort with a hazard ratio of 5.13 and p-value of 0.018.

In overview, 5m and compounds of the invention were shown to be brain penetrant and to retain extremely potent CBSI activity in vivo. Further, the ability to delay metastatic progression of breast cancer was demonstrated to include repressing metastasis to the brain, bone, spleen and lungs. In an independent study, these compounds were shown to increase OS due to their ability to inhibit metastasis.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:
1. A compound selected from the group consisting of:
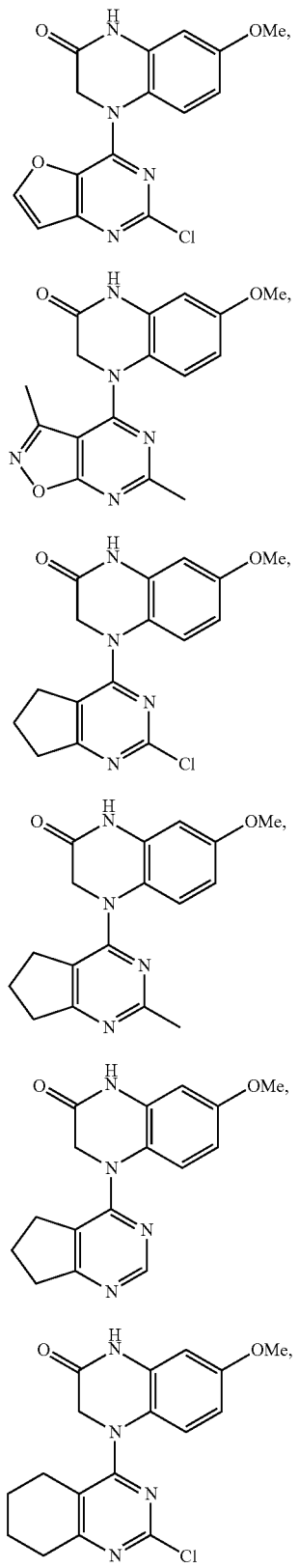
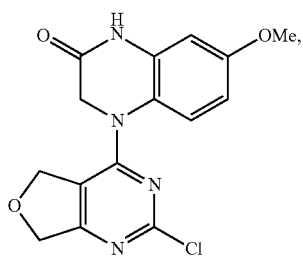
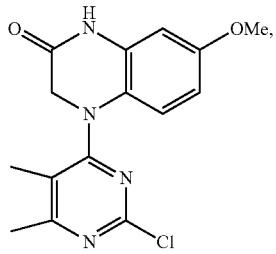
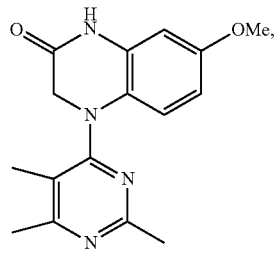
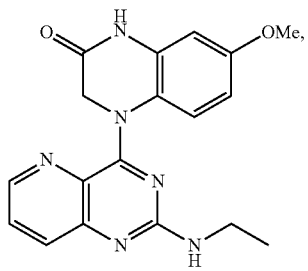
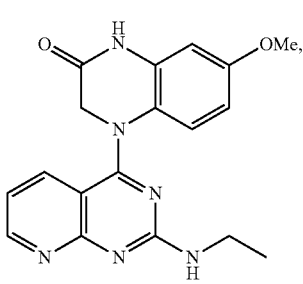
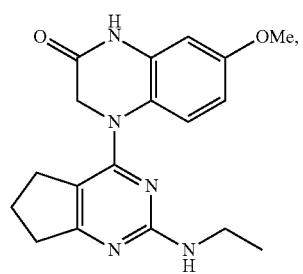

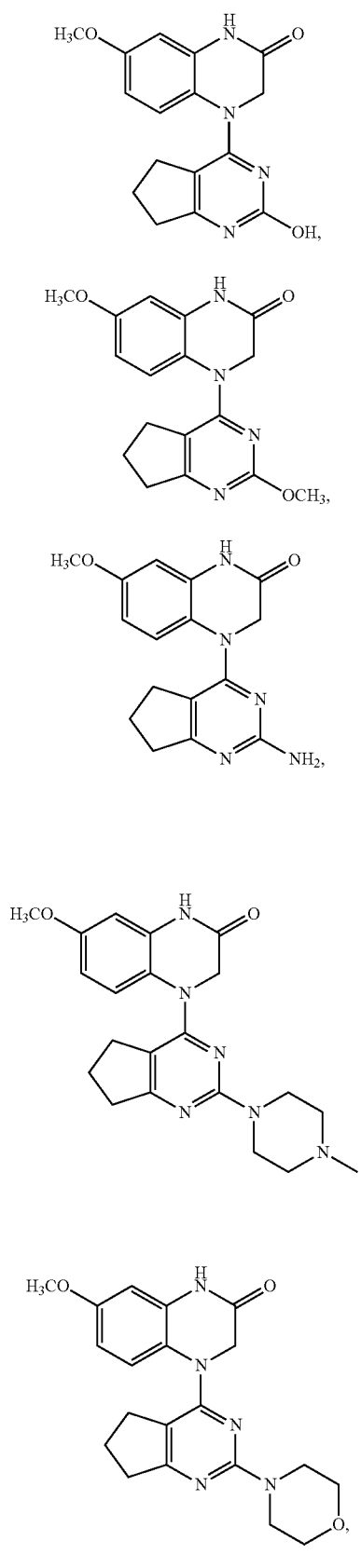
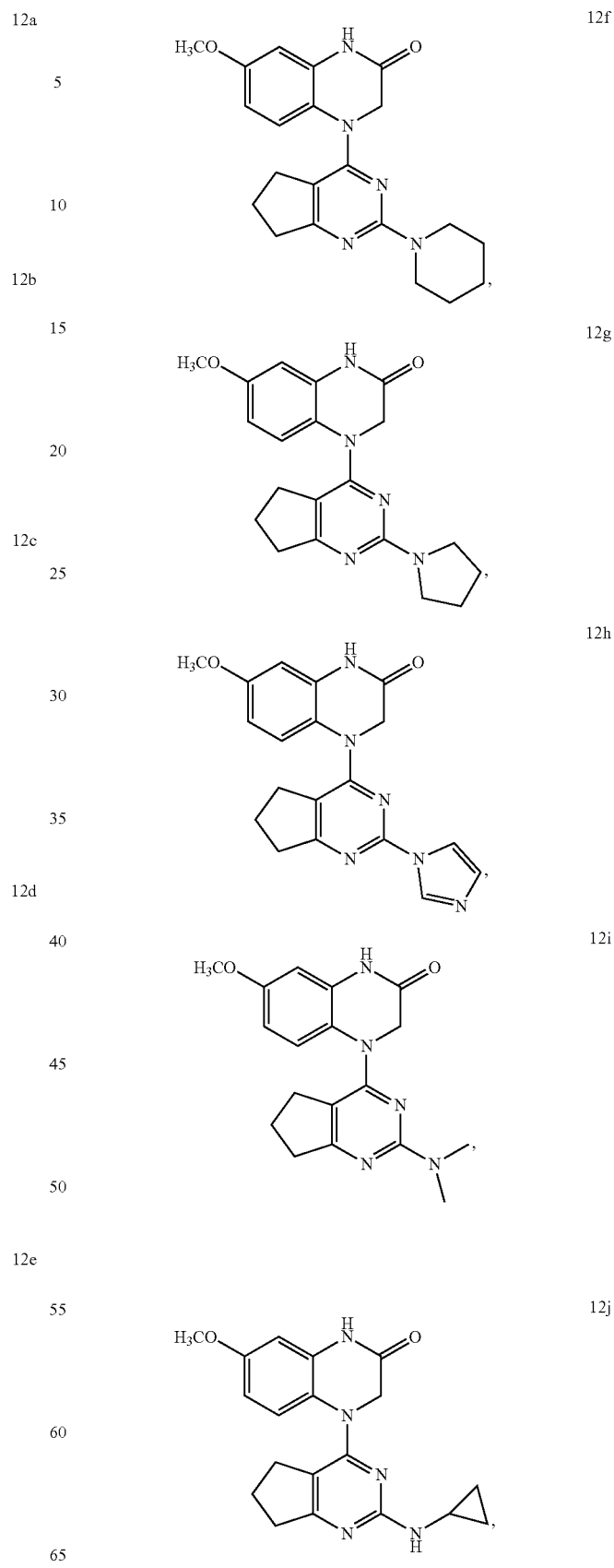

119
-continued

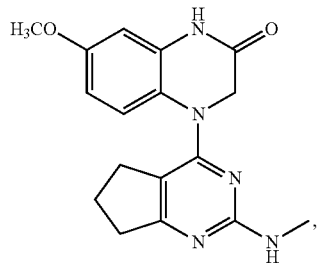
12k

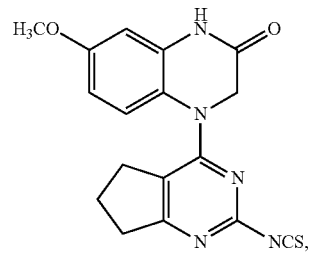
12l

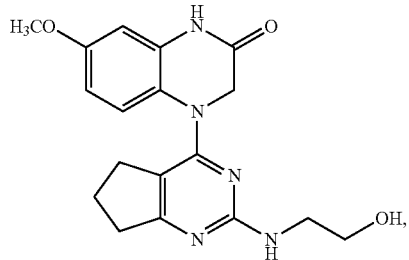
12m

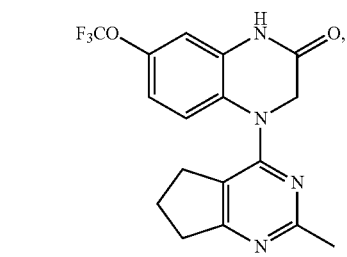
12o

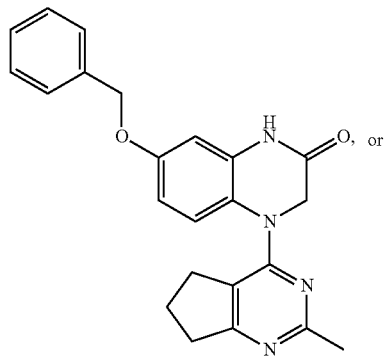
12p

120
-continued

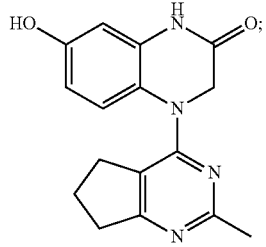
12q or a pharmaceutically acceptable salt, hydrate, N-oxide, or combinations thereof.

2. A compound having a structure of Formula III:

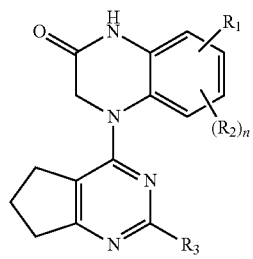

Formula III wherein $R_1$ is a halide, $C_1$-$C_4$ alkyl, $C_1$-$C_4$ alkoxy, $C_1$-$C_4$ haloalkyl, $C_1$-$C_4$ haloalkoxy, Ph, O($C_5$-$C_{10}$ aryl), OPh, ($C_1$-$C_3$ alkyl)phenyl, —O($C_1$-$C_3$ alkyl)phenyl, —NH$_2$, —NH($C_1$-$C_4$ alkyl), —N($C_1$-$C_4$ alkyl)$_2$, hydroxyl, cyano, or $C_2$-$C_5$ ether;

$R_2$ is at least one of hydrogen, halide, $C_1$-$C_4$ alkyl, $C_1$-$C_4$ alkoxy, $C_1$-$C_4$ haloalkyl, —NH$_2$, —NH($C_1$-$C_4$ alkyl), —N($C_1$-$C_4$ alkyl)$_2$, hydroxyl, cyano, or $C_2$-$C_5$ ether;

$R_3$ is hydrogen, halide, $C_1$-$C_4$ alkyl, $C_1$-$C_4$ alkoxy, $C_1$-$C_4$ haloalkyl, —NH$_2$, —NH($C_1$-$C_4$ alkyl), —N($C_1$-$C_4$ alkyl)$_2$, —NH($C_1$-$C_4$ heteroalkyl), —NHPh, —NH($C_3$-$C_{10}$ aryl), —NH($C_3$-$C_{10}$ heteroaryl), —NH($C_3$-$C_{10}$ cycloalkyl), —NH($C_3$-$C_{10}$ heterocyclyl), hydroxyl, cyano, NCS, $C_3$-$C_6$ heterocyclyl, or $C_2$-$C_5$ ether, wherein the heterocyclyl has at least one of O, N, or S, and wherein the heterocyclyl may optionally be substituted, wherein the substitutions of the heterocyclyl include halide, $C_1$-$C_4$ alkyl, $C_1$-$C_4$ alkoxy, $C_1$-$C_4$ haloalkyl, —NH$_2$, —NH($C_1$-$C_4$ alkyl), —N($C_1$-$C_4$ alkyl)$_2$, hydroxyl, cyano, or $C_2$-$C_5$ ether; and n is 1-3;

or a stereoisomer, pharmaceutically acceptable salt, hydrate, N-oxide, or combinations thereof.

3. The compound of formula III in claim 2 represented by one of the following compounds:

-continued

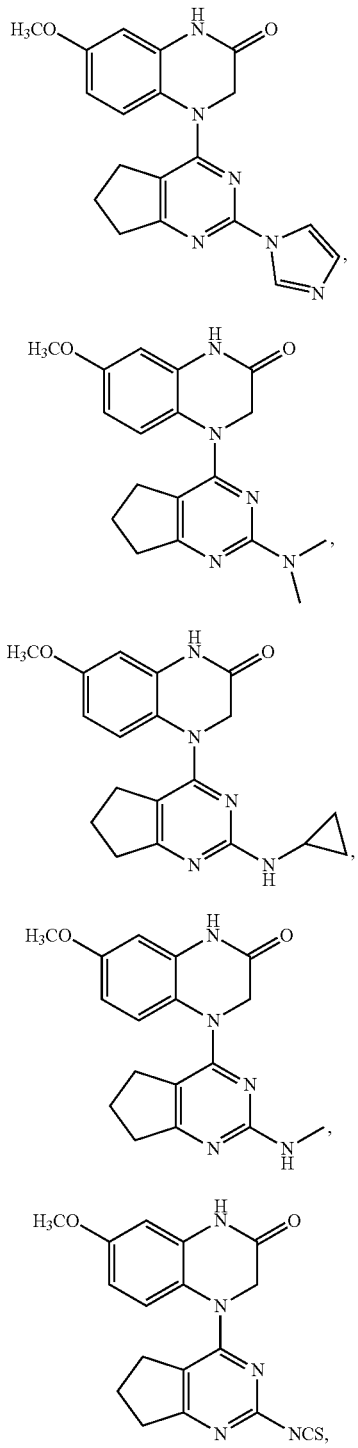
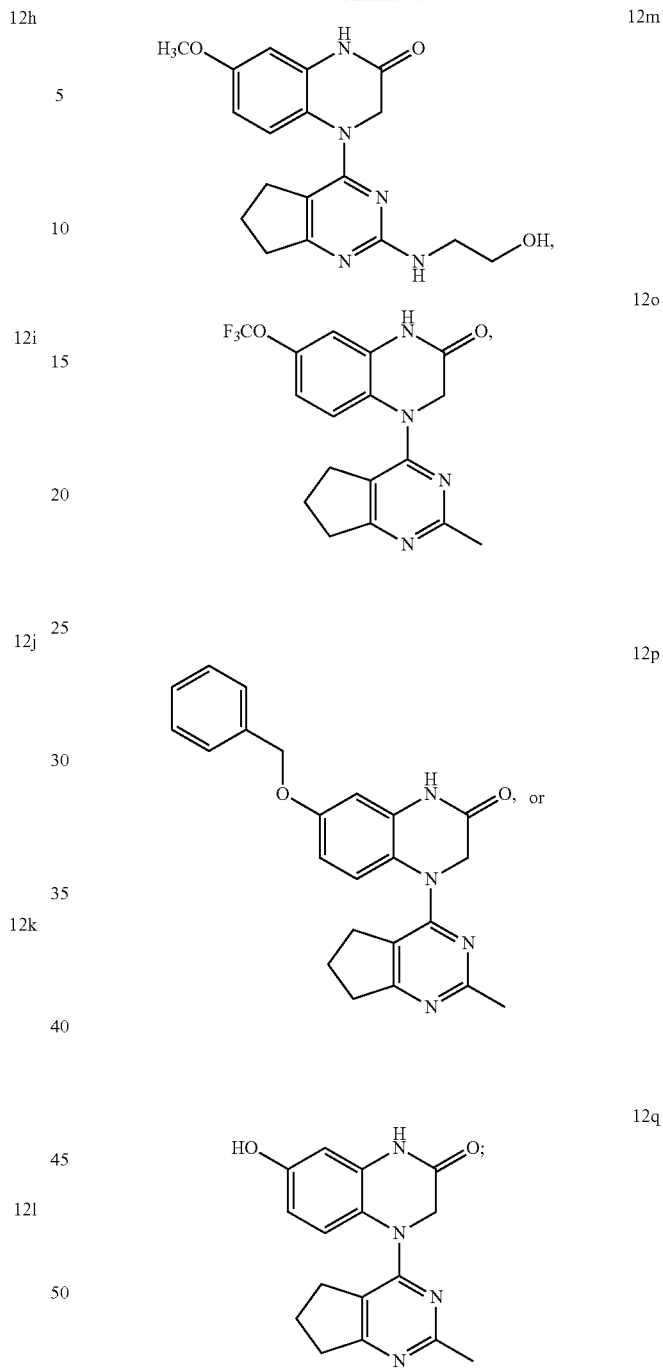
or a pharmaceutically acceptable salt, hydrate, N-oxide, or combinations thereof.
* * * * *